United States Patent
Cherkasov et al.

(10) Patent No.: US 9,994,894 B2
(45) Date of Patent: Jun. 12, 2018

(54) METHOD AND COMPONENTS FOR DETECTING NUCLEIC ACID CHAINS

(75) Inventors: Dmitry Cherkasov, Marburg (DE);
Claus Becker, Otigheim (DE); Norbert Basler, Gross Hansdorf (DE); Andreas Muller-Hermann, Munich (DE); Petra Van Husen, Eltville (DE)

(73) Assignee: AGCT GMBH, Luebeck (DE)

(*) Notice: Subject to any disclaimer, the term of this patent is extended or adjusted under 35 U.S.C. 154(b) by 205 days.

(21) Appl. No.: 14/114,506

(22) PCT Filed: Apr. 26, 2012

(86) PCT No.: PCT/EP2012/001787
§ 371 (c)(1),
(2), (4) Date: Jun. 12, 2014

(87) PCT Pub. No.: WO2012/146377
PCT Pub. Date: Nov. 1, 2012

(65) Prior Publication Data
US 2014/0295438 A1    Oct. 2, 2014

(30) Foreign Application Priority Data

Apr. 27, 2011  (DE) .................. 10 2011 018 663
Apr. 27, 2011  (DE) .................. 10 2011 018 664

(51) Int. Cl.
*C12Q 1/68*   (2018.01)
*C07H 21/02*  (2006.01)

(52) U.S. Cl.
CPC .......... *C12Q 1/686* (2013.01); *C12Q 1/6846* (2013.01)

(58) Field of Classification Search
CPC ............ C12Q 1/6846; C12Q 2525/101; C12Q 2563/149; C12Q 2563/179; C12Q 1/686
See application file for complete search history.

(56) References Cited

U.S. PATENT DOCUMENTS

| 4,792,520 A * | 12/1988 | Stambrook .............. C12Q 1/68 435/29 |
| 5,518,900 A * | 5/1996 | Nikiforov .............. C12N 15/10 435/810 |
| 5,739,311 A * | 4/1998 | Lackey ................. C12Q 1/686 435/5 |

(Continued)

FOREIGN PATENT DOCUMENTS

| WO | 2005/044836 A2 | 5/2005 |
| WO | 2006/097320 A2 | 9/2006 |

(Continued)

OTHER PUBLICATIONS

Putney, S.D. et al., PNAS USA, vol. 78, pp. 7350-7354 (1981).*

(Continued)

*Primary Examiner* — Teresa E Strzelecka

(57) ABSTRACT

The invention relates to a novel method for the enzymatic marking of nucleic acid chains (target sequences) by means of nucleotide conjugates. Said nucleotide conjugates are able, under reaction conditions, to specifically bind to the target sequence and integrate into the complementary growing strand by means of a polymerase. The nucleic acid chains marked by such conjugates can be bound to the solid phase. The marking can be carried out parallel to the enzymatic amplification of target sequences.

23 Claims, 56 Drawing Sheets

(56) References Cited

U.S. PATENT DOCUMENTS

| 6,682,887 B1* | 1/2004 | Singh | C07H 19/06 |
|---|---|---|---|
| | | | 435/6.1 |
| 2009/0155859 A1* | 6/2009 | Nelson | C12Q 1/6848 |
| | | | 435/91.53 |
| 2010/0029494 A1 | 2/2010 | Cherkasov et al. | |
| 2010/0093992 A1 | 4/2010 | Cherkasov et al. | |
| 2010/0304368 A1 | 12/2010 | Cherkasov et al. | |

FOREIGN PATENT DOCUMENTS

| WO | 2008/043426 A2 | 4/2008 |
|---|---|---|
| WO | 2011/050938 A1 | 5/2011 |

OTHER PUBLICATIONS

Cherkasov et al., "New Nucleotide Analogues with Enhanced Signal Properties," Bioconjugate Chemistry, vol. 21, No. 1, Jan. 20, 2010, pp. 122-129.

International Search Report for International Application No. PCT/EP2012/001787, dated Nov. 10, 2012, 3 pgs.

* cited by examiner

Nuc macromolecule

1) Nuc component
2) Linker component
3) Target domain of the nuc macromolecule
4) Anchor domain of the nuc macromolecule
5) Signaldomain of the nuc macromolecule Fig. 2
Basic structure of the nuc macromolecule
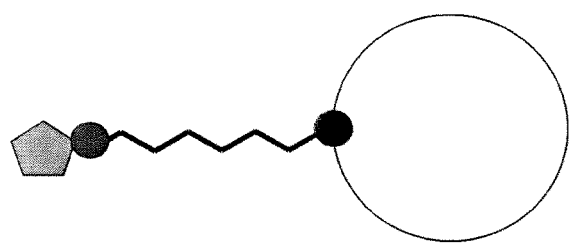
Legend
Nuc component
Linker component with
Coupling unit (L)
Polymer
coupling unit (T)
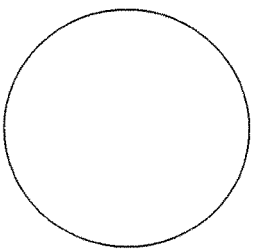
Markercomponent Primer-Template-complex 6) Primer
7) Template (target sequence)
8) Anchor domain of the primer
9) Signal domain of the primer

Fig. 6

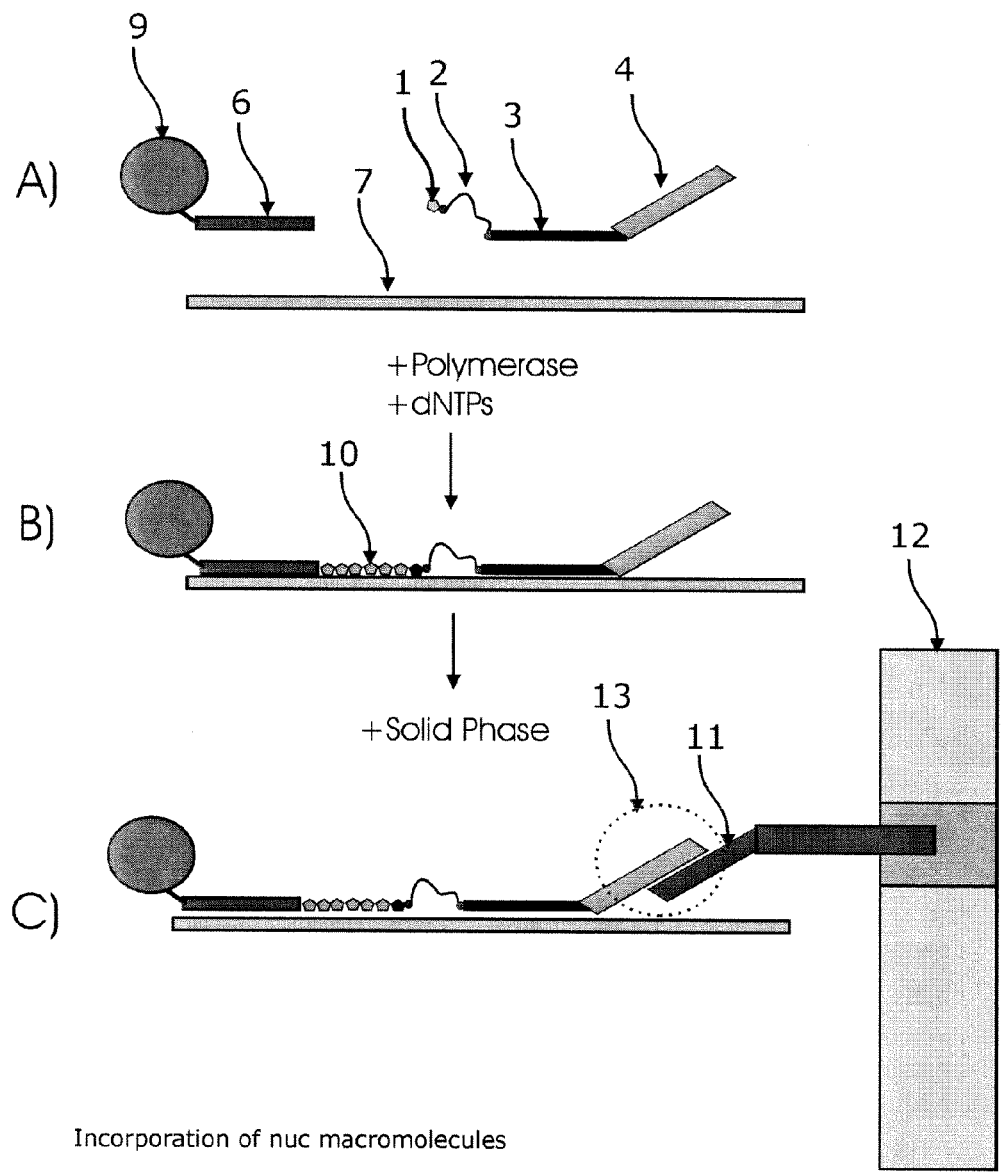

Incorporation of nuc macromolecules

1) Nuc compoent
2) Linker compoent
3) Target domain of the nuc macromolecule
4) Anchor domain of the nuc macromolecule
6) Primer
7) Template (target sequence)
9) Signal domain of the primer
10) non labeled nucleotides (incorporiert)
11) Binding partner of the anchor domain
12) solid Phase 1 (e.g. Lateral flow test strip with immobilized binding partners)
13) Binding between Anchor domain and binding partner on the solid phase Fig. 7
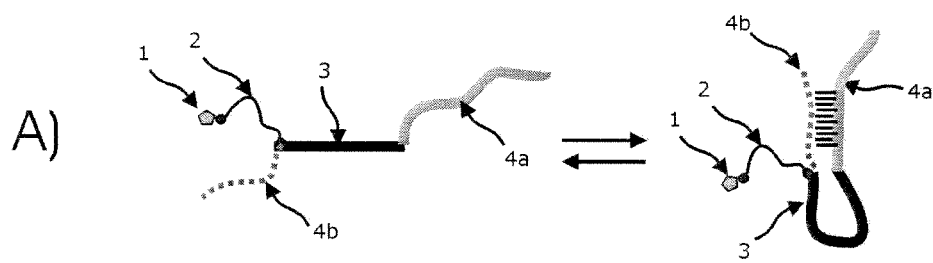
Labeling of target sequence with a nuc macromolecule with an antogonist to the anchor domain
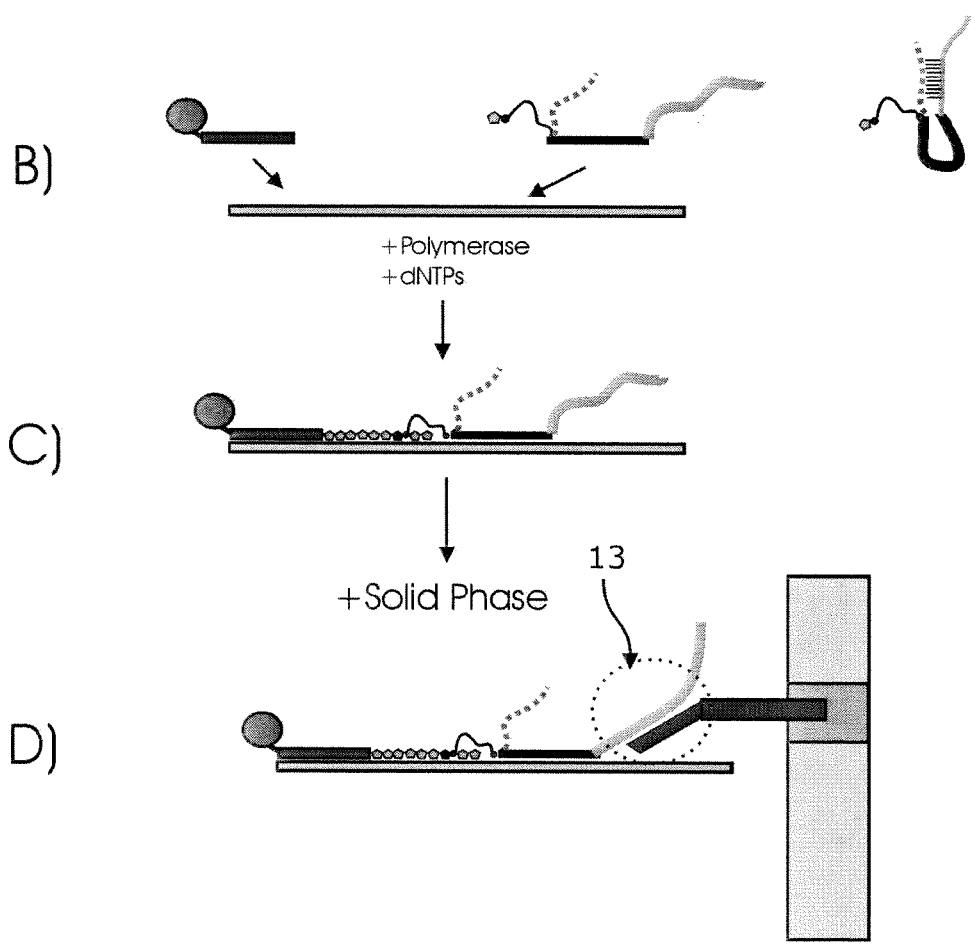

Fig. 9
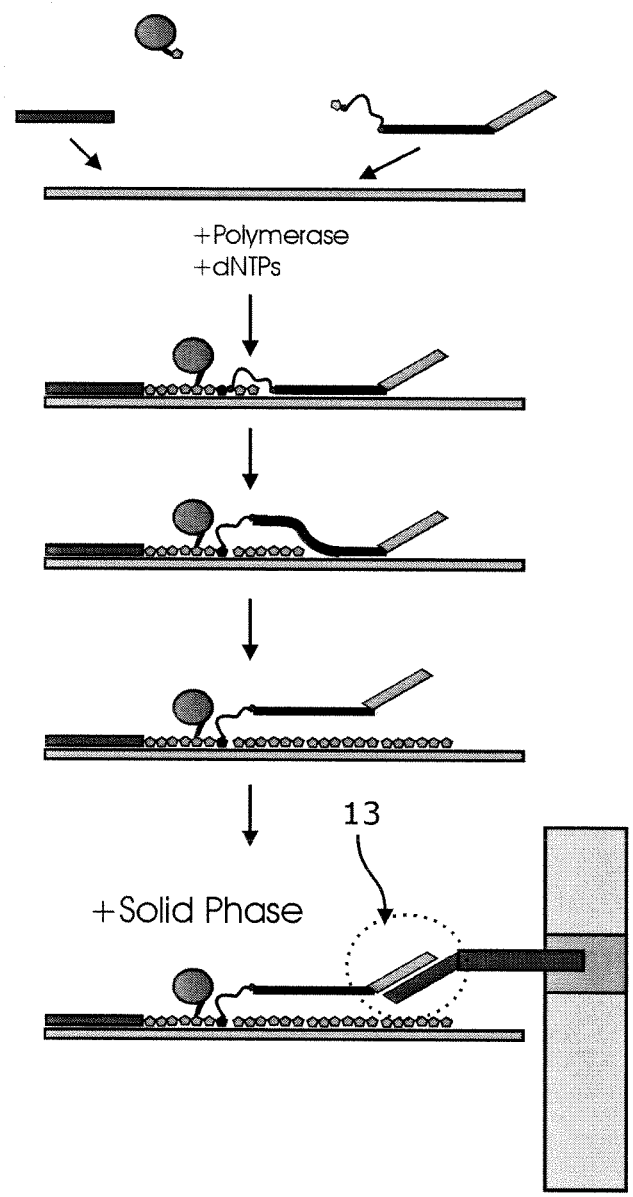
Legende
 Markiertes Nukleotid

Fig. 13

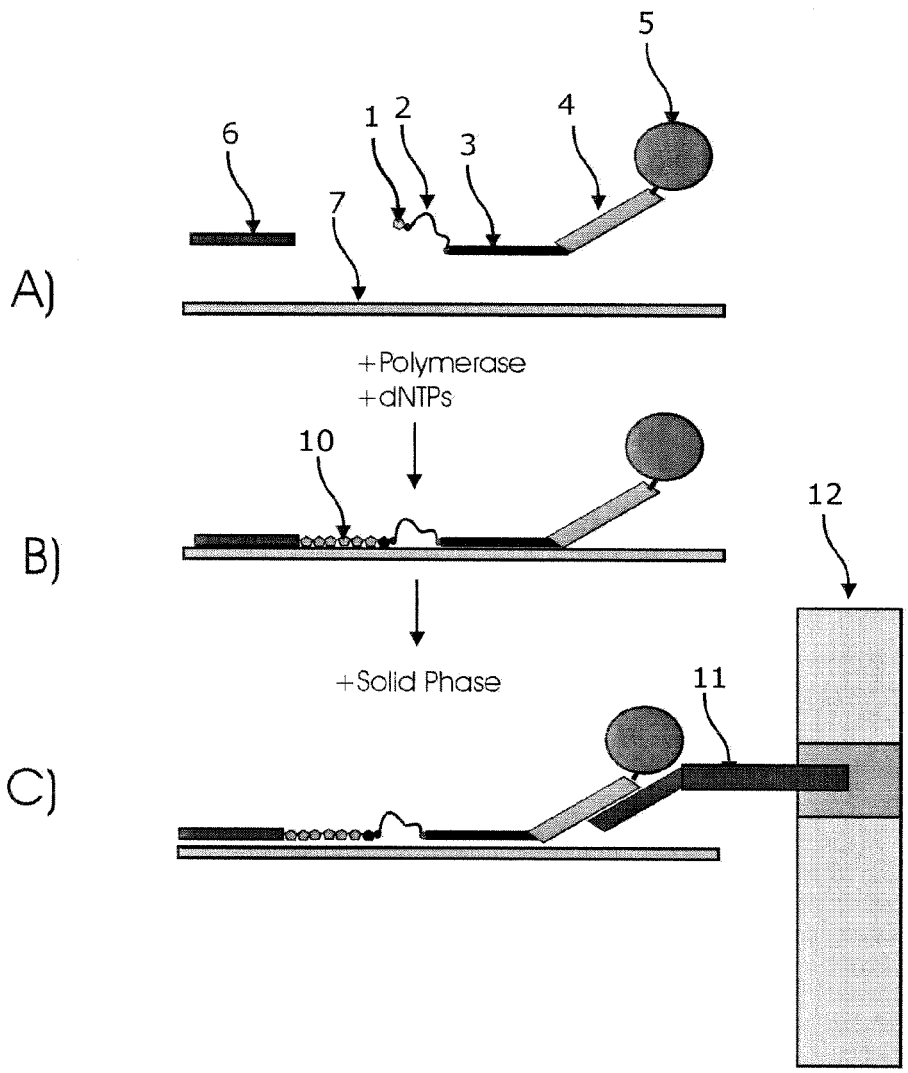

Incorporation of nuc macromolecules

1) Nuc compoent
2) Linker compoent
3) Target domain of the nuc macromolecule
4) Anchor domain of the nuc macromolecule
5) Signal domain of the nuc macromolecule
6) Primer
7) Template (target sequence)
10) non labeled nucleotides (incorporiert)
11) Binding partner of the anchor domain
12) solid Phase 1 (e.g. Lateral flow test strip with immobilized binding partners)

Fig. 14

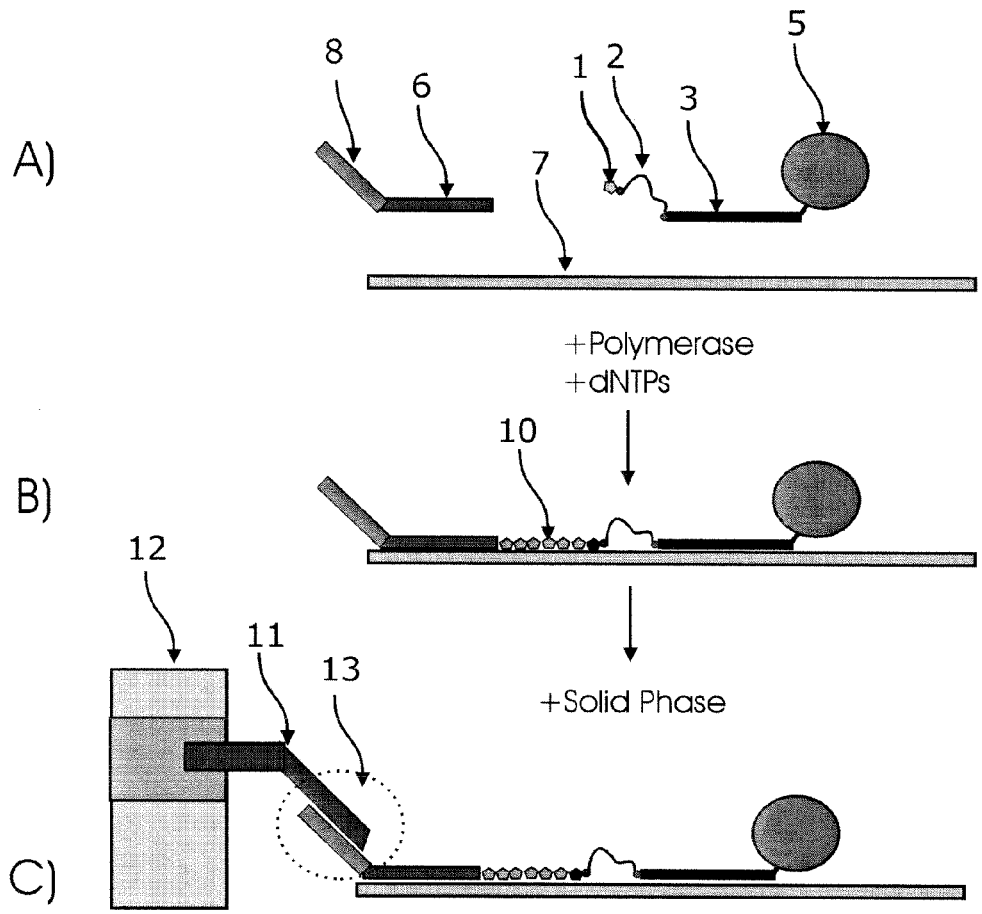

Incorporation of nuc macromolecules

1) Nuc compoent
2) Linker compoent
3) Target domain of the nuc macromolecule
4) Signal domain of the nuc macromolecule
6) Primer
7) Template (target sequence)
8) Anchor domain of the primer
10) non labeled nucleotides (incorporiert)
11) Binding partner of the anchor domain
12) solid Phase 1 (e.g. Lateral flow test strip with immobilized binding partners)
13) Binding between Anchor domain and binding partner on the solid phase

Fig. 15

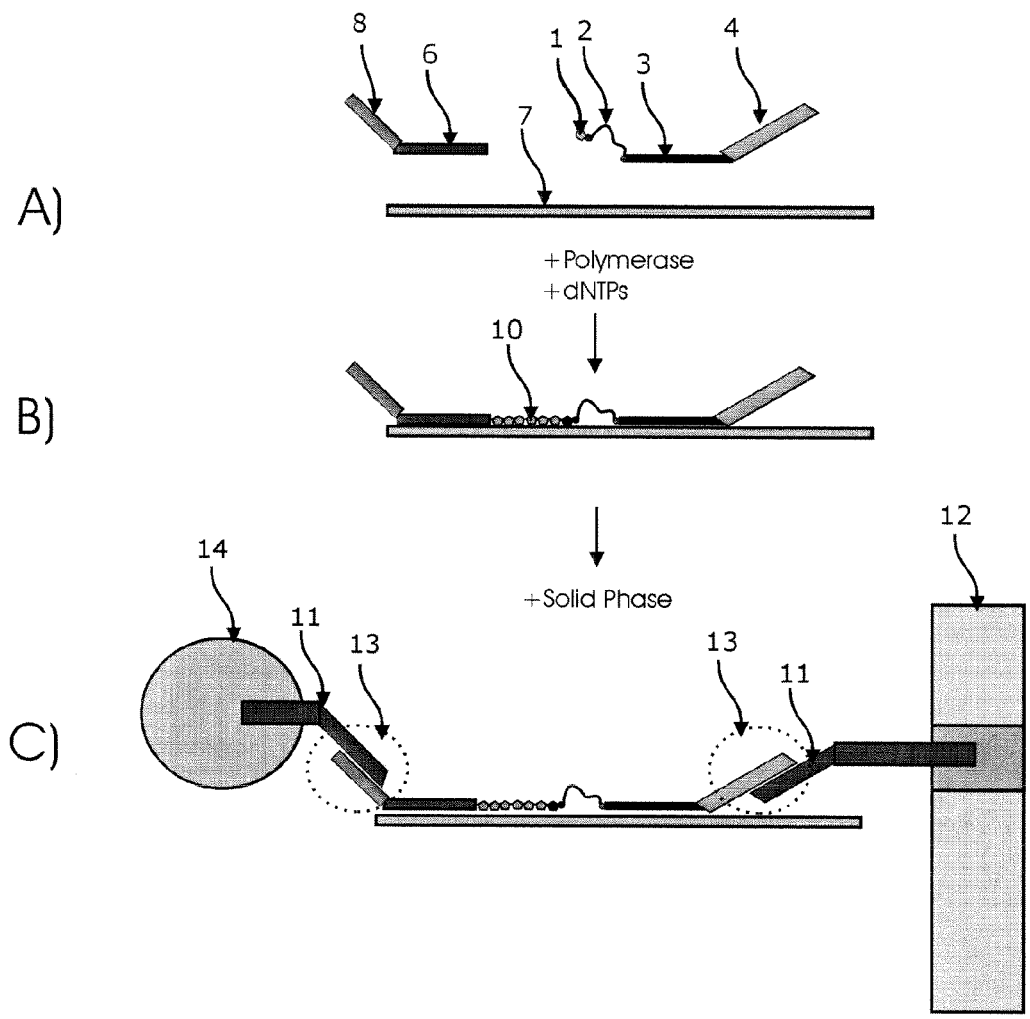

Incorporation of nuc macromolecules

1) Nuc compoent
2) Linker compoent
3) Target domain of the nuc macromolecule
4) Anchor domain of the nuc macromolecule
6) Primer
7) Template (target sequence)
8) Signal domain of the primer
10) non labeled nucleotides (incorporiert)
11) Binding partner of the anchor domain
12) solid Phase 1 (e.g. Lateral flow test strip with immobilized binding partners)
13) Binding between Anchor domain and binding partner on the solid phase
14) solid phase 2 ( e.g. Microparticles or nanoparticles)

Selection of the target sequence through the target domain, incorporation and addressable binding to the solid phase Parallel amplification and labeling of the target sequence Binding to the solid phase via anchor domain Parallel amplification and labeling of the target sequences Parallel amplification and labeling of the target sequences Fig. 22
A) 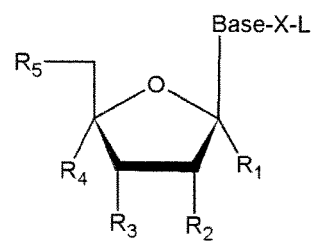
B) 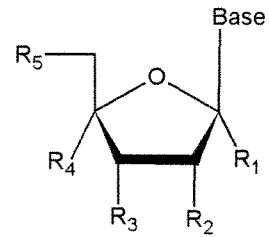

Fig. 23
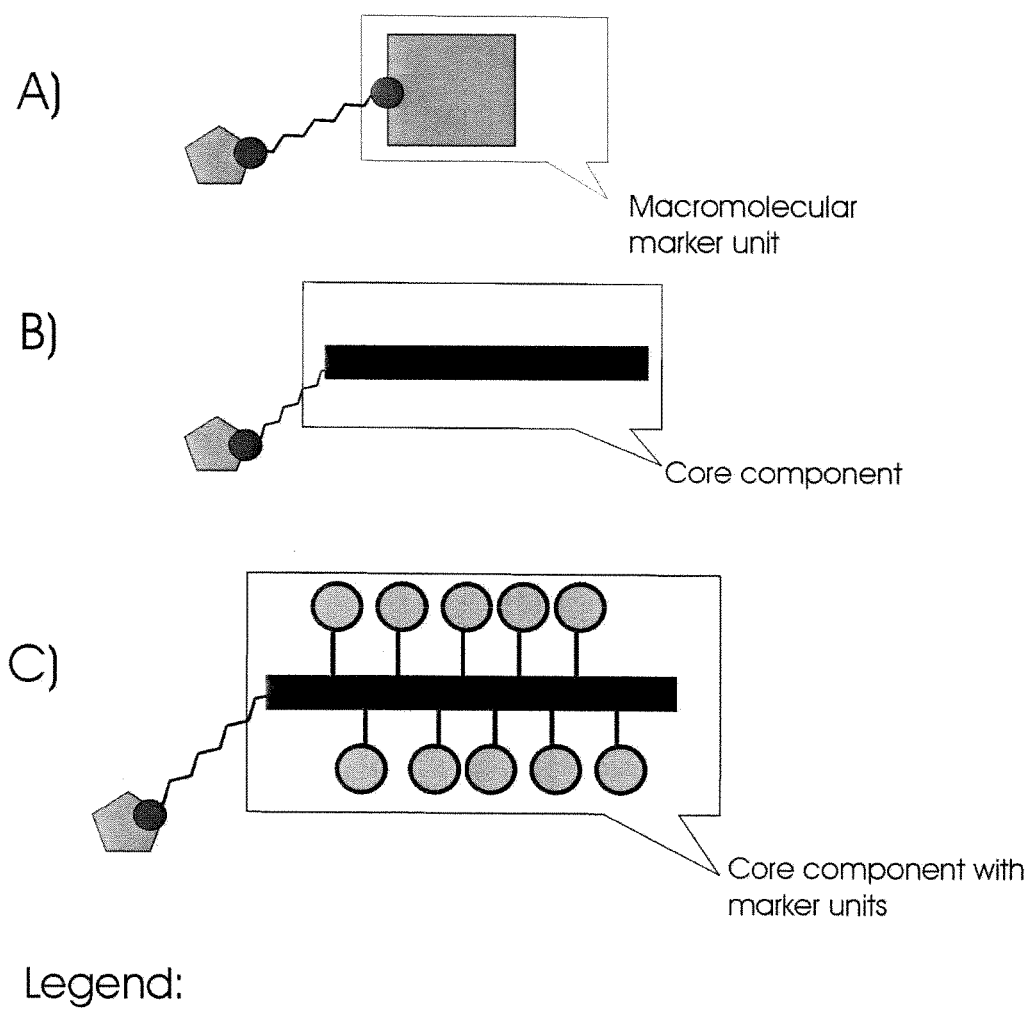
A) Macromolecular marker unit
B) Core component
C) Core component with marker units
Legend:
     
Nuc component     Linker component Fig. 24
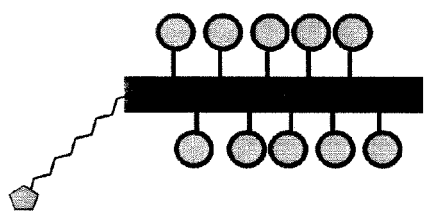
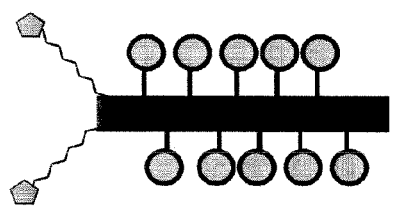
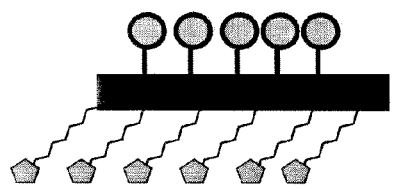
Legend:
         
Nuc component        Linker component        Core component        Marker unit with a linker Nucleic acid as a core component Legend:

| Nuc component | Linker component | Signal-giving marker unit | Nucleic acid with a signal-giving marker unit |

Fig. 28
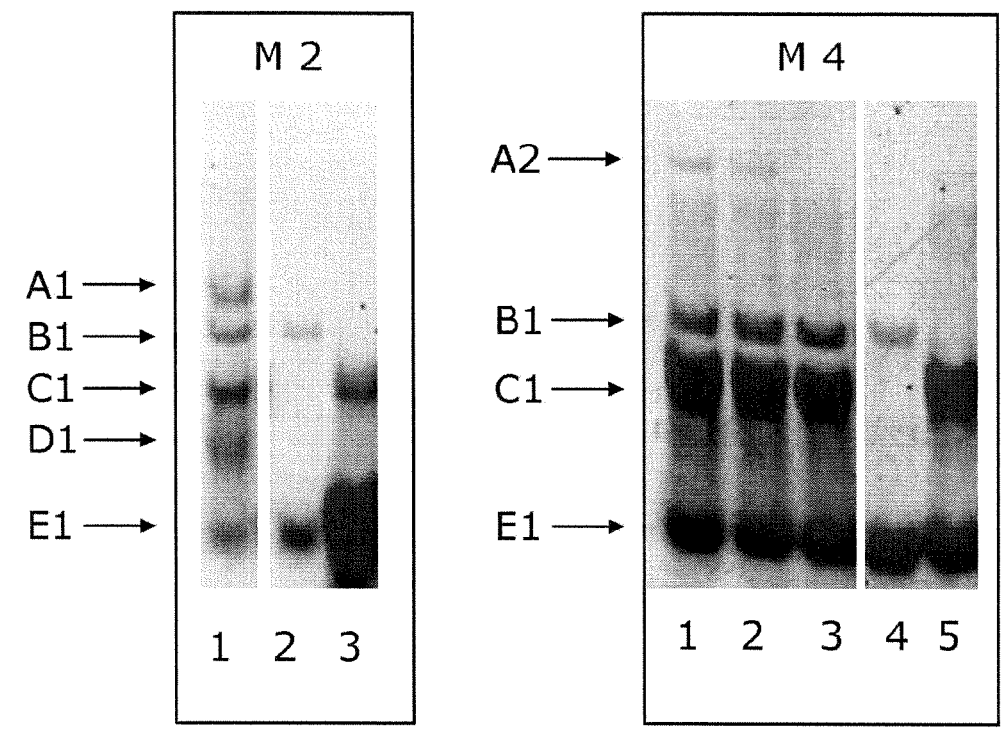
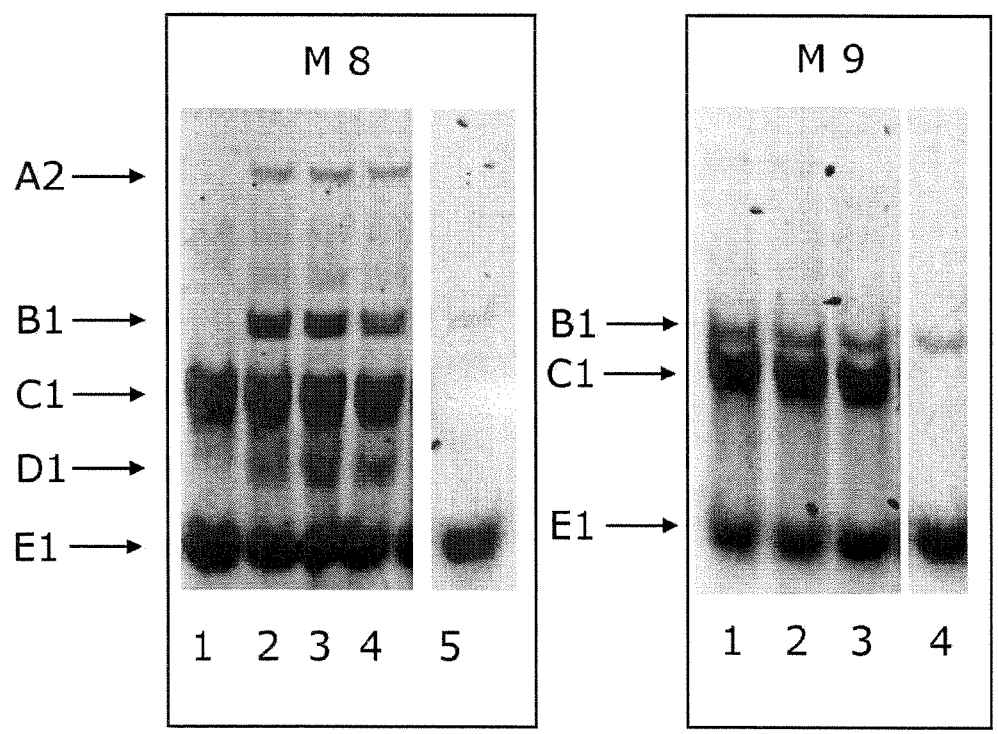

Fig. 32

Examples for nuc-macromolecules with oligonucleotides with a double-stranded structure (Molecular Beacon)

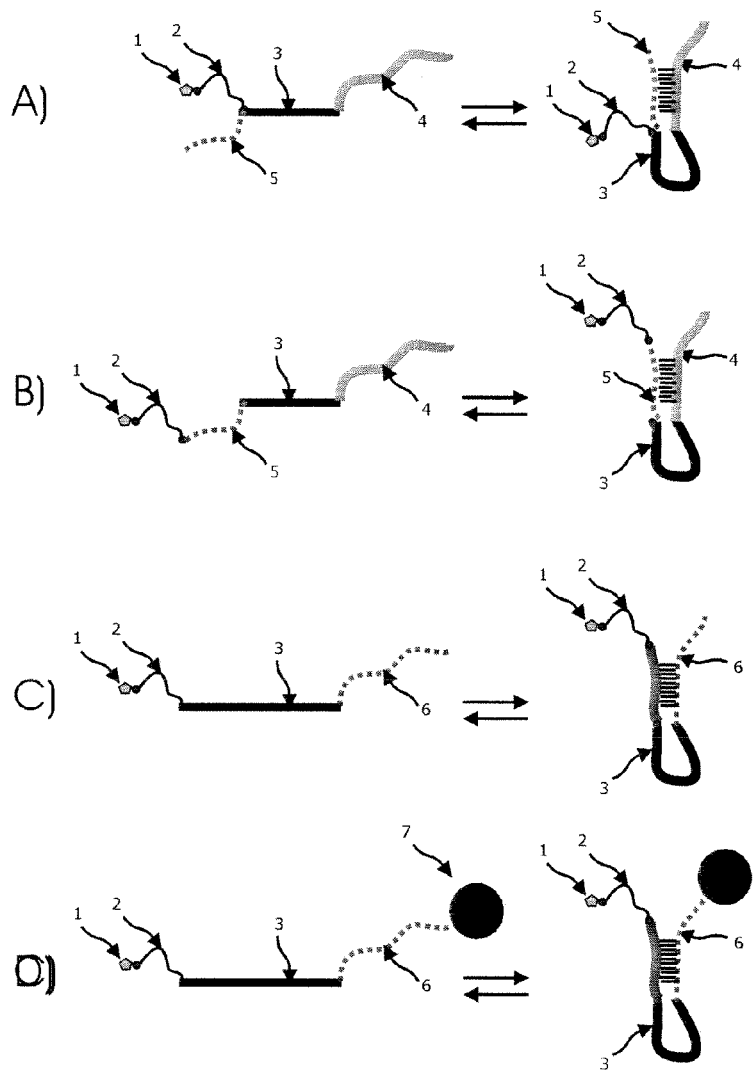

Legend:

"open" (left) and "closed" (right) state of nuc-macromolecules with self-complementary sequence fragments (1) Nuc-component, (2) Linker, (3) Target-Domain-oligonucleotide, (4,5) flanking sequences with reciprocal complementary fragments (6) flanking sequences with a fragment complementary to the target domain, (7) signal giving moiety

Fig. 33

Examples for nuc-macromolecules with
antagonist-oligonucleotides complementary bound
to the target domain of a nuc-macromolecule

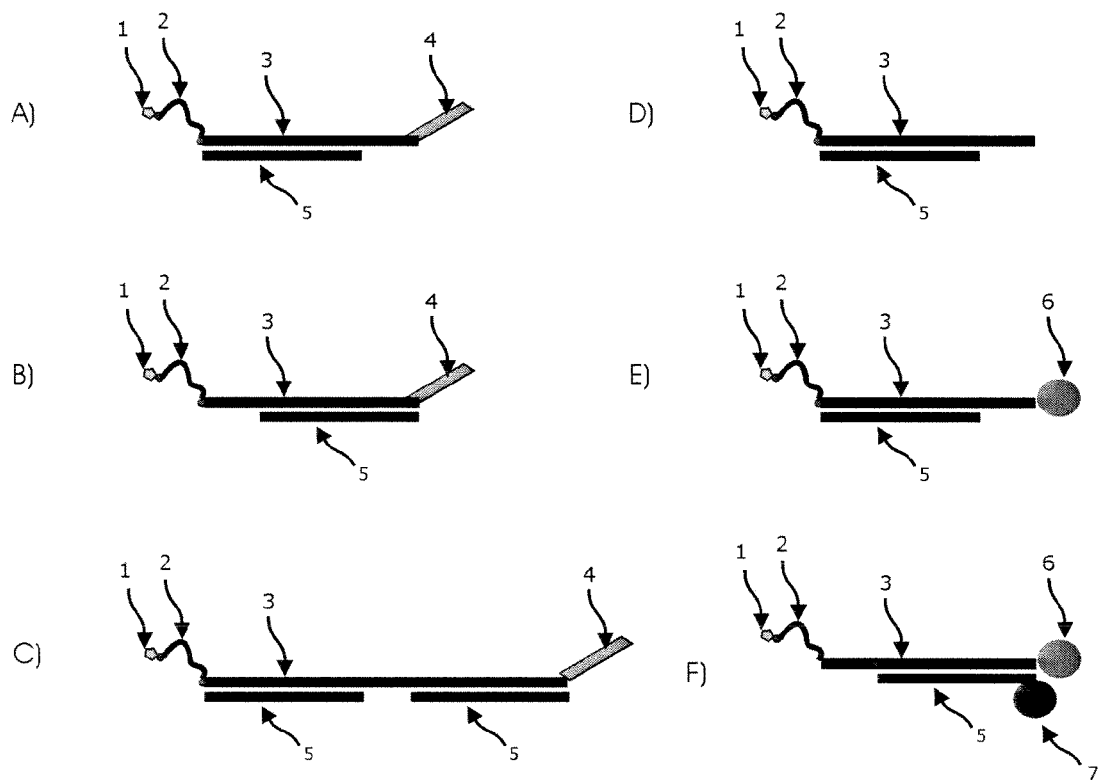

Legend:

1) Nuc-compoent
2) Linker compoent
3) Target domain of the nuc-macromolecule (oligonucleotide)
4) Anchor domain of the nuc-macromolecule (oligonuleotide)
5) Antagonist oligonucleotide
6) Signal domain (1) of the nuc-macromolecule (e.g. dye)
7) Signal domain (2) of the nuc-macromolecule (e.g. Quencher)

Parallel amplification and labeling of target sequences
with nuc-macromolecules comprising antagonist-oligonucleotides

Fig. 38

Example for combination of chain-terminating nuc-macromolecules
and their positioning within the target sequence
both strands are targets for the binding of nuc-macromolecules

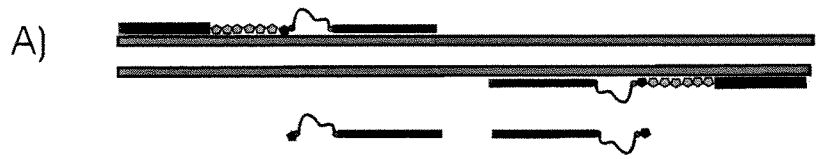

A)

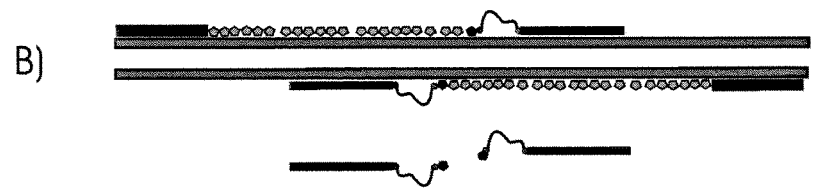

B)

A and B: both nuc-macromolecules bind to
non-overlapping parts of the target sequence

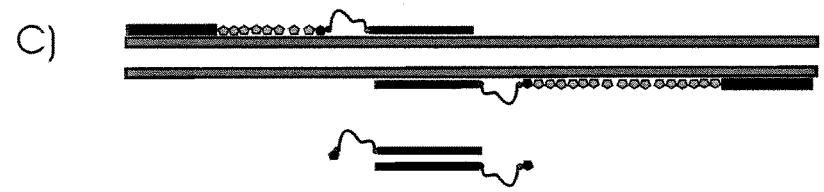

C)

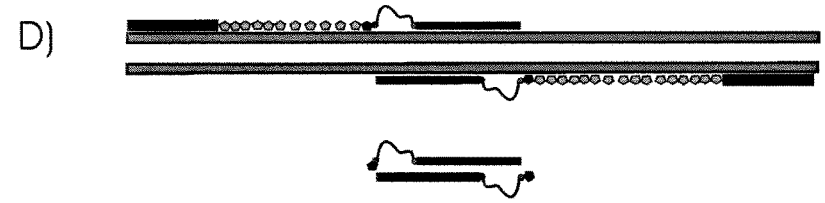

D)

E)

C, D and E: both nuc-macromolecules bind to fully or
partially overlapping parts of the target sequence Fig. 40
Termination of multiple sequences
A) 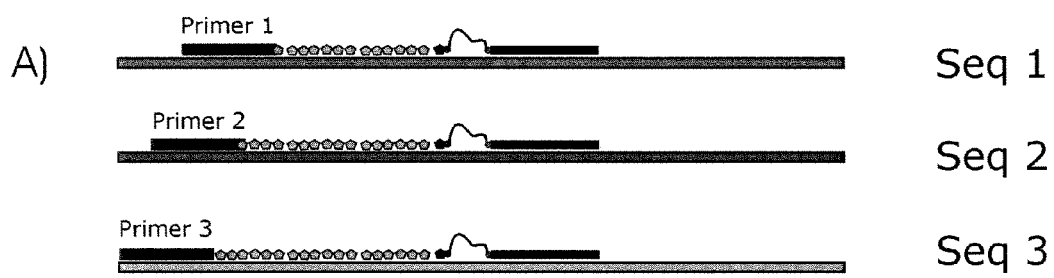
Suppression of the extenstion of multiple sequences via
nuc-macromolecules with the same or similar sequence of the target domain
B) 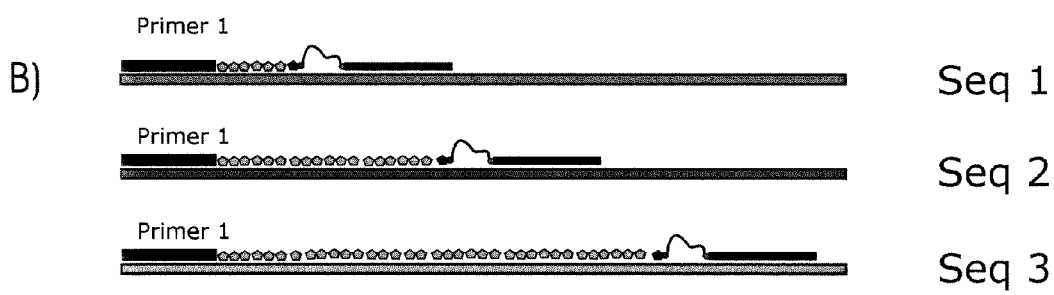
Suppression of the extenstion of multiple sequences via
nuc-macromolecules with different target domains

Fig. 41

Simulteneous extension and detection of the target sequences (A)
and termination of the target sequences (B)

A) 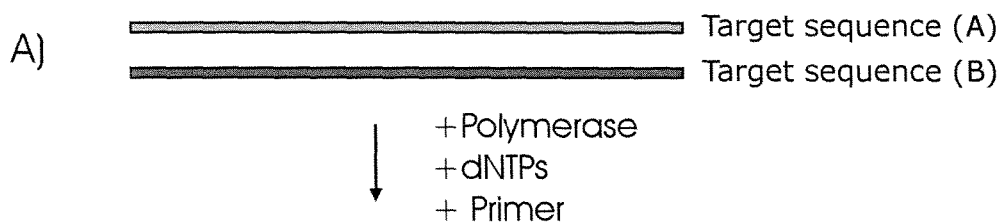

B)

Selective termination of the extension of both
complementary stands of the target sequence (B)

Selective amplification
of the target sequence (A)

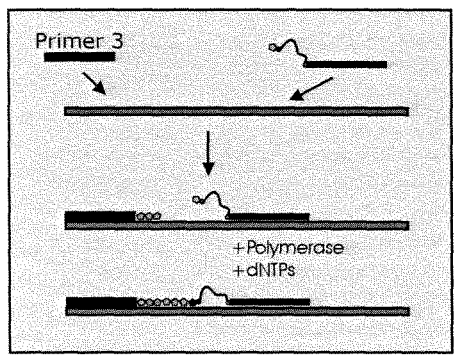 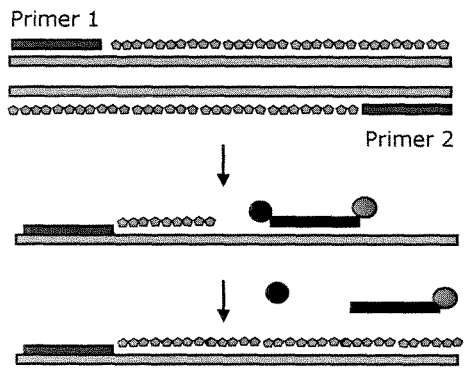

Selective amplification
of the target sequence (A)
and detection via 5´-exonuclease
degradation of the probe (Nuc-Linker)$_1$-[T]
with a chain-terminating nuc-component

Fig. 42

Simulteneous extension and detection of the target sequences (A)
and termination of the target sequences (B)

A)
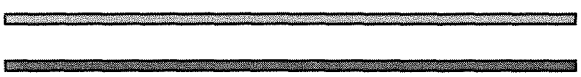
Target sequence (A)
Target sequence (B)

↓ +Polymerase
+dNTPs
+ Primer

B)

Selective termination of the extension of both
complementary stands of the target sequence (B)

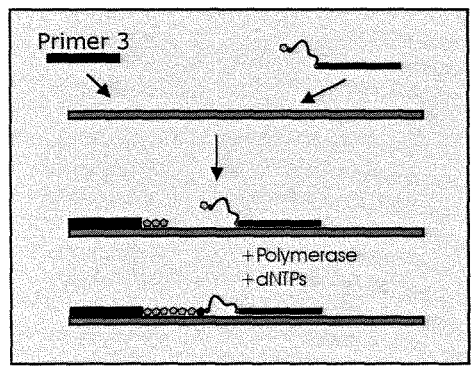

Selective amplification
of the target sequence (A)

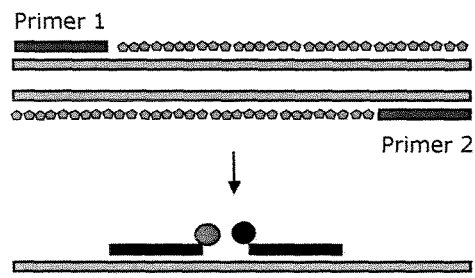

Detection of the target sequence (A)
via FRET between two labeled oligonucleotides

(Nuc-Linker)$_1$ -[T]
with a chain-terminating nuc-component

Fig. 43

Simulteneous extension and detection of the target sequences (A)
and termination of the target sequences (B)

A) ══════════════ Target sequence (A)
══════════════ Target sequence (B)

↓ +Polymerase
+dNTPs
+ Primer

B)

Selective termination of the extension of both
complementary stands of the target sequence (B)

Selective amplification
of the target sequence (A)

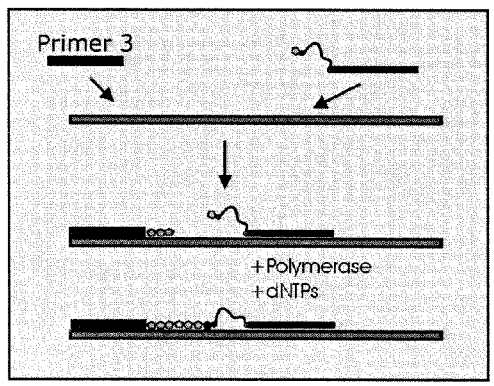

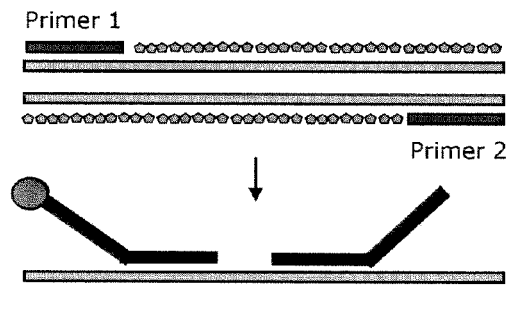

Detection via hybridization probes

 (Nuc-Linker)$_1$ -[T]
with a chain-terminating nuc-component

Simulteneous extension and detection of the target sequences (A)
and termination of the target sequences (B)

Fig. 45

Simulteneous extension and detection of the target sequences (A) and termination of the target sequences (B)

A)

Target sequence (A)
Target sequence (B)

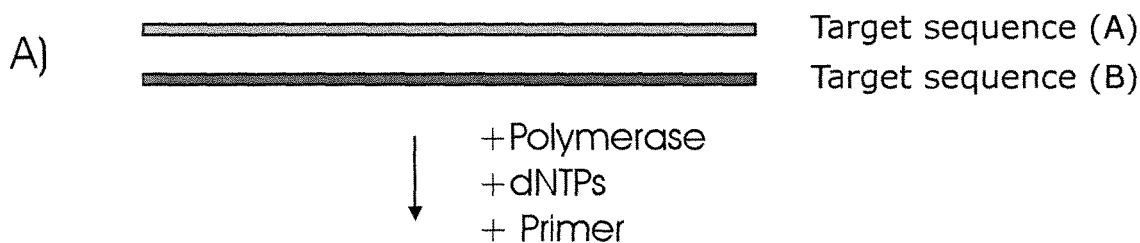

↓ +Polymerase
  +dNTPs
  + Primer

B)

Selective termination of the extension of both complementary stands of the target sequence (B)

Selective amplification of the target sequence (A)

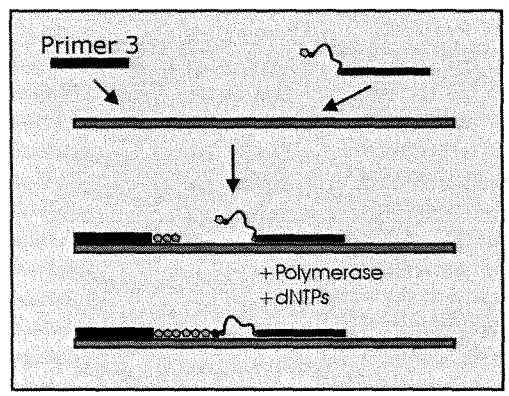

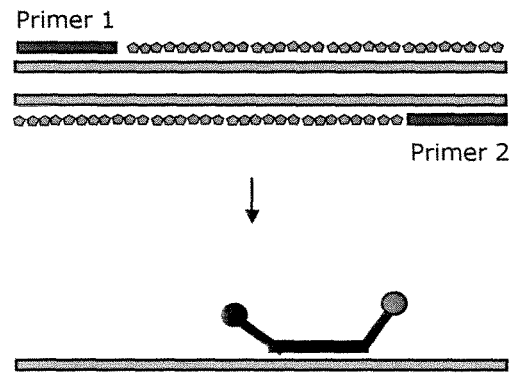

Detection of the target sequence (A) via probe of "Molecular beacon" type

Labeled DNA-fragment with
one nuc-macromolecule after
incorporation and following
isolation by means of nuclease Fig. 48
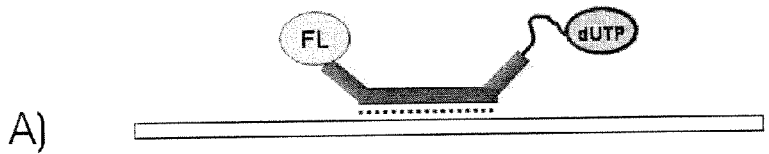
A)
Perfect match binding of a fully complementary
target domain of a nuc-macromolecule to the target DNA
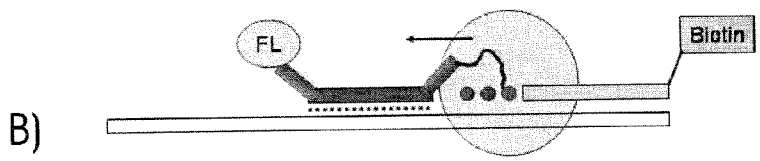
B)
Incorporation of the nuc-component
of the bound nuc-macromolecule
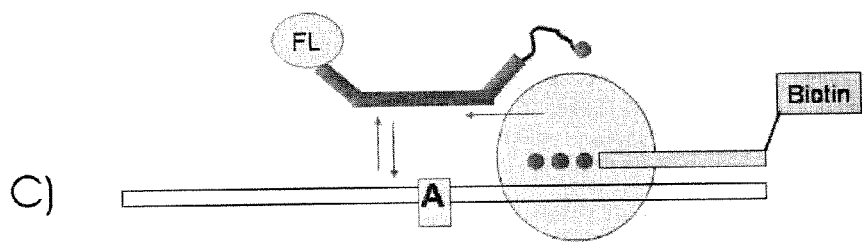
C)
Lack of binding of the target domain
of a nuc-macromolecule in case of
mismatch and lack of incorporation Fig. 49
A) Labeling of the target DNA in case of perfect match hybridization of the target domain of the nucleotide
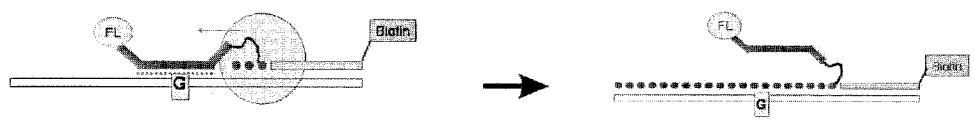
B) Lack of labeling of the target DNA in case of mismatch hybridization of the target domain of the nucleotide
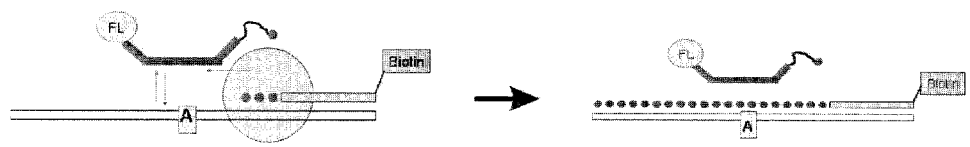

Fig. 50
Slowdown of the synthesis on labeled fragments
A) 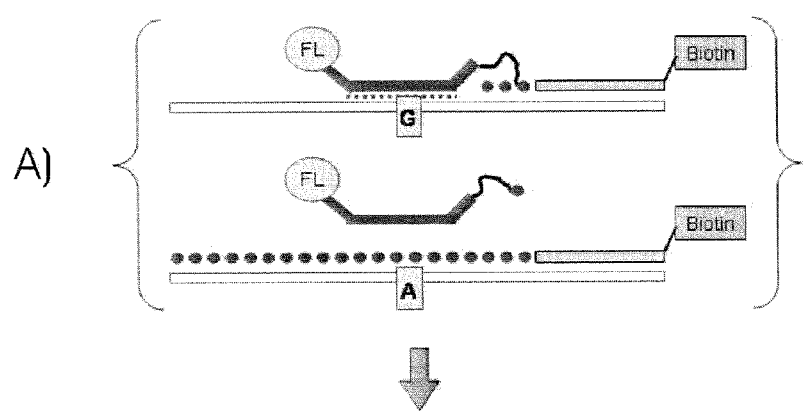
B) 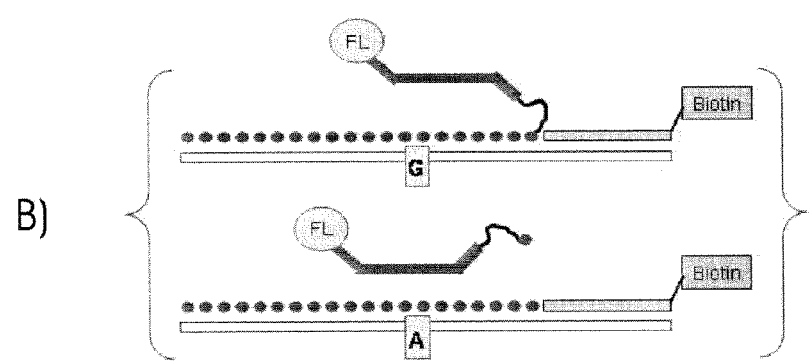

Fig. 51
Isolation of the labeled DNA
or ist fragments via nuclease
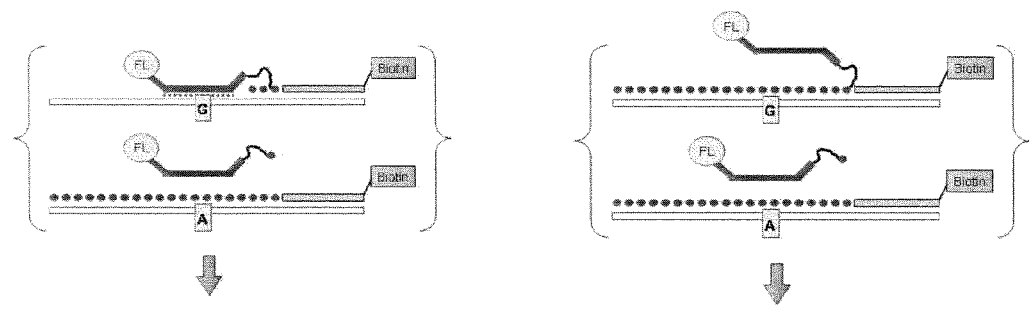
Degradation of the unprotected segments
of the synthesized nucleic acid chain via nuclease
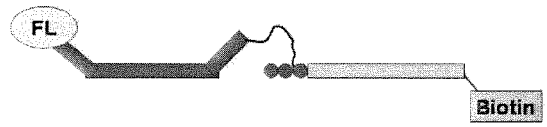

Fig. 52
Saturation of the target domain
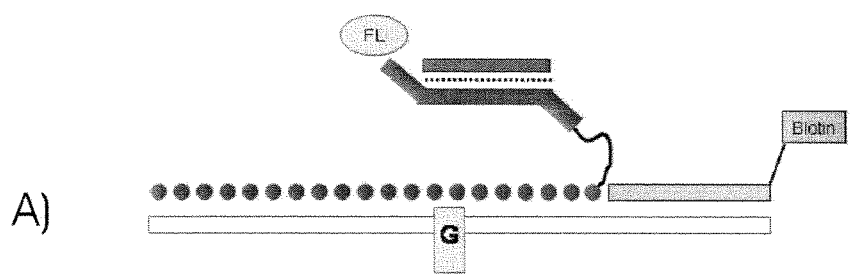
A)
Saturation of the target domain of the incorporated nucleotide in perfect match situation
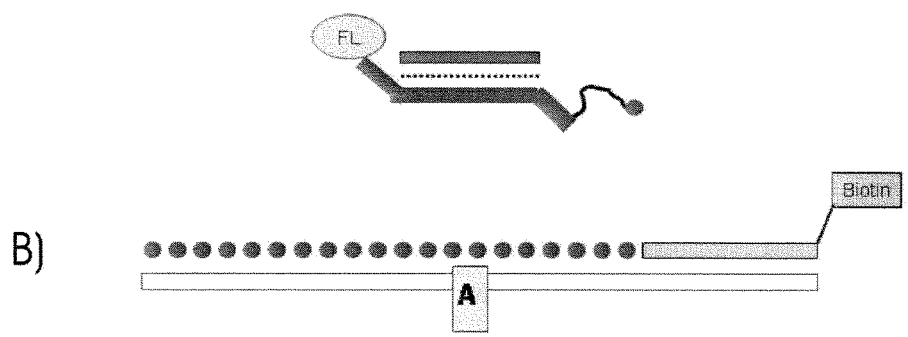
B)
Saturation of the target domain of a not-incorporated nucleotide in mismatch situation Detection of the labeled DNA
or the labeled DNA-fragment Binding of the labeled DNA-fragment to the solid phase and detection Identification of the correct version of the template sequence

METHOD AND COMPONENTS FOR DETECTING NUCLEIC ACID CHAINS

SEQUENCE LISTING

The instant application contains a Sequence Listing which has been submitted electronically in ASCII format and is hereby incorporated by reference in its entirety. Said ASCII copy, created on Sep. 9, 2016, is named 8315AG0001_SL.txt and is 12,545 bytes in size.

INTRODUCTION

1.1 State of the Art and Objects of the Invention

Often, analysis of nucleic acid chains is used for a detection of a specific sequence of an organism, such as pathogens in clinical material. This sequence is often referred to as the target sequence. Often, such target sequences are present not as isolated form, but embedded in a sample matrix, the material. Patient samples, food, or a part of an organism can represent material of interest. The objective of this analysis is therefore testing for the presence of the target sequence in such material.

It is known to a person skilled in the art that specific detection of nucleic acid chains can be of great medical importance.

Modern methods for analyzing nucleic acid chains involve several processes with the goal of detecting a specific signal (i.e., the information content of a nucleic acid chain). These processes usually include the following sub-processes: amplification, labeling, isolation and identification of nucleic acid chains.

Several interfering factors can lead to a poor signal-to-noise ratio, such as non-specific amplification of nucleic acids, non-specific labeling of nucleic acids or non-specific detection of nucleic acid chains. A poor signal-to-noise ratio can falsify the result of the entire analysis.

A person skilled in the art is familiar with many conventional methods for the amplification of one or more nucleic acid chains. Such conventional assays include the amplification methods of PCR, HDA, SDA or LAMP for example.

Under ideal conditions these amplification methods can specifically multiply specified DNA fragments. The varying reaction conditions found in the everyday reality of diagnostic work may deviate significantly from ideal conditions, resulting in a reduction of the quality of the assay, such as low specificity, loss of sensitivity, etc.

For this reason, the amplification of a DNA fragment alone is often not sufficient for a meaningful interpretation of the assay. Rather, an expert must verify the specificity of the amplified fragment, for example through hybridization with a specific probe under stringent conditions, or by sequencing.

Several methods for increasing the specificity of analysis or to improve the signal to noise ratio have been proposed, for example Real-time PCR with 5'-exonuclease degradation (Taqman, ABI), hybridization of oligonucleotides with FRET (LightCycler, Roche), or hybridization assay with several washing steps under stringent conditions, or detection of specific sequences via sequencing and alignment of several nucleotides in the sequence.

These methods often require sophisticated equipment however, which limits their application outside specialized laboratories.

The object of this invention is to provide components, compositions and methods for nucleic acid chain detection which allow for higher analytic specificity and a better signal-noise ratio in the assay.

This is achieved by providing methods and components (for in vitro analysis) for the visualization of the genetic information contained in at least one nucleic acid chain, wherein sequence-specific nucleotide conjugates are used in at least one of the following sub-steps of the visualization: generation, termination or suppression of the amplification, labeling, isolation, or detection.

New nuc-macromolecules are presented having new structures of the marker component and new functions. The nucleotide structures represent new variants of nuc-macromolecules with basic structure described in the applications Cherkasov et al WO2011050938, Cherkasov et al WO2005044836, Cherkasov et al WO2006097320, Cherkasov et al WO2008043426, Cherkasov et al DE 10356837, Cherkasov et al DE 102004009704. These applications are incorporated by reference.

Surprisingly, these structures, in combination with other assay components, enable a more efficient labeling, labeling specificity and detection. The present invention discloses such an advantageous combination for a labeling reaction of target sequences (e.g. primers, modified primers, target sequence, etc.) (FIG. 4), so that new assays can be developed for the nucleic acid analysis. The inventive method allows a greater variety of molecules to be bound to the nucleic acid chains in a sequence-specific manner. Therefore, methods in the field of nucleic acid analysis can benefit from this invention.

The subject of this application further includes methods for the manufacture, synthesis, or multiplication of one or more nucleic acid chains (target sequences), wherein at least one type of nucleotide conjugate according to the present invention is used.

The subject of this application further includes methods for labeling one or more nucleic acid chains (target sequences), wherein at least one type of nucleotide conjugate according to the present invention is used.

The subject of this application further includes methods for the isolation of one or more nucleic acid chains (target sequences), wherein at least one type of nucleotide conjugate according to the present invention is used.

The subject of this application further includes methods for the detection of one or more nucleic acid chains (target sequences), wherein at least one type of nucleotide conjugate according to the present invention is used.

The subject of this application further includes methods for modifying the nucleic acid chains in cells in vivo and in vitro.

1.2 Brief Description of the Objects of the Invention

The present invention provides novel components and compositions for the enzymatic synthesis of nucleic acid chains and methods for the application thereof. These components and compositions can be used for example for primer extension, amplification, labeling, isolation, and detection of nucleic acid chains. These components and compositions can be also used in diagnostic assays for the amplification or labeling or detection or sequence analysis of nucleic acid chains. Further, certain components can be used in order to influence gene expression or cell division in vivo. Components, Compositions and Methods for In Vitro Assays Both sequence-specific signal generation and sequence-specific signal suppression are of importance in an assay. A person skilled in the art should ensure that the assay design allows for the specific detection of signals from target sequences of interest, while unwanted signals are suppressed as far as possible. Therefore, it is possible to define sequences that are to be positively or negatively selected in an assay.

Signal Processing at the Level of Nucleic Acids

Modern genetics-based assays commonly include the following steps: amplification, labeling, isolation and detection. These steps can be partially combined within one method, or they can take place sequentially. In each of these steps, sequences can be selected positively or negatively in a variety of ways.

In one embodiment of the invention, target sequences that are to be positively selected are amplified during the amplification step, while the amplification of target sequences that are to be negatively selected is suppressed.

In a further embodiment of the invention, target sequences that are to be positively selected are labeled in a sequence specific manner during the labeling step, while the labeling of target sequences that are to be negatively selected is suppressed.

In a further embodiment of the invention, target sequences that are to be positively selected undergo sequence-specific enrichment during the isolation step, while target sequences that are to be negatively selected are de-selected.

In a further embodiment of the invention, target sequences that are to be positively selected undergo sequence-specific detection during the detection step, while the detection of target sequences that are to be negatively selected is suppressed.

A method for sequence-specific incorporation of nuc-macromolecules during enzymatic synthesis provides the basis for the components and methods described in this invention (Cherkasov et al. WO2011050938). Under this approach, sequence-specific nucleotide conjugates are incorporated into a strand that is complementary to a preselected sequence (called the target sequence) during enzymatic synthesis. Such sequence-specific nucleotide conjugates belong to the class of macromolecular nucleotide compounds (Cherkasov et al. WO2011050938, Cherkasov et al. WO2005044836, Cherkasov et al. WO2006097320). The macromolecular nucleotide compounds just mentioned are also referred to as nuc-macromolecules. Sequence-specific nucleotide conjugates represent a particular type of such nuc-macromolecules, also referred herein to as "smart nucleotides". The term "smart" is used to emphasize their ability to discriminate between nucleic acid sequences. This property distinguishes smart nucleotides from conventional dNTPs.

These sequence-specific nucleotide conjugates (smart nucleotides) comprise the following components for example:
  at least one nucleoside triphosphate (nuc-component),
  at least one oligonucleotide (target domain) for recognition of the target sequence,
  at least one linker between the nucleoside triphosphate and the oligonucleotide.
  Other domains can be bound to the smart nucleotides (signal domains, anchoring domains, etc.).

The composition of the oligonucleotide is matched to the sequence composition of at least one target sequence in the assay, so that the sequence-specific oligonucleotide can primarily bind or hybridize to the target sequence under assay conditions.

The overall properties of nucleotide conjugates are determined by the properties of the nuc-component, the oligonucleotide (target domain), as well as other structures.

In one preferred embodiment of the invention, nucleotide conjugates with sequence-specific terminating properties are used. After being incorporated into the growing strand of the nucleic acid, this type of sequence-specific nucleotide conjugates is capable of stopping or of significantly retarding further enzymatic synthesis by polymerase.

In a further preferred embodiment of the invention, nucleotide conjugates with sequence-specific labeling properties are used. This type of sequence-specific nucleotide conjugate bears a marker which becomes linked to the nucleic acid strand after the nucleotide conjugate has been incorporated into the growing strand of the nucleic acid.

In a further preferred embodiment of the invention, nucleotide conjugates with sequence-specific nuclease-protective properties are used. This type of sequence-specific nucleotide conjugate comprises a nuclease degradation resistant modification of nuc-components (for example an Alpha-Phosphorothioate-dNTP) or a nuclease degradation resistant oligonucleotide, e.g. target domain. This results in protection of a labeled nucleic acid chain against nuclease degradation after incorporation of such nucleotide conjugates into the growing strand of the nucleic acid chain.

Typical Reaction Mixture

In one advantageous embodiment of the invention, sequence-specific nucleotide conjugates are used in an assay, which comprises additional components: for example, at least one target sequence, at least one polymerase, at least one other type of substrate for polymerases (e.g. dNTPs), at least one other oligonucleotide (e.g. primer).

In a still further advantageous embodiment of the invention, nucleotide conjugates are used in an assay, which comprises further additional components: for example, at least two target sequences, at least one polymerase, at least four other types of substrates for polymerases (e.g. dATP, dGTP, dCTP, dTTP), at least two sequence-specific primers.

Mode of Action of Smart Nucleotides in Selectively Labeling a Sequence

In presence of primer-template complexes, dNTPs, and polymerase, primer extension takes place, i.e., the target sequence serves as a template for the synthesis of complementary strands. Sequence-specific nucleotide conjugates can only be incorporated during such a primer extension if they are able to bind complementarily to the target sequence via their target domain.

The concentration of natural dNTPs is chosen in such a way (preferably it is higher than 10 µmol/l, and is for example between 50 µmol/l and 1 mmol/l) that those nuc-nucleotides that are not bound to the target sequence are not incorporated by the polymerase. Their incorporation is competitively suppressed by natural dNTPs.

The resulting incorporation of smart nucleotides into the newly synthesized complementary strands of the target sequence is target-sequence-specific. DNA segments which do not undergo hybridization with the target domain of sequence-specific nucleotide analogues, are not labeled.

The enzymatic incorporation of sequence-specific nucleotide conjugates produces a modified DNA, which comprises at least one sequence-specific, covalently bound nucleotide conjugate. The covalent bond between newly synthesized complementary strands and incorporated nucleotide conjugates is highly stable. The properties of this DNA can accordingly be influenced by the selection of the properties of the sequence-specific nucleotide conjugates. The physical, chemical and especially biochemical properties of DNA labeled with nucleotide analogues can thus be modified.

Each component of the smart nucleotides can influence the properties of the labeled DNA in a sequence-specific manner. For example, modifications of nuc-components can lead to sequence-specific changes in the properties of the labeled nucleic acid. For example, ddNTPs result in sequence-specific termination of synthesis. Alpha-thio-triphosphates allow for sequence-specific incorporation of a nuclease-resistant nucleotide into the chain. Modifications of the target domain of the nucleotide conjugate (target sequence binding part of the oligonucleotide) such as PTO, PNA, LNA can, for example, lead to nuclease resistance.

The nature of the linkage between the nuc-component and the remaining structure of the nucleotide conjugate determines whether only the nuc-component or the entire structure of the nucleotide conjugate remains in the newly synthesized strand. For example, coupling of the target domain to the base of the nuc-component via a stable linker means that the incorporated nuc-component and the target domain remain bound to each other after incorporation. In contrast, coupling of the target domain to the gamma-phosphate group of a nuc-component via a linker means that the connection between the now incorporated nuc-component and the target domain is cleaved by polymerase after incorporation of the nuc-component, and that the target domain is no longer bound to the nuc-component.

As already mentioned, the specificity of the analysis, or the positive or negative selection of sequences or signals, can be influenced at several points in the process. Advantageous embodiments of the invention will be described below in which positive or negative selection of target sequences takes place in a particular step (amplification, labeling, isolation, detection) or through a combination of individual steps.

Selection of Nucleic Acids During Amplification or During Extension by Means of Sequence-Specific Nucleotide Conjugates With Chain-Terminating Properties The extension or amplification of one or more sequences (population N1-Nx) are known to one skilled in the art (for example, PCR, HDA, etc). A specific amplification of a nucleic acid fragment between two primers takes place under appropriate conditions. Sequences that are characterized by different sequence content between the two primers are co-amplified. Often, there is a requirement to amplify only one nucleic acid chain with one specific sequence, for example, sequences that harbor a mutation or a specific SNP-variant. The amplification of other sequences needs to be suppressed however.

In General, the Following Results Must be Achieved when Using a Method for the Amplification of Nucleic Acid Chains:

Extension or amplification of one or more sequences (population N1-Nx), i.e. such sequences should to be positively selected Suppression of extension or amplification of one or more sequences (population Z1-Zx), i.e. such sequences should be negatively selected Populations N1-Nx can be distinguished from population Z1-Zx by their sequence.

In one preferred embodiment of the invention, components and methods are provided for the sequence-specific suppression of the template-dependent synthesis of the sequences of population Z1-Zx In a further preferred embodiment of the invention, components and methods are provided for the sequence-specific suppression of the amplification of the sequences of population Z1-Zx In a still further preferred embodiment of the invention, components and methods are provided for the sequence-specific suppression of the template-dependent synthesis of the sequences of population Z1-Zx while still allowing simultaneously for template-dependent synthesis of the sequences of population N1-Nx.

In a still further preferred embodiment of the invention, components and methods are provided for the sequence-specific suppression of the amplification of the sequences of population Z1-Zx while still allowing simultaneously for amplification of the sequences of population N1-Nx.

The sequence-specific suppression of the extension or amplification of the population Z1-Zx is achieved by use of sequence-specific nucleotide conjugates with terminating properties. Such terminating nucleotide conjugates can bind to nucleic acid chains of population Z1-Zx in a sequence-specific manner via their target domains. During the synthesis of the complementary strand, the nuc-component of the bound nucleotide conjugates is incorporated by the polymerase. The structure of the nucleotide conjugates leads to a termination of synthesis, or to substantially slower synthesis, so that amplification of these sequences cannot take place.

In case of termination, no further nucleotides are incorporated after incorporation of such a terminating nucleotide conjugate. For example, such a conjugate comprises a dideoxy nuc-component (e.g. 2',3'-ddUTP). In case of significant slowdown in the synthesis of complementary strands, further nucleotides can be incorporated after terminating nucleotide conjugates have been conjoined; however, the rate of synthesis is significantly lower. As the time for an extension step during an amplification reaction is limited (e.g. 1 min during PCR), the complementary strand undergoes insufficient extension, resulting in premature termination of the primer extension. Amplification is thus inhibited.

Sequence-specific inhibition of the extension of the growing strand or termination or retardation of synthesis can be effected by means of the following components of nuc-macromolecules:

Properties of the nucleotide component:
  Nuc-components with strand-terminating properties can be used, such 2'-3'-dideoxy-nucleotides, for example ddUTP, ddCTP, ddATP, ddGTP. Other nucleotides with modifications of the sugar like 3'-azide, 3'-amine, 3'-mercapto etc. are also known to the expert. In summary these nucleotide structures have modified 3'-OH positions.
  In one embodiment, the target domain of a terminating nucleotide conjugate is coupled via a linker to the base of the nuc-component. Thus, after incorporation of the nucleotide in the newly synthesized strand, the target domain remains bound to the newly synthesized terminated strand. In a further embodiment, the target domain of the terminating nucleotide conjugate is bound via a linker to the gamma phosphate group of the nuc-component. Thus, the target domain is separated from the nucleotide during incorporation.

Properties of the remaining structure of the nuc-macromolecule, for example the structure of the marker, or a part thereof, or the structure of the target-domain. In such embodiments, the target domain has to remain bound to the incorporated nuc-component of the nucleotide conjugate and can have an influence on further synthesis. This influence can be determined by the following parameters of the nucleotide conjugate for example:

Chemical properties of the target domain, for example PNA or LNA. Such structures are known for their ability to cause stopping of synthesis after binding to the complementary nucleic acid chain.

Sequence composition of the oligonucleotide in the nuc-macromolecule: synthesis can be influenced, for example, by steric hindrance of the polymerases by double-stranded portions of the oligonucleotide (hairpin structures) within the nuc-macromolecule or a triplex formation of the oligonucleotide of the nuc-macromolecule with the template.

Certain components of the nucleotide conjugate, for example nano-particles, polymers, or proteins, etc. covalently linked to the target domain can sterically interfere with the reaction, and thereby obstruct or retard the synthesis reaction.

Selection of Nucleic Acids by Means of Sequence-Specific Nucleotide Conjugates with Labeling Properties During the Labeling Reaction In genetics-based testing there is a general need to label nucleic acid chains of only one specific sequence. Such labeling can be carried out during primer extension or can be combined with a method for the amplification of the nucleic acid chain. Labeling needs to be sequence-specific in order to obtain the following results:

specific labeling of one or more sequences (population N1-Nx), such sequences are positively selected.

no labeling at all of one or more sequences (population Z1-Zx), such sequences are negatively selected.

Populations N1-Nx can be distinguished from population Z1-Zx by their sequence.

One advantageous embodiment of the invention relates to the provision of components and processes for sequence-specific labeling of the sequences of population N1-Nx during a template-dependent synthesis of these sequences (population N1-Nx).

One further advantageous embodiment of the invention relates to the provision of components and processes for sequence-specific labeling of the sequences of population N1-Nx during amplification of these sequences (population N1-Nx).

One advantageous embodiment of the invention relates to the provision of components and processes for sequence-specific labeling of the sequences of population N1-Nx during a template-dependent synthesis of sequences of population N1-Nx and population Z1-Zx.

A further advantageous embodiment of the invention relates to the provision of components and processes for the sequence-specific labeling of the sequences of population N1-Nx during amplification of sequences of population N1-Nx and population Z1-Zx.

The labeling of the sequences (population N1-Nx) can be effected by the following structures of the nucleotide conjugate: target domain or signal domain or anchor domain.

The differences between labeled and non-labeled DNA fragments resulting from sequence-specific labeling may be utilized for example for isolation and detection of labeled DNA. Various methods can be used to separate labeled and non-labeled DNA fragments or to prevent interactions between labeled and non-labeled DNA fragments. Such "filter systems" or "filtering methods" provide a means for the better separation of the specific signal from the noise.

By way of example, the single-stranded part of the target domain is no longer needed after covalent incorporation of nuc-macromolecules. Other sequences in the assay also need not necessarily be present in a single stranded state: nucleotide conjugates are covalently bound into the newly synthesized DNA strands. This opens surprising new opportunities for improving the specificity of the analysis: further process steps and components can be used, which are usually not compatible with the analysis of nucleic acid chains.

In one advantageous embodiment, methods and components are used that lead to competitive saturation of the single-stranded regions of the target domain by additional oligonucleotides. The saturation of the target domain prevents potential non-specific interactions of the nucleotide conjugate with other sequences. This can improve the specificity of the analysis for example.

In a still further advantageous embodiment, methods and components can be used that provide a means for affinity isolation of the sequence-specifically labeled nucleic acid chains. For example, the isolation may be carried out via the anchor domain of the incorporated nucleotide conjugates.

In a further advantageous embodiment of the invention, nucleases are used to isolate labeled DNA fragments and to degrade of non-labeled DNA fragments. In this advantageous embodiment, sequence-specific nucleotide analogues comprise, for example, a target domain which is resistant to nucleases. This property of the nucleotide conjugates results in the labeled DNA or a part thereof also becoming resistant to nucleases. Degradation of non-labeled DNA fragments eliminates the possibility of non-specific interactions between labeled DNA fragments is with non-labeled strands. Thereby, the specificity of an assay can be increased.

Another essential part of this invention is DNA that has been labeled with sequence-specific nucleotide conjugates or its fragments labeled with sequence-specific nucleotide conjugates. This labeled DNA is created by enzymatic, template-dependent synthesis. The properties of the labeled DNA are determined by the properties of primer, dNTP and sequence-specific nucleotide analogues used in its preparation.

Another part of this invention are methods which describe the isolation of the labeled portion of this DNA. A further part of this invention relates to methods that describe the detection of the labeled DNA or the detection of the isolated and labeled portion of this DNA.

Modification of Nucleic Acid Chains In Vivo

The ability of sequence-specific nucleotide conjugates to control the extension of nucleic acid chains may also be used to control the functions of nucleic acid chains in vivo. Nucleotide conjugates in the present invention can be used, for example, in a similar manner to oligonucleotides in antisense technologies for controlling the extension of nucleic acid chains in cells. Examples of antisense applications of oligonucleotides are known to a person skilled in the art (Expert Opin Biol Ther. 2007 Jul.; 7(7):1021-34. The versatility of oligonucleotides as potential therapeutics. Eckstein F.)

A decisive advantage of the nucleotide conjugates in the present invention is that they can be covalently incorporated into the growing strand by cellular DNA-polymerases or RNA-polymerases and thus can irreversibly block the extension of these strands.

Sequence-specific terminating nucleotide conjugates thus combine the properties of antisense oligonucleotides, having a sequence-specific mode of action, with the chain-terminating properties of nucleoside or nucleotide-analogues, which have been used in medicine for some time.

Sequence-Specific Chain-Terminating Nucleotide Conjugates can be Used in the Following Areas:

Suppression of the extension of the DNA, or of the replication of particular segments of chromosomes and of genetically defined genome-parts of tumor cells. In this embodiment, terminating nuc-macromolecules are used that bind to defined DNA sequences of tumor cells which differ from wild-type DNA sequences. During replication, a replication terminating nucleotide analog is sequence-specifically incorporated, leading to termination of the replication of a chromosome. In this manner, chromosome-damage can be introduced into the tumor cells in a sequence-specific manner.

Change (reduce or increase) gene expression from particular segments of the chromosomes of tumor cells. In this embodiment, sequence-specific nuc-macromolecules are used that bind to sequences of tumor cells which differ from wild-type sequences. During replication, a transcription modifying nucleotide analogue is incorporated in a sequence-specific manner, resulting, not in termination of the replication of a chromosome, but in altered transcription by a RNA-Polymerase or altered binding of transcription factors.

Suppression of the extension of the DNA or RNA, or of the replication of the DNA or RNA of particular segments of viral genomes. In this embodiment, terminating nuc-macromolecules are used which bind to sequences of viruses. During replication, a terminating nucleotide analogue is incorporated in a sequence-specific manner, which leads to termination of the replication of the virus.

Sequence-specific nucleotide analogues directed against a double-stranded segment of chromosomal DNA or of a viral nucleic acid preferably include at least one oligonucleotide that is capable of binding to a double-strand (duplex invasion). Such oligonucleotides are well known to those skilled in the art. They comprise, for example, PNA or LNA sequence parts. The following literature examples show that oligonucleotides may have suppressive effects on cellular processes: Chem Biol. 2004 Jun.; 11(6):749-58. Recognition of chromosomal DNA by PNAs. Kaihatsu K, et al: Nucleic Acids Res. 2003 Feb. 1; 31(3):953-62. In vivo tumor growth inhibition and biodistribution studies of locked nucleic acid (LNA) antisense oligonucleotides. Fluiter K, et al; Biochemistry. 2007 Jun. 26; 46(25):7572-80. Epub 2007 May 31. Inhibiting gene expression with locked nucleic acids (LNAs) that target chromosomal DNA. Beane R L, et al; Biochemistry. 2007 Jun. 26; 46(25):7581-9. Epub 2007 May 31. Inhibiting gene expression with peptide nucleic acid (PNA)—peptide conjugates that target chromosomal DNA. Hu J, et al; Biochemistry. 2002 Aug. 6; 41(31):9973-81. Implications of high-affinity hybridization by locked nucleic acid oligomers for inhibition of human telomerase. Elayadi A N, et al;

Like antisense oligonucleotides, chain-terminating nucleotide analogs can be covalently or non-covalently modified with other structures, such as antibodies, cell-penetrating peptides, lipids, steroids, nucleus-localization signals (peptide). Such structures provide better cellular uptake and localization of the nucleotide analog in the cell, for example in the cell nucleus or cell cytoplasm. Examples of this are known (Expert Opin Biol Ther. 2007 Jul.; 7(7):1021-34. The versatility of oligonucleotides as potential therapeutics. Eckstein F.; Oligonucleotides. 2011 Mar.-Apr.; 21(2):55-75. Epub 2011 Mar. 21. Oligo/polynucleotide-based gene modification: strategies and therapeutic potential. Sargent R G, et al; Biochemistry. 2006 Dec. 19; 45(50):14944-54, Structural requirements for cellular uptake and antisense activity of peptide nucleic acids conjugated with various peptides. Wolf Y, et al; Adv Drug Deliv Rev. 2003 Feb. 10; 55(2):295-306. NLS bioconjugates for targeting therapeutic genes to the nucleus. Escriou V, et al; Int J Mol Sci. 2008 Jun.; 9(7):1276-320. Epub 2008 Jul. 16. Recent developments in peptide-based nucleic acid delivery. Veldhoen S, et al)

To achieve better uptake of nucleotide analogs into the cells, various techniques of so-called "targeted delivery" (or "targeted therapy") may be used. Many examples of this are known to an expert from the field of targeted delivery of antisense oligonucleotides and siRNA. Thus, covalent or affinity conjugates of the oligonucleotide component with a cell-specific ligand, e.g. with an antibody against a membrane receptor, can be used. On the other hand, nucleotide conjugates can be packaged into microparticles, such as liposomes, or form micelles with polymers such as polycations. Such macro-conjugates can likewise carry cell type-specific structures like antibodies, which enhance uptake into the cell as known for immuno-liposomes. J Pharm Sci. 2011 January; 100(1):38-52. Drug delivery trends in clinical trials and translational medicine: challenges and opportunities in the delivery of nucleic acid-based therapeutics. Xu L, et al; J Control Release. 2003 Feb. 21; 87(1-3):89-105. Cytoplasmic delivery and nuclear targeting of synthetic macromolecules. Jensen K D, et al.; J Control Release. 2009 Mar. 4; 134(2):132-40. Epub 2008 Nov. 12. Polymersome delivery of siRNA and antisense oligonucleotides. Kim Y, et al In the following, advantageous examples of components and methods for their use in detection or amplification processes are presented.

The subject of this application comprises methods for the detection of one or more nucleic acid chains (one or more target sequences), wherein modified nucleotides (nuc-macromolecules, FIG. 1) having one of the following structures are used:

(Nuc-linker)$_n$-marker wherein:

Nuc is a nucleotide (nuc-component)

Linker is a linker component wherein the linker links the nuc-component to a macromolecular marker component Marker is a marker component which comprises at least one nucleic acid sequence, called the "target domain," e.g. an oligonucleotide, which is completely or partially complementary to the target sequence (n) is a positive integer from 1 to 1000

Such a nuc-macromolecule is capable of sequence-specific binding to at least one target sequence in accordance with its complementary properties an assay. The binding of the "target domain" to the target sequence enhances the yield of a specific labeling reaction of the complementary strands of the target sequence because the nuc-component of the bound nuc-macromolecule is preferentially incorporated by a polymerase.

The inventive nuc-macromolecules are different from the natural nucleotides in several aspects:

In one advantageous embodiment of the invention, nuc-macromolecules comprising at least an oligonucleotide moiety are used. According to the invention, this oligonucleotide part can bind complementarily at one position of the target sequence (template) to form a double strand. Such an oligonucleotide part is called "the target domain" and is abbreviated as "T domain" (FIG. 1).

In another advantageous embodiment of the invention, nuc-macromolecules comprising at least one target domain and at least one anchor domain (abbreviated as "A-domain") are used (FIG. 1). A nuc-macromolecule can be bound to a solid phase via such an anchor domain. Examples of an anchor domain are biotin and oligonucleotides. A nuc-macromolecule can be bound to the solid phase via biotin or an oligonucleotide when this solid phase carries a streptavidin or a complementary oligonucleotide.

In another advantageous embodiment of the invention, nuc-macromolecules comprising at least one target domain and at least one signal domain (abbreviated as "S-domain") are used (FIG. 1). A nuc-macromolecule can be distinctively detected via such a signal domain. Fluorescent dyes represent examples of signal domains.

According to the inventive method, a labeling reaction, for example, can be carried out as follows (FIG. 5A): Providing of at least one target sequence (a nucleic acid template), at least one primer, at least one polymerase and at least one kind of the above mentioned nuc-macromolecules and incubating under conditions which allow for an enzymatic incorporation of the nuc-component of the nuc-macromolecule into the growing strand by a polymerase. The complementary strand of the target sequence is labeled through the specific binding of the nuc-macromolecules to the target sequence. The enzymatic coupling of such a nuc-macromolecule in the growing nucleic acid strand leads to the formation of a bond between the extended strand and different domains of a nuc-macromolecule.

In one embodiment of the present application, nuc-macromolecules can be used which comprise at least one domain (target domain) which is able to bind sequence-specifically to the target sequence and at least one other domain (anchor domain) that can bind to a binding partner on a solid phase. By the enzymatic incorporation of such a nuc-macromolecule, the anchor domain is also bound to the nucleic acid chain in a sequence-specific manner. Thus, during incubation of the labeled nucleic acid chains with a solid phase which includes at least one binding partner for the anchor domain, labeled nucleic acid chains can bind specifically to the solid phase.

As shown above, a nuc-macromolecule can comprise structures that are complementary to the target sequence. Therefore, it is advantageous to perform an incorporation reaction under conditions which allow binding of these components to a complementary position in the template. Thereby, a selective labeling of selected target sequences can be achieved.

In an advantageous embodiment, nuc-macromolecules can be used together with natural nucleotides (e.g. dNTPs or NTPs) in the same reaction. The invented nuc-macromolecules and corresponding dNTPs, which are complementary to the template, compete with each other for their incorporation by the polymerase at the 3' terminus of the growing complementary strand. A nuc-macromolecule being specifically bound to the target sequence via target domain outcompetes free nucleotides in the solution: it can be preferentially incorporated by the polymerase. Thus, the target sequence can be specifically labeled with nuc-macromolecules even in the presence of natural dNTPs.

The incorporation of nuc-macromolecules occurs preferentially in the vicinity of their binding site on the template. Sequence regions that are far away from this site or other sequences occurring in sample sequences ("non-target sequences") are not labeled. In an advantageous embodiment of the invention, the "non-target-sequences" remain unlabeled. This can be due to the lack of binding or only weak binding of nuc-macromolecules to those "non-target sequences": complementary growing strands of such non-target sequences are extended with dNTPs and are only weakly or not labeled with nuc-macromolecules.

The extended nucleic acid strand can gain affinity properties of the anchor domain of the nuc-macromolecule due to the specific, predetermined composition of the nuc-macromolecules. In analysis, a solid phase can be provided that comprises a suitable binding partner for the anchor domain of a nuc-macromolecule. After the labeling reaction, the labeled target sequences are incubated with a solid phase with a binding partner (e.g. oligonucleotide-oligonucleotide-pair or biotin-streptavidin-pair or antibody-hapten-pair), which results in the binding of the extended strand to this binding partner (FIG. 6).

There are particularly advantageous embodiments in which a plurality of different templates with specific primers is provided and nuc-macromolecules with corresponding oligonucleotide parts (target domains) that are specific to each template and specific anchor domains are provided. This allows for a sequence-specific incorporation of nuc-macromolecules into the complementary strands of respectively specific target sequences and a subsequent selective binding to the solid phase by using different and distinct anchor domains. Particularly advantageous embodiments describe specific binding partners for anchor domains which are immobilized on a solid phase in an addressable array. This allows for a specific distribution of extended nucleic acid on the solid phase on the basis of their sequence composition.

The binding properties of the anchor domain to the binding partner can be optimized.

For example, the anchor domains are designed in such a way that they do not include complementary sites to target sequence. Further, their binding strength and specificity can be optimized independently of the target sequence.

In the Following, Some Important Aspects of the Invention are Summarized.

1. Aspect of the invention relates to methods for the visualization of the genetic information in vitro of at least one nucleic acid chain, wherein sequence-specific nucleotide conjugates are used in at least one of the following partial steps of the visualization:

Positive selection during the synthesis of the nucleic acid chains or the equivalents of genetic information by primer extension or amplification
  Negative selection of nucleic acid chains or the equivalents of genetic information through targeted termination or targeted suppression
  Positive selection of nucleic acid chains or the equivalents of genetic information by labeling
  Positive selection of nucleic acid chains or the equivalents of genetic information by isolation
  Positive selection of nucleic acid chains or the equivalents of genetic information by detection and at least one of the sequence-specific nucleotide conjugates used has the following structure:

$$(Nuc\text{-}linker)_n\text{-}marker$$

wherein:
Nuc—is a nuc-component
Linker—is a linker component which connects the nuc-component and macromolecular marker component Marker—is a marker component which comprises at least one nucleic acid sequence complementary to the target sequence, the so-called target-domain n—is a number from 1 to 100

2. Aspect of the invention relates to methods for the enzymatic synthesis of at least one modified nucleic acid chain of Aspect 1, which includes the following steps:

Amplification of at least one nucleic acid chain

Labeling of said nucleic acid chain with sequence-specific nucleotide conjugates Where applicable, amplification and labeling take place simultaneously Where applicable, isolation of the labeled nucleic acid chain and comprises the following components:

At least one nucleic acid chain to be labeled as a template (target sequence)

At least one polymerase for enzymatic synthesis

At least one primer

At least one kind of sequence-specific nucleotide conjugate

At least one kind of other nucleotide

3. Aspect of the invention relates to a method for the isolation of at least one nucleic acid chain labeled with sequence-specific nucleotide conjugates according to Aspect 1, including the following steps:

Preparation of a nucleic acid chain labeled with sequence-specific nucleotide conjugates Incubation of said labeled nucleic acid chain in a reaction mixture with at least one nuclease under conditions allowing the degradation of non-labeled nucleic acid chains 4. Aspect of the invention relates to a method for the detection of at least one nucleic acid chain labeled with sequence-specific nucleotide conjugates according to Aspect 1, including the following steps:

Preparation of at least one labeled nucleic acid chain

Detection of the signals from at least one nucleic acid chain labeled with sequence-specific chain-conjugates Where applicable, comparison of this signals with a reference signal 5. Aspect of the invention relates to a method according to Aspect 2, wherein at least one sequence-specific nucleotide conjugate used in the labeling step has the following structure:

(Nuc-linker)n-marker wherein:

Nuc—is a nucleotide (nuc-component)

Linker—is a linker component which connects the nuc-component to the macromolecular marker component Marker—is a marker component which includes at least one oligonucleotide sequence that is fully or partially complementary to the corresponding nucleic acid chain to be labeled (target sequence) and this oligonucleotide includes at least one chemical nucleotide modification that is resistant to the nuclease of Aspect 3 n—is a number from 1 to 1000

6. Aspect of the invention relates to nucleotide conjugates according to Aspect 5, the marker component of which includes at least one oligonucleotide which comprises at least one of the following chemical modifications: PTO, LNA; PNA, morpholino, 2'-O-Me.

7. Aspect of the invention relates to sequence-specific nucleotide conjugates according to Aspect 2, the marker component of which includes at least one oligonucleotide which includes at least one sequence region which is capable of forming a double strand within the same oligonucleotide.

8. Aspect of the invention relates to sequence-specific nucleotide conjugates according to Aspect 2, the marker of which includes at least one oligonucleotide that is hybridized with at least one further complementary oligonucleotide to form a double-stranded region 9. Aspect the invention relates to a method according to the Aspect 2, wherein at least one primer includes at least one of the following modifications: PTO, LNA, PNA, morpholino, and 2'-O-Me.

10. Aspect of the invention relates to a method according to Aspect 2, wherein "other nucleotides" are selected from the group of naturally occurring nucleotides consisting of: dATP, dGTP, dCTP, dTTP, dUTP, ATP, GTP, CTP, UTP, and/or selected from the group of modified nucleotides consisting of: nucleotides labeled with biotin, such as dUTP-biotin dCTP-biotin, terminators, such as ddTTP, ddCTP, ddATP, ddGTP, or fluorescent dye labeled nucleotides, such as dUTP-Cy3 or dUTP-TAMRA, or alpha-phosphorothioate nucleotides, such as Sp-dATP-a-S, Sp-dCTP-a-S Sp-dGTP-a-S Sp-dUTP-a-S.

11. Aspect the invention relates to a method according to Aspect 2, wherein the method of amplification includes a polymerase chain reaction (PCR)

12. Aspect the invention relates to a method according to Aspect 2, wherein the method of amplification is an isothermal amplification 13. Aspect of the invention relates to a method according to Aspect 3, wherein one of the following nucleases is used: DNase I, Micrococcal nuclease, Exonuclease III (Exo III), Exonuclease I (Exo I), Mung Bean Nuclease, S1 Nuclease, a sequence-specific endonuclease 14. Aspect of the invention relates to a method for the production of a modified nucleic acid chain according to Aspect 2, wherein amplification step or labeling step also includes at least one of the following components:

An oligonucleotide comprising sequence segments which are fully or partially complementary to at least one target sequence, and wherein their binding site at the target sequence or at sequences similar to the target sequence fully or partially coincides with the binding site of the target domain of the sequence-specific nucleotide conjugate of Aspect 2.

An oligonucleotide comprising sequence segments which are fully or partially complementary to the target domain of at least one sequence-specific nucleotide conjugate according to Aspect 2

15. Aspect of the invention relates to a method for the detection of a modified nucleic acid chain according to Aspect 4, wherein at least one kind of oligonucleotide is bound to the target domain of the sequence-specific nucleotide conjugates via hybridization prior to or during the detection step, so that the target domain is rendered incapable of binding further nucleic acid chains via hybridization.

16. Aspect of the invention relates to a method for targeted termination of an enzymatic synthesis of nucleic acid chains according to Aspect 1, wherein sequence-specific nucleotide conjugates are enzymatically incorporated into the complementary strand, or its equivalent, of at least one target sequence to be terminated, wherein at least one of the nucleotide conjugates used (called terminating nucleotide sequence-specific conjugate) has the following structure:

(Nuc-linker)n-marker wherein:
Nuc—is nuc-component with modified 3'-OH-Position, resulting in termination of enzymatic synthesis
Linker—is a linker component which connects the nuc-component to the macromolecular marker component
Marker—is a marker component which includes at least one nucleic acid sequence complementary to a particular target sequence to be terminated, the so-called target domain,
n—is a number from 1 to 100

17. Aspect of the invention relates to a method for the selective suppression of the enzymatic synthesis of nucleic acid chains according to Aspect 1, wherein nucleotide conjugates are enzymatically incorporated into the complementary strand, or its equivalent, of at least one target sequence to be suppressed, wherein at least one of the nucleotide conjugates has the following structure:

(Nuc-linker)n-marker wherein:
Nuc—is a nucleotide (nuc-component)
Linker—is a linker component which connects the nuc-component to the macromolecular marker component
Marker—is a marker component which includes at least one oligonucleotide with a nucleic acid sequence complementary to the target sequence to be terminated and optionally includes a steric hindrance that has the effect of suppressing enzymatic synthesis.
n—is a number from 1 to 100

18. Aspect of the invention relates to a method according to the Aspect 1, wherein at least two different nucleic acid chains are present, and the synthesis of at least one of the nucleic acid chains is suppressed or terminated by the methods of Aspects 16 or 17.

19. Aspect of the invention relates to a method for enzymatic production according to Aspect 2, wherein at least two different nucleic acid chains (target sequences) are present, and the production or labeling of at least one of the nucleic acid chains is suppressed or terminated by the methods of Aspects 16 or 17.

20. Aspect relates to a kit for the visualization of the genetic information of nucleic acid chains according to method of any of the Aspects 1 to 19, including at least one kind of sequence-specific nucleotide conjugate (nuc-macromolecule) according to any of the preceding aspects, and at least one of the components selected from the following list:
   One or more types of polymerase
   Compositions for carrying out enzymatic reactions (amplification, labeling), including at least one required type of other nucleoside triphosphates, primers and buffer substances
   One or several nucleases for the isolation of labeled nucleic acid chains
   A solid phase for the detection of labeled nucleic acid chains
   A composition for binding labeled nucleic acid chains to the solid phase
   A composition for optical detection of signals on the solid phase 21. Aspect relates to a kit for the amplification and labeling of nucleic acid chain according to a method of any of the Aspects 1 to 20 which comprises one or several polymerases selected of the following group:
   Reverse Transcriptases: M-MLV, RSV, AMV, RAV, MAV, HIV
   DNA Polymerases: Klenow Fragment DNA Polymerase, Klenow Fragment exo minus DNA Polymerase, T7 DNA Polymerase, Sequenase 2, Vent DNA Polymerase, Vent exo minus DNA Polymerase, Deep Vent DNA Polymerase, Deep Vent exo minus DNA Polymerase, Taq DNA Polymerase and its modifications, e.g. hotstart polymerases, Tli DNA Polymerase, Pwo DNA Polymerase, Thermosequenase DNA Polymerase, Pfu DNA Polymerase 22. Aspect relates to a kit for the isolation of labeled nucleic acid chains according to a method of the Aspects 1 or 3 or 20 which comprises one or several nucleases selected of the following group: DNase I, Micrococcal nuclease, S1 Nuclease, Exonuclease III (Exo III), Exonuclease I (Exo I), Mung Bean Nuclease and a corresponding buffer.

23. Aspect of the invention relates to a method for selective termination or suppression of the enzymatic synthesis of nucleic acid chains of a virus in vitro or in vivo, wherein cells, including cells infected by virus, or tissues, or organisms are exposed to sequence-specific nucleotide conjugates, wherein the type of virus responsible for the said infection is known.

24. Aspect of the invention relates to a method according to Aspect 23, wherein at least one of the used nucleotide conjugates has the following structure:

(Nuc-linker)n-marker wherein:
Nuc—is a nucleotide (nuc-component)
Linker—is a linker component which connects the nuc-component to the macromolecular marker component
Marker—is a marker component which includes at least one oligonucleotide with a nucleic acid sequences complementary to a particular known virus-sequence to be terminated
n—is a number from 1 to 100

25. Aspect of the invention relates to a method according to Aspect 23, wherein at least one of the nucleotide conjugates used has the following structure:

(Nuc-linker)n-marker wherein:
Nuc—is a nuc-component with modified 3'-OH position, resulting in termination of enzymatic synthesis
Linker—is a linker component which connects the nuc-component to the macromolecular marker component
Marker—is a marker component which includes at least one oligonucleotide with a nucleic acid sequence complementary to a particular, known virus-sequence to be terminated, and optionally includes a signal domain for cellular uptake.
n—is a number from 1 to 100

26. Aspect of the invention relates to a method for targeted labeling of the chromosomal DNA of at least one cell type of a particular species during intracellular enzymatic synthesis (replication), wherein sequence-specific nucleotide conjugates are brought into contact with cells or tissues or organisms.

27. Aspect of the invention relates to a method according to Aspect 26, wherein at least one of the nucleotide conjugates used has the following structure:

(Nuc-linker)n-marker wherein:
Nuc—is a nuc-component
Linker—is a linker component which connects the nuc-component to the macromolecular marker component
Marker—is a marker component which includes at least one oligonucleotide with a nucleic acid sequence that is complementary to an intrachromosomal target sequence characteristic for this cell type, and optionally includes a signal domain for cellular uptake.

n—is a number from 1 to 100

28. Aspect of the invention relates to a method according to Aspect 26, wherein at least one of the nucleotide conjugates used has the following structure:

(Nuc-linker)n-marker wherein:

Nuc—is a nuc-component with modified 3'-OH position, resulting in termination of enzymatic synthesis Linker—is a linker component which connects the nuc-component to the macromolecular marker component Marker—is a marker component which includes at least one oligonucleotide with a nucleic acid sequence that is complementary to an intrachromosomal target sequence characteristic for this cell type, and optionally includes a signal domain for cellular uptake.

n—is a number from 1 to 100

29. Aspect of the invention relates to a method according to any of the above aspects, wherein the signal domain for cellular uptake comprises one of the following structures: "Nucleus Localising Sequence" (NLS), "Cell-Penetrating-Peptide", or an antibody or fragment of an antibody against a structure on the cell surface.

BRIEF DESCRIPTION OF THE DRAWINGS

FIG. 2 is a schematic of the basic structure of the nuc-macromolecule of the invention.

FEG. 4A, 4B and 4C are schematic depictions of various primer-template-complexes with the nuc-macromolecules of the invention.

Figure 5A:
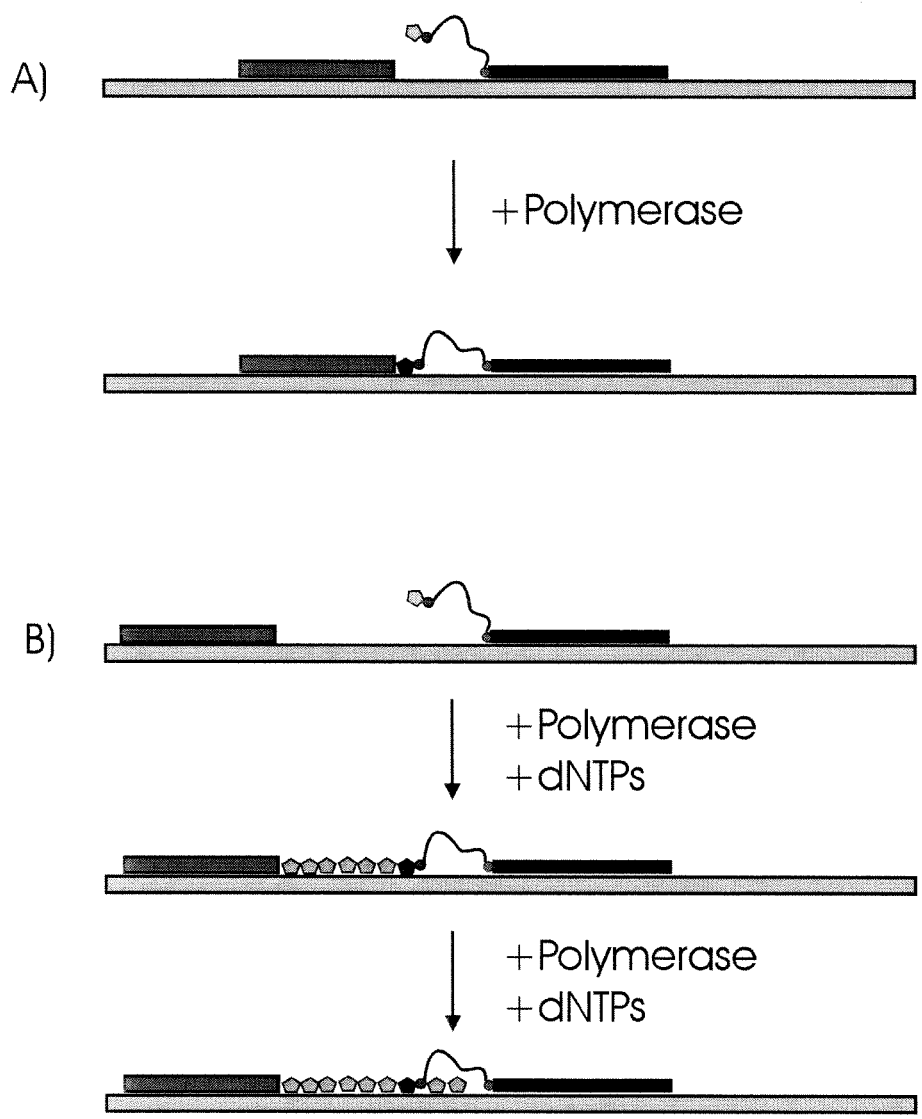
Figure 5B:
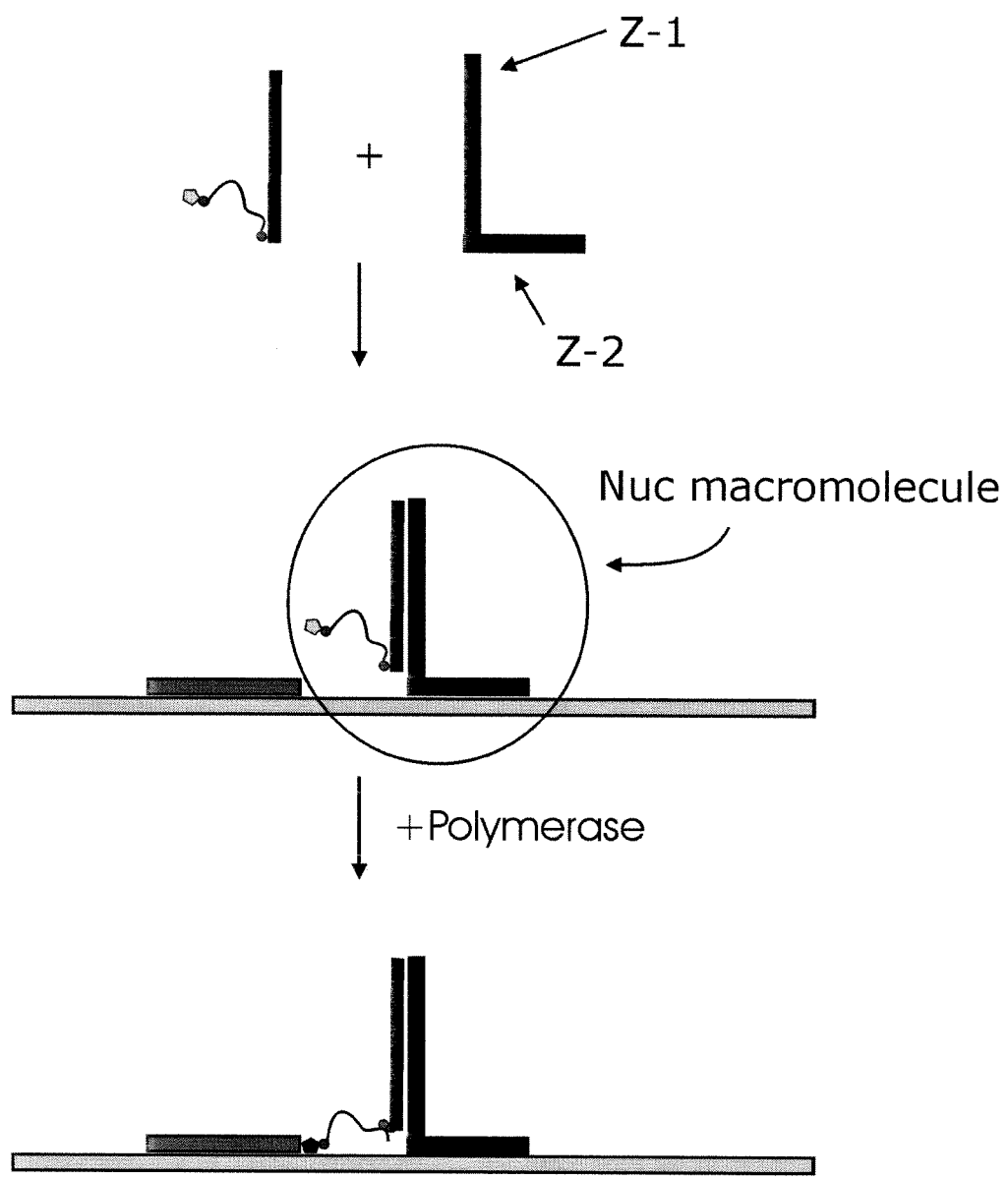

FIG. 5A and FIG. 5B depict a labelling reaction using a nuc-macromolecule of the invention.

FIG. 6 is an example of a labeling method for a target sequence or its equivalents with a subsequent binding to a solid phase. FIG. 6A illustrates one type of nuc-macromolecule with a target domain and an anchor domain, a single-stranded target sequence, one primer labeled with a signal domain, a DNA polymerase, and further nucleotides such as dNTPs. In FIG. 6B, these components are incubated under conditions that allow the polymerase to incorporate dNTPs and nuc-macromolecules into the growing strand. FIG. 6C depicts a reaction in which a solid phase provides a binding partner for the anchor domain.

FIG. 7 is a schematic of an example of a labeling method for a target sequence or its equivalents with a subsequent binding to a solid phase. In FIG. 7A the following components are provided: one type of nuc-macromolecules (1-4 in FIGS. 7A and 7B) with a target domain, an anchor domain (4a in FIG. 7A), and an antagonist of the anchor domain (4b in FIG. 7A). Further components such as single-stranded target sequence, one primer labeled with a signal domain, a DNA polymerase, and further nucleotides such as dNTPs are depicted in 7B. FIG. 7C illustrates an incubation of the various components to allow polymerase to incorporate dNTPs and nuc-macromolecules into the growing strand.

Figure 8:
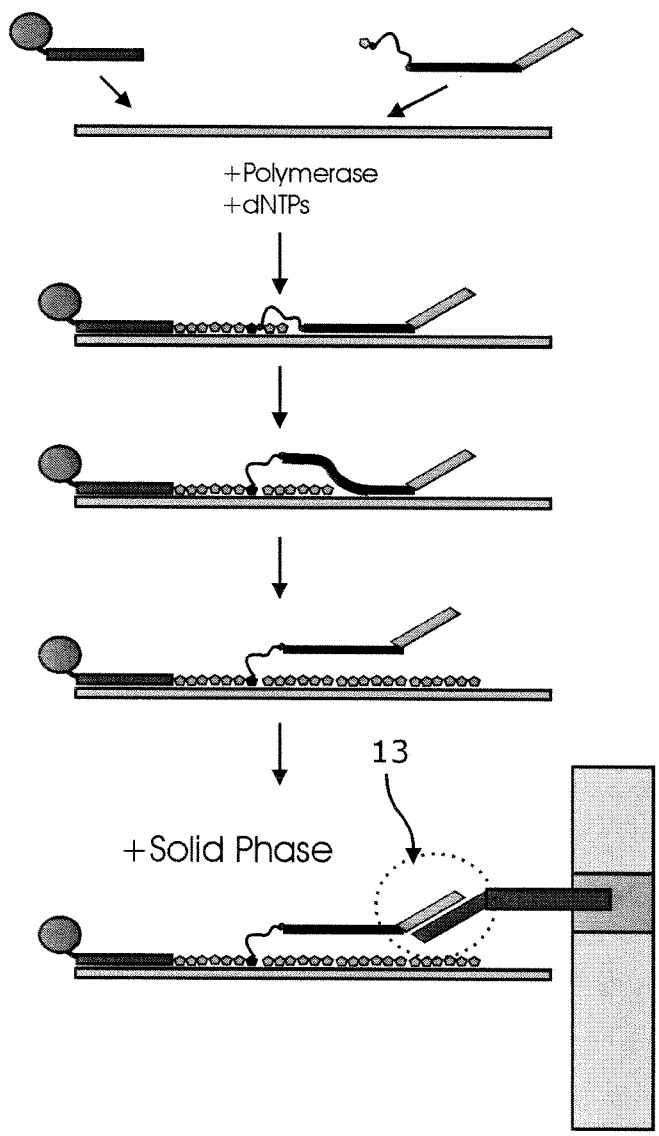

FIG. 8 is an illustration of a labeling method for a target sequence or its equivalents with a subsequent binding to a solid phase.

FIG. 9 is an illustration of a labeling method for a target sequence or its equivalents with a subsequent binding to a solid phase.

Figure 10:
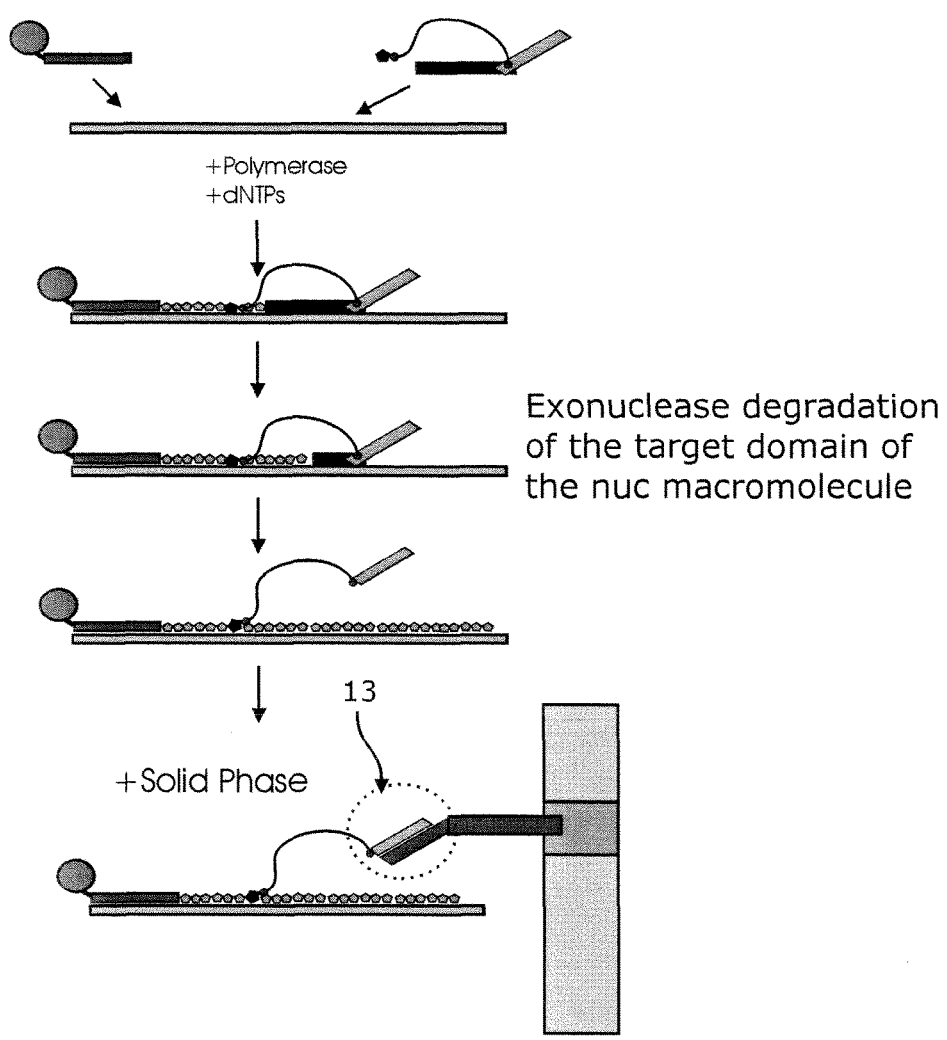

FIG. 10 is an illustration of a labeling method for a target sequence or its equivalents with a subsequent binding to a solid phase.

Figure 11:
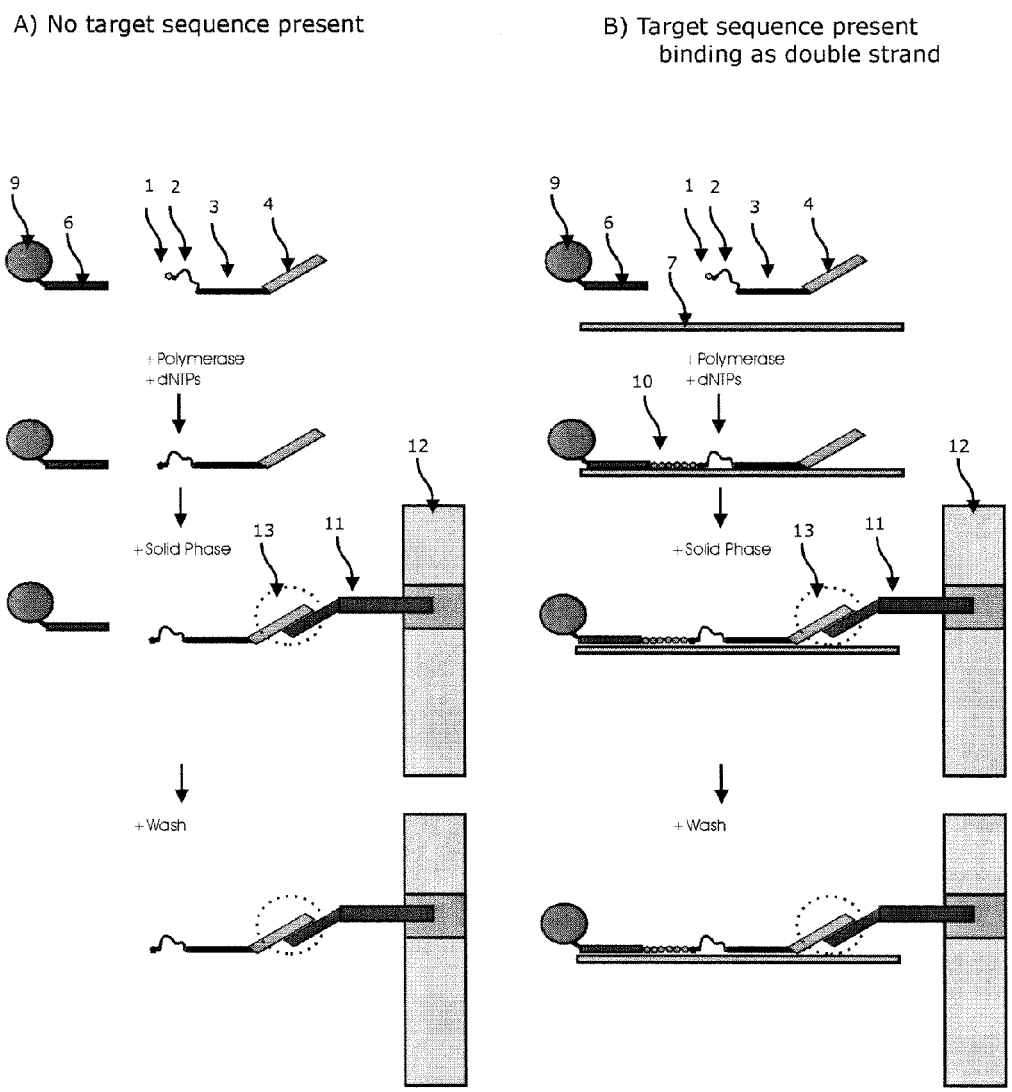

FIG. 11 illustrates a labelling reaction with a nuc-macromolecule of the invention. In 11A no target is present. 11B depicts a reaction in which the target sequence with the newly synthesized complementary strand is attached directly to the solid phase.

Figure 12:
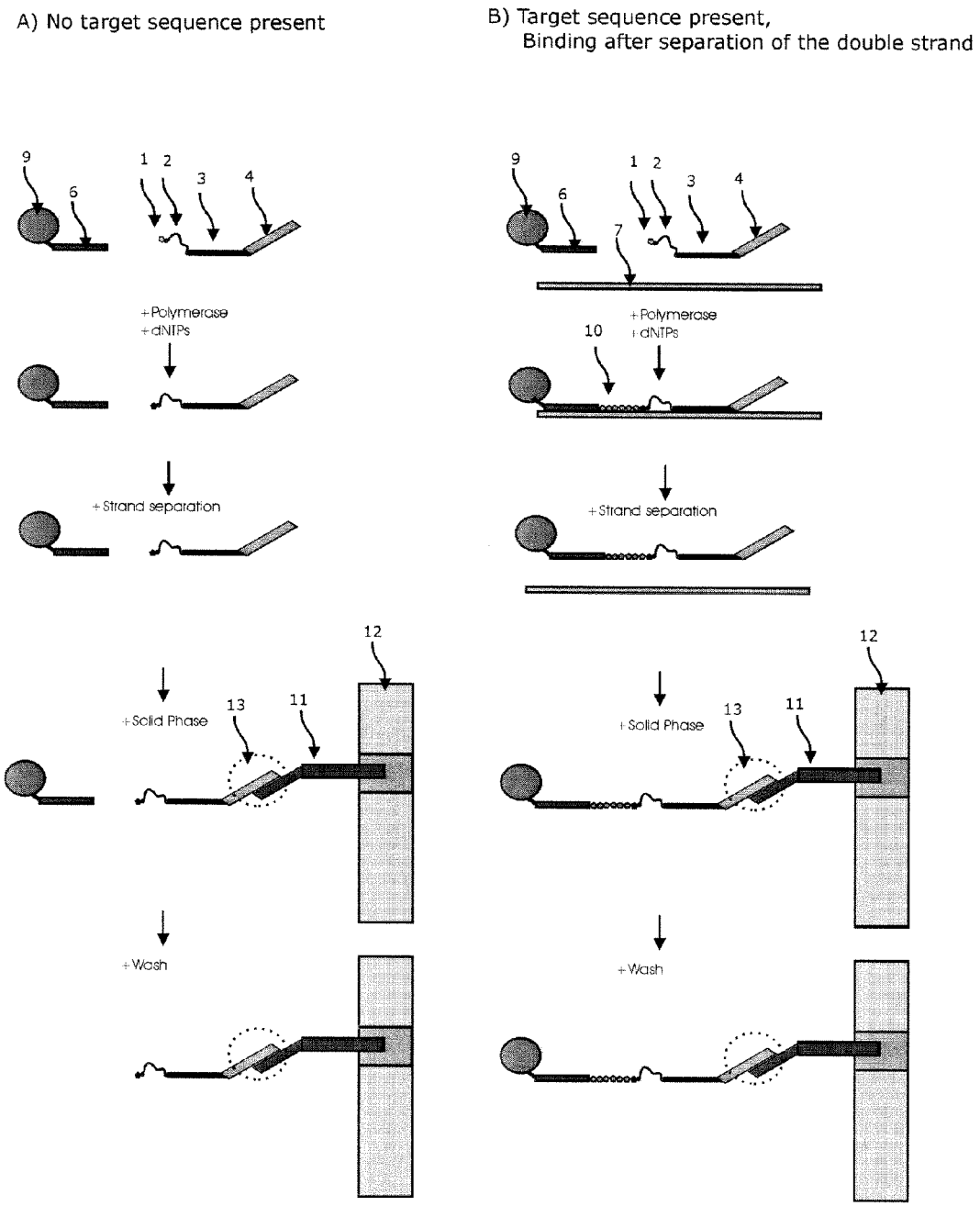

FIG. 12 illustrates a labelling reaction with a nuc-macromolecule of the invention. In 12A no target is present. In the method illustrated in FIG. 12B, a separation of the double strand is included.

FIG. 13 illustrates a labeling reaction with a nuc-macromolecule of the invention. In FIG. 13A, the various components are the reaction are illustrated. FIG. 13B depicts incorporation of dNTPs and nuc-macromolecules into the growing strand. In FIG. 13C, the labeled target sequence binds to the solid phase via the anchor domain of the incorporated nuc-macromolecule.

FIG. 14 illustrates a labeling reaction with a nuc-macromolecule of the invention. In FIG. 14A, the various components are the reaction are illustrated. FIG. 14B depicts incorporation of dNTPs and nuc-macromolecules into the arowina strand. In FIG. 14C, the labeled target sequence binds to the solid phase via the anchor domain of the primer.

FIG. 15 illustrates a labeling reaction with a nuc-macromolecule of the invention. In FIG. 15A, the various components are the reaction are illustrated. FIG. 15B depicts incorporation of dNTPs and nuc-macromolecules into the growing strand. In FIG. 15C, the labeled target sequence binds to the two solid phases included in the reaction. The first solid phase (solid phase-1) which comprises a binding partner for the anchor domain-1 of the nuc-macromolecule is provided, as well as the second solid phase (solid phase-2) which comprises a binding partner for the anchor domain-2 of the primer is provided.

Figure 16:
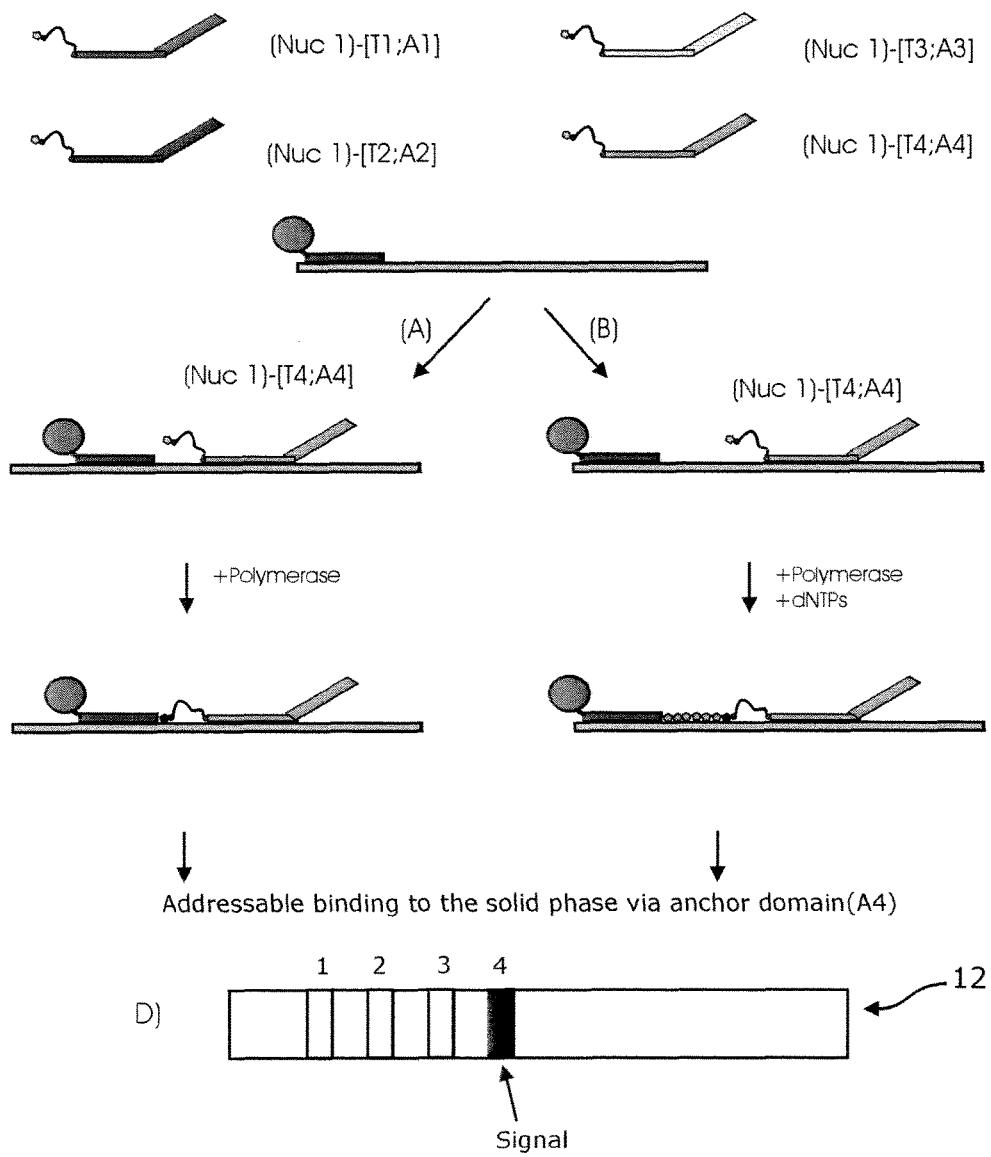

FIG. 16 illustrates an embodiment in which differentiation is carried out by the target domain of the nuc-macromolecules. Multiple nuc-macromolecules whose target domains are complementary to different variants of the target sequence (FIG. 16) are depicted.

Figure 17:
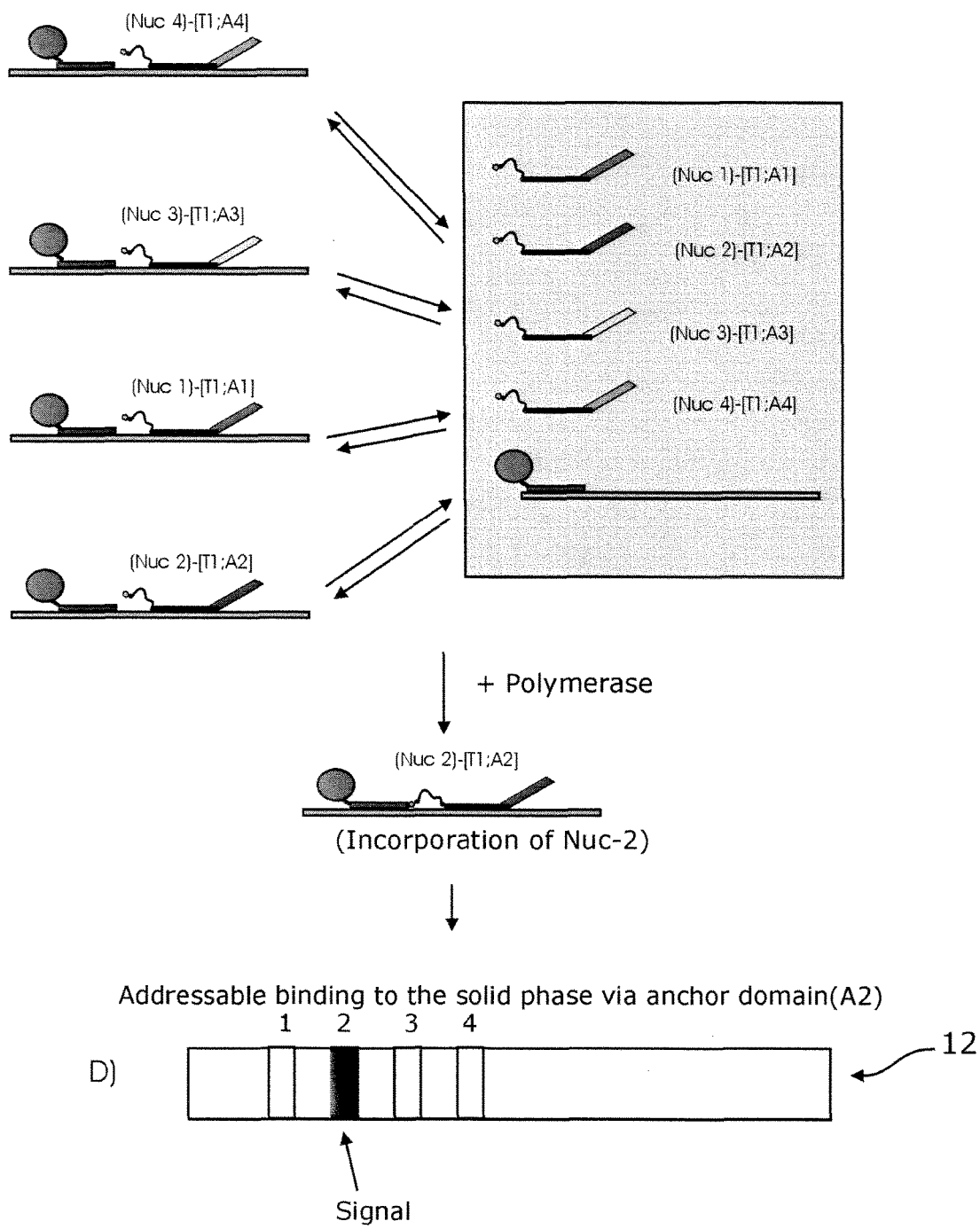

FIG. 17 illustrates an embodiment of the invention in which differentiation is achieved by the incorporation of a nuc-component of a nuc-macromolecule. The nuc-component is combined with a specific anchor domain or signal domain, which allows for a specific attribution of the incorporated nuc-component after the binding to a solid phase.

Figure 18:
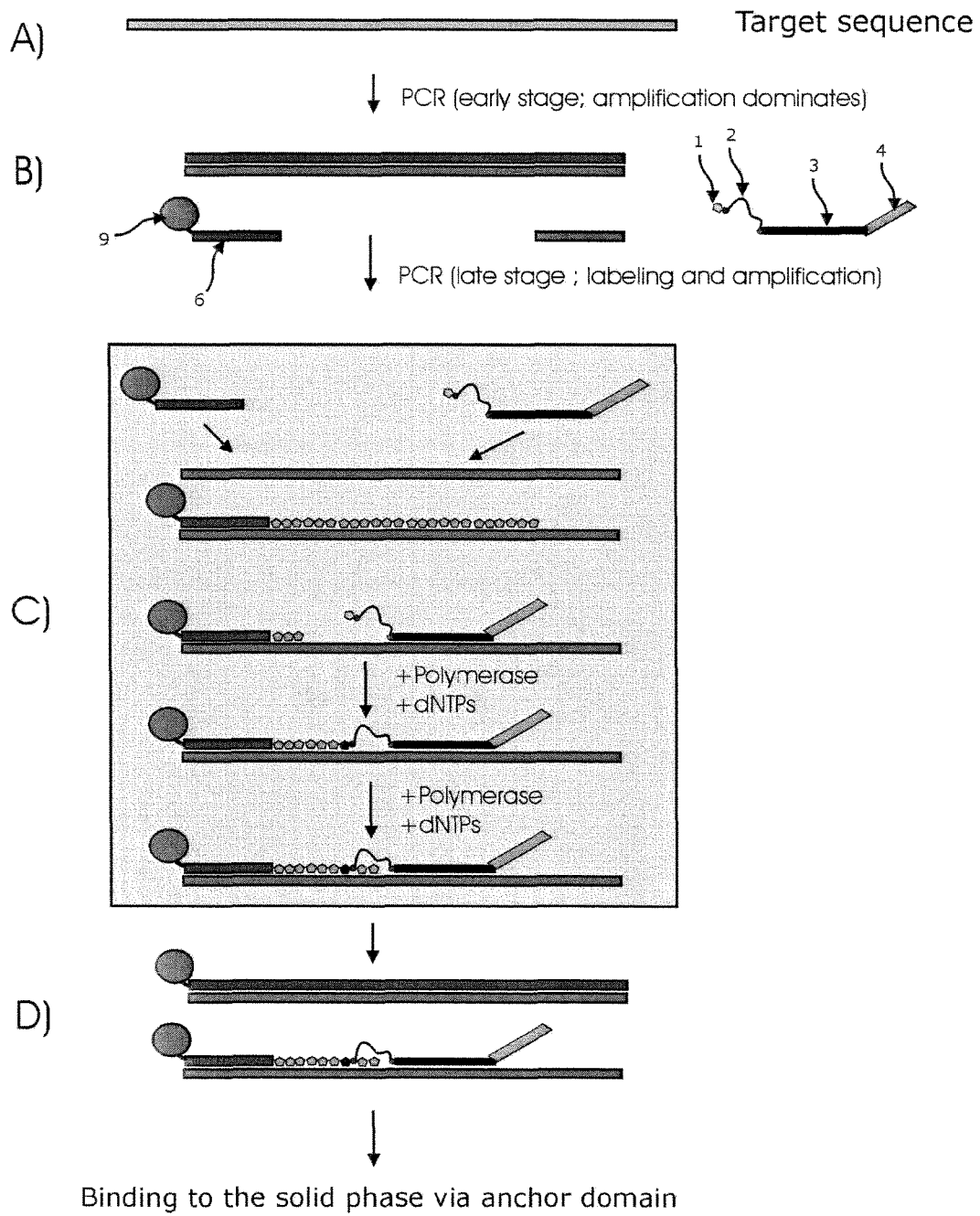

FIG. 18 illustrates an embodiment in which PCR is used as an amplification method. FIG. 18A depicts target sequence. FIG. 18B illustrates an early amplification stage and FIG. 18C and FIG. 18D depict the later amplification stage and reaction products, respectively.

Figure 19:
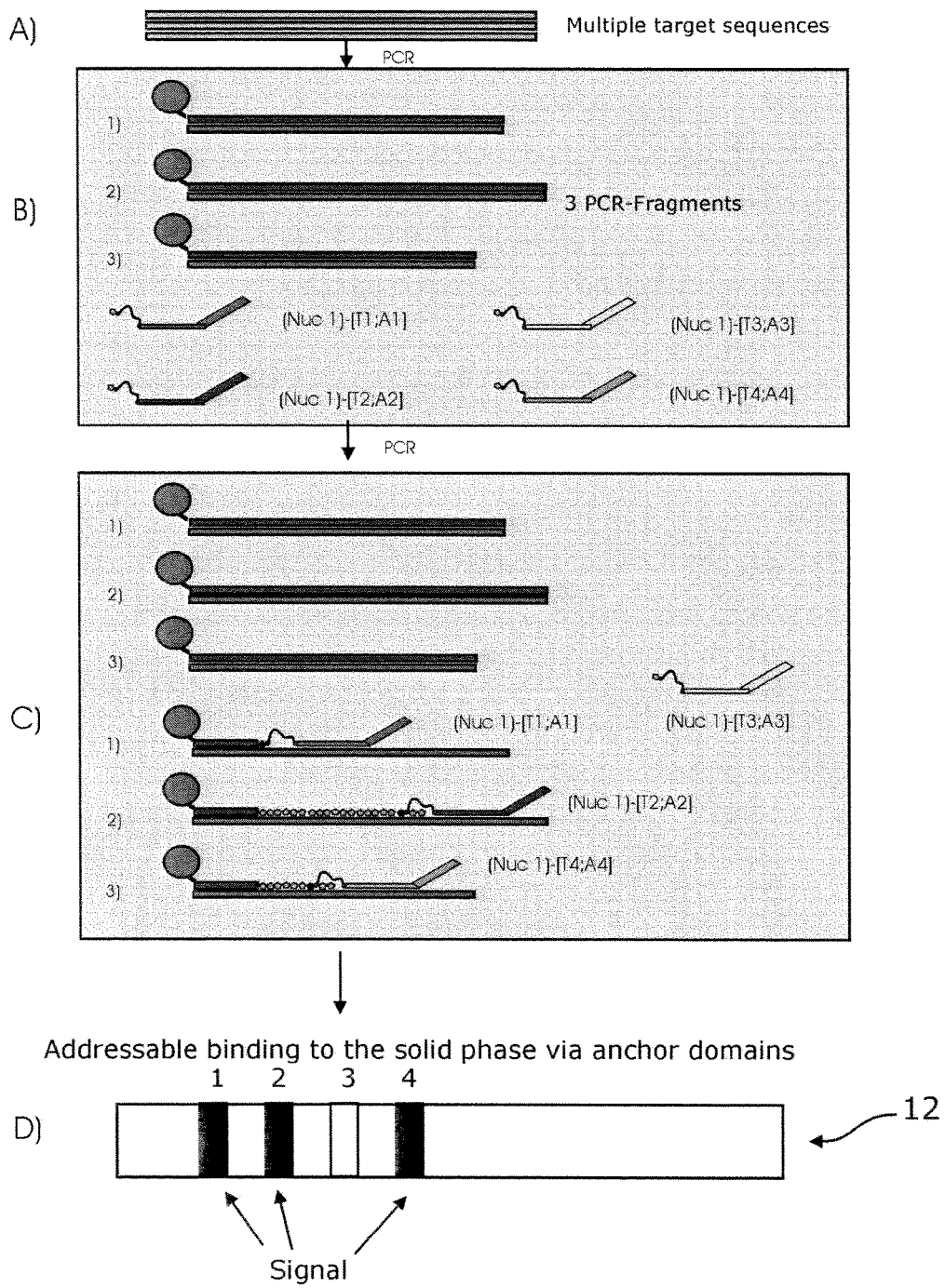

FIG. 19 illustrates multiple amplification in a single reaction using multiple nuc-macromolecules. 19A depicts multiple target sequences, which are amplified by means of PCR (FIG. 19B) In FIG. 19C the anchor domains of the nuc-macromolecules are specifically combined with the respective target domains so that respective anchor domain with the corresponding target domain of a nuc-macromolecule forms a specific pair. This is also depicted in FIG. 19D.

Figure 20:
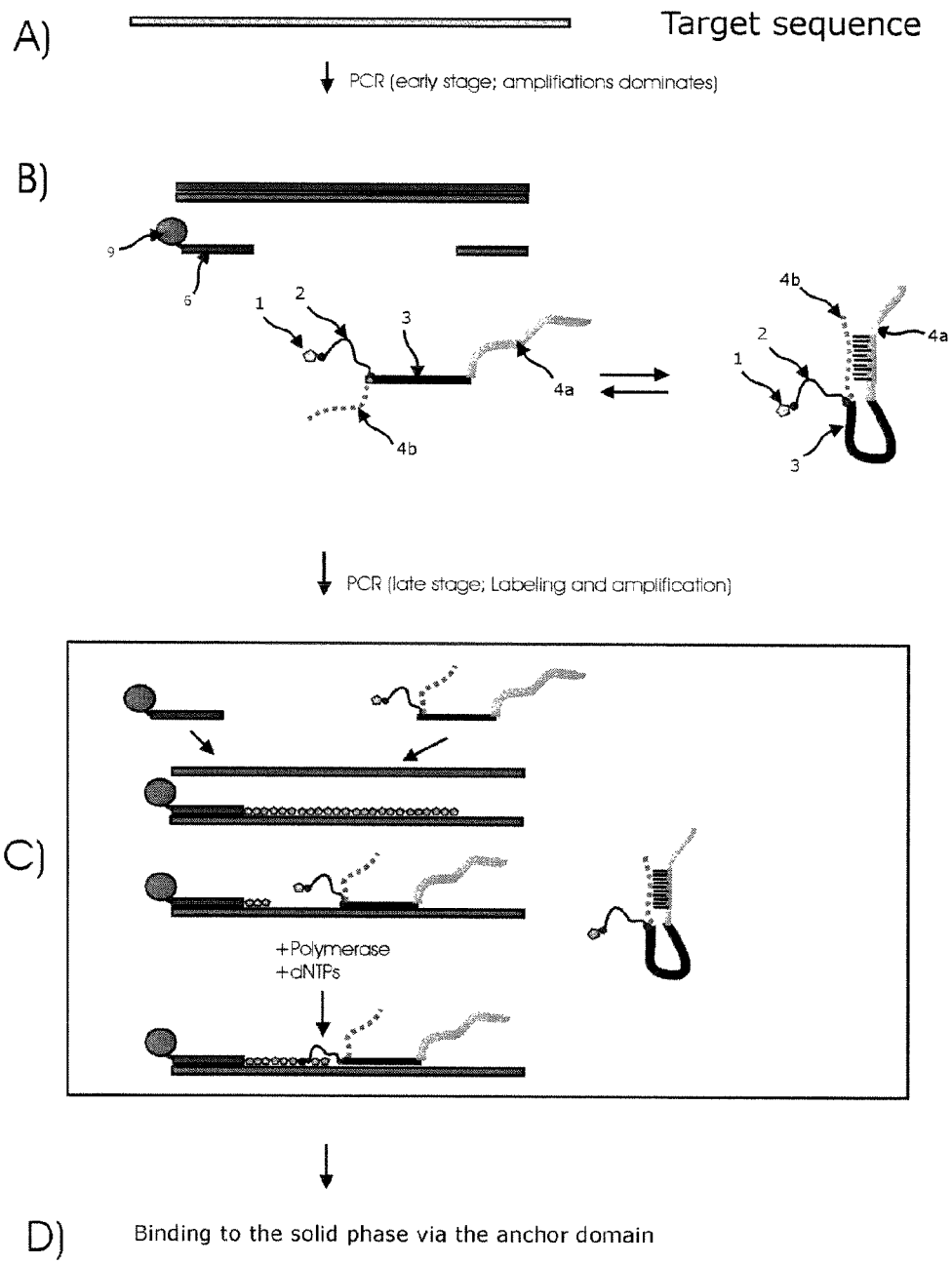

FIG. 20 illustrates an embodiment in which nuc-macromolecules comprising a target domain, an anchor domain and an antagonist to the anchor domain are used in a PCR reaction. Target is depicted in FIG. 20A; early amplification is depicted in FIG. 20B; and late stage PCR amplification and labelling is depicted in FIG. 20C. Binding of the product of the reaction is depicted in FIG. 20D.

Figure 21:
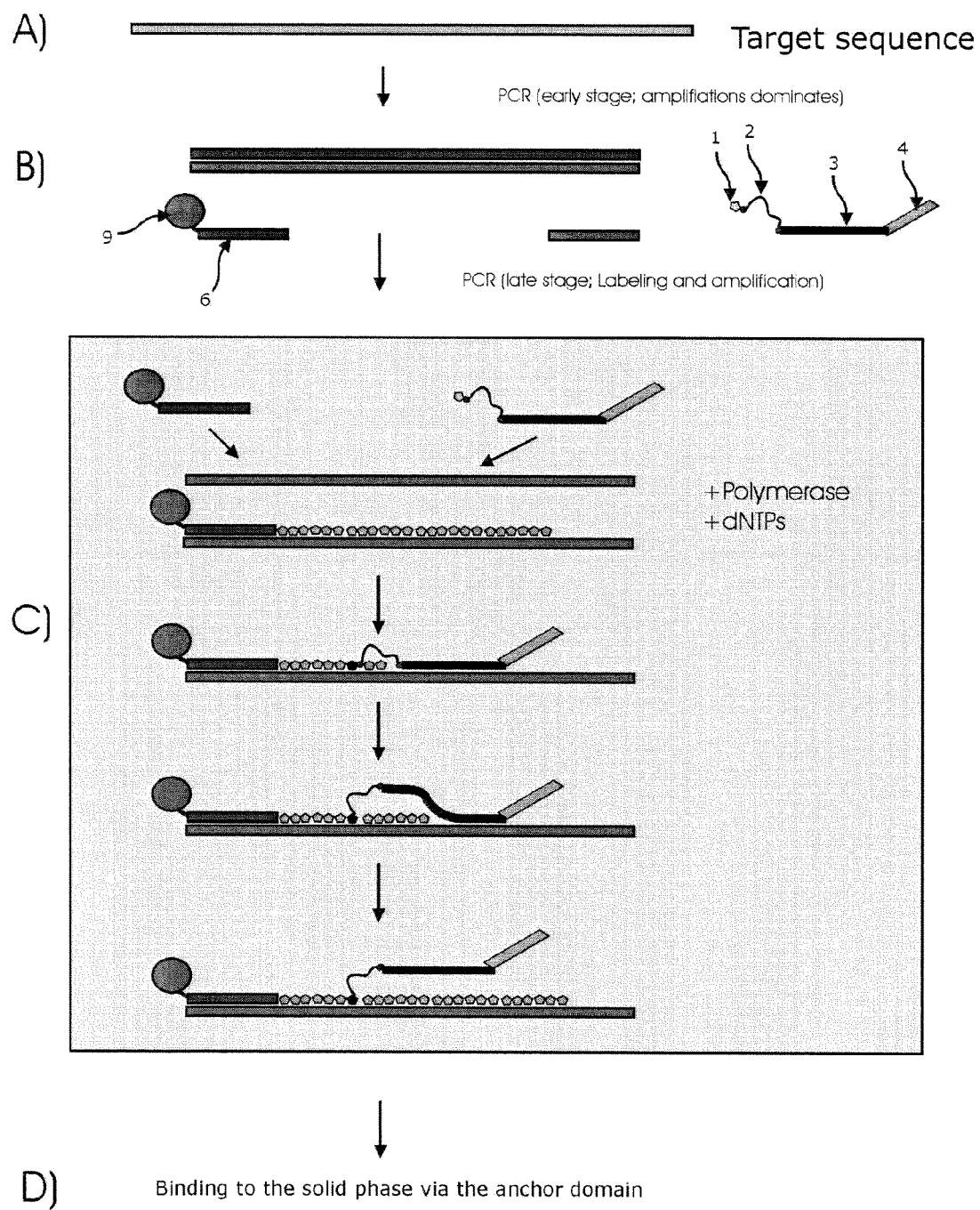

FIG. 21 illustrates an embodiment of the invention in which a polymerase having a strand displacement activity is used in the PCR reaction. FIG. 21A illustrates the target; early amplification is depicted in FIG. 21B; late stage PCR amplification and labelling is depicted in FIG. 21C; and binding to a solid support is depicted in FIG. 21D.

FIG. 22 depicts the base and sugar of the nuc-component (22B) with a linker (22A).

FIG. 23 depicts an embodiment of the invention where marker units are bound to a framework, the core component of the marker. 22A: a macromolecular marker unit; 23B: core composnet; 22C: core components with bound marker units.

FIGS. 24A-D illustrate the manner in which the core component connects one or several nuc-linker components.

FIGS. 25A-C illustrate embodiments in which signal-giving marker units are bound to core composnet consisting of polynucleotide.

Figure 26:
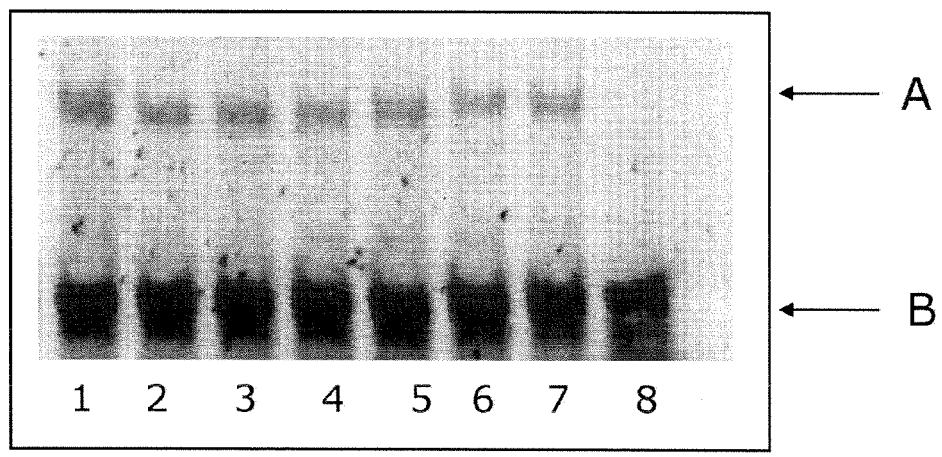

FIG. 26 is a gel imaae showing separation of labelled reaction products.

Figure 27:
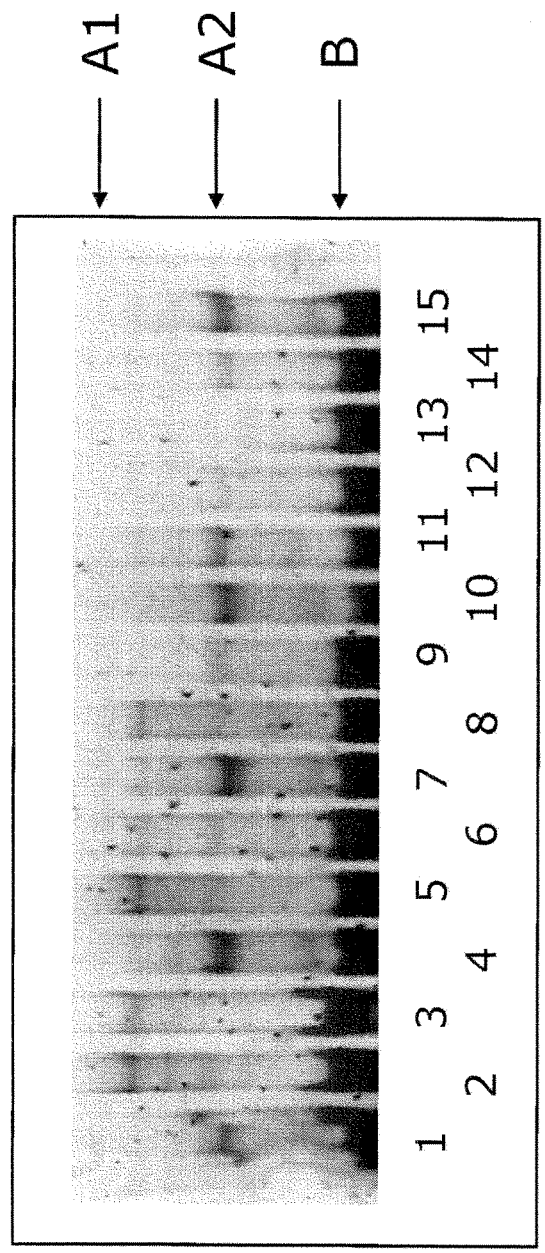

FIG. 27 is a gel image showing separation of labelled reaction products.

FIG. 28 shows gel image of newly synthesized nucleic acid strands in which nuc-macromolecules was bound to template using varied stringency conditions.

Figure 29:
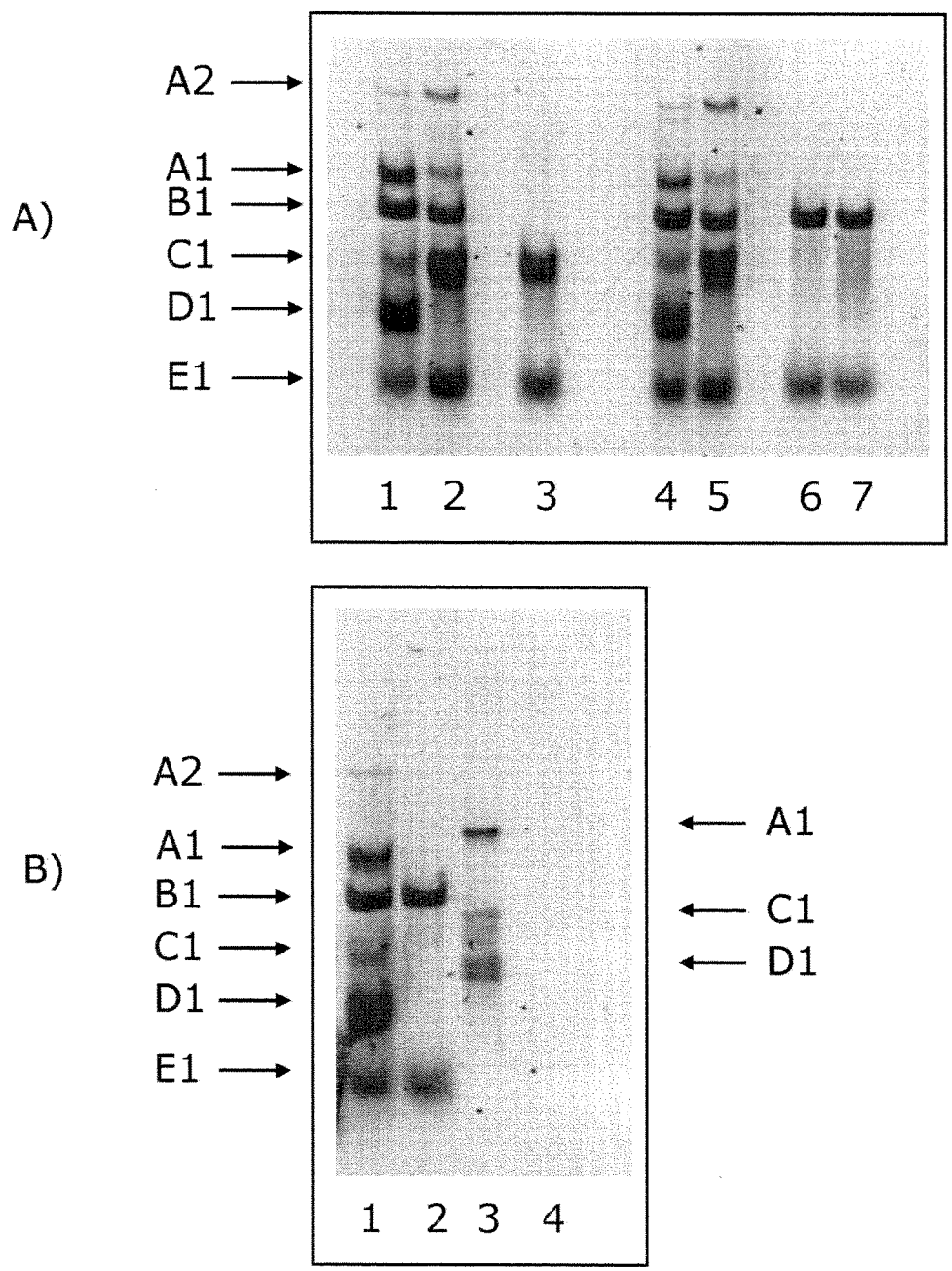

FIGS. 29A and B are gel image of reaction products: labeled nuc-macromolecules PCR products (Arrow Al and A2, FIG. 29 A) and PCR products without nuc-macromolecules (Arrow Bl, FIG. 29 A).

Figure 30:
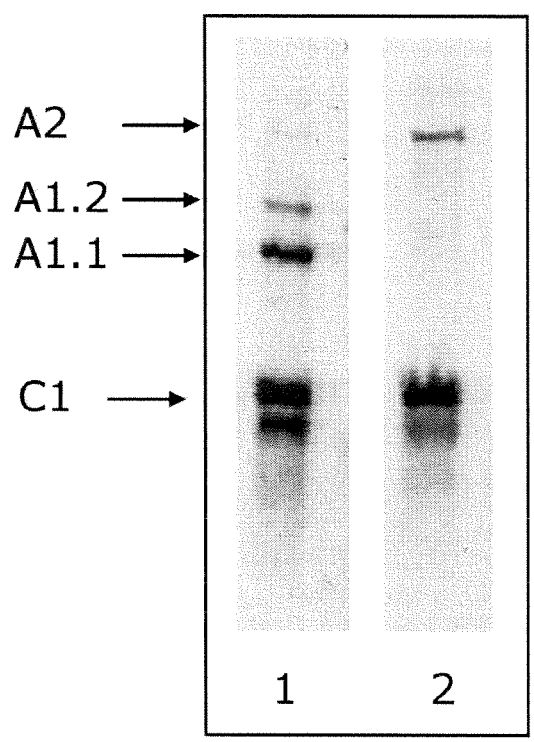

FIG. 30 is gel image showing the results of labeling of target sequences with solid-phase-Bound Nuc-Macromolecules.

FIGS. 31A and B are Images of a gel after electrophoretic separation of the reaction products. FIGS. 31A and B (first, imaaina of fluorescence signals from nuc-macromolecules was conducted (31B), then the gel was stained with ethidium bromide and a further imaae was made (31A).

FIGS. 32A-D illustrate examples of nuc-macromolecules with oligonucleotides with a double-stranded structure.

FIGS. 33A-F demonstrate couplings based on affinity, which is achieved by hybridization of the antagonist oligonucleotide to the oligonucleotide of the target domain.

Figure 34:
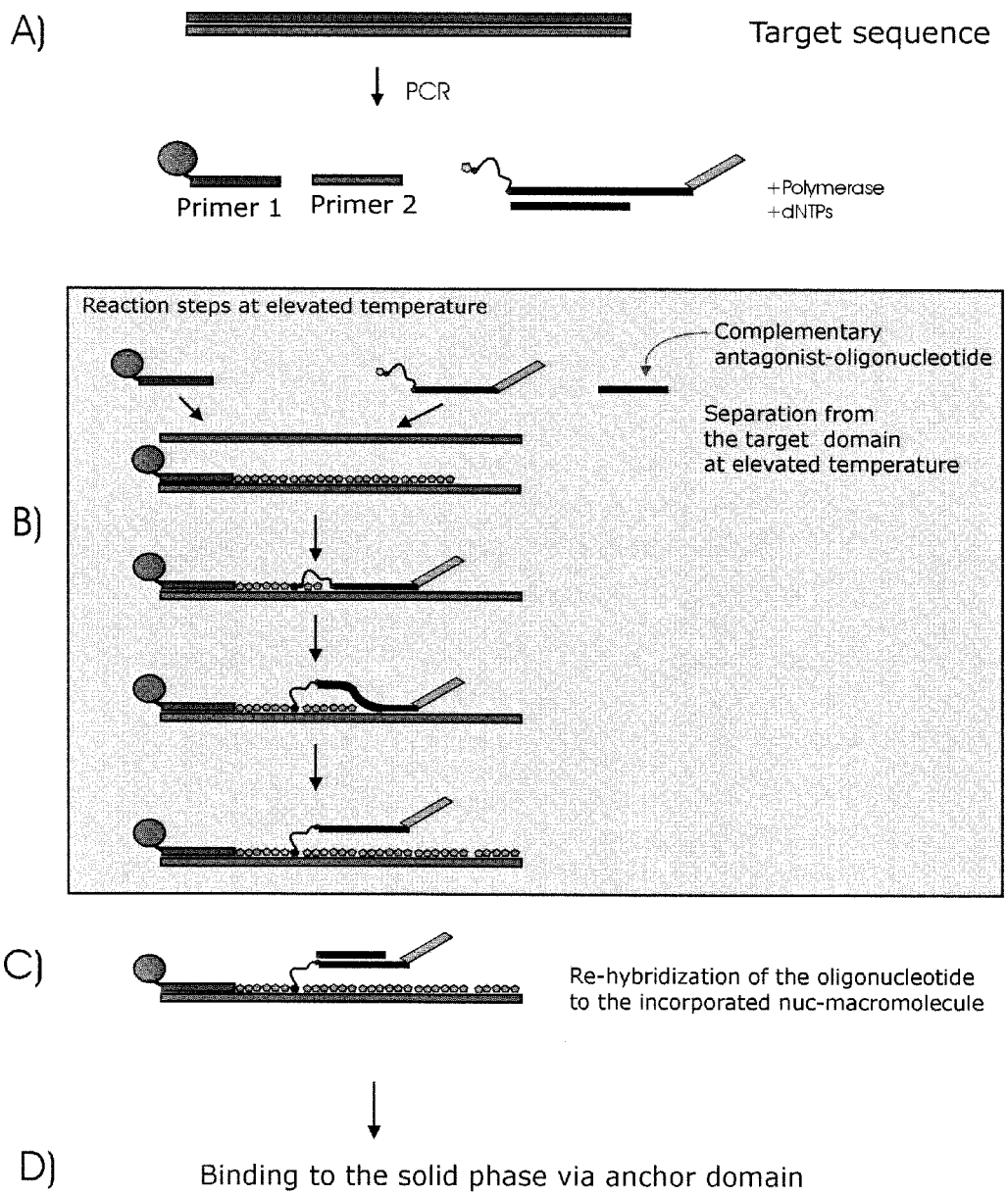

FIG. 34 illustrates parallel amplification and labelling of target sequences with nuc-macromolecules comprising antagonist-oligonucleotides. 33A: target sequence; 34B: PCR reaction steps; 34C: rehybridization; and 34D: binding to a solid support.

Figure 35:
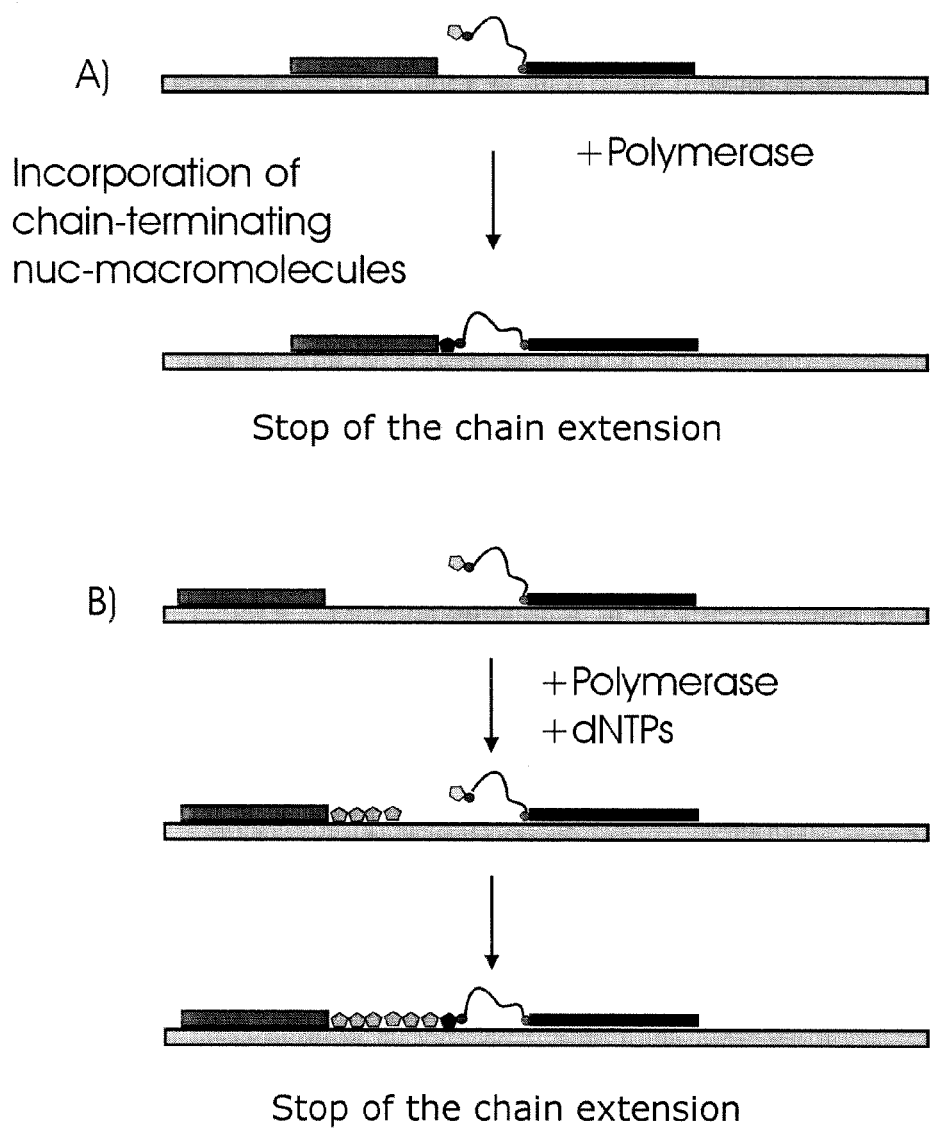

FIG. 35 illustrates incorporation of nuc-macromolecules into a newly synthesized nucleic acid chain. 35A: reaction plus polymerase; 35B: reaction plus polymerase and dNTPs.

Figure 36:
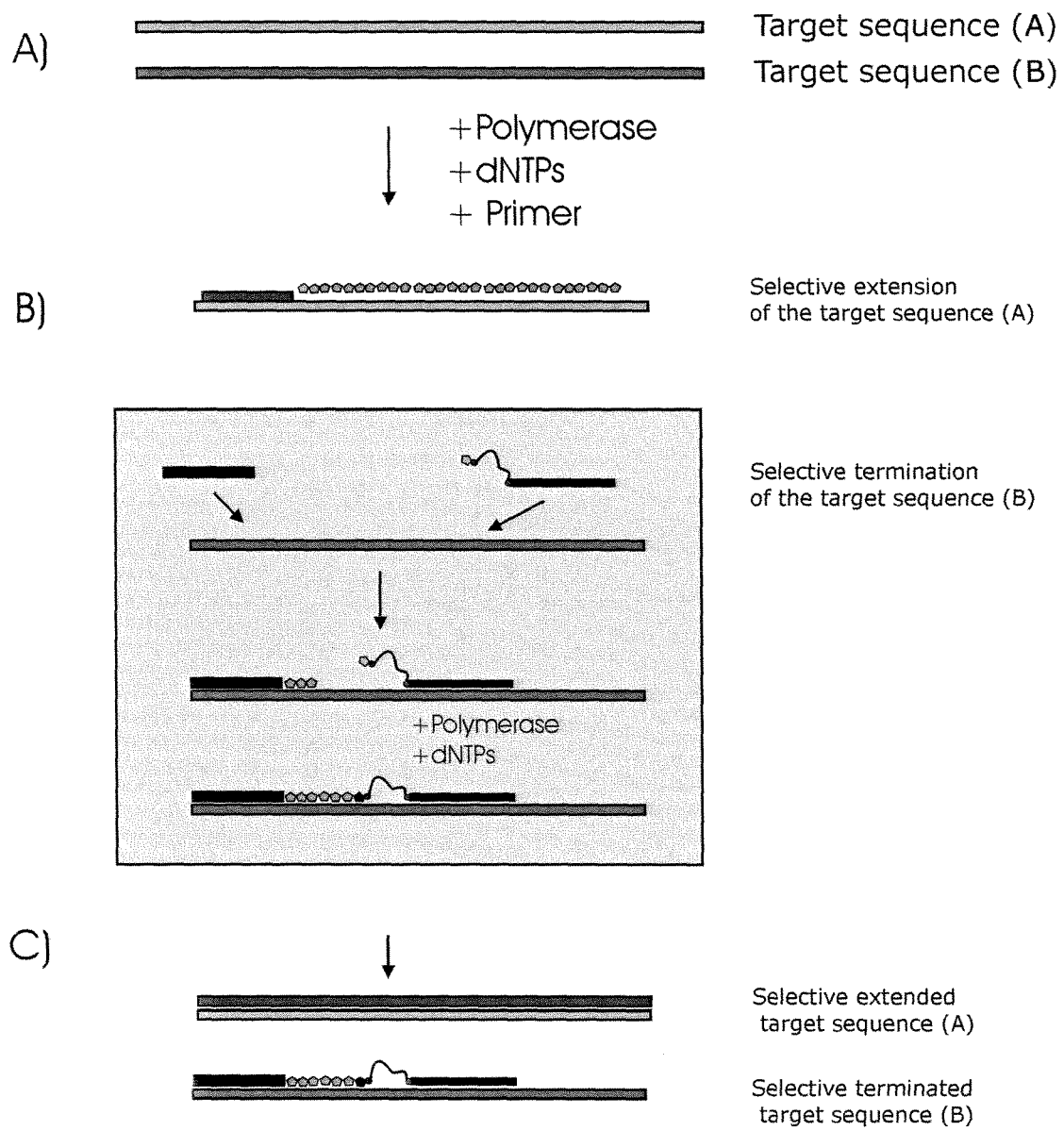

FIG. 36 illustrates simultaneous extension of one taraet sequence and termination of a different target sequence. 36A: shows target sequences and reaction components; 36B: selective extension of target A and selective termination of target B; 36C: reaction products.

Figure 37:
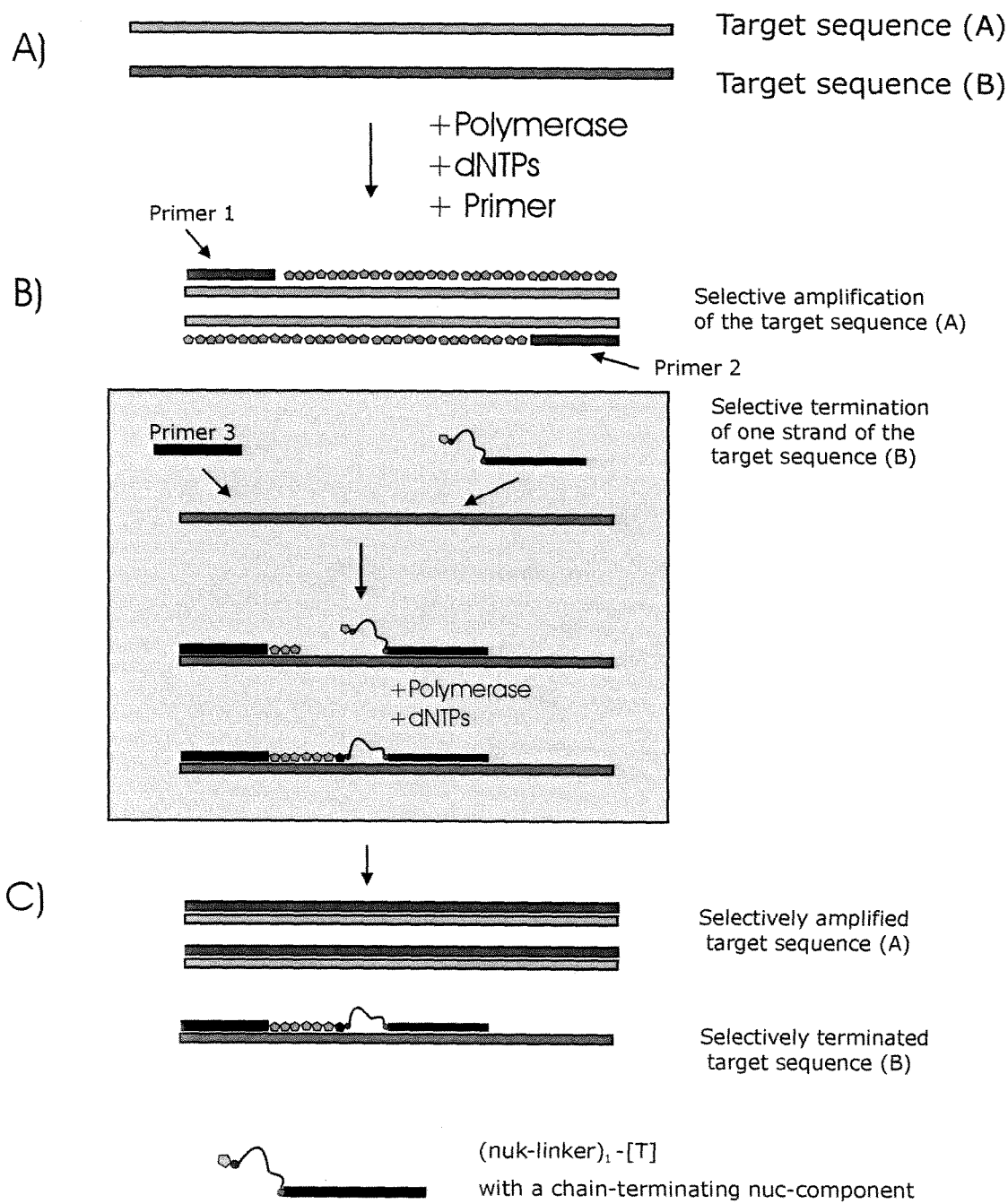

FIG. 37 illustrates simultaneous amplification of one target sequence and termination of a different target sequence. 37A: shows target sequences A and B and reaction components; 37B: selective amplification of target A and selective termination of target B; 37C: reaction products.

Figure 39:
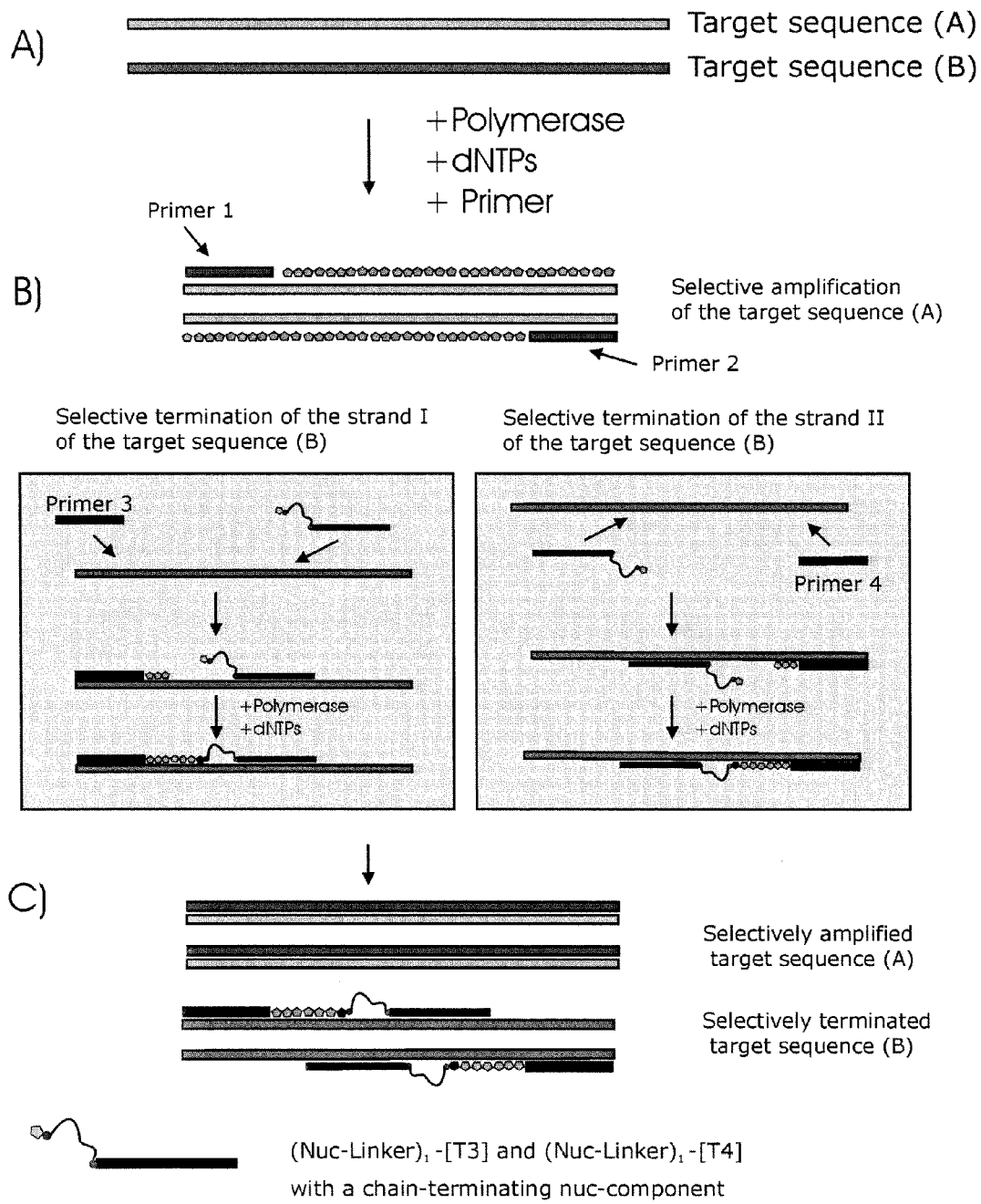

FIG. 38A-E illustrate at least two nuc-macromolecules each with different target domain oligonucleotides binding to both strands of a target sequence. In each of 38A-E, each nucleotide conivaate with its sequence-specific target domain binds to one strand of the target sequence FIG. 39 illustrates simultaneous amplification of target sequence A and termination of taraet sequence B. 39A: shows taraet sequences A and B and reaction components; 39B: selective amplification of target A and selective termination of strand I and strand II taraet B; 39C: reaction products.

FIG. 40 illustrates termination of multiple sequences. 40A: suppression of extension of three sequences with nuc-macromolecules where the targets have the same or similar sequence; 40B: suppression of extension of three sequences with nuc-macromolecules where the targets have different sequences.

FIG. 41 illustrates simultaneous extension and detection of target sequence A and termination of target sequence B. 41A: target sequence A and B and reaction components; 41B: selective termination of both complementary strands of target B and selective amplification of target A.

FIG. 42 illustrates simultaneous extension and detection of target sequence A and termination of target sequence B. 42A: target sequence A and B and reaction components; 42B: selective termination of both complementary strands of target B and selective amplification of target A.

FIG. 43 illustrates simultaneous extension and detection of taraet sequence A and termination of target sequence B. 43A: target sequence A and B and reaction components; 43B: selective termination of both complementary strands of tartlet B and selective amplification of target A.

Figure 44:
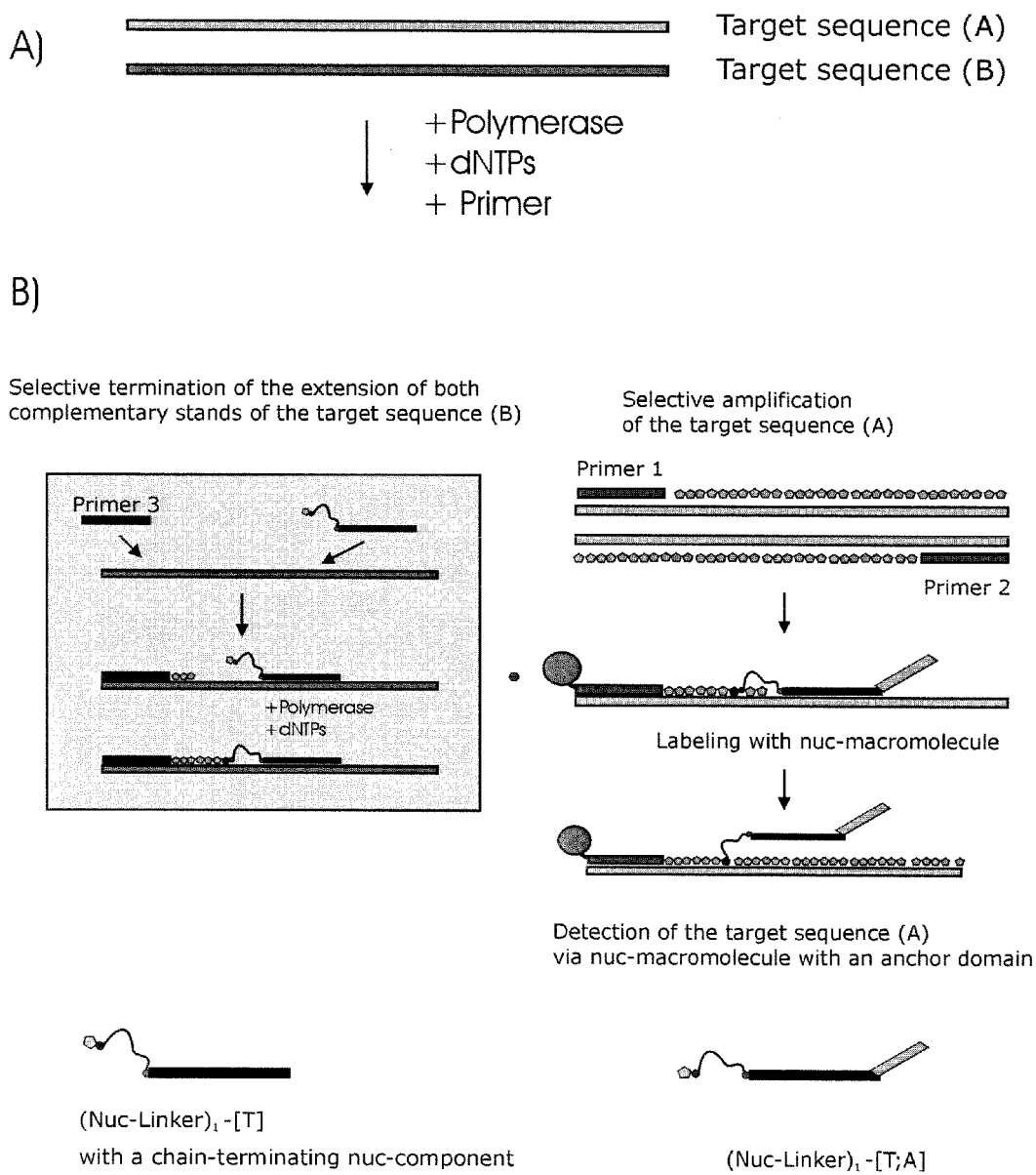

FIG. 44 illustrates simultaneous extension and detection of target sequence A and termination of target sequence B. 44A: target sequence A and B and reaction components; 44B: selective termination of both complementary strands of target B and selective amplification of target A.

FIG. 45 illustrates simultaneous extension and detection of target sequence A and termination of target sequence B. 45A: target sequence A and B and reaction components; 45B: selective termination of both complementary strands of target B and selective amplification of target A.

Figure 46:
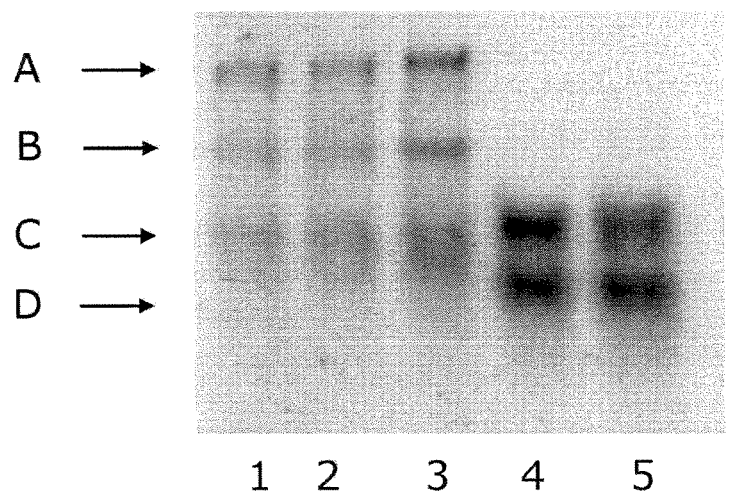

FIG. 46 is gel image of separated reaction mixture products.

Figure 47:
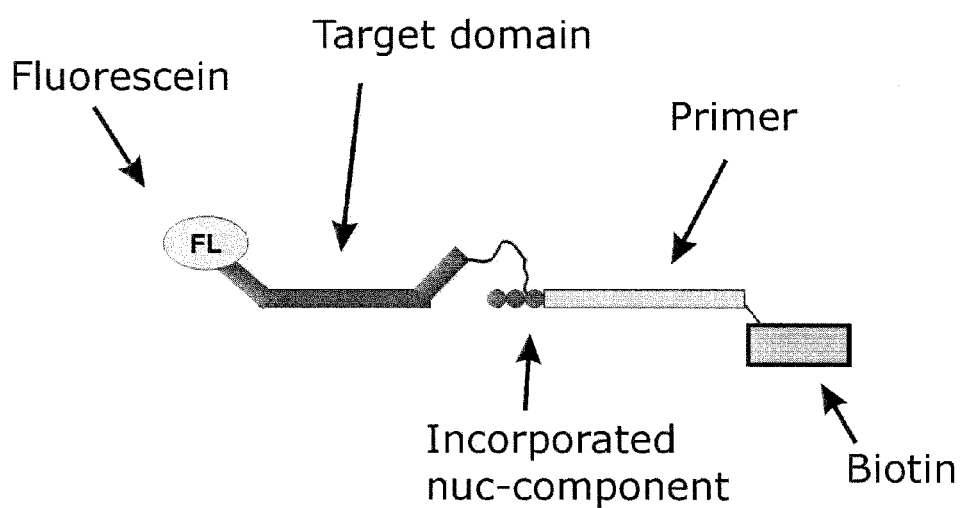

FIG. 47 is an illustration of the synthesis of a nuclease-resistant information carrier ("smart DNA").

FIG. 48A illustrates binding of a fully complementary target domain to a nuc-macromolecule; 48B illustrates incorporation of the nuc-component of the nuc-macromolecule into the newly synthesized nucleic acid chain. 49C illustrates lack of binding and incorporation due to a mismatch in the target domain of a nuc-macromolecule.

FIG. 49 illustrates labelling of target in the case of a perfect match of the target domain; 49B: illustrates lack of labelling in the case of a mismatch with the target domain.

FIG. 50 illustrations retardation of the synthesis of labeled fragments. 50A: incorporation of the nuc-components of nuc-macromolecules; 50B: illustrates a decrease in the rate of synthesis.

FIG. 51 illustrates the separation of labelled fragments from non-labelled fragments by means of nuclease degradation.

FIG. 52 illustrates saturation of the target domain after an incorporation reaction. 52A: perfect match; 52B: mismatch.

Figure 53:
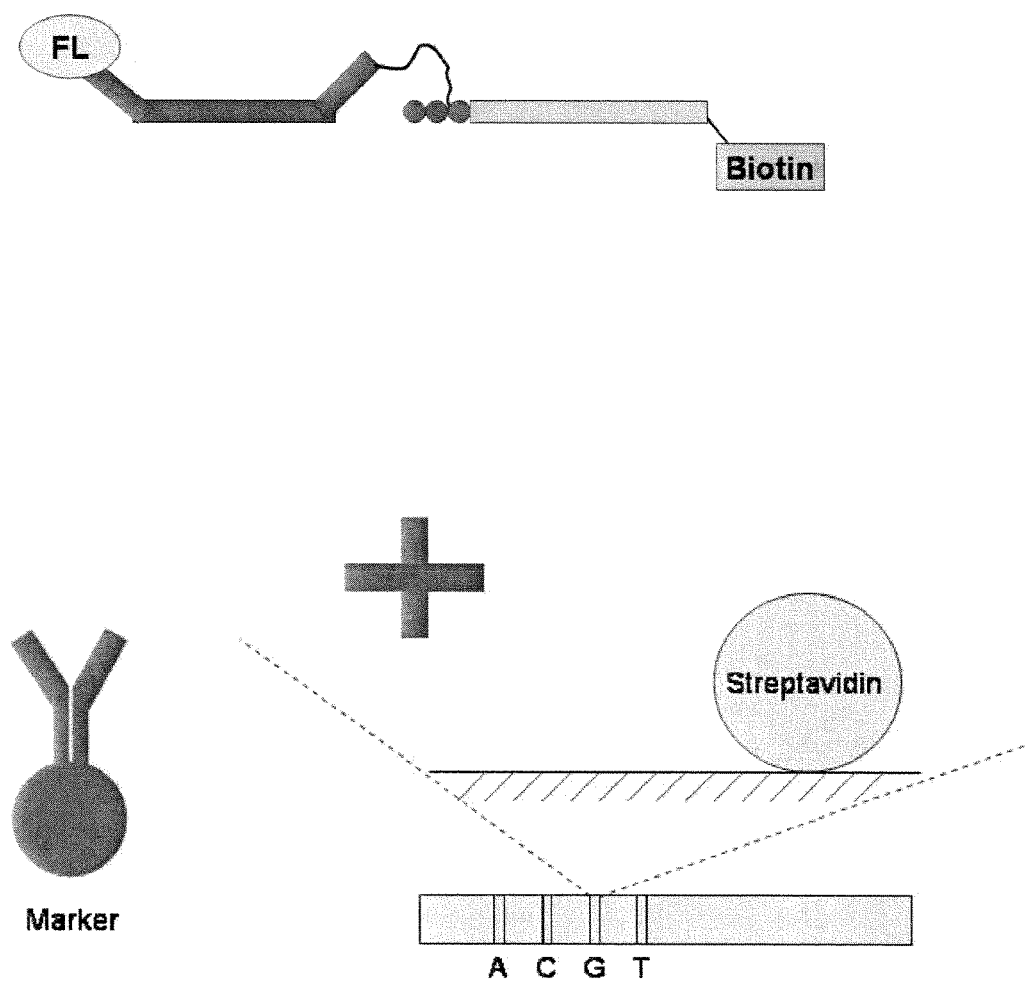

FIG. 53 illustrates detection of labelled DNA or labelled DNA fragmant.

Figure 54:
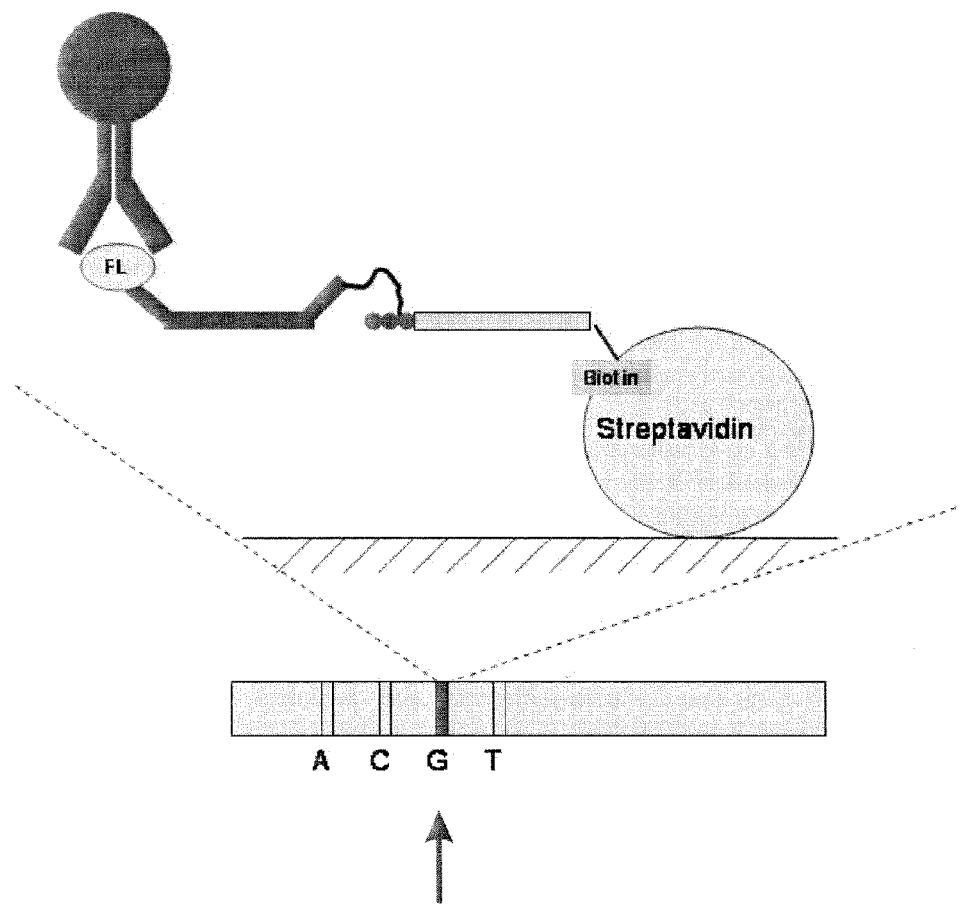
Figure 55:
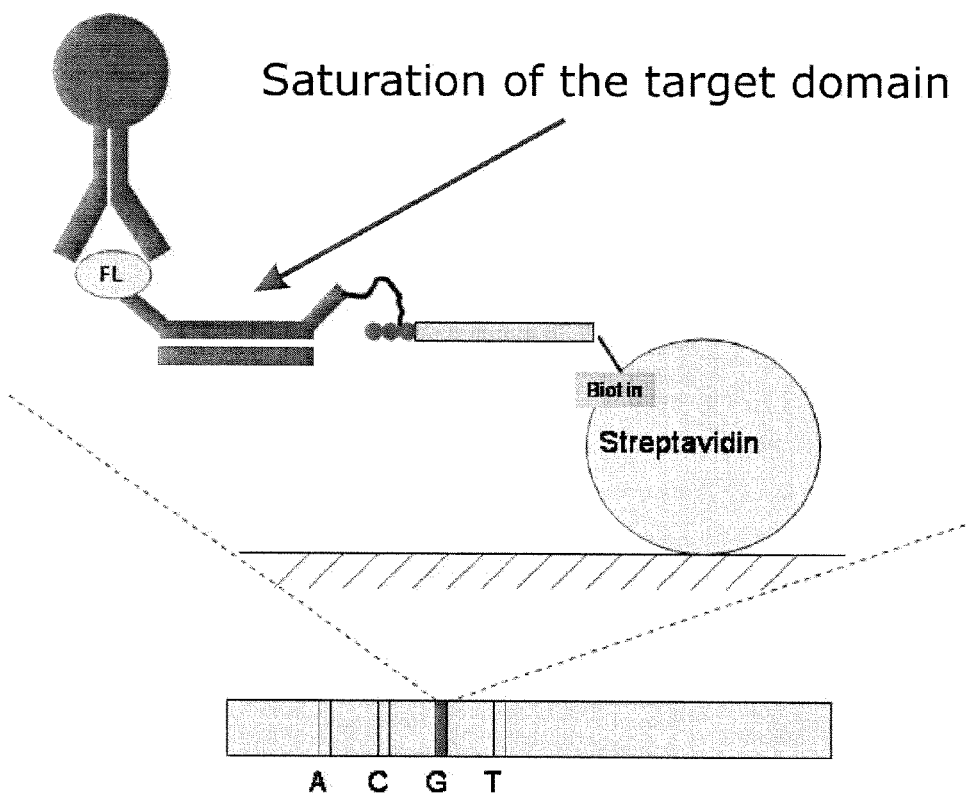

FIG. 54 illustrates binding of labelled DNA to a solid phase and detection

DETAILED DESCRIPTION OF THE INVENTION

1.3 Terms and Definitions

1.3.1 Macromolecular Compound a molecule or complex of molecules or a nanocrystal or nanoparticle, which has a molecular weight between 2 kDa and 20 kDa, 2 kDa and 50 kDa, 2 kDa and 100 kDa, 100 kDa and 200 kDa, 200 kDa and 1000 kDa or 1 MDa and 100 MDa or 100 MDa and 100 Gda. Examples of macromolecular compounds are nucleic acids, e.g. oligonucleotides with a length of more than 7 nucleotides, polynucleotides, polypeptides, proteins or enzymes, quantum dots, polymers like PEG, Mowiol, dextran, polyacrylate, nanogold particles and complexes comprising several macromolecules.

1.3.2 Low-Molecular Compound a molecule or a molecule complex, which has a mass smaller than 2000 Da (2 kDa), e.g. biotin, natural nucleotides, dATP, dUTP, many dyes, like Cy3, rhodamine, fluorescein and conventionally modified nucleotides, like biotin-16-dUTP.

Figure 1:
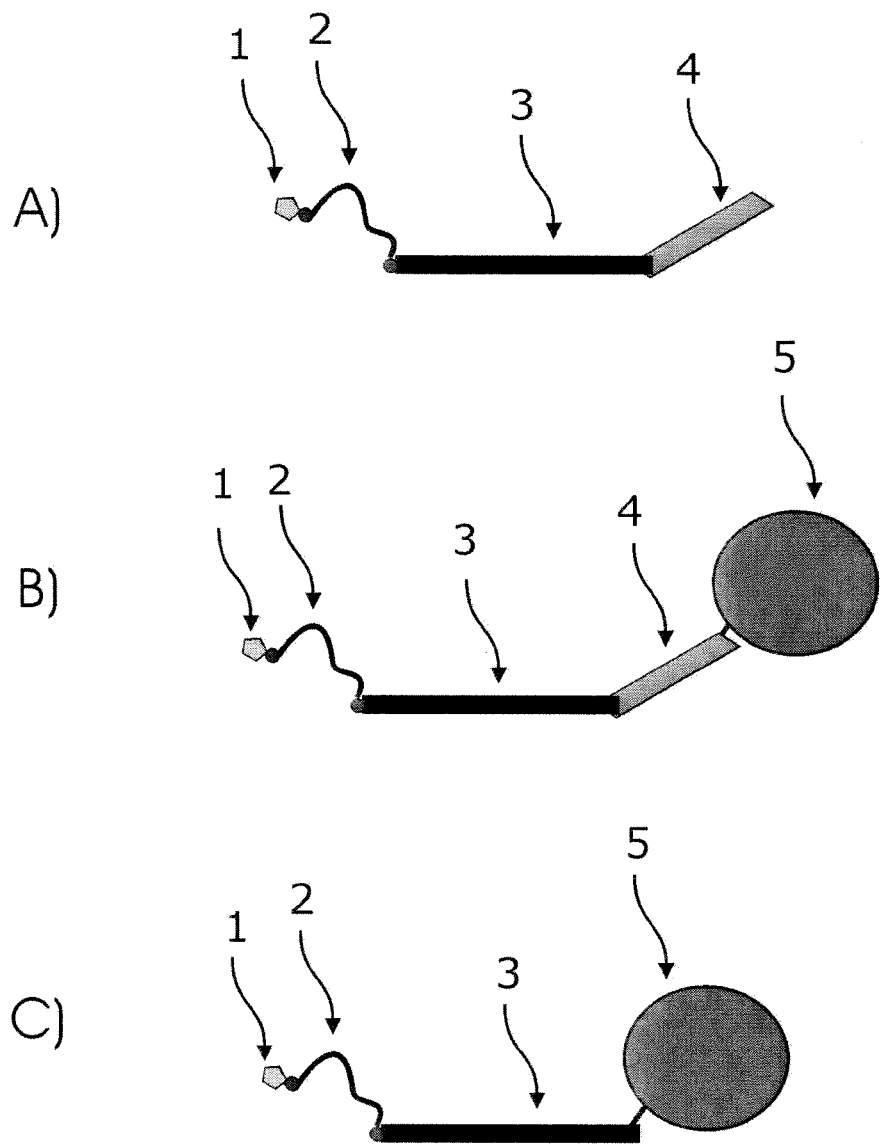
FIG. 1 A, FIG. 1B and FIG. 1C provide schematic depictions of three embodiments of the nuc-macromolecules of the invention.
Figure 3:
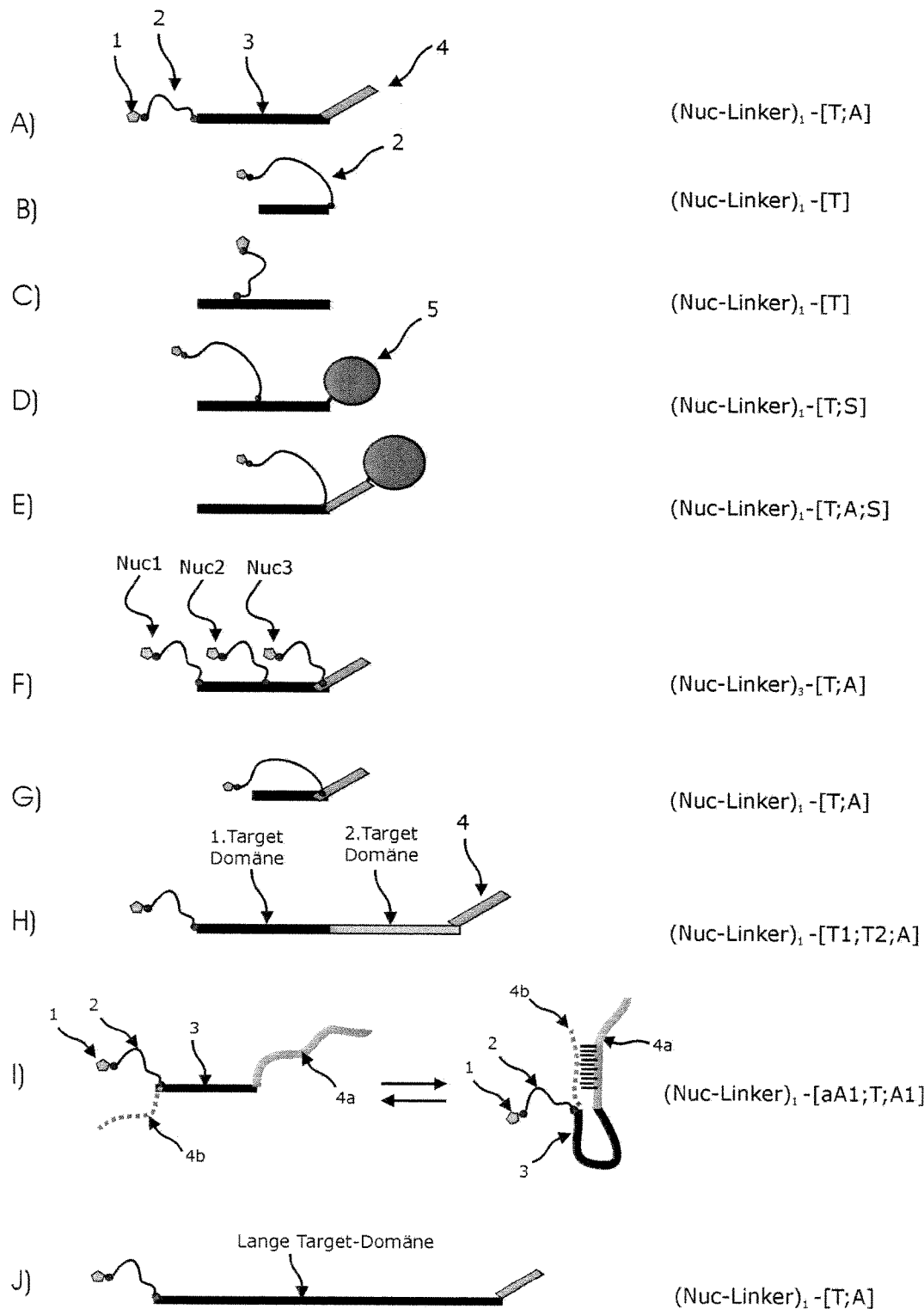
FIGS. 3A-J are schematic depictions of various embodiments of the nuc-macromolecules of the invention.
Figure 4:
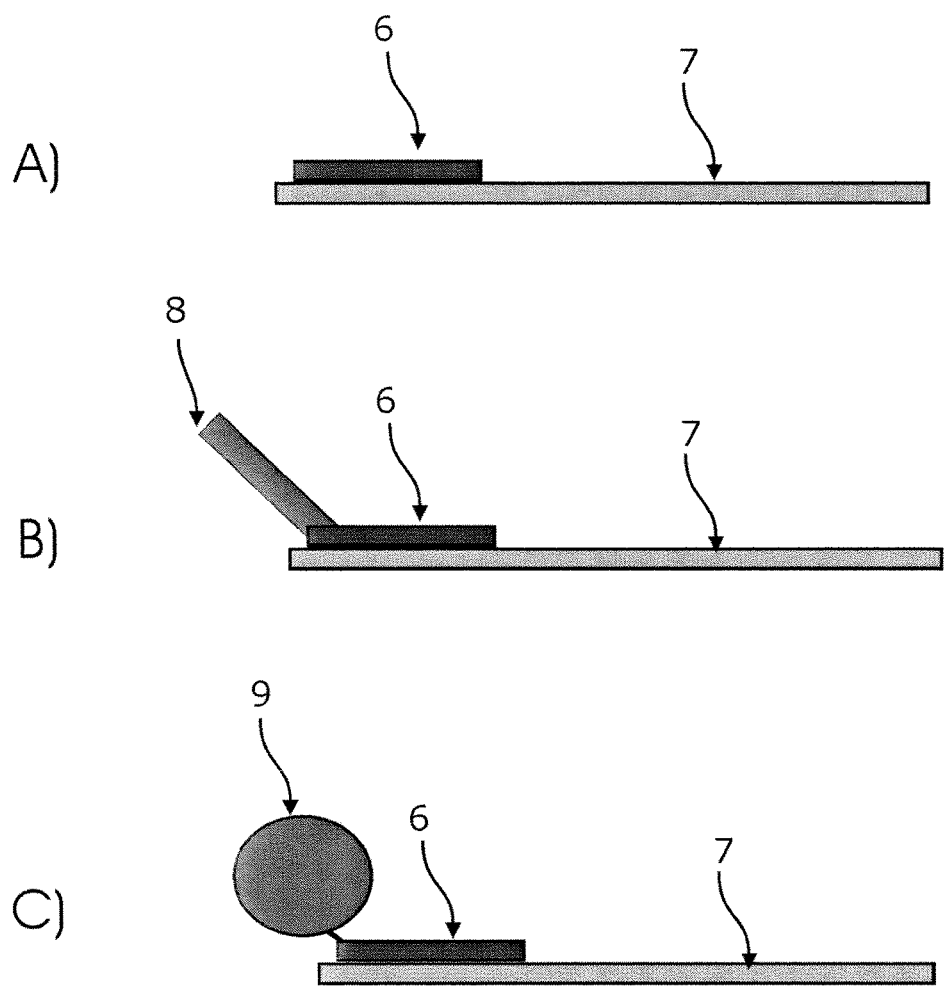

1.3.3 A Nuc-Macromolecule within the meaning of this application is a chemical structure (a nucleotide analog or a nucleotide conjugate), which comprises one or more nuc-components, one or more linker components, and at least a marker component, (FIGS. 1 to 3):

(Nuc-Linker)$_n$-Marker wherein:
Nuc is a nuc-component
Linker is a linker component
Marker is a marker component
n is a positive integer from 1 to 10000
Nuc is a Nucleotide or a Nucleoside Monomer (a Nuc-Component)

Linker has a composition which is not restricted as long as substrate properties of the nucleotides are not lost. Its length ranges between 5 and 10000 chain atoms.

Marker is a marker component, which can comprises one or several domains. For example a target domain, anchor domain, signal domain.

n is a positive integer from 1 to 10000, wherein (n) can be an average number.

In a further embodiment, the linker component comprises a coupling unit (L) for coupling the linker to the nuc-component, a hydrophilic, water soluble polymer and a coupling unit (T) for coupling the linker to the marker component. In this preferred embodiment, a nuc-macromolecule has the following structure, FIG. 1 or 2:

(Nuc-L-Polymer-T)$_n$-Marker wherein:
Nuc is a nucleotide monomer or a nucleoside monomer (nuc-component)

Linker comprises a coupling unit (L), a hydrophilic polymer and a coupling unit (T), wherein (L) is a part of the linker which connects the nuc and the linker-moiety (coupling unit L), and (T) is a part of the linker which connects the linker-moiety and the marker (coupling unit T).

Polymer is a part of the linker, which is hydrophilic, water soluble polymer with an average length between 5 and 100000 atoms.

(Coupling unit L, Polymer, coupling unit T are combined in this applications as a linker component).

Marker is a marker component, which can comprises one of several domains, for example a target domain, an anchor domain, a signal domain.

n is a positive integer from 1 to 10000, wherein (n) can represent an average number.

Examples for the synthesis of nuc-macromolecules are presented in the applications: Cherkasov et al WO2011050938, Cherkasov et al WO 2005044836, Cherkasov et al WO2006097320, Cherkasov et al WO 2008043426, Cherkasov et al DE 10356837, Cherkasov et al DE 102004009704.

1.3.3.1 Nuc-Component

Nuc-component is a substrate for nucleotide or nucleoside accepting enzyme. A nuc-component can represent a nucleotide as well as a nucleoside. In the following, nucleotides will be described as example for both classes of the substances. Nucleosides can be converted into a nucleotide form with corresponding enzymes or via chemical methods.

In one embodiment, the nuc-component is a nucleotide monomer or a nucleoside monomer, which is coupled to the linker component. In principle, all conventional nucleotide variants that are suitable as a substrate for nucleotide-accepting enzymes can serve as nuc-component of the nuc-macromolecule so that naturally occurring nucleotides as well as modified nucleotides (nucleotide analogs) can be considered for the nuc-component. Modified nucleotides comprise base-, sugar- or phosphate-modified nucleotide analogs. Many examples are known to the person skilled in the art ("Nucleoside Triphosphates and their Analogs", Morteza Vaghefi, 2005, ISBN 1-57444-498-0; "Deoxynucleoside analogs in cancer therapy" Godefridus 3. Peters, 2006, ISBN 1-58829-327-0; "Chemistry of nucleosides and nucleotides" Leroy B. Townsend, 1991, ISBN 0-306-43646-9; "Advanced organic chemistry of nucleic acids", 1994, Shabarova, ISBN 3-527-29021-4; "Nucleotide Analogs" Scheit, 1980, ISBN 0-471-04854-2; "Nucleoside and Nucleic Acid Chemistry", Kisakürek 2000, "Anti-HIV Nucleosides" Mitsuya, 1997, "Nucleoside Analogs in cancer therapy", Cheson, 1997). further examples for modifications of the nucleotides will also be cited in the text.

The nuc-component preferentially comprises a base part (base), a sugar part (sugar) and optionally a phosphate part (phosphate). Base, sugar and phosphate can be modified, i.e. the basic structure resembles the natural occurring nucleotides, but comprises e.g. additional chemical groups. Examples for combinations of different nucleotide components are known to the person skilled in the art. Such nuc-components can be used in a variety of enzymatic and chemical reactions (G. Wright et al. Pharmac. Ther. 1990, v. 47, p. 447-).

In a preferred embodiment, the nuc-component is a substrate for DNA polymerase. In a another preferred embodiment, the nuc-component is a substrate for RNA polymerase. Variations of the nucleotides, which allow for such substrate properties, can be used as nuc-components. For example, substrates for nucleotide accepting enzymes, which lack a part of a conventional nucleotide, e.g. acyclic nucleotide analoga, can be used as nuc-components, too.

1.3.3.1.1 Variations of the Phosphate

In one embodiment the nuc-component is a nucleoside. In another embodiment the nuc-component represents a nucleoside-monophosphate. In another embodiment the nuc-component represents a nucleoside-diphosphate. In another embodiment the nuc-component is a nucleoside-triphosphate. Still higher numbers of phosphate groups in a nucleotide (e.g. tetraphosphate, pentaphosphate etc.) can be used.

The said phosphate modifications can be located at the 5'-position of the sugar, like nucleoside-triphosphates, or also at other positions of the sugar part of the nucleotide, e.g. at the 3'-position.

Optionally, the phosphate part of the nucleotide can comprise modifications, in one embodiment such modifications comprising a linker, for example (D. Jameson et al. Methods in Enzymology 1997, v. 278, p. 363-, A. Draganescu et al. J. Biol. Chem. 2000 v. 275, p. 4555-). In another embodiment of the invention, the phosphate part of the nuc-component comprises thiotriphosphate derivates (Burges et al. PNAS 1978 v. 75, p. 4798-).

In another embodiment of the invention, the phosphate part of the nuc-component comprises protected phosphate groups (e.g. phosphoroamidites).

In one embodiment, the phosphate part represents a linkage between the nuc-component and the linker component of the nuc-macromolecule.

1.3.3.1.2 Variations of the Base

The nuc-component can be natural nucleotide or nucleoside occurring in the nucleic acids in nature or their analogs, preferentially participating at the Watson-Crick base-pairing, e.g. adenine, guanine, thymine, cytosine, uracil, inosine or modified bases like 7-deazaadenine, 7-deazaguanine, 6-thioadenine (as referred above). Optionally, the base comprises modifications. In one embodiment, such modifications comprise for example a linker, e.g. amino-propargyl-linker or amino-allyl-linker. Further examples of linkers are known (Ward et al. U.S. Pat. No. 4,711,955, G. Wright et al. Pharmac. Ther. 1990, v. 47, p. 447-, Hobbs et al. U.S. Pat. No. 5,047,519 or other linkers e.g. Kievan U.S. Pat. No. 4,828,979, Seela U.S. Pat. No. 6,211,158, U.S. Pat. No. 4,804,748, EP 0286028, Hanna M. Method in Enzymology 1996 v. 274, p. 403, Zhu et al. NAR 1994 v. 22 p. 3418, Jameson et al. Method in Enzymology, 1997, v. 278, p. 363-, Held et al. Nucleic acid research, 2002, v. 30 p. 3857-, Held et al. Nucleosides, nucleotides & nucleic acids, 2003, v. 22, p. 391, Short U.S. Pat. No. 6,579,704, Odedra WO 0192284). In one embodiment, a linker coupled to the base represents a connection part between the nuc-component and the linker component of the nuc-macromolecule. Further modifications of the base are described for example in the catalogue of Trilink Biotechnologies, Inc. San Diego, USA, and are presented in "Nucleoside triphosphates and their analogs", Morteza Vaghefi, 2005 ISBN 1-57444-498-0.

1.3.3.1.3 Variations of the Sugar

Different variations of the sugar part of the nucleotides, which are used e.g. in the diagnostics, therapy or research, are known to the person skilled in the art. Such variations comprise ribose, 2'-deoxyribose or 2',3'-dideoxyribose. Optionally, the sugar part comprises modifications (M. Metzker et al. Nucleic Acid Research 1994, v. 22, p. 4259-, Tsien WO 91/06678). In one embodiment, such modifications comprise for example a linker. The modifying group can be optionally be reversibly coupled to the sugar part (Hovinen et al. J. Chem. Soc. Prking Trans. 1994, s. 211-, Canard U.S. Pat. No. 5,798,210, Kwiatkowski U.S. Pat. No. 6,255,475, Kwiatkowski WO 01/25247, Ju et al. U.S. Pat. No. 6,664,079, Fahnestock et al. WO 91066678, Cheeseman U.S. Pat. No. 5,302,509, Parce et al. WO 0050642, Milton et al. WO 2004018493, Milton et al. 2004018497).

In one embodiment, the linker coupled to the sugar part represents the connection between the nuc-component and the linker component of the nuc-macromolecules.

In another embodiment, the sugar part comprises for example the following modifications: optionally the 3'-OH-Group or the 2'-OH-Group can be substituted by the following atoms or groups: halogen atoms, hydrogen atoms, amino- or mercapto- or azido groups (Beabealashvilli et al. Biochem Biophys Acta 1986, v. 868, p. 136-, Yuzhanov et al. FEBS Lett. 1992 v. 306, p. 185-).

In another embodiment, the nuc-component comprises acyclic nucleotide or nucleoside modifications (A. Holy Current Pharmaceutical Design 2003 v. 9, p. 2567-, G. Wright et al. Pharmac. Ther. 1990, v. 47, p. 447-). In another embodiment, the sugar part comprises a double bond.

In this application, the following abbreviations will be used for 2'-deoxynucleotides: dUTP for 2'-deoxyuridine-triphosphate, dCTP for 2'-deoxycytidine-triphosphate, dATP for 2'-deoxyadenosine-triphosphate, dGTP for 2'-deoxyguanosine-triphosphate.

Ability of nuc-component or its lack to be further extended by a polymerase is an important property of nucleotide conjugates. In one preferable embodiment of invention, nucleotide analoga are used as terminators of the enzymatic synthesis. An example for such analoga are ddNTP-Analoga, e.g. 2',3'-dideoxy-UTP. A person skilled in the art should know other examples for terminators.

1.3.3.1.4 Linking of the Nuc-Component and Linker

The nuc-component is linked to the linker at a coupling position. This coupling position of the linker on the nuc-component is preferably located on the base. The linker can be attached also on the sugar (e.g. ribose or deoxyribose) or on the phosphate part. The linkage between the linker component and the nuc-component is preferentially covalent.

If the coupling position is on the base, then the following positions are preferable: position 4 or 5 for pyrimidine bases and positions 6, 7, 8 for purine bases. (Ward et al. U.S. Pat. No. 4,711,955, G. Wright et al. Pharmac. Ther. 1990, V. 47, S. 447-, Hobbs et al. U.S. Pat. No. 5,047,519 or other linker e.g. Klevan U.S. Pat. No. 4,828,979, Seela U.S. Pat. No. 6,211,158, U.S. Pat. No. 4,804,748, EP 0286028, Hanna M. Method in Enzymology 1996 v. 274, S. 403, Zhu et al. NAR 1994 v. 22 S. 3418, Jameson et al. Method in Enzymology, 1997, v. 278, S. 363-, Held et al. Nucleic acid research, 2002, v. 30 3857-, Held et al. Nucleosides, nucleotides & nucleic acids, 2003, v. 22, S. 391, Short U.S. Pat. No. 6,579,704, Odedra WO 0192284). Further examples for modifications on the base are represented in "Nucleoside triphosphates and their analogs", Morteza Vaghefi, 2005 ISBN 1-57444-498-0; On sugar, positions 2', 3', 4' or 5' can serve as coupling positions. The coupling to the phosphate groups can proceed for example via alpha, beta, or gamma phosphate groups. Examples for coupling positions on the base are described in Short WO 9949082, Balasubramanian WO 03048387, Tcherkassov WO 02088382 (also see commercially available nucleotides e.g. from Amersham, Roche, Trilink Technologies, Jena Bioscience), on the ribose in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Parce WO 0050642, on phosphate groups in Jameson et al. Method in Enzymology, 1997, v. 278, p. 363.

The location of the coupling position depends on the area of application of the nuc-macromolecules. For example, coupling positions on the sugar or on the base are preferable in cases where the marker is intended to stay coupled to the nucleic acid strand. The coupling to the gamma or beta phosphate groups can be used for example in cases where the marker has to be separated during the incorporation of the nuc-macromolecule.

The linking between the nuc-component and the linker component results for example via a coupling unit (L) that is a part of the linker component.

In one embodiment, the linkage between the nuc-component and the linker is stable, e.g. resistant to temperatures up to 130° C., pH-ranges from 1 to 14 and/or resistant to hydrolytical enzymes (e.g. proteases or esterases). In another embodiment of the invention, this linkage between the nuc-component and the linker component is cleavable under mild conditions.

This cleavable linkage allows removal of the linker components and the marker components. This can be advantageous for example for methods of sequencing by synthesis, like pyrosequencing, BASS (base addition sequencing schema) (Canard et al. U.S. Pat. No. 5,798,210, Rasolonjatovo Nucleosides & Nucleotides 1999, v. 18, p. 1021, Metzker et al. NAR 1994, v. 22, p. 4259, Welch et al. Nucleosides & Nucleotides 1999, v. 18, p. 19, Milton et al. WO 2004018493, Odedra at al. WO 0192284) or single molecule sequencing Tcherkassov WO 02088382. The choice of the cleavable linkage is not restricted insofar as it remains stable under conditions of enzymatic reaction, does not result in irreversible damage of the enzyme (e.g. polymerase) and is cleavable under mild conditions. "Mild conditions" is understood to mean conditions that do not result in damage of nucleic acid-primer complexes wherein, for example, the pH-range is preferentially between 3 and 11 and the temperature is between 0° C. and the temperature value (x). This temperature value (x) is dependent upon the Tm of the nucleic acid-primer complex (where Tm is the melting temperature) and is calculated for example as Tm (nucleic acid primer complex) minus 5° C. (e.g. Tm is 47° C., then the (x)-value is 42° C.; ester, thioester, acetales, phosphoester, disulfide linkages and photolabile compounds are suitable as cleavable linkages under these conditions).

Preferentially, the said cleavable linkage comprises chemical or enzymatic cleavable linkages or photolabile compounds. Ester, thioester, tartrate, disulfide and acetal linkages are preferred as examples of chemical cleavable groups (Short WO 9949082, "Chemistry of protein conjugation and crosslinking" Shan S. Wong 1993 CRC Press Inc., Herman et al. Method in Enzymology 1990 v. 184 p. 584, Lomant et al. J. Mol. Biol. 1976 v. 104 243, "Chemistry of carboxylic acid and esters" S. Patai 1969 Interscience Publ., Pierce Catalog). Examples for photolabile compounds are described in Rothschild WO 9531429, "Protective groups in organic synthesis" 1991 John Wiley & Sons, Inc., V. Pillai Synthesis 1980 p. 1, V. Pillai Org. Photochem. 1987 v. 9 p. 225, Dissertation "Neue photolabile Schutzgruppen für die lichtgesteuerte Oligonucleotidsynthese" H. Giegrich, 1996, Konstanz, Dissertation "Neue photolabile Schutzgruppen für die lichtgesteuerte Oligonucleotidsynthese" S. M. Bühler, 1999, Konstanz).

1.3.3.1.5 Number of the Linked Nuc-Components

In one embodiment of the invention, only one nuc-component is coupled per nuc-macromolecule. In another embodiment of the invention, several nuc-components are coupled per nuc-macromolecule. If several nuc-components are coupled, they can be identical or different, whereas the average number of the nuc-components per nuc-macromolecule can range for example from 2 to 5, 5 to 10, 10 to 25, 25 to 50, 50 to 100.

1.3.3.2 Linker Component

The function of the linker is to link a nuc-component and a marker component in such a way that substrate properties of the nuc-component are retained for nucleotide accepting enzymes even after the coupling of a macromolecular marker.

The terms "linker" and "linker component" will be used synonymously in this application and comprise the whole structural part of the nuc-macromolecule between the nuc-component and the marker component. The exact composition of the linker is not limited and can vary. In one embodiment, the linker is preferentially hydrophilic.

1.3.3.2.1 Linker Length

An average linker length ranges between 2 to 5, 5 to 10, 10 to 20, 20 to 30, 30 to 40, 40 to 50, 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 atoms (chain atoms), so that an average linker length amounts to between 2 to 5, 5 to 10, to 20, 20 to 30, 30 to 40, 40 to 50, 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 angstroms (measured on a molecule potentially stretched-out as much as possible).

If a nuc-macromolecule comprises several linker components, these linker components can be of the same or different lengths relative to each other.

Some parts of the linkers can comprise rigid areas and other parts can comprise flexible areas.

1.3.3.2.2 Short Linker

In a preferred embodiment, nuc-macromolecules have a short linker. Its length comprises the ranges between 2 to 5, 5 to 10, 10 to 20, 20 to 30, 30 to 40, 40 to 50 chain atoms. Such linkers can carry functional groups, as for example amino, carboxy, mercapto, hydroxy groups, alkyn-, isothiocyanat-, aldehyd- or azid-group. Such group can be provided in reactive form such as NHS-ester for carboxy group. Further molecules can be coupled to these groups. In one embodiment, cross-linker are bound to the short linker so that resulting nuc-component can be further reacted with other substances such as macromolecular linker component or marker component. Examples of short linkers coupled to the nucleotides are known to the person skilled in the art ("Nucleoside triphosphates and their analogs", Morteza Vaghefi, 2005 ISBN 1-57444-498-0, Ward et al. U.S. Pat. No. 4,711,955, G. Wright et al. Pharmac. Ther. 1990, V. 47, S. 447-, Hobbs et al. U.S. Pat. No. 5,047,519 or other linker e.g. Klevan U.S. Pat. No. 4,828,979, Seela U.S. Pat. No. 6,211,158, U.S. Pat. No. 4,804,748, EP 0286028, Hanna M. Method in Enzymology 1996 v. 274, S. 403, Zhu et al. NAR 1994 v. 22 S. 3418, Jameson et al. Method in Enzymology, 1997, v. 278, S. 363-, Held et al. Nucleic acid research, 2002, v. 30 3857-, Held et al. Nucleosides, nucleotides & nucleic acids, 2003, v. 22, S. 391, Short U.S. Pat. No. 6,579,704, Odedra WO 0192284). The linker can contain one or several units of polymers, as for example amino acids, sugars, PEG units or carboxylic acids. The coupling unit (L) of a long linker can serve as further examples of short linkers (see below). Examples for cross-linker are known to an expert ("Chemistry of protein conjugation and crosslinking" Shan S. Wong 1993). Many cross-linker are commercially available, e.g. from Invitrogen (Lifescience Technologies, Pierce Biotech, Iris-Biotech). Examples of coupling of different substances to macromolecules such as oligonucleotides are also known (Y. Singh et al Chem. Soc. Rev. 2010, 39, 2054-). It should be obvious to an expert that the linker between the nuc-component and the marker component can be assembled in several chemical steps.

Still further examples for short linkers between a nuc-component and a marker are represented by an example of linkage between a nucleoside triphosphate and an oligonucleotide:

NUC—NH—OLN, NUC—O—OLN, NUC—S—OLN, NUC—SS—OLN, NUC—CO—NH—OLN, NUC—NH—CO—OLN, NUC—CO—O—OLN, NUC—O—CO—OLN, NUC—CO—S—OLN, NUC—S—CO—OLN, NUC—P(O)$_2$—OLN, NUC—Si—OLN, NUC—(CH$_2$)$_n$—OLN, NUC—(CH$_2$)$_n$—OLN, NUC-A-(CH$_2$)$_n$—OLN, NUC—(CH$_2$)$_n$—B—OLN, NUC—(CH=CH—)$_n$—OLN, NUC-(A-CH=CH—)$_n$—OLN, NUC—(CH=CH—B—)$_n$—OLN, NUC-A-CH=CH—(CH$_2$—)$_n$—OLN, NUC—(—CH=CH—CH$_2$)$_n$—B—OLN, NUC—(—CH=CH—CH$_2$—CH$_2$)$_n$—B—OLN, NUC—(—O—CH$_2$—CH$_2$)$_n$—B—OLN, NUC-A-(—O—CH$_2$—CH$_2$)$_n$—OLN, NUC-A-(—O—CH$_2$—CH$_2$)$_n$—B—OLN, NUC—(C≡C—)$_n$—OLN, NUC-(A-C≡C—)$_n$—OLN, NUC—(C≡C—B—)$_n$—OLN, NUC-A-C≡C—(CH$_2$—)$_n$—OLN, NUC—(—C≡C—CH$_2$)$_n$—B—OLN, NUC—(—C≡C—CH$_2$—CH$_2$)$_n$—B—OLN, where NUC is the nuc-component; OLN is an oligonucleotide; A and B comprises the following structural elements: —NH—, —O—, —S—, —SS—, —CO—NH—, —NH—CO—, —CO—O—, —O—CO—, —CO—S—, —S—CO—, —P(O)$_2$—, —Si—, —(CH$_2$)$_n$—, a photolabile group; (n) is a number from 1 to 5

This examples are presented only for illustration purpose without intention to limit the structure of the linker.

1.3.3.2.3 Langer Linker

In another preferred embodiment of the invention, a long linker having a length of more than 50 chain atoms is used. The linker component has in its structure, for example, the following components:
1) coupling unit (L)
2) hydrophilic or water soluble polymer
3) coupling unit (T)

The subdivision of the linker in separate parts is purely functional and should serve merely for better understanding of the structure. Depending on the approach, particular structures can be considered as one functional part or as another.

The coupling unit (L) has the function of linking the linker component and the nuc-component. Short, non-branched compounds from 1 to 20 atoms in length are preferred. The particular structure of the coupling unit (L) depends on the coupling position of the linker to the nucleotide and on the particular polymer of the linker.

Several examples of coupling units (L) are shown in examples 1 to 33 of this application. Many conventionally modified nucleotides comprise a short linker; these short linkers are further examples of coupling units (L), e.g. short linker on the base: Short WO 9949082, Balasubramanian WO 03048387, Tcherkassov WO 02088382 (see also commercially available nucleotides from e.g. Amersham or Roche), short linker on the ribose as described in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Ju et al. U.S. Pat. No. 6,664,079, Parce WO 0050642, and short linker on phosphate groups as described in Jameson et al. Method in Enzymology, 1997, v. 278, p. 363.

Still further examples for the coupling unit (L) are presented in the following:

R$_6$—NH—R$_7$, R$_6$—O—R$_7$, R$_6$—S—R$_7$, R$_6$—SS—R$_7$, R$_6$—CO—NH—R$_7$, R$_6$—NH—CO—R$_7$, R$_6$—CO—O—R$_7$, R$_6$—O—CO—R$_7$, R$_6$—CO—S—R$_7$, R$_6$—S—CO—R$_7$, R$_6$—P(O)$_2$—R$_7$, R$_6$—Si—R$_7$, R$_6$—(CH$_2$)$_n$—R$_7$, R$_6$—(CH$_2$)$_n$—R$_7$, R$_6$-A-(CH$_2$)$_n$—R$_7$, R$_6$—(CH$_2$)$_n$—B—R$_7$, R$_6$—(CH=CH—)$_n$—R$_7$, R$_6$-(A-CH=CH—)$_n$—R$_7$, R$_6$—(CH=CH—B—)$_n$—R$_7$, R$_6$-A-CH=CH—(CH$_2$—)$_n$—R$_7$, R$_6$—(—CH=CH—CH$_2$)$_n$—B—R$_7$, R$_6$—(—CH=CH—CH$_2$—CH$_2$)$_n$—B—R$_7$, R$_6$—(C≡C—)$_n$—R$_7$, R$_6$-(A-C≡C—)$_n$—R$_7$, R$_6$—(C≡C—B—)$_n$—R$_7$, R$_6$-A-C≡C—(CH$_2$—)$_n$—R$_7$, R$_6$—(—C≡C—CH$_2$)$_n$—B—R$_7$, R$_6$—(—C≡C—CH$_2$—CH$_2$)$_n$—B—R$_7$, where R$_6$ is the nuc-component; R$_7$ is a polymer; A and B comprises the following structural elements: —NH—, —O—, —S—, —SS—, —CO—NH—, —NH—CO—, —CO—O—, —O—CO—, —CO—S—, —S—CO—, —P(O)$_2$—, —Si—, —(CH$_2$)$_n$—, a photolabile group; (n) is a number from 1 to 5

The coupling unit L is covalently linked to the nuc-component on the one side. On its other side further parts of the linker, for example, a hydrophilic polymer or directly the coupling unit (T) or directly the marker can be bound.

In the following, the coupling of the polymer, as a part of the linker is explained as example. The character of the linkage with the polymer depends on the kind of polymer. In a preferred embodiment, the ends of the polymer comprises reactive groups, for example NH2 (amino), OH (hydroxy), SH (mercapto), COOH (carboxy), CHO (aldehyde), acrylic, maleimide, or halogen groups, or alkyn-, Isothiocyanat- or Azid-Group. Such groups can be provided as a reactive form, e.g. NHS-ester for carboxy-group. Such polymers are commercially available (e.g. Fluka, Iris-Biotech, Nanocs inc, Pierce Biotech). Some examples for the coupling of polymers to the coupling unit are shown in the examples.

In a preferred embodiment, the water-soluble polymer represents the major part of the linker component. It is a polymer, preferentially hydrophilic, consisting of the same or different monomers.

Examples of suitable polymers are polyethylene-glycol (PEG), polyamides (e.g. polypeptides), polysaccharides and their derivates, dextran and its derivates, polyphosphates, polyacetates, poly(alkyleneglycols), copolymers with ethylenglycol and propyleneglycol, poly(olefinic alcohols), poly (vinylpyrrolidones), poly(hydroxyalkylmethacrylamides), poly(hydroxyalkylmethacrylates), poly(x-hydroxy acids), polyacrylic acid and their derivates, poly-acrylamide and its derivates, poly(vinylalcohol), polylactic acid, polyglycolic acid, poly(epsilon-caprolactones), poly(beta-hydroxybutyrates), poly(beta-hydroxyvalerate), polydioxanones, poly (ethylene terephthalates), poly(malic acid), poly(tartronic acid), poly(ortho esters), polyanhydrides, polycyanoacrylates, poly(phosphoesters), polyphosphazenes, hyaluronidate, and polysulfones.

In one embodiment, the polymer-part comprises branched polymers. In an other embodiment, the polymer-part comprises non-branched or linear polymers. The polymer can consist of several parts of different length, each part consisting of the same monomers with the monomers in different parts being different. To a person skilled in the art, it should seem obvious that for a macromolecular linker, it is often possible to determine only an average mass, so that the data regarding the mole masses represent an average ("Makromoleküle, Chemische Struktur and Synthesen", Volume 1, 4, H. Elias, 1999, ISBN 3-527-29872-X). For this reason, often there is no exact mass information for nuc-macromolecules.

In one preferred embodiment, the linker component comprises a linear, non-branched polymer that is not modified with further sterically demanding chemical structures such as dyes, fluorescent dyes, or ligands. Such linker components lead to a low sterical hindrance, e.g. in an enzymatic recognition of the nuc-components.

In another preferred embodiment, the polymer of the linker component is linear but the linker component is modified with one or several sterically demanding chemical groups, for example dyes. The presence of the sterically demanding group allows for a control of the enzymatic reaction in some analytic processes (Tcherkassov WO 02088382).

Further examples of sterically demanding groups are shown in the chapter 1.3.19.

Sterically demanding ligands or structures can be coupled to different linker parts. The average number of the sterically demanding ligands coupled to the linker can vary and amounts, for instance, between 1 and 3, 3 and 5, 5 and 20, 20 and 50. In the coupling of sterically demanding groups, it is necessary to take into consideration that a space-demanding structure coupled in the direct proximity of nucleotide-component can lead to the loss of the substrate properties. Sterically demanding ligands can be coupled uniformly or randomly over the entire length of the linker, or they can be coupled to the linker at a certain distance from the nuc-component. The distance between the nuc-component and the steric hindrance amounts, for instance, to 10 to 15, to 15 to 20, 20 to 25, 25 to 30, 30 to 35, 35 to 40, 40 to 45, 45 to 50, 50 to 55, 55 to 60, 60 to 70, 70 to 80, 80 to 90, 90 to 100, 100 to 200, 200 to 1000, 1000 to 5000 chain atoms. The sterically demanding group can be considered as a part of the linker or as a part of the marker. Which way to consider it can depend, for instance, on whether or not the sterically demanding group possesses certain signal properties.

1.3.3.2.3 Linker Coupling in a Nuc-Macromolecule

The linker is connected to the nuc-component on one side and to the marker component on the other side. The linker can have coupling units at his ends which fulfill this connecting function. The connection to the nuc-component was discussed above. The connection between the linker and the marker components is provided by coupling unit T. Short, non-branched connections no more than 20 atoms in the length are preferred. The respective structure of the coupling unit T depends upon the coupling position on the marker component and upon the respective polymer of the linker.

The coupling unit T is covalently connected to the polymer. The kind of the coupling depends on the kind of the polymer. In a preferred embodiment, the polymer has reactive groups at its ends such as NH2 (amino), OH (hydroxy), SH (mercapto), COOH (carboxy), CHO (aldehyde), acrylic, maleimide, or halogen groups, or alkyn-, Isothiocyanat- or Azid-Groups. Such groups can be provided as a reactive form, e.g. NHS-ester for carboxy-group. Such polymers are commercially available (e.g. Fluka, Iris-Biotech, Nanocs inc, Pierce Biotech). Some examples of the coupling units L are shown in Cherkasov et al WO 2005044836, Cherkasov et al WO2006097320, Cherkasov et al WO 2008043426, Cherkasov et al DE 10356837, Cherkasov et al DE 102004009704. For further examples of the chemical and affine connections please refer to the literature: "Nucleoside triphosphates and their analogs", Morteza Vaghefi, 2005 ISBN 1-57444-498-0; "Chemistry of protein conjugation and crosslinking" Shan S. Wong in 1993, "Bioconjugation: protein coupling techniques for the biomedical sciences", M. Aslam, in 1996.

The linker can also comprise other functional groups or parts, for example one or several groups that are cleavable under mild conditions, see also Cherkasov et al WO 2005044836, Cherkasov et al WO2006097320, Cherkasov et al WO 2008043426, Cherkasov et al DE 10356837, Cherkasov et al DE 102004009704.

A cleavable group within the linker allows the removal of a part of the linker and the marker component. After a cleavage reaction, a linker residue remains coupled to the nuc-component. Examples of cleavable groups are shown in Section 1.3.3.1.4.

1.3.3.3 Marker Component

The structure of the marker component is particularly adapted to its functions.

In the present application, the marker component particularly has one or more of the following functions: a) recognition of one or more target sequences, b) binding to a solid phase, c) generation or transmitting of a specific signal, d) binding to a structure on a cell surface, e) penetration into a cell, f) control of an intracellular transport, g) anchoring of a nuc-macromolecule within a transport visicle (e.g. liposome). These functions are performed by different parts of the marker component.

In this application, the term "domain" is used. This term is used to describe a part or group of parts of the nuc-macromolecule with a common function. Individual parts of the domain can be referred to as marker units. In this case, a domain consists of one or more marker units with the same function. The term "domain" should provide a person skilled in this area with a better overview of the possible combinations of individual structures and their functions. This term is not intended to be restricted to certain structures.

The term "marker unit" is used to describe structures fulfilling a certain function, and is an appropriate term to designate certain structures that will be well known to a person skilled in this area, e.g. biotin; dyes, including fluorescent dyes; oligonucleotides; quantum dots; nanoparticles; and reactive groups.

For example, a dye or a microparticle or an amino group will be a known element to the expert. As in the field of polymer chemistry, individual marker units represent building blocks of a macromolecular structure. For the purpose of creating a clear and simple description, marker units with similar functions can be combined into domains. In the simplest case, a domain consists of only one marker unit, such as an anchor domain consisting of a biotin. However, several biotin molecules can be combined to form an anchor domain.

According to the invention, a marker component of the nuc-macromolecules can comprise the following domains: one or more target domains, one or more anchor domains, and one or more signal domains. In a further embodiment, nuc-macromolecules include suitable antagonists for respective domains. In one embodiment, nuc-macromolecules with sequence-specific terminating properties comprise at least one target domain.

Target Domain:

the recognition of a target sequence or a plurality of target sequences is provided by a part of the marker component called a "target domain". Examples of target domains are nucleic acid chains (e.g. DNA-oligonucleotides or RNA-oligonucleotides) or their analogs (e.g. PNA-oligonucleotides or LNA-oligonucleotides) which can bind to the target sequence. Different target sequences can be recognized by different specific target domains or by a target domain with a broad sequence recognition pattern.

Anchor Domain:

binding to a solid phase is enabled by a further part of the marker component, a so-called "anchor domain". This anchor domain is capable of binding to a solid phase via an affine or covalent binding. Other examples of anchor domains are nucleic acid chains, such as oligonucleotides, which can bind to the complementary partner immobilized on a solid phase (complementary binding of nucleic acid chains or aptamer-protein binding). Further examples of anchor domain include biotin or haptens (e.g. dyes, digoxigenin, and DNP) or proteins with the ability to bind other molecules (such as streptavidin (SA), antibodies, and lectins). Many examples of affine binding are known to an expert. Generally, one partner of a binding pair is a constituent of a marker component (anchor domain), while another partner is an element of the solid phase (binding partner).

The signal domain of a marker component mediates for example the specific recognition or detection of nuc-macromolecules. Otherwise, a signal domain can have still further functions, like for example binding to a structure on a cell surface, enabling of a penetration into a cell, control of transport within a cell. Several examples are given below, and are known to a person skilled in the area.

Antagonists of Individual Marker Domains

In one embodiment, the marker component comprises structures which inactivate the function of a particular domain reversibly. Such structures are designated as an antagonist to the respective domain. The effect of the antagonist is reversible, so that the properties of the domains can be restored.

Target Domain Antagonist

In one embodiment, a nuc-macromolecule comprises at least one target domain antagonist (e.g. filter-2-oligonucleotide). This can be an oligonucleotide with a sequence composition that is partially or completely complementary to the sequence of the oligonucleotide of the target domain for example. The length of the antagonist oligonucleotide may vary. Preferably, it is between 5 and 7, 7 and 10, 10 and 15, 15 and 20, 20 and 25, 25 and 30, or 30 and 40 nucleotides in length. The antagonist oligonucleotide is preferably coupled to the target domain of the nuc-macromolecule. In one embodiment, this coupling is of a covalent nature. This covalent coupling can be achieved via the 3'-end or the 5'-end of the oligonucleotide of the target domain (FIG. 32). In a further embodiment, such a coupling is based on affinity and is achieved by hybridization of the antagonist oligonucleotide to the oligonucleotide of the target domain (FIG. 33). A greater discrimination of target sequences can be achieved though the introduction of such an antagonist.

Antagonist of the Anchor Domain:

The purpose of the anchor domain is to convey binding to the solid phase. In some embodiments, the anchor domain comprises oligonucleotides which bind via hybridization to a complementary immobilized binding partner. An antagonist of such an anchor domain, for example, represents a complementary oligonucleotide in the nuc-macromolecule, which can reversibly bind the anchor domain and thereby prevents interaction with the binding partner on the solid phase (FIG. 3i). The effect of the antagonist is reversed, for example, due to binding of a nuc-macromolecule to the target sequence and the incorporation of the nuc-component (FIG. 7). Thus, the anchor domain with regained/restored binding capability can bind to the solid phase. In a further embodiment of the invention, an antagonist of the anchor domain of a nuc-macromolecule can be cleaved off by chemical or enzymatic reaction.

Antagonist of the Signal Domain:

Quencher molecules represent examples of antagonists for signal domains with fluorescence properties. These antagonists can be brought into the proximity of the marker units having fluorescent properties via a cleavable chemical bond or via a hairpin-like structure of the nucleic acid chains ("molecular beacons", FRET pairs). By these means the signal is reduced or completely suppressed. After cleaving off of the quencher or through destruction of the hairpin structure of the nucleic acids, the distance between a quencher and the fluorescent dye increases. This leads to increase of the signal.

In the description of the invention, the antagonists will be discussed together with the respective domains that they reversibly block.

The individual domains and their antagonists are integrated into a marker component. The integration can be accomplished by coupling individual domains to each other or they can be connected using linkers or individual domains are linked to another structure, such as a core component of the marker.

Individual domains can comprise one or more marker units. In one embodiment a domain comprises only one marker unit. For example, a target domain comprises only one oligonucleotide that can bind to a target sequence. An example of an anchor domain having only one structural unit is biotin or an oligonucleotide. An example of a signal domain having only one structural unit is one fluorescent dye or one quantum dot.

In a further embodiment, a domain comprises several marker units. For example, several identical or different oligonucleotide sequences can be coupled in a nuc-macromolecule and bind to the same position in the target sequence. In this case, the individual oligonucleotides represent marker units and their entirety represents a target domain. Similarly, several oligonucleotides or several biotin molecules can be combined to an anchor domain.

A nuc-macromolecule can also comprise several target domains or multiple anchor domains or multiple signal domains. This is the case if the domains of a group differ in their function. For example, different target domains of a nuc-macromolecule bind to different sites of a target sequence or to different target sequences. The function of binding to the solid phase can also be achieved by only one or a plurality of different anchor domains.

A nuc-macromolecule can comprise a marker component which has only a single function or a combination of two or more functions. The composition of individual nuc-macromolecule types depends on these particular functions.

The manner of presentation of the composition of the marker is in accordance with the patent application Cherkasov et al WO2011050938.

Each domain can be connected with another directly or with the aid of the core component.

Below, some examples of structures and functions of individual domains of the marker component will be discussed in more detail.

1.3.3.3.1 Target Domain

In one embodiment, the target domain comprises an oligonucleotide. This oligonucleotide can comprise DNA, PTO, RNA, PNA, LNA, or other modifications of nucleic acid chains that are capable of base paring. In a further embodiment, a target domain comprises mixed oligonucleotides, for example DNA and PTO.

In another embodiment, a target domain comprises a peptide or protein with sequence recognition properties, such as a transcription factor.

In one embodiment, the purpose of the target domain is to bind the entire nuc-macromolecule to a target sequence in a predominantly sequence-specific manner, in another embodiment the binding to a target sequence is fully specific. Nuc-macromolecules can bind the target sequence by means of a sequence-specific target-domain before or during the enzymatic reaction.

The target domain preferably binds to a single strand of the target sequence. The target sequence can be present in single-stranded form in its entire length, or it can be partially double-stranded.

In a further embodiment of the invention, the target domain binds sequence-specifically to a double strand of the target sequence. This can involve strand invasion by the target domain (as known, for example, for PNA) or the target domain binds to the double-strand without concomitant strand separation, for example with the help of sequence-recognizing proteins. Depending on the structure of the target sequence (double-stranded or single-stranded), various structures can be used as the target domain (e.g. oligonucleotides, or sequence-specific nucleic acid binding proteins such as transcription factors).

In the following, the binding of the target domain to a single strand of the target sequence is considered by way of an example. In such an embodiment, an oligonucleotide that is complementary to the target sequence can be used as the target domain. Similarly, a skilled person can select other structures as the target domain, if sequence-specific binding to a double strand is required. Examples of such structures are known to a person skilled in the art.

In one embodiment, a target domain is an oligonucleotide and consists of different nucleobases. Nucleobases like adenine, cytosine, guanine, thymine, and uracil (abbreviated as A, C, G, T, U) or analogs thereof linked to a sugar-phosphate backbone in the form of DNA or RNA or analogs thereof, such as PNA and LNA, can bind sequence-specifically to the nucleic acid strands. Various nucleic acid chains, such as DNA, PTO, RNA, protein nucleic acids (PNA), morpholino, and their analogs can represent the nucleic acid portion of the target domain. Generally speaking, substances capable of entering into a preferentially or a strongly sequence-specific binding to a single- or a double-stranded nucleic acid chain are suitable for the target domain. Usually, such substances have nucleobases (A, C, T, G, U) or their derivatives which allow sequence-specific binding. The backbone can have a natural composition (sugar-phosphate backbone) or a variation thereof, such as PNA, PTO, 2'-O-Methyl-modification. Single target domains within a single species of nuc-macromolecules can consist of one type of building blocks, for example DNA only or PNA only, or be a polymer with mixed composition, wherein at certain positions of sequence DNA, PTO, RNA, PNA, morpholino, LNA, or other modifications are introduced into the same chain.

In a case in which multiple target domains are combined within a single type of nuc-macromolecules, individual domains can consist of different types of monomers; for example, one target domain can be composed of DNA, another of PNA, and still another of RNA.

To simplify the description, nucleic acid chains representing a target domain are discussed in detail in the form of DNA. Other types of nucleic acid chains can be constructed and used according to rules known by an expert in accordance with the examples with DNA oligonucleotides.

The length of the segment of the oligonucleotide that is designed to hybridize with the target sequence, i.e. the length of the target domain, must be adjusted to the particular assay conditions. This length falls in the following ranges (measured in the nucleobases): 6 to 8, 8 to 10, 10 to 15, 15 to 20, 20 to 25, 25 to 30, 30 to 40, 40 to 50, 50 to 70, 70 to 100, 100 to 150, more than 150.

Depending on the nature of the target domain (i.e., for example DNA, PTO, RNA, PNA or LNA), the specificity of binding to a particular target sequence may vary. A person skilled in the art knows that PNA-based oligonucleotides have a stronger affinity to complementary segments than DNA-based oligonucleotides of the same length and composition.

DNA-based oligonucleotides, for example, exhibit a relatively higher specificity when they are between about 15 and 25 nucleotides in length. An increase in the length of the target domain, may lead to a decrease in specificity. This means that longer target domain oligonucleotides are more tolerant of single nucleotide variations in the target sequence than shorter target domain oligonucleotides. However, it may also be advantageous that longer target domain oligonucleotides can tolerate greater sequence variations (e.g. insertions or deletions).

In a further embodiment, the linking of the target domain within a nuc-macromolecule is achieved at one of its two ends such as via the 5' end or via the 3' end. Examples of the linking of an oligonucleotide via one of the ends will be known to a person possessing skills in the area. In another embodiment of the invention, the linking of another parts of nuc-macromolecules (e.g. nuc-component) is achieved through the internal position/region of the target domain.

The particular linker between the nuc-component and an oligonucleotide can, for example, be bound to one of the bases of the oligonucleotide, or to a monomer of the backbone (e.g. to a sugar or a phosphate group in a DNA backbone, or to an amino acid in a PNA backbone, or to a sulfur group of a phosphorothioate backbone, PTO). A person skilled in the art knows different ways of attaching moieties to an oligonucleotide at various positions.

The target domain can be coupled via a linker directly to the nuc-component, or it can be coupled to the core component of the nuc-macromolecule. A core component may for example consist of a linear or branched polymer (see below).

The segment of the oligonucleotide which is complementary to the target sequence, i.e. the actual target domain, can be flanked at the 5'-end or 3'-end by other sequence segments that do not bind to the target sequence. These flanking regions may consist of the same monomers as the target domain (for example DNA, PTO, PNA, LNA, RNA) or they may be of a different composition than the target domain. The length of these flanking sequence segments can range from 1 to 5, 5 to 10, 10 to 15, 15, to 20, 20 to 30, from 30 to 100, or can be more than 100 nucleobases. They can serve as spacers or, for example, perform functions of the marker domain or anchor domain (see below).

A linker that links a nuc-component with the oligonucleotide of the target domain can be attached to such a flanking region for example.

The oligonucleotides of the target domain may comprise partially self-complementary regions, such as structures known as hairpins or loops. In a preferred embodiment of the invention, the target domain participates in the formation of a type of structure known as a "molecular beacon" (for details about the properties of molecular beacons see: Bonnet et al PNAS 1999 v 96. 6171-). In this embodiment, the part of the target domain sequence that is actually complementary to the target sequence is surrounded by flanking nucleic acid strands, which are mutually complementary. Such a structure allows the binding specificity of the target domain to the target sequence to be increased. The self-complementary regions of such molecular beacons are generally between 3 to 6, 6 to 8, 8 to 10, 10 to 15 nucleotides in length, and the target domain sequence is about 10 to 15, 15 to 20, 20 to 30, 30 to 40 nucleotides long.

In one embodiment, one arm of the double-stranded portion of the arrangement of the type "molecular beacon" is involved in binding the target sequence (on this topic, see: "Shared stem molecular beacons", see Tsourkas et al NAR 2002, V. 30 4208-). In this case, the oligonucleotide sequence of the target domain is flanked by a segment which is complementary to the sequence of the target domain.

Regions that are self-complementary to the target domain can be considered as "antagonists" to the target domain: they impede low specificity interactions of the target domain, while allowing the target domain oligonucleotide to undergo higher specificity hybridization with the target sequence at higher temperatures.

A person skilled in the art knows other oligonucleotide modifications which can influence binding with complementary segments in the target sequence. Such modifications include, for example, "minor groove binders". Such modifications can be attached to the target domain.

In one embodiment, the 3'-OH end of the oligonucleotide of the target domain (or of the flanking oligonucleotide) is blocked by chemical group. A person skilled in the art knows many examples of modifications of the 3'-OH position of oligonucleotides, including for example the following moieties: 2',3'-dideoxy-ribose, a phosphate group, a biotin moiety, an amino linker, a fluorescent dye, a peptide chain, or a quencher. In place of the 3'-OH group, various modifications may be incorporated into an oligonucleotide, such as an amino group, a halogen atom, an azido group, etc. In this embodiment such an oligonucleotide cannot be extended by a polymerase and consequently has no primer function.

In another embodiment, the 3'-OH end of the oligonucleotide of the target domain is not blocked and can be extended by a polymerase.

In one embodiment of the application, the target domain is completely or partially degradable by the 5' to 3' exonuclease activity of a polymerase. The structure of the nuc-macromolecules can be designed in such a way that the incorporated nuc-component with the remainder of the nuc-macromolecule remains in the extended complementary strand. This can be achieved, for example, through a coupling of the nuc-component via a linker at the 3'-end of the target domain or in its vicinity.

In a further embodiment of the application, the target domain is resistant to a exonuclease activity of a polymerase or a nuclease. This can be achieved, for example, through the use of PTO, PNA, 2'-O-Me or LNA-monomers or other modifications.

In one embodiment, the target domain includes at least one such modification at either end (e.g. at the 5'- or at the 3'-end).

In one embodiment, the target domain includes at least one such modification in an internal region of the sequence of the target domain, In one embodiment, the target domain includes such modification at either end and in internal regions of the sequence of the target domain, and modifications can alternate with natural nucleotide monomers, resulting for example in PTO-DNA mixed polymer.

In one embodiment, the target domain comprises such modification over its entire length.

In one embodiment, the target domain comprises more than one type of modification over its entire length, resulting in a mixed polymer, e.g. of PNA and PTO.

The binding of the target domain to the target sequence can be carried out with the formation of double strands (according to the rules of Watson-Crick base pairing); in another embodiment, triple strands are formed (according to Hoogsteen rules).

Examples of sequence-specific binding of nucleic acid chains will be known to a person possessing skills in the area. The length and the composition of the target domain are adjusted to such a degree that the target domain can bind to the target sequence under the respective reaction conditions. Binding of primers to target sequences or binding of probes to target sequences are well known examples of hybridization between oligonucleotides and target sequences.

Hereinafter, binding to a single strand is considered as an example. The composition of a target domain can be designed to be completely complementary to the target sequence ("perfect match") or differ in some positions ("mismatch").

For a given target sequence, there are several methods that will be known to a person skilled in the composing of an appropriate sequence for the target domain. Because the target domain has to bind within the target sequence, rules may be applied, for example, which are used for the construction of a real-time PCR probe (see literature section amplification). On the other hand, rules for the design of microarray-oligonucleotides that will also be known to an expert can be applied. For example, for a known target sequence an appropriate complementary sequence with a length of about 10 to 50 nucleobases or about 15 to 30 nucleobases can be selected to bind to a single-stranded stretch of the respective target sequence.

Preferentially, a target domain of nuc-macromolecules comprises nucleic acid chains with lengths in the following ranges: from 3 to 6, 6 to 9, 9 to 12, 12 to 14, 14 to 16, 16 to 18, 18 to 20, 20 to 25, 25 to 30, 30 to 40, 40 to 50, 50 to 60, 60 to 70, 70 to 100, 100 to 200, and 200 to 500 nucleobases. If a plurality of target domains is integrated within a nuc-macromolecule, these may have different lengths. Individual target domains can be integrated within one continuous nucleic acid chain or represent stand-alone marker units within a nuc-macromolecule.

In one embodiment of the application, the sequences of a target domain are complementary only to a target sequence and can only bind the target sequence.

In a further embodiment of the application, the sequence of a target domain is able to bind a plurality of different target sequences. This can be achieved for example by the use of target domain with sufficient long length.

In a further embodiment of the application, a nuc-macromolecule comprises several target domain oligonucleotides consisting of different sequences, wherein said target domains are able to bind to different target sequences.

In a preferred embodiment of the application, sequences of the target domain are selected not to bind to anchor domain sequences under applied reaction conditions and not to bind the respective partner sequences provided with the solid phase.

In a further embodiment of the application, the sequence of the target domain of one type of nucleic macromolecules is selected in such a way that it is not able to bind to further target domains or anchor domains or other constituents of the same type of nuc-macromolecules under conditions used in the reaction.

In a further embodiment of the application, the sequence of the target domain of one type of nucleic macromolecules is selected in such a way that it is not able to bind to further target domains or anchor domains or other constituents of the other nuc-macromolecules used in the same reaction.

In a further embodiment of the application, the length and sequence composition of the target domain of one type of nuc-macromolecules are designed so that it can discern changes in the target sequence under stringent reaction conditions (such as reaction temperature). These changes could be, for example, nucleotide exchange (e.g. adenosine instead of guanosine or instead of cytosine), nucleotide deletions, or nucleotide additions. For example, the target domain can, under given reaction conditions, discern changes in the target sequence in the following ranges: 1 to 2 nucleotides or 2 to 5 nucleotides or 5 to 10 nucleotides or 10 to 20 nucleotides or 20 to 50 nucleotides. The changed nucleobases may be localized at a single location in the target sequence or may be distributed over several locations in the target sequence.

In a further embodiment of the application, the length and sequence of the target domain of one type of nuc-macromolecules is designed so that it can tolerate changes in the target sequence under less stringent reaction conditions (such as reaction temperature). These changes could be, for example, nucleotide exchange (e.g. adenosine instead of guanosine or instead of cytosine), nucleotide deletions, or nucleotide additions. For example, the target domain can, under given reaction conditions, tolerate changes in the target sequence in the following ranges: 1 to 2 nucleotides or 2 to 5 nucleotides or 5 to 10 nucleotides or 10 to 20 nucleotides or 20 to 50 nucleotides. These changes may be localized at a single position in the target sequence or may be distributed over several positions in the target sequence. In this embodiment, therefore, not only target sequences are labeled, but also other nucleic acid chains which are similar to a target sequence.

A target domain may be composed of a plurality of individual oligonucleotides which are integrated into one nuc-macromolecule. A nuc-macromolecule may also comprise several target domains; for example, oligonucleotides having different sequences can be arranged within a nuc-macromolecule. Several target domains may be integrated within a single oligonucleotide chain. They can be linked in "end-to-end" manner or sequences of each target domain may even overlap each other or additional sequences may be located between individual domains to separate them.

The individual target domains can be within one type of nuc-macromolecules of the same kind or different kinds of nucleic acid structure. For example, DNA-based target domains can be combined with PNA-based target domains within one type of nuc-macromolecules. The synthesis of mixed nucleic acid chains consisting of, for example, DNA and PNA is known.

A target domain may comprise additional modifications, such as signal-emitting or signal-conveying molecules, such as dyes, including fluorescent dyes, or biotin or macromolecular substances such as enzymes or nanocrystals. Modified oligonucleotides can be purchased commercially, for example from MWG Biotech.

A target domain can perform the function of a core component providing a linkage between individual parts of the marker of a nuc-macromolecule. The linker component may be coupled directly to the target domain.

In the following, an expert can find literature resources for the chemical synthesis of oligonucleotides and their modifications which can form target domains:

Singh et al Chem Soc Rev, 2010, v. 39, 2054-, "Oligonucleotide synthesis, methods and applications" Piet Herdewijn, 2004, ISBN 1-58829-233-9, "Protocols for oligonucleotide conjugates, synthesis and analytical techniques" Sudhir Agrawal, 1993, ISBN 0-89603-252-3, "Protocols for oligonucleotide conjugates, synthesis and properties" Sudhir Agrawal, 1993, ISBN 0-89603-247-7, "The aptamer handbook" Sven Klussmann, 2006, ISBN 10: 3-527-31059-2, "Pharmaceutical aspects of oligonucleotides" Patrick Couvreur, 2000, ISBN 0-748-40841-X, "Triple Helix forming Oligonucleotides" Claude Malvy, 1999, ISBN 0-7923-8418-0, "Artificial DNA, methods and applications" Yury E. Khudyakov, ISBN 0-8493-1426-7

In a further advantageous embodiment of the application, the target domain and other domains (e.g. anchor domain and/or signal domain) are positioned inside of a single nucleic acid chain. The target domain is positioned, for example, at the 5'-end part and the anchor domain or signal domain are at or near the 3'-end part of the nucleic acid chain. Such an arrangement of domains allows for a simultaneous synthesis of two domains during the synthesis of the oligonucleotide portion of the nuc-macromolecule. In other embodiments, one or more target domains may be surrounded by a plurality of anchor domains or signal domains within a single nucleic acid chain. One or more signal domains can also be surrounded by target domains.

In an advantageous embodiment of the invention, the sequences constituting the target domain and the anchor domain or the signal domain are overlapping. In this embodiment, some of the nucleobases belongs to at least two domains. The length of the sequence that encodes the common fragment of the target and anchor domains or target and signal domains can, for example, comprise 5% to 80% of the sequence of one of the domains.

In a further advantageous embodiment of the invention, sequences of the target domain and the anchor domain or the signal domain are separated by one or more spacer sequences. In one embodiment of the invention, such a spacer sequence has signal-conveying properties. In a further embodiment of the invention, a spacer sequence comprises a sequence complementary to a target domain or to an anchor domain or signal domain. These parts within the spacer sequence can be completely or only partially complementary to one of the domains. In such embodiments, such a spacer sequence has the function of an antagonist.

In another embodiment, the target domain of a nuc-macromolecule binds to a hybridization probe (Z) prior to or during the reaction instead of binding to a target sequence (FIG. 5B). Such a probe preferentially comprises an oligonucleotide. This oligonucleotide can bind both the target domain of the nuc-macromolecule (via sequence part Z-1) and the target sequence (via sequence part Z-2). Sequence part Z-2 is thus specific to the target sequence. In another embodiment, one type of nuc-macromolecules having a target domain specific to the hybridization probe is brought into contact with a plurality of hybridization probes, each of them having identical binding sites (Z-1) for the target domain of a nuc-macromolecule, but different binding sites for the target sequence (Z2). With this method it is possible to label different target sequences with a single type of nucleic macromolecules. Preferentially, the binding between the nuc-macromolecule and the hybridization probe is stable under the conditions of a labeling reaction. This can be achieved, for example, by the sequence choice for the sequence segment (Z-1) and the target domain of the nuc-macromolecules having a higher Tm, as compared to the Tm of the Z-2 segment of the hybridization probe.

The entire construct in FIG. 5B, consisting of nuc-components covalently bound to each other, the linker, the oligonucleotide and oligonucleotides attached via affinity binding (hybridization probe binding caused by base pairing between two nucleic acid strands) can be referred to as a nuc-macromolecule. According to this embodiment of the application, the synthesis/formation of a nuc-macromolecule suitable for reaction is occurring just before or during the labeling reaction. The oligonucleotide, which is covalently bound to the nuc-component, may be referred to as a core component (see below), because of its function as a binding partner between different functionalities, i.e. a nuc-component and a target domain.

Positioning of the Target Domain with Respect to the Target Sequence

The position for hybridization of the target domain with respect to the target sequence preferably lies downstream of a 3'-primer end. This positioning makes it possible for a polymerase to incorporate the nuc-component, which is bound to the target domain, during synthesis of a strand that is complementary to the target sequence. In one embodiment, it is located within the first 1-5, 1-10, 1-20, 20-30, 30-50 nucleotides from the primer binding site, in a further embodiment, it is located within the first 50 to 200 nucleotides from the primer binding site, in a further embodiment, the binding site for the target domain is separated by more than 200 nucleotides from the primer binding site.

If at least two primers are used in an assay, for example for amplification of the target sequence, the binding position of the target domain is located between the binding sites of the two primers on the target sequence.

The functional significance of the target sequence may be taken into account when choosing the positioning of the target domain with respect to a target sequence, in one embodiment for example, the position is chosen within a promoter region of a gene (+/−5000 nucleotides up- or downstream), or within an exon or intron of a gene.

The binding site of the target domain oligonucleotide in a target sequence may harbor a potential mutation site or an SNP site. In one embodiment of this kind, such a mutation is preferably located centrally within a binding site for the target domain. This choice of position can lead to better discrimination in binding between target domain and target sequence, which would contribute to higher assay specificity.

Several nuc-macromolecules can bind the same target sequence sequence-specifically within one assay. In one embodiment, the sequence composition of the target domain oligonucleotides is adjusted such that the respective nuc-macromolecules bind to the same strand of the target sequence. The binding sites of different nuc-macromolecules to a target sequence can be overlapping, or nuc-macromolecules can bind one behind the other on a strand of the target sequence without overlapping.

In another embodiment, at least two nuc-macromolecules each with different target domain oligonucleotides bind to both strands of the target sequence, and in particular each nucleotide conjugate with its sequence-specific target domain binds to one strand of the target sequence (FIG. 38-39). Such binding is advantageous, for example, when using amplification methods in which both strands of the target sequence are amplified, such as in PCR, HDA or LAMP. In one embodiment, the target domain oligonucleotides of the two types of nuc-macromolecules are at least partially complementary to each other (FIG. 38) and can form a double strand. The length of the complementary region of the two target domain oligonucleotides of different types of nuc-macromolecules can, for example, be 10 to 15, 15 to 20, 25 to 30, 30 to 50, or greater than 50 nucleobases. In a further embodiment, target domains of two types of nuc-macromolecules are not complementary to each other.

In a further embodiment, several nuc-macromolecules are used in an assay wherein at least two nuc-macromolecules bind to each respective strand of the target sequence. For example, either 2 to 4, 4 to 10, 10 to 20 nuc-macromolecules can bind to the first strand of the target sequence, and either 2 to 4, 4 to 10, 10 to 20 nuc-macromolecules can bind to the second, complementary strand of the target sequence. The respective target domain sequences lie in 3'-direction of a primer bound to the corresponding strand.

If such nuc-macromolecules are used in an amplification assay that involves at least two primers, then, in one embodiment, the binding sites of the target domain oligonucleotides are located between the binding sites of the two primers.

If multiple primers are used in an assay (e.g. nested PCR with at least one outer primer pair and at least one inner primer pair), then the binding site of at least one target domain oligonucleotide can be located between the binding sites of an outer primer and an inner primer.

In a further embodiment of the invention, the binding site of at least one target domain oligonucleotide overlaps partially or completely with a primer binding site.

In a further embodiment of the invention, the binding site of at least one target domain oligonucleotide overlaps partially or completely with the binding site of an oligonucleotide probe.

Discrimination Between Multiple Sequences.

There is often a need to distinguish one target sequence from other target sequences within an assay. Such target sequences differ from one another in at least one position e.g. by a single nucleotide or by differences that involve a run of several nucleotides.

The composition of the particular target domain oligonucleotides of the types of nuc-macromolecules to be used should allow for specific hybridization of the respective type of nuc-macromolecule to the corresponding target sequence in an assay. A person skilled in the art knows that oligonucleotides can discriminate even single nucleotide differences under appropriate stringent conditions. Target domain oligonucleotides with partially self-complementary structures in a "molecular beacon" arrangement (see above) allow for better discrimination between sequences, for example.

A person skilled in the art will appreciate that the following embodiments illustrate how sequence-specific events (such as sequence-specific termination or sequence-specific labeling, etc.) can be used during the detection, labeling, or amplification of one or several target sequences.

In one embodiment, multiple target sequences are differentially labeled with respectively specific nuc-macromolecules, wherein each type of nuc-macromolecule has distinct marker properties, such as different propensity of binding to the solid phase via the anchoring domain (see below), or different signal domain spectral characteristics (see below). The sequence-specific incorporation of differently labeled nuc-macromolecules makes it possible to differentially label and, where necessary, detect multiple target sequences in one assay.

In another embodiment, multiple target sequences are differentially labeled with respectively specific nuc-macromolecules, wherein at least one type of nuc-macromolecule comprises at least one type of terminating nuc-component, e.g. ddUTP. The target domain oligonucleotides are specifically designed for each corresponding target sequence. Sequence-specific binding by a terminating nuc-macromolecule and incorporation of a terminating nuc-component result in termination of the synthesis of one or several target sequences. Labeling and detection of these sequences is thereby avoided. Other target sequences that were not terminated can be labeled and detected however.

In another embodiment, multiple target sequences are amplified and simultaneously differentially labeled with respectively specific nuc-macromolecules, wherein at least one type of nuc-macromolecule comprises at least one type of terminating nuc-component, e.g. ddUTP. The target domain oligonucleotides are specifically designed for each corresponding target sequence. Amplification ceases after incorporation of a terminating nuc-component. In this manner, particular target sequences can be excluded from amplification. However, other target sequences in the same assay can be amplified before sequence-specific labeling and/or detection.

Target Domain Antagonists (Antagonist Oligonucleotides)

In one embodiment of the invention, nucleotide conjugates comprise oligonucleotides complementary to the target domain (FIG. 33). These oligonucleotides hybridize with target domain oligonucleotides and block them from binding to nucleic acid chains, including those of the corresponding target sequence. These oligonucleotides are referred to as target domain antagonists. Their purpose is to increase the binding specificity of a target domain oligonucleotide to its respective target sequence in an assay.

Non-specific binding of the target domain to nucleic acid sequences at low reaction temperatures can be avoided through the use of antagonist oligonucleotides (Gidwani et al. Analyst, 2009, v. 134, 1675-, Huang et al. NAR, 2007, v. 35, e101 "Thermodynamically modulated partially double stranded DNA probe design for homogeneous real time PCR"). This relationship can be used to increase the binding specificity of the target domain to the corresponding target sequence.

Structure of Antagonist Oligonucleotides

In one embodiment, the antagonist oligonucleotide consists of nucleobases. Nucleobases such as adenine, cytosine, guanine, thymine, uracil (abbreviated as A, C, G, T, U), or analogs thereof, linked to a sugar-phosphate backbone as in the case of DNA or RNA, or analogues thereof, such as PTO, PNA, LNA, can bind nucleic acid strands in a sequence-specific manner. Different types of nucleic acid chains, such as DNA, PTO, RNA, protein nucleic acids (PNA), morpholinos and their analogues, can constitute the nucleic acid content of the target domain. Individual segments of the antagonist oligonucleotides can be composed of the same kind of monomer, for example DNA only or PNA only, or can be composed of a mixed polymer, wherein DNA, RNA, PNA, morpholinos, LNA or other modifications are combined to form a single chain.

If more than one antagonist oligonucleotide is present within one kind of nuc-macromolecule, individual domains can be composed of different types of monomers, e.g. one antagonist oligonucleotide consists of DNA, another of PNA, etc.

For simplicity of exposition, antagonist oligonucleotides of the DNA type were discussed in detail. Other types of nucleic acid chains can be constructed and used in accordance with rules based on the paradigm of DNA oligonucleotides, which are known to a person skilled in the art.

The segment of the oligonucleotide which is complementary to the target domain, i.e., the actual antagonist sequence, can be flanked at the 5'-end or at the 3'-end by further sequence segments that do not bind the target domain. These flanking regions may consist of the same monomers as the antagonist oligonucleotide (e.g. DNA, PTO, PNA, LNA, RNA) or may be of a different composition from the antagonist oligonucleotide. These flanking sequence segments can range in their length, for example, from 1 to 5, 5 to 10, 10 to 15, 15, BSI 20, from 20 to 30, or they be longer than 30 nucleobases in length. They can serve as spacers or, for example, bind to marker domains or anchor domains and thus act as antagonists to these domains.

These antagonist oligonucleotides are preferably constructed in such a way that the binding of respective target domains oligonucleotides to antagonist oligonucleotides is weaker than the perfect match hybridization of target domain to target sequence.

In one embodiment of the invention, these antagonist oligonucleotides are shorter than the target domain. For example, differences in length between the target domain and the corresponding antagonist domain include the following ranges (measured in the nucleobases): 1-3, 3-5, 5-7, 7-10, 10-13, 13-15, 15 to 18, 18 to 20, 20 to 30, 30 to 40 or longer than 40.

The length of the oligonucleotide of the target domain is 25 nucleobases for example, and the length of the antagonist-oligonucleotide is 18 nucleobases. The difference in length is thus 7 nucleobases.

If the target domain has a total length of more than 20 nucleobases, then several antagonist oligonucleotides can bind to such a target domain. For example, two antagonist domains of 20 nucleobases each can be hybridized to a target domain of a total length of 40 nucleobases.

During the design of antagonist oligonucleotides the respective hybridization conditions of the reaction (e.g. temperature, buffer etc.) and hybridization properties of the target domain to the target sequence should be taken into account. A person skilled in the art can find support for adjusting the length and composition of the antagonist oligonucleotide precisely to the respective target domain in the following reference: Gidwani et al. Analyst, 2009, v. 134, 1675-, Huang et al. NAR, 2007, v. 35, e101 "Thermodynamically modulated partially double stranded DNA probe design for homogeneous real time PCR".

The composition of antagonist oligonucleotides may involve different modifications of the nucleobases, such as DNA, RNA, PNA, LNA, etc. that are known to a person skilled in the art.

Depending on the composition of the antagonist oligonucleotide (i.e. DNA, RNA, PNA or LNA), the strength of binding the respective target domain can vary for a given length of the oligonucleotide antagonists. A person skilled in the art knows for example that PNA-based oligonucleotides have a stronger affinity to complementary regions the DNA-based oligonucleotides of the same composition and length.

A person skilled in the art should know further oligonucleotide modifications which can influence the binding between complementary nucleic acid chains. Such modifications include, for example, "minor groove binder". Such modifications can be attached to the antagonist oligonucleotides.

In one embodiment, the 3'-OH end of the antagonist oligonucleotide (or of the flanking oligonucleotide) is blocked by a chemical group. A person skilled in the art knows many examples of modifications of the 3'-OH position of oligonucleotides, including for example the following moieties: 2',3'-dideoxy-ribose, a phosphate group, a biotin moiety, an amino linker, a fluorescent dye, a peptide chain, or a quencher. Various modifications may be incorporated into an oligonucleotide in place of the 3'-OH group, such as an amino group, a halogen atom, an azido group, etc. In this embodiment, such an oligonucleotide cannot be extended by a polymerase, and consequently has no primer function.

The antagonist oligonucleotides may comprise partially self-complementary segments, such as structures known as hairpins or loops. In one embodiment of the invention, the antagonist oligonucleotide participates in the formation of a type of structure known as "molecular beacon" (for details about the properties of molecular beacons: Bonnet et al PNAS 1999 v 96. 6171-). In this embodiment, the antagonist oligonucleotide sequence that is actually complementary to the target domain is surrounded by flanking the nucleic acid strands, which are mutually complementary. Such a structure allows the binding specificity of the antagonist oligonucleotide to the target domain to be increased. The length of self-complementary regions of such molecular beacons ranges generally between 3 to 6, 6 to 8, 8 to 10, 10 to 15 nucleotides, wherein the antagonist oligonucleotide is about 10 to 15, 15 to 20, 20 to 30, 30 to 40 nucleotides long.

In one embodiment, one arm of the double stranded portion of the arrangement of type the "molecular beacon" is involved in binding to target domain (on this topic, see "Shared stem molecular beacons", see Tsourkas et al NAR 2002, V. 30 4208-).

Preferably, antagonist oligonucleotides are resistant to the exonuclease activities of polymerases (e.g. 5'-3' exonuclease or 3'-5'-exonuclease). This may be achieved for example by introduction of PNA analogues at both ends of the antagonist oligonucleotides. A person skilled in the art knows further modifications of oligonucleotides which impart such a resistance to exonucleases.

Binding of Antagonist Oligonucleotides to the Target Domain Oligonucleotides of Nuc-Macromolecules The antagonist oligonucleotides are preferably hybridized to the target domain before nuc-macromolecules are used in a labeling reaction. Hybridization between the target domain and an antagonist oligonucleotide can be carried out under reaction conditions known to those skilled in the art which are conducive to the specific binding of nucleic acid chains to each other (e.g. by heating and cooling of nuc-macromolecules together with a target domain and antagonist oligonucleotides in a buffer solution).

In a further embodiment, binding of this type is conducted under assay conditions, i.e. nuc-macromolecules bearing a target domain and antagonist oligonucleotides are separately added to the assay. This means that the binding of antagonist oligonucleotides to the respective target domain only occurs in the assay mixture.

Function of the Antagonists

The binding of antagonist oligonucleotide to the respective target domain is not of a covalent nature and is reversible, for example, at higher temperatures. At higher temperatures, the antagonist oligonucleotides separate from the target domain, thus vacating and enabling the target domain to bind to the target sequence.

In one approach, the target sequence and the antagonist oligonucleotides compete in binding the target domain. Owing to stronger interaction between target domain and target sequence (caused for example by length differences between the target domain and antagonist oligonucleotide) nuc-macromolecules preferentially bind to the target sequence.

Non-specific binding of the target domain to the nucleic acid sequences at low reaction temperatures can be avoided through the use of antagonist-oligonucleotides. After the reaction, antagonists can bind the target domain once again, and thereby prevent non-specific binding to other nucleic acid chains. The specificity of the detection can be increased in this way.

1.3.3.3.2 The Anchor Domain of a Nuc-Macromolecule and the Combination with the Solid Phase The purpose of the anchor domain is to provide a specific binding to a solid phase for a particular type of nuc-macromolecule or a nucleic acid strand which is labeled with such a molecule. Nuc-macromolecules or nucleic acid strands labeled with nuc-macromolecules (e.g. target sequences or their equivalents) can bind to a solid phase by means of an anchor domain, before or during or after an enzymatic reaction.

The following application Cherkasov et al WO2011050938 provides examples for anchor domain, their function and linking within nucleotide conjugates, antagonists of an anchor domain and different examples of a solid phase for the analysis.

1.3.3.3.3 Signal Domain (Functions and Composition)

Function of a Signal Domain

In one embodiment, the signal domain can have a signaling function. In another embodiment, it has a signal-transmitting function. In another embodiment, it has a catalytic function. In a further embodiment, the signal domain has more than one function and combines for example both signaling and signal-transmitting functions.

Other combinations are obvious. Further examples of methods of detection are given in section 1.3.25.

The signal domain having signaling function comprises constituents which have been assembled within a nuc-macromolecule during the chemical synthesis of a nuc-macromolecule: for examples see the applications Cherkasov et al WO 2005044836, Cherkasov et al WO2006097320, Cherkasov et al WO 2008043426, Cherkasov et al DE 10356837, Cherkasov et al DE 102004009704.

A signal domain having signal transmitting function develops its signaling properties only after having reacted with signaling molecules. For example, a marker consists of several molecules of biotin, e.g. 100 biotin molecules. After the incorporation of the nuc-macromolecules, a detection reaction is carried out with modified streptavidin molecules. In another example, the nucleic acid chains comprise the signal-transmitting function: after the incorporation of nuc-macromolecules, a hybridization of uniform oligonucleotides with detectable moieties such as fluorescent dyes (MWG Biotech) to the marker is conducted. In another example, amino or mercapto groups, for example 50 amino groups per marker, have the signal-transmitting function. After the incorporation of the nuc-macromolecules into the nucleic acid chain, a chemical modification with reactive components is conducted, for example modification of incorporated allyl-amino-dUTP by dyes described in Diehl et al. Nucleic Acid Research, 2002, V. 30, Nr. 16 e79.

In another embodiment, the signal domain has a catalytic function (in the form of an enzyme or ribozyme). Here, different enzymes can be used, such as peroxidase or alkaline phosphatase. Due to the linkage to the nuc-component, the respective enzyme becomes covalently bound to the nucleic acid strand after a nuc-macromolecule has been incorporated.

In one embodiment, a signal domain comprises one low molecular weight marker unit. In a further embodiment, the signal domain comprises one macromolecular marker unit. In a further embodiment, the signal domain comprises several low molecular weight marker units. In a further embodiment, the signal domain comprises multiple macromolecular marker units. In a further embodiment, the signal domain comprises a combination of low molecular and macromolecular units. The signal domain can have a signaling or signal-transmitting function.

These units can be molecules with low molecular mass, e.g. less than 2000 Da, or they can be also macromolecules. The number of the signal-giving or signal-transmitting units, which are combined into one signal domain, comprises the following ranges: 1 and 2, 2 to 5, 5 to 20, 20 to 50, 50 to 100, 100 to 500, 500 to 1000, 1000 to 10000, 10000 to 100000.

If several marker units are combined into one signal domain, then in one embodiment these units are bound to a framework, the core component of the marker (FIG. 23). This core component connects the units together. The core component can provide the connection to one or several nuc-linker components (FIG. 24). The core component can comprise low-molecular or macromolecular compounds.

1.3.3.3.3.1 Structure of the Signal-Giving or the Signal-Transmitting Units of the Signal Domain The structural marker units comprise the following groups:

1.3.3.3.3.1.1 Structures with Low Molar Mass

Biotin molecules, hapten molecules (e.g. digoxigenin or dinitrophenol (DNP), radioactive isotopes (e.g., $P^{32}$, $J^{313}$) or their derivatives, rare earth elements, dyes, fluorescent dyes, quencher of the fluorescence (e.g. dabsyl) (many of these molecules are commercially available, e.g., from Molecular Probes, Inc or from Sigma-Aldrich) with the same or different spectral properties, groups of dyes undergoing FRET. Thermochromatic, photochromatic or chemoluminescent substances are available for example from Sigma-Aldrich, chromogenic substances are described for example as substrates for peptidases in "Proteolytic enzymes Tools and Targets", E. Sterchi, 1999, ISBN 3-540-61233-5).

Also chemically reactive groups, as for example amino-, carboxy-, merkapto-, aldehyde, iodine acetate, acrylic, dithio-, thioester-groups, can serve as signal-transmitting structural units. These reactive groups can be modified with signal-giving elements, such as dyes with suitable reactive groups (for instance, NHS esters, mercapto-, amino groups), e.g. after incorporation of nuc-macromolecules. General rules for the choice of a suitable pair of reactive groups are shown in "Chemistry of protein conjugation and crosslinking" Shan S. Wong 1993.

In a special embodiment, a combination comprising one nuc-component, one macromolecular linker component and one signal domain with a low molecular weight already fulfils the requirements of the present invention. Such compounds are also subject matter of this invention. They can be used both as intermediate compounds for the chemical synthesis of nuc-macromolecules with one macromolecular marker, e.g., dUTP-PEG-biotin, and as independent compounds for enzymatic reactions, as, for example, nucleotides labeled with only one dye.

Different fluorescent dyes can be used, and their choice is not limited as long as their influence of the enzymatic reaction is not substantial. Examples of such dyes are Rhodamine (Rhodamine 110, Tetramethylrhodamine, available from Fluka-Sigma), cyanine dyes (Cy2, Cy3, Cy3.5, Cy5, Cy5.5, Cy7 available from Amersham Bioscience), coumarine, Bodipy, fluorescein, Alexa Dyes: e.g., Alexa 532, Alexa 548, Alexa 555 (Molecular Probes). Many dyes are commercially available, for instance, from Molecular Probes Europe, Leiden, the Netherlands (hereinafter called Molecular Probes) or from Sigma-Aldrich-Fluka (Taufkirchen, Germany).

Various substances (e.g. sugars, dyes, or hormones) can also serve as markers by virtue of being ligands of proteins with recognition properties (e.g. antibodies or their fragments, lectins, receptors). Several haptens (digoxigenin or fluorescein), hormones, or small peptides can be attached to the marker as marker units. Such molecular structures can be detected through the addition of a labeled protein, for example of a labeled antibody.

"Signaling Domain for Cellular Uptake" of Low Molecular Mass

Molecular structures of low molecular mass (e.g. lipids, cholesterol, mono- or disaccharides) may support cellular uptake or targeted intracellular transport. Here they will be referred to as a "signaling domain for cellular uptake". Examples of the modification of oligonucleotides (e.g. antisense oligonucleotides or siRNA) or proteins with such ligands, as well as their application in the context of cells are known to a person skilled in the art. (J Biol Chem. 1999 Jul. 2; 274(27):19087-94. Mannose polyethylenimine, conjugates for targeted DNA delivery into dendritic cells. Diebold S S, et al; Carbohydr Res. 2009 Nov. 2; 344(16):2137-43. Epub 2009 Aug. 31. Synthesis and characterization of mannosylated oligoribonucleotides. Zhao Y, et al; Expert Opin Drug Deliv. 2008 Jun.; 5(6):703-24. Mannose-targeted systems for the delivery of therapeutics. Irache J M, et al.; Nat Biotechnol. 2007 Oct.; 25(10):1149-57. Epub 2007 Sep. 16. Mechanisms and optimization of in vivo delivery of lipophilic siRNAs. Wolfrum C, et al; Bioorg Med Chem Lett. 2004 Oct. 4; 14(19):4975-7. Steroid and lipid conjugates of siRNAs to enhance cellular uptake and gene silencing in liver cells. Lorenz C, et al; J Med Chem. 2008 Aug. 14; 51(15):4374-6. Epub 2008 Jul. 8. Lipid-conjugated oligonucleotides via "click chemistry" efficiently inhibit hepatitis C virus translation. Godeau G, et al; AAPS J. 2009 Dec.; 11(4):639-52. Epub 2009 Sep. 9. Lipidic systems for in vivo siRNA delivery. Wu S Y, et al; FASEB J. 2002 Sep.; 16(11):1426-8. Epub 2002 Jul. 1. Gene delivery by a steroid-peptide nucleic acid conjugate. Rebuffat A G, et al; Mol Cell Biochem. 2005 August; 276(1-2):61-9. Cholesterol conjugated oligonucleotide and LNA: a comparison of cellular and nuclear uptake by Hep2 cells enhanced by streptolysin-O. Holasovà S, et al; Proc Natl Acad Sci USA. 1989 September; 86(17):6553-6. Cholesteryl-conjugated oligonucleotides: synthesis, properties, and activity as inhibitors of replication of human immunodeficiency virus in cell culture. Letsinger R L, et al; J Pharmacol Exp Ther. 2002 August; 302(2):619-26. bis-Cholesteryl-conjugated phosphorothioate oligodeoxynucleotides are highly selectively taken up by the liver. Bijsterbosch M K, et al.; Biochem Pharmacol. 2001 Sep. 1; 62(5): 627-33. Delivery of cholesteryl-conjugated phosphorothioate oligodeoxynucleotides to Kupffer cells by lactosylated low-density lipoprotein. Bijsterbosch M K, et al; Bioconjug Chem. 2009 Sep.; 20(9):1729-36. Phospholipid conjugate for intracellular delivery of peptide nucleic acids. Shen G, et al)

In one embodiment, the signal domain comprises several marker units. These marker units can have the same or different properties. For instance, fluorescent dyes with different spectral qualities can be used. In one embodiment, the fluorescent dyes that can form FRET pairs are selected.

1.3.3.3.3.1.2 Structures with High Mass (Macromolecules)

Nanocrystals

Nanocrystals, e.g. quantum dots, can serve as signal domain. Quantum dots with the same or different spectral qualities can be used within the same marker component. Examples of quantum dots are presented in U.S. Pat. No. 6,322,901, U.S. Pat. No. 6,423,551, U.S. Pat. No. 6,251,303, U.S. Pat. No. 5,990,479.

Nano- or Micro-Particles

Nano- or micro-particles can serve as signal domains. The diameters of these particles can range from 1 nm to 2 nm, from 2 nm to 5 nm, from 5 nm to 10 nm, from 10 nm to 20 nm, from 20 nm to 50 nm, from 50 nm to 100 nm, from 100 nm to 200 nm, from 200 nm to 500 nm, from 500 nm to 1000 nm, from 1000 nm to 5000 nm. The material of these particles can, for instance, be pure metals such as gold, silver, aluminum (as instances of particles capable of surface plasmon resonance), Protein-gold_conjugates: J. Anal. Chem. 1998; v. 70, p. 5177-, Nucleic acid-gold_conjugates: J. Am. Chem. Soc. 2001; v. 123, p. 5164-, J. Am. Chem. Soc. 2000; v. 122, p. 9071-, Biochem. Biophys. Res. Commun 2000; v. 274, p. 817-, Anal. Chem. 2001; v. 73, p. 4450-, latex (e.g., Latex-Nano-particles), Anal. Chem. 2000; v. 72, p. 1979-, plastic (Polystyrene), paramagnetic compounds: Zhi Z L et al. Anal. Biochem, 2003; v. 318 (2): p. 236-43, Dressman D et al. Proc Natl Acad Sci U.S.A. 2003, v. 100 (15): p. 8817-22, metal particles, magnetic compounds: Jain K K. Expert Rev Mol Diagn. 2003; v. 3 (2): p. 153-61, Patolsky F et al. Angew Chem Int Ed Engl 2003; v. 42 (21), p. 2372-2376, Zhao X et al. Anal Chem. 2003; v. 75 (14): p. 3144-51, Xu H et al. J Biomed Mater Res. 2003 Sep. 15; v. 66A(4): p. 870-9, Josephson U.S. Patent No. 2003092029, Kliche WO0119405.

Peptides and Protein Molecules

Peptides and Protein molecules can serve as signal domain. The proteins comprise the following groups: enzymes (e.g. peroxidase, alkaline phosphotase, urease, beta-galactosidase, peptidases), fluorescing proteins (e.g. from GFP-family or phycobiliproteins (e.g. Phycoerythrin, Phycocyanin) available e.g. from Molecular Probes Inc.), antigen-binding proteins (e.g. antibodies, tetramers, affibodies (Nord et. al Nature Biotechnology, 1997, v. 15, p. 772-) or their components (e.g. Fab fragments), nucleic acid-binding proteins (e.g. transcription factors).

Peptides or proteins can also be used as target antigens for antibodies. Nucleotide conjugates bearing such antigens can be specifically recognized by appropriate antibodies. This property can be used during detection for example. Means of coupling proteins to oligonucleotides is known to a person skilled in the art. Chem Soc Rev. 2010 June; 39(6):2054-70. Epub 2010 Apr. 14. Recent developments in oligonucleotide conjugation. Singh Y, et al; Bioconjug Chem. 2010 Feb. 17; 21(2):187-202. Chemical strategies for the synthesis of peptide-oligonucleotide conjugates. Lu K, et al; Bioconjug Chem. 1992 Jan.-Feb.; 3(1):74-9. Selective modification of cytosines in oligodeoxyribonucleotides. Miller P S, et al; Nucleic Acids Res. 1990 Sep. 25; 18(18):5419-23. Site specific functionalization of oligonucleotides for attaching two different reporter groups. Agrawal S, et al; Bioconjug Chem. 1990 Jan.-Feb.; 1(1):71-6. Use of maleimide-thiol coupling chemistry for efficient syntheses of oligonucleotide-enzyme conjugate hybridization probes. Ghosh S S, et al; Bioconjug Chem. 2000 Sep.-Oct.; 11(5): 605-18. Preparation and applications of peptide-oligonucleotide conjugates. Tung C H, et al; Chembiochem. 2010 Jul. 26; 11(11): 1493-500. Delivery of oligonucleotides and analogues: the oligonucleotide conjugate-based approach. Marlin F, et al; Methods Mol Biol. 2011; 683:219-30. Characterization of cellular internalization pathways for CPP-mediated oligonucleotide delivery. Guterstam P, et al; Methods Mol Biol. 2011; 683:453-63. Multifunctional CPP polymer system for tumor-targeted pDNA and siRNA delivery. Dohmen C, et al; Bioconjug Chem. 1999 Jul.-Aug.; 10(4):598-606. Peptide-oligonucleotide phosphorothioate conjugates with membrane translocation and nuclear localization properties. Antopolsky M, et al; Bioconjug Chem. 1998 Mar.-Apr.; 9(2):168-75. Hybridization characteristics of biomolecular adaptors, covalent DNA—streptavidin conjugates. Niemeyer C M, et al; Bioconjug Chem. 2008 Dec.; 19(12): 2304-7. Design of DNA-conjugated polypeptide-based capture probes for the anchoring of proteins to DNA matrices. Schweller R M, et al; Bioconjug Chem. 2010 Sep. 15; 21(9):1642-55. Versatile phosphoramidation reactions for nucleic acid conjugations with peptides, proteins, chromophores, and biotin derivatives. Wang T P, et al; Bioconjug Chem. 2010 May 19; 21(5):921-7. Conjugation of fluorescent proteins with DNA oligonucleotides. Lapiene V, et al. "Signaling Domain for Cellular Uptake" of High Molecular Mass In addition, peptides (e.g. Nucleus Localizing Signal, or Cell penetrating peptides) or proteins (for example antibodies, transferrin) can facilitate improved cellular uptake or support a targeted intracellular transport. Many examples of improved cellular uptake via membrane-protein or receptor-dependent mechanisms are known to a person skilled in the art. Various cell membrane receptors bind and translocate particular ligands into the cell, e.g. Fc-receptor and substances coupled to antibodies, folate receptor and substances modified with folate, lectins (e.g. mannose-receptor, DC-SIGN-Receptor and corresponding molecules that bear sugar moieties).

The company Solulink (www.solulink.com) provides a number of reagents for coupling oligonucleotides and proteins (e.g. antibodies). Below, some examples from the literature are cited that illustrate the current state of the art in these areas.

Literature on oligonucleotide antibody coupling, and examples of applications: Bioconjug Chem. 2010 Dec. 15; 21(12):2190-6. Epub 2010 Nov. 24. An approach to multiplexing an immunosorbent assay with antibody-oligonucleotide conjugates. Han K C, et al; Biopolymers. 2004 Apr. 5; 73(5):621-30. Efficient strategies for the conjugation of oligonucleotides to antibodies enabling highly sensitive protein detection. Kozlov I A, et al; AAPS J. 2009 Mar.; 11(1):195-203. Epub 2009 Mar. 19. Targeted delivery systems for oligonucleotide therapeutics. Yu B, et al.;

Literature on coupling oligonucleotides and peptides (cell penetrating peptides), and examples of applications: Br J Pharmacol. 2009 May; 157(2):195-206. Epub 2009 Mar. 20. Twenty years of cell-penetrating peptides: from molecular mechanisms to therapeutics. Heitz F, et al; Methods Mol Biol. 2011; 764:75-89. Cell-penetrating peptides-based strategies for the delivery of splice redirecting antisense oligonucleotides. El Andaloussi S, et al.; J Mol Biol. 2002 Apr. 26; 318(2):237-43. A biological transporter for the delivery of peptide nucleic acids (PNAs) to the nuclear compartment of living cells. Braun K, et al.; Adv Drug Deliv Rev. 2003 Feb. 10; 55(2):267-80. Cellular delivery of peptide nucleic acid (PNA). Koppelhus U, et al; Biochemistry. 2006 Dec. 19; 45(50):14944-54. Structural requirements for cellular uptake and antisense activity of peptide nucleic acids conjugated with various peptides. Wolf Y, et al; Expert Opin Biol Ther. 2009 Aug.; 9(8):975-89. Prospects for antisense peptide nucleic acid (PNA) therapies for HIV. Pandey V N, et al; Methods Mol Biol. 2005; 298:131-41. Cellular delivery of peptide nucleic acid by cell-penetrating peptides. Kilk K, et al; Blood Cells Mol Dis. 2007 January-February; 38(1):1-7. Epub 2006 Nov. 17. RNA targeting with peptide conjugates of oligonucleotides, siRNA and PNA. Turner J J, et al.; Nucleic Acids Res. 2005 Nov. 30; 33(21):6837-49. Print 2005. Cell-penetrating peptide conjugates of peptide nucleic acids (PNA) as inhibitors of HIV-1 Tat-dependent trans-activation in cells. Turner J J, et al; Methods Mol Biol. 2009; 480:85-99. Peptide-based delivery of steric-block PNA oligonucleotides. Abes S, et al; Adv Drug Deliv Rev. 2008 Mar. 1; 60(4-5):517-29. Epub 2007 Oct. 22. Cell penetrating peptide conjugates of steric block oligonucleotides. Lebleu B, et al A coupling between a peptide or protein and a target-domain within a nucleotide conjugate can impart additional properties to the whole sequence-specific nucleotide conjugate construct.

Examples of a targeted application (e.g. application involving a particular cell type) of nucleic acid-based therapeutics are known to an expert. Some examples of a so-called "targeted delivery" are shown in the following: Mol Pharm. 2007 Jan.-Feb.; 4(1):58-72. Epub 2007 Jan. 17. Receptor-mediated delivery of antigens to dendritic cells: anticancer applications. Proudfoot O, et al; Mol Pharm. 2006 Sep.-Oct.; 3(5):579-88. Targeted delivery of antisense oligodeoxynucleotide and small interference RNA into lung cancer cells. Li S D, et al; Trends Pharmacol Sci. 2012 April; 33(4):186-92. Epub 2012 Mar. 15. Peptides for cell-selective drug delivery. Svensen N, et al; Nucleic Acids Res. 2008 May; 36(8):2764-76. Epub 2008 Mar. 26. Intracellular delivery of an anionic antisense oligonucleotide via receptor-mediated endocytosis. Alam M R, et al; Bioconjug Chem. 2008 Nov. 19; 19(11):2182-8. Cellular delivery and biological activity of antisense oligonucleotides conjugated to a targeted protein carrier. Kang H, et al; Bioconjug Chem. 2011 Aug. 17; 22(8):1673-81. Epub 2011 Jul. 20. Multivalent cyclic RGD conjugates for targeted delivery of small interfering RNA. Alam M R, et al; Antisense Nucleic Acid Drug Dev. 2002 Apr.; 12(2):51-63. Cell-dependent differential cellular uptake of PNA, peptides, and PNA-peptide conjugates. Koppelhus U, et al.

Several monographs describe couplings between nucleic acids and peptides, as well as their use in the cells or tissues or organisms: "Handbook of Cell-Penetrating Peptides", p 309-, Ülo Langel, Taylor&Francis Group, 2007, ISBN-13: 978-0-8493-5090-0; Methods in Molecular Biology v. 208, Peptide Nucleic Acids, ed. P. E. Nielsen 2002.

Like in the examples cited above, sequence-specific nucleotide conjugates that comprise appropriate oligonucleotides and peptides can also exhibit biological activity in cells. In an advantageous embodiment of the invention, nucleotide conjugates comprise a "signaling domain for cellular uptake" for a better uptake into the cells. As described above, such a domain can be represented by various moieties.

Nucleic Acid Chains

Figure 25:
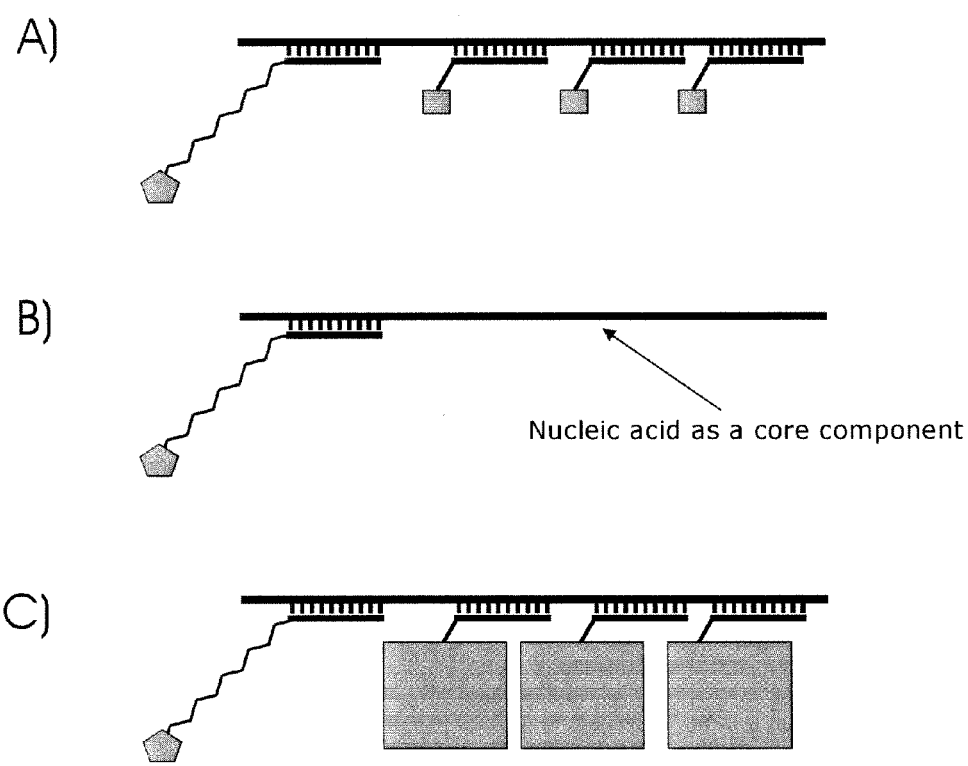

Nucleic acid chains, including oligonucleotides (modified and non-modified), can act as signal domains. The length of these nucleic acid chains should fall preferentially within the following ranges (number of nucleotide monomers in a chain): 10 to 20, 20 to 50, 50 to 100, 100 to 200, 200 to 500, 500 to 1000, 1000 to 5000, 5000 to 10000, 10000 to 100000. Labeled and unlabeled DNA, PTO, RNA, Morpholino or PNA molecules can be used. Nucleic acid chains can carry additional modifications, such as, for example, free amino groups, dyes and other signal-giving molecules, e.g. macromolecular substances, enzymes or nanocrystals (FIG. 25). Modified nucleic acid chains are also commercially available, e.g. from MWG-Biotech, Trilink Biotechnologies. Further examples of macromolecules or macromolecular complexes which can be used, according to the scope of the present invention, as a marker or marker units in the marker component are described in the U.S. Pat. No. 4,882,269, the U.S. Pat. No. 4,687,732, WO 8903849, the U.S. Pat. No. 6,017,707, the U.S. Pat. No. 6,627,469.

Preferentially, the 3' end of the signal domain is blocked so that the target domain can not act as a primer.

Preferentially, the signal domain does not comprise sequences complementary to the target sequence or to the target domain or to the anchor domain or to the used primers.

1.3.3.3.4 Core Component of the Marker

Examples for core component and for linkage of individual marker units to the core component can be found in patent application Cherkasov et al WO2011050938, Cherkasov et al WO2005044836, Cherkasov et al WO2006097320.

1.3.3.3.5 Coupling of the Marker Units or Domains

Marker units or domains can be bound to the core component or to the linker component by a covalent bond, for example, via a crosslinker (Chemistry of protein conjugation and cross linking, S. Wang, 1993, ISBN 0-8493-5886-8, "Bioconjugation: protein coupling techniques for the biomedical sciences", M. Aslam, 1996, ISBN 0-333-58375-2), or via an affine bond, for example, biotin-streptavidin connection or hybridizing of nucleic acid chains or antigen-antibody interaction ("Bioconjugation: protein coupling techniques for the biomedical sciences", M. Aslam, in 1996, ISBN 0-333-58375-2).

In one embodiment, the coupling of the marker units to the core component is conducted already during the synthesis of the nuc-macromolecules.

In another embodiment, the chemically synthesized nuc-macromolecules comprise a marker component consisting only of a core component without marker units. The coupling of marker units to the core component is conducted after the nuc-macromolecules have been incorporated in the nucleic acid chain. Due to the large number of potential binding positions within the core component, the probability of the coupling of the marker units to the core component of incorporated nucleotides is therefore substantially larger in comparison to conventional nucleotide structures. The coupling chemistry depends in detail on the structure of the marker units and the structure of the core component.

Covalent Coupling:

In one embodiment, the connection between the marker units and the core component can be resistant, e.g. to temperatures up to 100° C., to pH ranges between 3 and 12, and/or resistant to hydrolytical enzymes (e.g., esterases). In another embodiment of the invention, the connection is cleavable under mild conditions.

Examples of the coupling of nucleic acids to dendrimers (this corresponds to a coupling of marker units to the core component) are described, e.g., in Shchepinov et al. Nucleic Acids Res. 1999; v. 27 (15):p 3035-41, Goh et al. Chem Commun (Camb). 2002; (24): p 2954.

1.3.3.3.6 Coupling Between Linker and Marker

The connection between the linker component and the marker depends on the respective structures of the marker units or the structure of the core component. In one embodiment, the linker component is bound directly to the signal-giving or signal-transmitting marker unit. The marker can consist of only one or several marker units.

In a further embodiment, one or several linker components are bound to the core component of the marker.

The connection between the linker component and the marker can be covalent as well as affine. Many examples are known to the specialist, e.g. "Bioconjugation: protein coupling techniques for the biomedical sciences", M. Aslam, in 1996, ISBN 0-333-58375-2. "Chemistry of protein conjugation and crosslinking" Shan S. Wong in 1993 CRC Press Inc).

Covalent Coupling:

In one embodiment, the connection between the linker component and the marker can be resistant to, e.g., temperatures up to 130° C., pH ranges between 1 and 14, and/or resistant to hydrolytic enzymes (e.g. proteases, estarases). In another embodiment, the connection is cleavable under mild conditions.

According to some embodiments of this invention, macromolecular compounds used for the labeling of nucleotides comprise water-soluble polymers (see above). The linker of the nuc-macromolecules comprises water-soluble polymers too. A person skilled in the art should recognize that assignment of individual polymers to the linker or to the marker has a descriptive character.

1.3.3.3.7 Ratio of Nuc-Components in a Nuc-Macromolecule

One nuc-macromolecule can comprise on average 1 to 2, 2 to 5, 5 to 10, 10 to 30, 30 to 100, 100 to 1000, or more than 1000 nuc-components.

In one embodiment, all nuc-macromolecules have the same number of nuc-components per one nuc-macromolecule. For instance, a maximum of 4 biotin molecules can be bound per one strepavidin molecule; at a saturating concentration of nuc-linker components, a uniform population of nuc-macromolecules can be obtained.

In another embodiment, a nuc-macromolecule population has a defined average number of nuc-components per one nuc-macromolecule, however, in the population itself there is dispersion in the actual occupation of the nuc-macromolecules by nuc-components. In this case, the number of nuc-components per one nuc-macromolecule displays an average.

1.3.3.3.8 Ratio of Marker Units in a Nuc-Macromolecule

The number of marker units in one nuc-macromolecule falls within the following ranges: 1 and 2, 2 and 5, 5 and 20, 20 and 50, 50 and 100, 100 and 500, 500 and 1000, 1000 and 10000, 10000 and 100000, or more than 100000. In one embodiment, nuc-macromolecules have a definite number of signal-giving units per one marker. In another embodiment, a population of nuc-macromolecules has a varying number of marker units per one nuc-macromolecule and it does not need to have a definite value for every single nuc-macromolecule in a population.

In one embodiment, all the nuc-macromolecules have the same number of marker units per one nuc-macromolecule. For instance, a maximum of 4 biotin molecules can be bound per one strepavidin molecule, see "Avidin-Biotin-Technology", Methods in Enzymology v. 184, 1990.

In another embodiment, a nuc-macromolecule population has a defined average number of marker units per one nuc-macromolecule, however, in the population itself, there is dispersion in the actual occupation of the nuc-macromolecules by marker units. An increasingly more uniform occupation of the nuc-macromolecules by marker units can be achieved by the use of saturating concentration during the synthesis of the marker component.

For instance, in cases where only qualitative detection is important, the exact number of marker units per one nuc-macromolecule has a subordinate role. In such cases the availability of a stable signal is important in itself.

To an expert in the field it should be evident that the said marker components have substantially greater molecule size and molecule measures, than the respective nuc-components themselves. Other examples of macromolecular marker components should readily suggest themselves to an expert in the field.

1.3.3.4 Substrate Properties of the Nuc-Macromolecules

1.3.3.4.1 Substrate Properties of the Nuc-Component

Incorporation of the First Nuc-Component of a Sequence-Specific Nucleotide Conjugate.

The nuc-component integrated in a nuc-macromolecule can serve as a substrate for different enzymes. For instance, a nucleoside triphosphate as the nuc-component serves as a substrate for a polymerase, so that the nuc-component can be incorporated in a growing strand by a polymerase and therefore the whole nuc-macromolecule can be coupled covalently to the strand.

On one hand, the substrate properties of the nuc-component determine the substrate properties of the nuc-macromolecules. For example, a nuc-component can be a 2'-deoxynucleoside-triphosphate and thus represent a potential substrate for DNA polymerases or a ribonucleoside-triphosphate and therefore be a potential substrate for RNA polymerases. Further, the nuc-component can serve as a terminator, so that only a single nuc-macromolecule can be incorporated.

Nucleotides with modified sugar moieties, described in Section 1.3.3.1.3 Variations on sugar, represent examples of terminating nuc-components. Further extension of the same strand is not possible after incorporation of such nucleotides.

In another embodiment, the nuc-component serves as a reversible terminator that allows a controlled stepwise elongation reaction to be carried, such as described for example in Ju et al. U.S. Pat. No. 6,664,079, Tcherkassov WO 02088382.

If the marker is coupled to the base of the nuc-component, then it can be covalently bound to the newly synthesized strand. As a result, its properties can influence the properties of the newly synthesized nucleic acid, for example its extendibility, cleavability, affinities etc.

By coupling the marker to the gamma phosphate group of the nuc-component, the marker can be cleaved from the remainder of the incorporated nuc-component during the incorporation of the nucleotide conjugates by polymerase. This allows only the nuc-component to be incorporated into the newly synthesized strand.

On the other hand, the marker (e.g. the target domain bound to the target sequence) can have a significant influence on the properties of nuc-components: due to the binding of the target domain to the target sequence, the local concentration of nuc-components can increase significantly. This increase in the local concentration can have an effect on the acceptance of the nuc-component of the nuc-macromolecule that is bound to the target sequence by a polymerase. For example, the discriminating capability of the polymerase regarding the nucleobase or other modifications of the nuc-component can be changed. In addition, the competition between natural nucleotides available in the solution in a free state (such as dNTPs) and the nuc-component of the nuc-macromolecule that is bound to the target sequence can be shifted in favor of the incorporation of the nuc-component.

These changes in the local concentration of the nuc-component—a strong increase in the vicinity of the bound target domain—make it possible to use a much broader range of nucleotide analogues as nuc-components, for example those which have very little incorporation efficiency under usual reaction conditions.

Further, the target domain provides the possibility of preferred labeling in favor of target sequences. This is particularly advantageous in the presence of strong contamination with unwanted nucleic acid chains, i.e., interfering DNA: the specific yield of a reaction can be increased as compared with known, conventionally labeled nucleotides.

Coupling of antiviral nucleotide analogues as nuc-components within the nuc-macromolecule permits the selective suppression of viral polymerases.

The substrate properties of nuc-macromolecules can be strongly affected by the presence of natural nucleotides. If no binding of the target domain to the target sequence has occurred, the presence of competing nucleotides in the reaction can prevent or greatly reduce the incorporation of nuc-macromolecules into the growing strand. Conversely, if the target domain is bound to the target sequence, nuc-components of the nuc-macromolecules are incorporated into the growing strand despite the presence of highly concentrated competing nucleotides.

Consequences of the Incorporation of a Nuc-Component for Subsequent Incorporation Reaction in the Same Strand Incorporation of one or several nuc-components from a sequence-specific nucleotide conjugate can influence the next or subsequent steps of primer extension in a number of ways. The following conditions can be achieved:

Irreversible Stop/irreversible loss of the ability to undergo further synthesis (termination)

Reversible Stop/reversible loss of the ability to undergo further synthesis (reversible termination)

Continuation of primer extension with normal or slightly reduced speed (no or slight suppression of the ability to undergo further synthesis).

Continuation of primer extension with greatly reduced speed (suppression of the ability to undergo for further synthesis).

Temporal termination of the reaction through a combination of a temporal limitation of the primer extension reaction with much reduced speed of the reaction. The reaction produces prematurely terminated nucleic acid chains (FIG. 50).

Specifically, these results can be achieved through different combinations of nucleotide conjugate and/or polymerase selection and/or reaction conditions. Some examples are provided below:

Termination or irreversible stop of primer extension
  Use of 3'-deoxy-nucleotide triphosphates as nuc-component (modified 3'-OH position of the nuc-component),
  Incorporation of multiple nuc-components (for example between 5-10) of a nucleotide conjugate behind each other,
  Use of nucleotide conjugates bearing a bulky marker as a steric hindrance to polymerase, such as an oligonucleotide having a double-stranded portion, or a peptide or protein
  Use of relatively long target domains and polymerases that lack strand displacement activity
  Use of low concentrations of natural dNTP, for example in ranges below 50 µmol/l Reversible termination or reversible stop of primer extension:
  Cleavage of the linker between the nuc-component and the marker Continuation of primer extension with normal or slightly reduced speed (no or slight suppression of the ability to undergo further synthesis).
  Use of optimal conditions for the incorporation reaction
  Use of polymerase with high strand displacement activity
  Use of high concentrations of polymerases
  Incorporation of no more than two nuc-components directly behind each other
  Use of relatively high concentrations of natural dNTPs, for example above 50 µmol/l
  Use of relatively short target domains Continuation of primer extension at a greatly reduced speed (suppression of the ability to undergo further synthesis).
  Use of polymerases lacking or possessing only low strand displacement activity
  Use of non-optimal conditions for the incorporation reaction Incorporation of 3 to 5 nuc-components behind each other A person skilled in the art should be able to achieve optimum results in the incorporation reaction by changing individual parameters.

1.3.4 Low Molecular Marker of a conventially modified nucleotides is a state-of-the-art labeling for nucleotides, for instance, with one or two biotin molecules, one or two dye molecules, one or two hapten molecules (e.g., digoxigenin).

1.3.5 Conventionally Modified Nucleotide a nucleotide with a linker (average length between 5 and 30 atoms) and a marker. A conventionally modified nucleotide usually carries a marker with low molecular weight, e.g. one dye molecule or one biotin molecule or one hapten molecule (e.g. DNP or Digoxigenin).

These modifications can be used as the signal or anchor domain. Nucleic acid chains can be attached to a solid phase via biotin (function of an anchor domain), or a streptavidin labeled with a dye or an enzyme can be coupled via biotin (function of a signal domain).

1.3.6. Enzymes

1.3.6.1 Polymerases

In one embodiment, the nuc-macromolecules can be used as substrates for enzymes. Polymerases represent frequently used enzymes, which utilize nucleotides as substrates. They will be dealt with further as representative examples of other nucleotide-utilizing enzymes. One of the central abilities of polymerases consists in covalent coupling of nucleotide monomers to a polymer. Furthermore, the synthesis can be template-dependent (as for example DNA or RNA synthesis with DNA- or RNA-dependent polymerases) as well as independent of templates, e.g. terminal transferases (J Sambrook "Molecular Cloning" 3. Ed. CSHL Press in 2001).

If RNA is used as a substrate (e.g., mRNA) in the sequencing reaction, commercially available RNA-dependent DNA polymerases can be used, e.g. AMV reverse transcriptase (Sigma), M-MLV reverse transcriptase (Sigma), HIV reverse transcriptase without RNAse activity. For Klenow Fragment DNA polymerase a function as reverse transcriptase is also described. For certain applications, reverse transcriptases can be essentially free of RNAse activity ("Molecular cloning" in 1989, Ed. Maniatis, Cold Spring Harbor Laboratory), e.g. for use in mRNA labeling for hybridisation applications.

If DNA is used as a substrate (e.g. PCR-fragment), all the following polymerases are suitable in principle: DNA-dependent DNA polymerases with or without 3'-5' exonuclease activity ("DNA-Replication" in 1992 Ed. A. Kornberg, Freeman and company NY), e.g. modified T7-Polymerase for example of the type "Sequenase version 2" (Amersham Pharmacia Biotech), Klenow fragment of the DNA-Polymerase I with or without 3'-5' exonuclease activity (New England Biolabs), T4 DNA Polymerase, phi29 DNA Polymerase, polymerase Beta of different origin ("Animal Cell DNA polymerases" in 1983, Fry M., CRC Press Inc, commercially available from Chimerx), thermostable polymerases such as, for example, Taq-Polymerase (New England Biolabs), Vent Polymerase, Vent exo minus Polymerase, Deep Vent Polymerase, Deep Vent exo minus Polymerase, Pfu Polymerase, Tli Polymerase, Tfl Polymerase, Tth Polymerase, Thermosequenase, Pwo-Polymerase, Terminator, Terminator I, Terminator II, Terminator III, Bst DNA Polymerase, Bst DNA Polymerase, Large Fragment, Phusion® High-Fidelity DNA Polymerase, Phusion® High-Fidelity Hot Start DNA Polymerase, Phire® Hot Start DNA Polymerase, Phire® Hot Start II DNA Polymerase, Phusion® Flash High-Fidelity DNA Polymerase, Crimson Taq DNA Polymerase, DyNAzyme™ EXT DNA Polymerase, DyNAzyme™ II Hot Start DNA Polymerase, 9° $N_m$ DNA Polymerase etc. (for example from New England Biolabs, or from Promega, or from Roche, or from Qiagen).

Using modern genetic engineering methods, it is possible to construct polymerases which differ in their capabilities from naturally occurring enzymes, for example by the absence of certain activities or improved enzymatic parameters such as precision or processivity. An increasing number of companies manufacture such thermolabile and thermostable polymerases, which are used as optimized enzymes for PCR or other amplification or labeling methods. The basic functions of polymerases are retained, however: they are able to incorporate nucleotides into complementary strands during the synthesis. Such polymerases can also be used for the methods described. An expert is aware of how to bring about an optimization of the reaction conditions.

In one embodiment of the application, polymerases without strand displacement activity (no strand displacement) are preferred. Such polymerases may preferably be used for terminating reactions.

In a further embodiment of the application, polymerases with strand displacement activity (strand displacement) are preferred, for example Klenow exo minus, Vent polymerase exo minus, Bst-Polymerase large fragment, Phi 29 polymerase. Such polymerases may be used in assays that are based on a non-terminating reaction.

In one embodiment of the application, polymerases without 5'-3'-exonuclease activity are preferred, for example Vent exo minus, Bst polymerase large fragment. These polymerases do not degrade or cleave oligonucleotides that are bound to the target sequences. Nuc-macromolecules with target domain oligonucleotides consisting of DNA can be used with such polymerases.

In one embodiment of the application, polymerases without a 3'-5'-exonuclease activity are preferred, for example Taq polymerase or Klenow fragment exo minus. These polymerases are not able to remove nucleotides that have already been incorporated, such as terminating nucleotides for example (e.g. ddUTP used as nuc-component).

In one embodiment of the application, polymerases with a 5'-3-exonuclease activity are preferred, for example Taq polymerase or Bst polymerase. This activity can be utilized for example for the detection of target sequences by degradation of labeled probes (Taqman probes).

In one embodiment of the invention, polymerases that possess 5'-3'-exonuclease activity are used together with nucleotide conjugates whose function is not affected by the 5'-3'-exonuclease activity of polymerases. In one embodiment, this can be achieved by attaching the linker, which connects the nuc-component and target domain oligonucleotide, at an internal position in the oligonucleotide or at the 3'-position of the oligonucleotide. The nuc-component is thereby coupled to a part of the oligonucleotide that is not degraded by the exonuclease activity of the polymerase.

The chemical composition of the target domain oligonucleotide may include nucleotide analogs or different types of chemical bonding between the individual monomers in the oligonucleotide, which are insensitive to exonuclease activity, such as phosphorothioate nucleic acids (PTO), peptide nucleic acids (PNA), or locked nucleic acids (LNA) or phosphorothioate backbone. Other examples of oligonucleotides that can withstand exonuclease degradation are known to a person skilled in the art.

In a further embodiment, polymerases with 3'-5'-exonuclease activity are used. This can for example help to increase the accuracy of synthesis. In such an embodiment, nuc-components are preferably used which can withstand 3'-5'-exonuclease activity of a polymerase after their incorporation into the growing complementary strand. This can be achieved for example through the use of alpha-phosphorothioate nucleotide analogs.

DNA-dependent RNA polymerases can also be used, for example E coli RNA polymerase, T7 RNA polymerase, or SP6 RNA polymerase.

RNA-dependent RNA polymerases (RNA replicase) can be used for the amplification and labeling RNA, e.g. phi6 RNA polymerase (e.g. Q-beta replicase, polio replicase, 3Dpol, or replicase of hepatitis C virus, NS5b).

In the application, DNA-dependent DNA polymerases are considered as examples of polymerases.

Further literature sources and examples for selecting a proper polymerase, reaction conditions, etc. are presented in the chapter "Amplification Methods".

1.3.7 Cleavable Compound

A compound which is cleavable under mild conditions. This compound can represent a part in the linker and can be cleavable in one or several positions. It can be a chemically cleavable bond, such as, for example, disulfide, acetal, oxidative cleavable bonds (e.g. Linker comprising tartrate bond), thioester bonds (Short WO 9949082, Tcherkassov WO 02088382). It can also be a photo-chemically cleavable compound (Rothschild WO 9531429). It can also be an enzymatically cleavable compound (for instance, a peptide or polypeptide bond, Odedra WO 0192284), cleavable by peptidases, a poly- or oligo-saccharide bond, cleavable by disaccharidases, whereas the cleavage can be achieved by a specific enzyme between certain monomers of the cleavable bonds.

Several examples of cleavable compounds are known. The synthesis of such a compound is described, for instance, in (Tcherkassov WO 02088382, Metzker et al. Nucleic Acid Research 1994, v. 22, p. 4259-, Canard et al. Genes, 1994, v. 148, p. 1, Kwiatkowski U.S. Pat. No. 6,255,475, Kwiatkowski WO 0125247, Parce WO 0050642, Milton et al. WO 2004018493, Milton et al. 2004018497). A cleavable compound can be a part of the linker or can form the connecting part of the linker to the nucleotide, or the connecting part of the linker component to the marker component, or the connection between marker units and the core component.

1.3.8 DNA

Deoxyribonucleic acid of different origin and different length (e.g. oligonucleotides, polynucleotides, plasmides, genomic DNA, cDNA, ssDNA, dsDNA)

1.3.9 PTO

Nucleic acids with phosphorothioate backbone

1.3.10 PNA

Peptide Nucleic Acid

1.3.11 LNA locked nucleic acids

1.3.12 Nucleotides

Nucleotides serve as substrates for polymerases in a template dependent synthesis reaction. They can be incorporated into a complementary strand.

dNTP—2'-deoxynucleoside triphosphate or their analoga, as a substrate for DNA polymerases and reverse-transcriptases, e.g. dATP, dGTP, dUTP, dTTP, dCTP, dITP or their analoga like 7-Deaza-dATP or 7-Deaza-dGTP. Also other analoga of naturally occurring 2'-deoxinucleoside-triphosphates can be used as substrates by DNA-polymerases.

NTP—Ribonucleoside triphosphate or their analoga, as a substrate for RNA polymerases, UTP, CTP, ATP, GTP.

Abbreviation "NT" is used for the description of the length of a particular nucleic acid sequence, e.g. 1000 NT. In this case "NT" means nucleoside monophosphates.

The plural is formed by the addition of the suffix "-s"; "NT" means, for example, "one nucleotide", "NTs" means "several nucleotides".

Concentration of Nucleotides in an Assay

In the absence of unlabeled nucleotides (e.g. dNTP), nuc-macromolecules of the same base type can be incorporated by a polymerase in a sequence-specific manner as well as in a manner lacking sequence-specificity. Target-sequence-specificity is favored unexpectedly strongly when the target domain oligonucleotide of a nuc-macromolecule hybridizes to the target sequence. The presence of dNTP of the same base type as the base type of nuc-component creates a situation in which natural nucleotides and nuc-components of the nuc-macromolecule compete for incorporation. With increasing concentration of dNTP, the incorporation of nuc-macromolecules that lacks target sequence specificity is initially suppressed competitively by dNTP. This can be achieved at concentrations of the natural nucleotide of 1 to 100 μmol/l for example. At still higher natural nucleotide concentrations, for example at a concentration of 1 mmol/l to 100 mmol/l, sequence-specific incorporation of nuc-macromolecules bound to the target sequence is also increasingly suppressed.

The concentration of substrates for polymerases (e.g. dNTP) in an assay is chosen in such a way that the sequence-nonspecific incorporation of nuc-macromolecules with a target domain is completely suppressed, while sequence-specific incorporation is not significantly affected.

1.3.13 NAC

Nucleic acid chain (NSK abbreviation stands for German "Nukleinsäurekette"), DNA or RNA.

1.3.14 Term "the Whole Sequence"

The whole sequence is the sum of all the sequences to be analyzed in one experiment; it can comprise originally one or several NACs. Also, the whole sequence can display parts or equivalents of another sequence or sequence populations (e.g., mRNA, cDNA, Plasmid DNA with insert, BAC, YAC)

and can originate from one species or various species. The "whole sequence" can comprise one or several target sequences.

1.3.15 NACF

The nucleic acid chains fragment (NSKF abbreviation stands for German "Nukleinsäurekettenfragment") (DNA or RNA) which corresponds to a part of the whole sequence, NACFs—the plural form—nucleic acid chain fragments. The sum of the NACFs forms an equivalent to the whole sequence. The NACFs can be, for instance, fragments of the whole sequence (DNA or RNA), which result after a fragmentation step.

1.3.16 Primer Binding Site (PBS)

A PBS is the part of the target sequence to which the primer binds.

1.3.17 Reference Sequence

A reference sequence is an already known sequence, divergences from which in the analysed sequence or sequences (e.g. whole sequence) have to be determined. Reference sequences can be found in databases, such as, for example, the NCBI database.

1.3.18 Tm

Melting temperature

1.3.19 Steric Hindrance, Sterically Demanding Group or Ligand

A sterically demanding group or ligand which (by its chemical structure) changes the properties of the nucleotides coupled with this group in such a way that these nucleotides cannot be inserted successively by a polymerase in an extension reaction. One or several sterically demanding groups coupled to the nucleotide base can lead to the stop or to the impedance of further synthesis. Many of the markers, currently used in research, represents a sterical hindrance for the enzymes. Biotin, digoxigenin and fluorescent dyes like fluorescein, tetramethylrhodamine, Cy3-dye, are examples of such sterically demanding groups (Zhu et al. Cytometry in 1997, v. 28, p. 206, Zhu et al. NAR 1994, v. 22, p. 3418, Gebeyehu et al., NAR 1987, v. 15, p. 4513, Wiemann et al. Analytical Biochemistry in 1996, v. 234, p. 166, Heer et al. BioTechniques 1994 v. 16 p. 54). Further examples for sterically demanding groups can be linear or branched polymers with a compact three-dimensional structure, as for example proteins, nucleic acid chains, nanoparticles or dendrimers.

Another example for steric hindrance and its application is given in Cherkasov et al WO 2008043426.

1.3.20 Solid Phase Analysis

Solid phase is provided for the binding of labeled target sequences. A distinction is made between a direct and an indirect, i.e., transmitted binding of target sequences to the solid phase. Examples for solid phase are given in application Cherkasov et al WO2011050938.

1.3.21 Target Sequences

A target sequence is a sequence of a nucleic acid chain which is to be amplified or detected or analyzed. In modern biotechnology and medicine, many examples of the analysis of selected sequences are known. In one embodiment, the analysis consists of the detection of the presence of a particular target sequence or several target sequences. In another embodiment, the analysis consists of the detection of the sequential arrangement of bases in the target sequence, wherein said sequence is of interest. In another embodiment, the analysis consists in measurement of the amount of the target sequence.

The target sequence of organisms may be present as DNA or RNA. In modern research and industry, modified nucleic acid chains can be used, so that a target sequence may also be an artificial sequence, with or without modifications.

In an analytical test, multiple target sequences can be present. Examples of complex mixtures of target sequences are mRNA or cDNA mixtures or target sequences which have been generated in a multiplex PCR or mixtures of fragments of genomic DNA. Viral nucleic acid chains such as mixtures of viral variants, e.g. HIV sequences, may also represent mixtures of target sequences. Isolates from the patient also provide a mixture of nucleic acid chains, which may contain multiple target sequences, such as viral and bacterial target sequences.

An amplification reaction is often used for the detection or analysis of a target sequence or multiple target sequences (e.g. conducted by means of a polymerase chain reaction, PCR; a ligase chain reaction, LCR; or an isothermal amplification like HAD or LAMP). By these methods, equivalents of a target sequence can be generated, for example, as PCR fragments or LCR fragments. These amplification methods are conducted in such a way that the equivalents comprise the same information as the original target sequences. This allows an expert to draw conclusions regarding the target sequences in later steps of the analysis. For this reason, the amplified nucleic acid chains derived from a target sequence can also be considered and referred to as target sequences or equivalents of target sequences.

Owing to its great length, a target sequence can be represented by a plurality of amplified fragments. In one embodiment, the sum of the amplified fragments can be referred to as a target sequence. In a further embodiment, individual fragments are considered as independent target sequences.

An expert will recognize a similar situation with transformation of a target sequence from one format into another format, e.g. from DNA to RNA (transcription) or vice versa, generation of cDNA from mRNA by a reverse transcriptase. Those sequences which have been generated as a result of transformation are also referred to as target sequences or their equivalents.

In summary, target sequences or their equivalents can be considered as all kinds of sequences which have been derived from the original target sequence or have maintained original information from the starting target sequence and therefore allow conclusions regarding this initial target sequence to be drawn.

The target sequences can be derived from different species or belong to different genetic elements. Many organisms have been studied extensively in recent years. Thus, target sequences may represent, for example, PCR products or mRNA mixtures or small-RNA or plasmids. Many amplification and isolation methods have been established in order to enrich specific genetic elements.

The length of the target sequences can vary. For example, whole genomes can be considered as target sequences (e.g. the HIV genome), or several mRNA in a transcription profile. On the other hand, individual base variations at a single position in the genome can be of interest (SNP analysis). In the later case, a fragment of the sequence around the position of interest (SNP) is selected and amplified. This fragment can then be referred to as the target sequence.

Often, there is a need for the analysis of multiple target sequences, e.g. while searching for a pathogen. In such a case, an occurrence of specific target sequences in a material is of interest.

The choice of the target sequence is dependent upon the task. As mentioned above, sequences of different origins can represent target sequences. In the following, some examples of organisms which provide a source for selection of target sequences are listed.

The origin of the target sequence can be any organism; examples are viruses, prokaryota, archea, and eukaryota. Within eukaryota, protozoa or multicellular organisms, such as animals, including fishes, and plants can serve as sources of target sequences.

In an advantageous embodiment of the application, target sequences are selected from the following organisms: human organisms comprising, for example, protein coding sequences, for example, receptors, oncogenes, MHC, blood groups, and/or regulatory regions of the genome. Furthermore, target sequences can originate from farm animals, research animals and pets, for example cattle, pigs, horses, dogs, cats, mice, rats, rabbits, and monkeys. Fishes can serve as a source of target sequences. Sequences originating from trees and plants, either in their natural form or in genetically modified versions, can represent target sequences of interest, e.g. rice, maize, wheat, colza.

Fungi and bacteria of importance for human medicine or for veterinary, agricultural, industry or military applications can represent the origin of target sequences. Examples of such bacteria are *Staphylococcus aureus, Streptococcus pyogenes, Streptococcus pneumoniae, Pseudomonas* sp., *Salmonella, Shigella, Yersinia, Campylobacter, Helicobacer, Legionella, Mycobacteria, Chlamydia, N. gonorrhea, Yersinia, Francisella tularensis, B. antracis, Aspergillus fumigatus*. Examples of viruses are human pathogens: HIV, HSV, HPV, CMV, HBV, HCV, influenza, SARS, FSME. Examples of parasites are causative agents of malaria (Plasmodiidae), *Leishmania, Toxoplasma.*

The target sequences can be derived from a genomic fragment or from plasmids or mobile genetic elements.

In one embodiment, sequences are selected from genes which are responsible for resistance to antibiotics. Examples include organisms such as MRSA or VRE or carriers of ESBL resistances or quinolone resistance. In another embodiment, target sequences are selected from genes which are responsible for pathogenetic elements such as toxin-coding or invasins or adhesins, for example diphterotoxin, shiga toxin, or TSST.

In another embodiment, target sequences are selected from organisms which are of significance in the food industry, such as brewer's yeast or dairy products such as cheese or yogurt cultures.

In many analytical approaches control sequences are included in a particular test. This helps to control the quality of a reaction. Such control sequences can also represent target sequences.

For examples of applications for the design of diagnostic assays, wherein the invented nucleotides and methods can be of advantage, an expert is referred to the following literature:
"PCR Protocols for Emerging Infectious Diseases", 1996, ISBN 1-55581-108-6

"Molecular Diagnostic PCR Handbook" Gerrit J. Viljoen, 2005 ISBN 1-4020-3403-2
"PCR Detection of Microbial Pathogens" Konrad Sachse, 2003, ISBN 1-58829-049-2
"Clinical Applications of PCR" Y. M. Dennis Lo, 2006, ISBN 1-58829-348-3
"Microarrays in Clinical Diagnostics" Thomas O. Joos, 2005, ISBN 1-58829-394-7
"Molecular Diagnostics" William B. Coleman, 2006, ISBN 1-58829-356-4
"Single Nucleotide Polymorphisms, Methods and Protocols" Pui-Yan Kwok, 2003, ISBN 0-89603-968-4
"Molecular Microbiology, Diagnostic Principles and Practice" Fred C. Tenover, 2004, ISBN 1-55581-221-X
"Rapid Detection of Infectious Agents", Steven Specter, 1998, ISBN 0-306-45848-9
"Nucleic Acid Amplification Technologies, Applications to Disease Diagnosis" H. Lee, 1997, ISBN 1-881299-04-X
"PCR Primers, a Laboratory Manual" Carl W. Dieffenbach, 2003, ISBN 0-87969-653-2
"Real-Time PCR, Current Technology and Applications" Julie Logan, 2009, ISBN 978-1-904455-39-4
"Rapid Cycle Real-Time PCR, Methods and Applications" S. Meuer, 2001, ISBN 3-540-66736-9
"PCR Primer Design" Anton Yuryev, 2004, ISBN 978-1-58829-725-9
"PCR Troubleshooting, the Essential Guide" Michael L. Altshuler, 2006, ISBN 1-904455-07-7
"PCR in Bioanalysis" Stephen J. Meltzer, 1998, ISBN 0-89603-497-6
"PCR Protocols" John M. S. Bartlett, ISBN 0-89603-642-1
"PCR Technology Current Innovations" Thomas Weissensteiner, 2004, ISBN 0-8493-1184-5

1.3.21.1 Positive Selection of Target Sequences Vs. Negative Selection of Target Sequences Target sequences can be present as a part of mixture of nucleic acids, which contains variants of a target sequence, or sequences that are substantially similar to a target sequences. In biological samples, target sequences are often present in a much lower copy number than sequences that are very similar to these target sequences.

Examples of such mixtures of nucleic acids include: nucleic acid chains with mutations from a tumor and non-mutated, so-called wild-type nucleic acid chains from normal surrounding tissue; mutated genome parts of a virus (e.g. HIV virus) and the predominant sequence variant of a viral genome; circulating fetal DNA in the maternal bloodstream; nucleic acid chains of a bacterial or viral or fungal pathogen are often contaminated by nucleic acid chains of the normal flora.

A person skilled in the art is often aware of the composition of interfering sequences. One example of such known sequences concerns the wild-type sequences of an organism from which a tumor originates, the nucleic acid chains of which require analysis. Further, the position of presumed sequence variant of interest within the target sequence is often known, for example the sequence of a receptor in a tumor tissue.

The predominant variant in the sequence population of the HIV virus represents another example. A still further example concerns sequences of maternal DNA in the maternal bloodstream, wherein the fetal cells represent the target object. Germs of the normal flora can also represent interfering sequences of known composition. Such known sequences can interfere with the sensitivity of the analysis considerably.

There is thus not only a need for targeted, positive selection of target sequences (e.g. amplification, labeling, detection, sequence analysis), but also for targeted, negative selection (e.g. suppression of amplification or of labeling or of detection) of particular nucleic acid chains of known composition.

By definition, two groups of target sequences can be defined within an assay comprising such a mixture of nucleic acids: the first group includes one or more sequences that need to be positively selected, and the second group includes one or several sequences that should be negatively selected.

Prior art methods for the specific selection of target sequences are often inadequate for achieving selective enrichment of the target sequence from such a mixture. Especially when it is not possible to isolate the target sequence by means of sequence-specific primers, there is a great need for methods for suppressing the amplification or labeling or detection of associated nucleic acid chains that resemble the target sequence.

In one embodiment of the invention, chain-terminating sequence-specific nuc-macromolecules are used to suppress amplification of target molecules that are to be negatively selected.

In one embodiment of the invention, chain-terminating nuc-macromolecules are used to suppress labeling of target molecules that are to be negatively selected.

1.3.22 Primer

A primer is usually an oligonucleotide which is capable of binding to a complementary position in the target sequence and can be recognized by a polymerase. Nucleotides are incorporated into the 3' end of such primers.

A specialist knows many examples of primers. They are used for amplification of nucleic acid chains as well as for labeling reactions. They can sequence-specifically bind to the nucleic acid chains. Through the introduction of uniform primer binding sites and the use of appropriate uniform primers, many different nucleic acid chains can be amplified or labeled in one reaction. Hexamer primers are examples of nonspecific labeling. Other examples will be known to a person skilled in the area (see the literature references for PCR and microarrays). Primers can bind to the target sequences more or less specifically. In one embodiment, a primer is completely complementary to the target sequence and binds only to such a target sequence. In another embodiment, a primer comprises sequences which allow for binding to a plurality of target sequences.

In one embodiment, the primer is resistant towards one or several types of nucleases. Such primers can comprise various modifications, for example PTO, PNA, 2'-O-Me, or LNA monomers or other modifications. A person skilled in the art is familiar with such modifications.

In one embodiment, a primer comprises at least one such modification at one of its ends (e.g. at the 5'- or the 3'-end).

In one embodiment, a primer comprises at least one such modification in an internal position of the sequence of the target domain.

In one embodiment, a primer comprises such modification at either end and in internal regions of its sequence, wherein modifications can alternate with natural nucleotide monomers, resulting for example in a PTO-DNA mixed polymer. In one embodiment, a primer comprises such modification over its entire length.

In one embodiment, a primer comprises more than one type of modification over its entire length, resulting in a mixed polymer, e.g. of PNA and PTO.

In this application, primers can be used for a labeling reaction as well for an amplification. Depending on the application, primers can be used only for one task (either labeling or amplification) or they can be used for both. A specialist should recognize in which situations which primer should be used.

A primer can be modified through the coupling of further structures. These structures can be used, for example, for signaling or for binding to the solid phase. Such a modified primer comprises, for example, at least one signal domain or least one anchor domain.

The structures of the anchor domain or the signal domain of a modified primer can be composed in accordance with the same principles as described for domains of a nuc-macromolecule (see section on anchor domain and signal domain).

In one embodiment, for example, an anchor domain consisting of nucleic acid chain (such as DNA, PNA, LNA) is attached to the 5' end of the primer. In another embodiment, a biotin residue or a dye molecule, for example, can be coupled to the primer (as a signal or an anchor domain).

The use of modified primers allows the binding of nucleic acid chains to the solid phase. Primers labeled with a signal domain can be used for detection. Some examples are given below.

An expert can find examples of primer design in the following literature sources:

"Nucleic Acid Amplification Technologies, Applications to Disease Diagnosis" H. Lee, 1997, ISBN 1-881299-04-X "PCR Primers, a Laboratory Manual" Carl W. Dieffenbach, 2003, ISBN 0-87969-653-2

"Real-Time PCR, Current Technology and Applications" Julie Logan, 2009, ISBN 978-1-904455-39-4

"Rapid Cycle Real-Time PCR, Methods and Applications" S. Meuer, 2001, ISBN 3-540-66736-9

"PCR Primer Design" Anton Yuryev, 2004, ISBN 978-1-58829-725-9

"PCR Troubleshooting, the Essential Guide" Michael L. Altshuler, 2006, ISBN 1-904455-07-7

"PCR in Bioanalysis" Stephen J. Meltzer, 1998, ISBN 0-89603-497-6

"PCR Protocols" John M. S. Bartlett, ISBN 0-89603-642-1

"PCR Technology Current Innovations" Thomas Weissensteiner, 2004, ISBN 0-8493-1184-5

"PCR Protocols for Emerging Enfectious Diseases", 1996, ISBN 1-55581-108-6

"Molecular Diagnostic PCR Handbook" Gerrit J. Viljoen, 2005 ISBN 1-4020-3403-2

"PCR Detection of Microbial Pathogens" Konrad Sachse, 2003, ISBN 1-58829-049-2

"Clinical Applications of PCR" Y. M. Dennis Lo, 2006, ISBN 1-58829-348-3

"Microarrays in Clinical Diagnostics" Thomas O. Joos, 2005, ISBN 1-58829-394-7

"Molecular Diagnostics" William B. Coleman, 2006, ISBN 1-58829-356-4

"Single Nucleotide Polymorphisms, Methods and Protocols" Pui-Yan Kwok, 2003, ISBN 0-89603-968-4

"Molecular Microbiology, Diagnostic Principles and Practice" Fred C. Tenover, 2004, ISBN 1-55581-221-X "Rapid Detection of Infectious Agents", Steven Specter, 1998, ISBN 0-306-45848-9

The following sources show examples of modified oligonucleotides which can be used as a primer or can be bound to primers:

"Oligonucleotide Synthesis, Methods and Applications" Piet Herdewijn, 2004, ISBN 1-58829-233-9

"Protocols for Oligonucleotide Conjugates, Synthesis and Analytical Techniques" Sudhir Agrawal, 1993, ISBN 0-89603-252-3

"Protocols for Oligonucleotide Conjugates, Synthesis and Properties" Sudhir Agrawal, 1993, ISBN 0-89603-247-7

"The Aptamer Handbook" Sven Klussmann, 2006, ISBN 10: 3-527-31059-2

"Pharmaceutical Aspects of Oligonucleotides" Patrick Couvreur, 2000, ISBN 0-748-40841-X "Triple Helix Forming Oligonucleotides" Claude Malvy, 1999, ISBN 0-7923-8418-0

"Artificial DNA, Methods and Applications" Yury E. Khudyakov, ISBN 0-8493-1426-7

1.3.23 Methods for Amplification of Nucleic Acid Chains

There are a variety of known methods which are used for the amplification of nucleic acid chains. Examples are isothermal amplification and PCR and their various modifications, such as hot start PCR and multiplex PCR. In an analytical approach, target sequences can be used as such or equivalents of target sequences (see above) or products of an amplification, the amplificats (equivalents of target sequences). In this application, some methods are described. They are intended to illustrate the invention, not provide a limitation.

Examples of amplification of target sequences, or their equivalents, will be known to a person skilled in the area. Many scientific papers describe the amplification of target sequences using a PCR or an isothermal amplification (for example SDA, strand displacement amplification), HDA (helicase-dependent amplification) or LAMP (loop-mediated isothermal amplification). Reaction conditions for such an amplification for a particular target sequence can be found in databases, for example in the NCBI database, PubMed. In such literature resources, the primer sequences as well as amplification conditions are indicated. Many target sequences are amplified using commercially available kits. Using examples of real-time PCR, sequences for probes can also be selected. Many examples of amplification methods which can potentially be used for replication of target sequences or can be combined with a labeling reaction are shown in the following sources.

"Nucleic Acid Amplification Technologies, Applications to Disease Diagnosis" H. Lee, 1997, ISBN 1-881299-04-X "PCR Primers, a Laboratory Manual" Carl W. Dieffenbach, 2003, ISBN 0-87969-653-2

"Real-Time PCR, Current Technology and Applications" Julie Logan, 2009, ISBN 978-1-904455-39-4

"Rapid Cycle Real-Time PCR, Methods and Applications" S. Meuer, 2001, ISBN 3-540-66736-9

"PCR Primer Design" Anton Yuryev, 2004, ISBN 978-1-58829-725-9

"PCR Troubleshooting, the Essential Guide" Michael L. Altshuler, 2006, ISBN 1-904455-07-7

"PCR in Bioanalysis" Stephen J. Meltzer, 1998, ISBN 0-89603-497-6

"PCR Protocols" John M. S. Bartlett, ISBN 0-89603-642-1

"PCR Technology Current Innovations" Thomas Weissensteiner, 2004, ISBN 0-8493-1184-5

"PCR Protocols for Emerging Infectious Diseases", 1996, ISBN 1-55581-108-6

"Molecular Diagnostic PCR Handbook" Gerrit J. Viljoen, 2005 ISBN 1-4020-3403-2

"PCR Detection of Microbial Pathogens" Konrad Sachse, 2003, ISBN 1-58829-049-2

"Clinical Applications of PCR" Y. M. Dennis Lo, 2006, ISBN 1-58829-348-3

"Microarrays in Clinical Diagnostics" Thomas O. Joos, 2005, ISBN 1-58829-394-7

"Molecular Diagnostics" William B. Coleman, 2006, ISBN 1-58829-356-4

"Single Nucleotide Polymorphisms, Methods and Protocols" Pui-Yan Kwok, 2003, ISBN 0-89603-968-4

"Molecular Microbiology, Diagnostic Principles and Practice" Fred C. Tenover, 2004, ISBN 1-55581-221-X "Rapid Detection of Infectious Agents", Steven Specter, 1998, ISBN 0-306-45848-9

According to the present invention, incorporation of sequence-specific nuc-macromolecules into the complementary strand of one or several target sequences can be combined with amplification of at least one target sequence by means of one known amplification method.

An advantageous example is the use of least one type of nuc-macromolecule (nucleotide conjugate) comprising at least one target domain oligonucleotide that is complementary to the target sequence in a PCR reaction, in which this target sequence is amplified. The nucleotide conjugate is incorporated during the extension of the complementary strands in one step of the PCR. The result is an amplified target sequence that has been labeled with one type of nucleotide conjugate.

Another beneficial example is the use of at least two different types of nuc-macromolecules (nucleotide conjugates) with respectively different target domain oligonucleotides that are complementary to one target sequence in a PCR reaction, in which this target sequence is amplified. The nucleotide conjugates are incorporated during the extension of the complementary strands in one step of the PCR. The result is an amplified target sequence that has been labeled with at least two types of nucleotide conjugate.

Another beneficial example is the use of at least two different types of nuc-macromolecules (nucleotide conjugates) with respectively distinct target domain oligonucleotides directed to distinct target sequences in a multiplex PCR reaction, in which at least two distinct target sequences are amplified. The nucleotide conjugates are incorporated during the extension of the complementary strands in one step of the PCR. This results in two amplified target sequences, each of which is labeled with a specific nucleotide conjugate.

Another beneficial example is the use of one type of nuc-macromolecule (nucleotide conjugate) with chain-terminating properties (e.g. with ddUTP as the nuc-component) and a target-domain oligonucleotide in a PCR, wherein the amplification of at least one known target sequence is to be suppressed (suppression of co-amplification). In a case where a target sequence (A) and a target sequence (B) are simultaneously present, only target sequence (A) is to be amplified. Target sequences (A) and (B) are sufficiently different from each other so that the target domain oligonucleotide binds differently to the two sequences. The sequence of target domain oligonucleotide is designed to be complementary to the target sequence (B). The sequence-specific chain-terminating nucleotide conjugate is incorporated during the extension of the complementary strands in one step of the PCR. After incorporation, chain elongation is terminated. The amplification of target sequence (B) is thus suppressed. Only target sequence (A) emerges as an amplification product of the PCR.

Instead of PCR, other amplification techniques can also be used, such as helicase-dependent amplification (HDA), or loop-mediated isothermal amplification (LAMP), or SDA (strand displacement amplification), or modifications of these techniques, such as real-time PCR, COLD-PCR (co-amplification at lower denaturation temperature PCR), or SMART 2 Amplification.

During such amplification procedures, nucleotide conjugates can bind via their target domains to corresponding target sequences and can be incorporated during extension of a complementary strand by polymerases. The use of terminating nuc-macromolecules can result in sequence-specific suppression of amplification of one or more target sequences. Otherwise, the use of non-terminating nuc-macromolecules leads to sequence-specific labeling of the amplified target sequence. The sequence-nonspecific labeling of nucleic acid chains by sequence-specific nuc-macromolecules is suppressed in the presence of sufficiently high concentrations of other substrates for polymerases (e.g. dNTPs: dATP, dGTP, dCTP, dTTP) (see below).

The result of amplification can be analyzed with end-point methods (for example by means of gel electrophoresis or sequencing), or with real-time methods (e.g. SYBRgreen-based methods).

1.3.25 Methods of Detection

An expert knows many detection methods which are currently used in analysis of nucleic acid chains.

Thus, direct detection methods (signal imaging methods) and indirect methods (signal transmitting methods), single-step methods, or multi-step methods, as well as physical, enzymatic, chemical, or electrochemical methods can be used for detection. Many signal-amplification methods are also known. It is up to an expert to choose which method of detection is better suited for a particular application. In this application, some examples are given. These examples are intended to demonstrate and not to restrict a potential diversity of detection methods which are compatible with the described structures of nuc-macromolecules and methods of their use according to this invention.

For example, fluorescence-based methods, methods based on color generation by an enzymatic reaction, like ELISA, or methods based on particles (such as colloidal gold or agglutination) can be used. Other examples are given in the chapter describing the signal domain of markers of nuc-macromolecules.

Many detection methods are described in literature sources for solid phase and amplification (see the corresponding chapters).

1.3.26 Hybridization Probe

In an advantageous embodiment, a combination of at least one sequence-specific nuc-macromolecule and at least one further oligonucleotide, a hybridization probe, is used in a reaction.

A hybridization probe is an oligonucleotide which is capable of sequence-specific binding to the target sequence. Examples of the application of such probes are known to those skilled in the art, for example as "Taqman probes" or "LightCycler probes". Some examples for the detection of nucleic acid chains by means of sequence-specific oligonucleotide probes described in the following references:

"Nucleic acid amplification technologies, applications to disease diagnosis" H. Lee, 1997, ISBN 1-881299-04-X "Real-Time PCR, current technology and applications" Julie Logan, 2009, ISBN 978-1-904455-39-4

"Rapid cycle Real-Time PCR, methods and applications" S. Meuer, 2001, ISBN 3-540-66736-9

"PCR Troubleshooting, the essential guide" Michael L. Altshuler, 2006, ISBN 1-904455-07-7

"PCR in Bioanalysis" Stephen J. Meltzer, 1998, ISBN 0-89603-497-6

"PCR Protocols" John M. S. Bartlett, ISBN 0-89603-642-1

"PCR Technology current innovations" Thomas Weissensteiner, 2004, ISBN 0-8493-1184-5

"PCR Protocols for emerging infectious Diseases", 1996, ISBN 1-55581-108-6

"Molecular Diagnostic PCR Handbook" Gerrit J. Viljoen, 2005 ISBN 1-4020-3403-2

"PCR Detection of microbial Pathogens" Konrad Sachse, 2003, ISBN 1-58829-049-2

"Clinical Applications of PCR" Y. M. Dennis Lo, 2006, ISBN 1-58829-348-3

"Molecular Diagnostics" William B. Coleman, 2006, ISBN 1-58829-356-4

"Single nucleotide polymorphisms, methods and protocols" Pui-Yan Kwok, 2003, ISBN 0-89603-968-4

"Molecular Microbiology, diagnostic principles and practice" Fred C. Tenover, 2004, ISBN 1-55581-221-X "Rapid detection of infectious Agents", Steven Specter, 1998, ISBN 0-306-45848-9

"Nucleic acid amplification technologies" Lee et al 1997, ISBN 0-8176-3921-7

"Advanced technologies in diagnostic microbiology" Tang et al. 2006, ISBN 10: 0-387-29741-3, "Molecular diagnostics for the clinical laboratories" Coleman, 2006, ISBN 1-58829-356-4

"Fluorescent Energy Transfer Nucleic Acid Probes" Vladimir V. Didenko, 2006, ISBN 1-58829-380-7

"Protocols for nucleic acid analysis by nonradioactive probes" Elena Hilario, 2006, ISBN 1-58829-430-7

"Nonisotopic DNA Probe Techniques" Larry J. Kricka, 1992, ISBN 0-12-426295-3

"Handbuch Immunchemische Färbemethoden", 2003, DakoCytomation, ISBN 3-00-011868-3

In one embodiment, the hybridization probe can be used as a means for a detection reaction (e.g., probes for 5'-3'-exonuclease assay). In a further embodiment of the invention, hybridization probes can be used to attach the labeled nucleic acid chains to the solid phase.

In a further embodiment of the invention, hybridization probes are used which are capable of competing with at least one target domain of a nucleotide conjugate for the binding to the target sequence.

A hybridization probe can be constructed similar to a nuc-macromolecule, but without a nuc-component. Consequently, such a hybridization probe cannot be incorporated into the complementary strand by a polymerase.

A hybridization probe comprises at least one target domain which is complementary to a target sequence (e.g. an oligonucleotide). In a further embodiment of the invention, a hybridization probe comprises at least one target domain complementary to a target sequence (e.g. an oligonucleotide), and optionally at least one signaling domain (e.g. fluorescent dye) and/or at least one anchoring domain (e.g. another oligonucleotide).

The structures (e.g. sequence length, composition, modifications to the 3'-end and the 5'-end) of the target domains, of the anchor domains, and of the signaling domains of a hybridization probe can be assembled according to the same principles as described for domains of a nuc-macromolecule (see corresponding sections on nuc-macromolecules). A significant difference is that a hybridization probe does not include a nuc-component, which means that it cannot be covalently attached to the growing strand by any polymerase.

The structure of an oligonucleotide probe can be described via the composition of its domains; for example [T1;A1] is a probe with a target domain oligonucleotide directed against target sequence (1) and an anchor domain (e.g. an oligonucleotide or a biotin-moiety). In another example, a hybridization probe consists of a target domain oligonucleotide and a marker (e.g. fluorescent dye). Such a hybridization probe can be described as [T1;S1].

A combination of labeled hybridization probes provides an example of sequence-specific detection of target sequences. Within such a combination, hybridization probes may have the following structures for example: hybridization probe 1 [T1;S1] in combination with hybridization probe 2 [T2;S2], wherein both target domain oligonucleotides [T1] and [T2] bind at adjacent, non-overlapping positions of a target sequence and their signaling domains (S1 and S2) may represent fluorescent dyes that form a FRET pair with each other. When both probes [T1;S1] and [T2;S2] bind to one target sequence, a fluorescent signal is generated. This signal is detected and indicates the presence of target sequence in an assay. A plurality of probe pairs can be used, so that a multiplexed analysis is possible.

Another example of sequence-specific detection of target sequences is provided by a combination of a labeled hybridization probe (1) [T1;S1] and a hybridization probe (2) [T2;A1]. The anchor domain [A1] of hybridization probe (2) facilitates binding to the solid phase (see section on anchor domains of nuc-macromolecules). The target domain oligonucleotides of both probes bind to one strand of a target sequence, the anchor domain [A1] allows for binding to the solid phase, and signal-domain [S1] allows for detection, for example through the binding of gold nanoparticles. A plurality of probe pairs can be used, so that a multiplexed analysis is possible.

Hybridization probes of the type "molecular beacon" represent yet another example of sequence-specific detection of target sequences.

Hybridization probes of the type "partially double-stranded linear DNA probes" represent yet another example of sequence-specific detection of target sequences ("Thermodynamically modulated partially double stranded linear DNA probe design for homogeneous real time PCR" Huang et al. NAR, 2007, v. 35 e101).

Yet another example for a sequence-specific detection of target sequences is the 5'-3-exonuclease assay (also known as Taqman assay). A polymerase with 5'-3'-exonuclease activity can cleave individual nucleoside monophosphates from the 5'-end of a nucleic acid fragment. The assay is set up as follows: use a hybridization probe (an oligonucleotide) complementary to a target sequence with a reporter dye at one end and a quencher moiety at the other end. The reporter dye and quencher form a FRET pair, and the distance between the two modifications is chosen in such a manner that the signal from the reporter dye is partially or completely suppressed (quenching). Upon binding to the target sequence, the polymerase can degrade the probe, resulting in spatial separation between the reporter dye and the quencher molecule. The signal from the reporter dye can be detected. When there is strand extension by the polymerase and an interaction between the probe and the target sequence the intensity of the signal increases.

In an advantageous embodiment of the invention, the hybridization probes mentioned above are used together with nuc-macromolecules in the same assay. A key advantage of using nuc-macromolecules in combination with known hybridization probes is that nuc-macromolecules are covalently bound to the growing strand of the target sequences, and this is associated with robustness in subsequent processes (e.g. labeling, termination, introduction of an anchor domain).

By way of example, sequence-specific terminating nucleotide conjugates can be used to prevent the amplification of a target sequence. This advantageous embodiment involves a combination of at least one type of hybridization probe directed to one target sequence and at least one type of terminating nuc-macromolecules (e.g. with ddUTP as nuc-component) directed to a different target sequence. The use of such a combination in an amplification assay (e.g. with simultaneous detection of amplification in real-time PCR) ensures amplification and detection of the first target sequence while amplification of another target sequence can be specifically suppressed.

In a further embodiment, hybridization probes are used in combination with sequence-specific nucleotide conjugates for detection. In such a combination the nuc-macromolecule can optionally function as a marker (e.g. nuc-macromolecules with the following structure: nuc-linker-[T1;S1]) or facilitate binding to a solid phase (e.g. nuc-macromolecules with the following structure: nuc-linker-[A1;T1].

In one embodiment of the invention, nucleotide conjugates are used together with polymerases with 5'-3'-exonuclease activity, wherein the function of said nucleotide conjugates are not affected by the exonuclease activity. This can be achieved for example by coupling of the linker, which connects the oligonucleotide and the nuc-component, at an internal position in the oligonucleotide, or at the 5'-position of the oligonucleotide. The nuc-component is thereby coupled to a part of the oligonucleotide that is not degraded by the exonuclease activity of the polymerase. The chemical composition of the target domain (i.e., the oligonucleotide complementary to the target sequence) may comprise nucleotide analogs or different types of chemical bonding between the individual monomers in the oligonucleotide, which are insensitive to exonuclease activity, such as phosphorothioate backbone (PTO), peptide nucleic acids (PNA), or locked nucleic acids (LNA). Other examples of oligonucleotides that can withstand exonuclease degradation are known to person skilled in the art.

In a further embodiment, hybridization probes are used in combination with sequence-specific nucleotide conjugates, wherein the hybridization probe can compete with nucleotide conjugates in binding to at least one target sequence. In such an embodiment, the hybridization probe and the target domain of the nucleotide conjugate differ, for example, in one position of the corresponding sequence. Such a hybridization probe may reduce or prevent a mismatch binding of the target domain to a sequence similar to the target sequence. Use of such hybridization probes is shown in the section Examples (filter-1-oligonucleotides).

1.3.27 Further Enzymes

Different enzymes are used in modern diagnosis and research for labeling and amplification methods. These enzymes and their effect on the reactions will be known to a person skilled in the area. Their use can also be advantageous in combination with methods described in this application. Here are some examples:

Uracil-N-glycosidase is often used to avoid cross-contamination. The enzyme is thermolabile and is inactivated by PCR conditions.

Ligases are used for linking nucleic acid strands. Ligases can be added as thermolabile or thermostable variants into a reaction.

Pyrophosphatases can be supportive of a reaction due to the hydrolysis of pyrophosphate, the by-product of a reaction to the incorporation of nucleotides. Thermolabile or thermophilic forms can be purchased.

Helicase unfold the double strand. Their use is preferred for amplification under isothermal conditions.

Single-strand binding protein binds to single-stranded DNA and prevents the formation of secondary structures.

Some of these proteins or enzymes require cofactors or an energy carrier such as ATP. It will be obvious to an expert that these substances should be added to the appropriate reaction.

Within the optimization procedure of a reaction, the above-mentioned proteins or enzymes as well as their substrates/co-factors can be used.

In one embodiment, kits for labeling reactions comprise these enzymes and their substrates/cofactors.

1.3.28 Nucleases

Different types of nucleases are known to a person skilled in the art ("Nucleases, Molecular Biology and Application" (published by, N. C. Mishra, Wiley Interscience 2002, ISBN 0-471-39461-0).

In preferred embodiments of the present invention, nucleases are used for the isolation of nucleic acids labeled with sequence-specific nucleotide conjugates. The use of nucleases in combination with nucleotide conjugates that have particular properties (such as resistance to degradation by nucleases) may make it possible for a person skilled in the art to increase the specificity of analysis, or to accelerate or simplify the isolation process.

Sequence-specific labeling of nucleic acid chains with nucleotide conjugates, which are fully or partially able to withstand a nuclease degradation, is a means for changing the properties of DNA that has been labeled in this manner. The introduction of nuclease-resistant nucleotide conjugates (e.g. target domain comprises: PTO and/or LNA and/or PNA) in the newly synthesized DNA can lead to the protection of the newly synthesized DNA from nucleases.

As sequence-specific nucleotide conjugates exclusively or at least preferentially label target sequences, only those sequences are protected from nuclease degradation. The remaining, non-target sequences may be degraded by nucleases, as they are not protected. In this way, sequence-specific protection of the target sequences against nuclease degradation can be achieved.

The feature of protecting particular nucleic acid chains against nuclease attack can be used for a simplified isolation of the labeled DNA from the remaining components of the reaction mixture. Nuclease degradation can, for example, be used for purification of labeled, protected nucleic acids from non-labeled nucleic acids. This is advantageous, for example, in applications where there is a high potential for non-specific amplification of nucleic acid chains (for example in multiplex analysis) or where high specificity is required of the analysis (for example discrimination of sequence down to a single nucleotide). The target sequences are protected by the covalently incorporated, protective sequence-specific nucleotide conjugates and survive the nuclease degradation step. The non-specific amplified nucleic acids have different sequences and are not protected by protective nucleotide conjugates. Consequently, they are degraded in the nuclease degradation step.

Such isolation of labeled nucleic acid chains is fast (for example, the step of nuclease treatment lasts for only 5 sec to 30 sec, 30 sec to 2 min, 2 min up to 10 min, or longer than 10 min), simple (addition of an enzyme), and can be carried out under simple field conditions (many nucleases tolerate fluctuations of temperature and buffer conditions). This type of isolation of labeled nucleic acid chains is therefore particularly well suited for point-of-care procedures.

Preferably the following parameters for primer extension or amplification with sequence-specific nucleotide conjugates can be combined with the use of nucleases for the isolation of labeled nucleic acid chains:

Primer extension or amplification and sequence-specific labeling of nucleic acid chains by means of nucleotide conjugates with a target domain Chemical composition of individual components of the nucleotide conjugates (e.g. choice of the chemistry of the target domain, and/or anchor domain and/or signal-to-domain, such as PTO, LNA, PNA, 2'-O-Me, etc.) is adjusted to the particular nuclease Nucleases with a particular profile of substrate properties (e.g. DNA nucleases, RNA nucleases, exo-nucleases, endo-nucleases, double-strand (ds-nucleases) and single stranded (ss-nucleases)) are chosen for a particular type of isolation Combinations of primers and dNTP with nuclease protective properties can be used to produce longer segments of labeled nucleic acid chains In advantageous embodiments, particular segments of the labeled nucleic acid chain are isolated by means of selection of suitable combinations of protective nucleotide conjugates, protective primers, natural or protective dNTP, and nucleases with suitable substrate properties Degradation of non-labeled fragments of DNA (e.g. non-labeled portions of the target sequence or non-specifically amplified nucleic acid chain fragments during PCR) is preferably performed before a detection step.

In one embodiment, the following combinations of components for sequence-specific primer extension or amplification and sequence-specific labeling are preferably used for example:

At least one target sequence: for example DNA

At least one primer which comprises at least one nuclease-protective modification, such as PTO At least one sequence-specific nucleotide conjugate with a target domain, wherein the target domain comprises at least one of the following variants of the nucleic acid backbone: PTO, LNA, PNA, morpholino, 2'-O-Me. These modifications can be used individually or as a mixed-polymer in combination with DNA or RNA At least one alpha-phosphorothioate-dNTP At least one natural dNTP At least one DNA polymerase with the ability to extend nuclease-protected primers The resulting labeled nucleic acid chains are brought into contact with at least one nuclease that has the following properties:

Degradation of non-labeled fragments (e.g. DNase I or Micrococcal nuclease)

Lack of degradation of labeled portions of the nucleic acid chain

After the degradation reaction, the mixture in which labeled nucleic acid chains are present can be analyzed, for example by means immunochromatographic assays.

In an advantageous embodiment, nucleases are used for the decontamination of the reaction mixture by means of complete destruction of non-labeled nucleic acid chains. This step ensures that all matrices capable of amplification are eliminated after an amplification reaction.

In one preferred embodiment, ds- and ssDNA-specific nucleases are used (e.g. DNase I). In a further embodiment, ss-specific nucleases are preferably used. In another embodiment, non-specific nucleases are preferably used (e.g. micrococcal nuclease). In a further embodiment, exonucleases are preferably used, e.g. 3'-exonuclease or 5'-exonuclease. In a further embodiment, sequence-specific endonucleases are preferably used.

Many nucleases are commercially available, for example from New England Biolabs (NEB) or Fermentas.

In particular, the following nucleases from different organisms can be used: deoxyribonucleases (e.g. DNase I, II, III, IV, V, VI, VII, VIII), ribonucleases, restriction endonucleases of type II (e.g. EcoRI, BamH1, HindIII), exonucleases (e.g. exonuclease I, II, III, IV, V, VI, VII), endonucleases (e.g. endonuclease I to VII). These and other examples of nucleases are described in "Nucleases, Molecular Biology and Application" (published by, N. C. Mishra, Wiley Interscience 2002, ISBN 0-471-39461-0.

Nucleases are preferably used for the isolation of labeled fragments in suitable buffers together with the co-factors necessary for their function (e.g. metal ions).

EXAMPLES 1.5.1 General Procedure of the Incorporation Reaction

As an example for an incorporation reaction, the labeling of a single stranded DNA with nuc-macromolecules can be considered. For a labeling reaction, nucleic acid chains are provided and contacted with a primer, and a polymerase, and at least one kind of nuc-macromolecules and incubated under conditions which allow the primer to be extended by the polymerase. Through the incorporation of nuc-macromolecules into the growing strand, domains of nuc-macromolecules are coupled to those growing strands of nucleic acid chains.

In an advantageous embodiment of the application, the nucleic acid chains are labeled with nuc-macromolecules, which comprise at least one target domain specific for the target sequence. This domain binds to the target nucleic acid chain to be labeled at the 3'-side of the primer allowing the nuc-macromolecules to bind in a sequence-specific way to the nucleic acid chain to be labeled.

The nuc-component of the nuc-macromolecule is preferentially chosen so that it is capable of forming a complementary base pair with at least one nucleotide in the target sequence. Such nucleotide is located preferentially in the 3' direction of the hybridized primer, so that a polymerase is capable of incorporation of the nuc-component into the growing strand during the extension of the 3' end of the primer.

Due to the high local concentration of the nuc-component in the vicinity of the target domain, it is also possible to use a nuc-component which does not makes a base-pair with a nucleotide in the target sequence but is incorporated anyway by a polymerase disregarding the proper base pairing.

In a further advantageous embodiment of the application, nucleic acid chains are labeled with nuc-macromolecules which comprise at least one target domain, and at least one anchor domain. The anchor domain is able to bind to a binding partner on a solid phase. After a labeling reaction, a solid is provided which comprises such a binding partner. Labeled nucleic acid chains can be specifically bound to this solid phase by incubation with such a solid phase.

In a further advantageous embodiment of the application, nucleic acid chains are labeled with nuc-macromolecules which comprise at least one target domain and at least one signal domain. After a labeling reaction, the labeled nucleic acid sequence can be detected based on the specific signal to the signal domain. In the following, individual components of the labeling reaction and examples of their combinations are discussed individually.

1.5.2 Examples of Nucleic Acid Chain/Starting Material/Target Sequences

Different nucleic acids can be used as a template for the synthesis of complementary strands. Many methods are known to one skilled in the art, how to isolate nucleic acids from the material and to provide a target sequence therefrom.

Either DNA or RNA can serve as a template. Using appropriate amplification techniques, target sequences can be provided in sufficiently high concentrations (see the "amplification").

The length of the target sequences, for example, ranges between 20 and 50, 50 and 200, 200 and 500, 500 and 2000, 2000 and 10000, 10000 and 1000000 nucleotides or is over one million nucleotides. Individual segments of a gene or a complete genome can be defined as the target sequence.

Double stranded nucleic acid chains and single stranded nucleic acid chains or mixtures of double and single stranded nucleic acid chains can be provided. In a preferred embodiment of the invention, only one target sequence is provided.

In a further preferred embodiment of the invention, multiple target sequences can be provided. The number of different target sequences ranges preferentially from 2 to 5, 5 to 10, 10 to 20, 20 to 50, 50 to 100, 100 to 500, 500 to 1000, 1000 to 10000, more than 10000.

In a further preferred embodiment of the invention. further control sequences are added to the target sequences in order to control the quality of the analysis. The use of such control sequences is known to an expert.

In a further preferred embodiment of the invention, multiple target sequences are provided, whose number is greater than 1000. For example, such mixture can be a mRNA mixture or a cDNA mixture.

The target sequences can be amplified with different techniques (e.g. PCR, LCR, isothermal amplification, or by TMA (transcription mediated amplification).

The amplification of target sequences can be carried out in solution or on a solid phase.

In one embodiment of the invention, target sequences for a labeling reaction are already provided in an amplified form, for example, as products of a PCR reaction, or an LCR reaction, or an isothermal amplification or plasmids. The nucleic acid chains to be labeled can be provided in single-stranded or double stranded form. Further examples of the amplification of nucleic acids are known to a person skilled in the art.

In one embodiment, the amplification and the labeling of target sequences with nuc-macromolecules is conducted in separate reactions.

In a further preferred embodiment, the amplification and the labeling of target sequences with nuc-macromolecules in done a single reaction.

Before analysis, target sequences can be preselected using other techniques such as hybridization to microarrays.

The target sequences can be provided in a solution or attached to a solid phase.

The attachment to a solid phase can be covalent or affine. The solid phase can be in the form of, for example, flat surfaces, or beads, or nanoparticles, or gels. The attached target sequences can be used with a solid phase in certain combinations, for example, they can form an array on the solid phase, or the solid phase can comprise coding elements which allow a subsequent assignment of the solid phase and the target sequence. The coding can be done via in color.

In one embodiment of the invention, target sequences are provided in purified form. Several methods and techniques known to a person skilled in the art of how to purify nucleic acid chains (see the "amplification"). In another embodiment, the target sequences can be provided as a part of a sample material, such as blood, secretions, reaction mixture etc. Such materials are often referred to as a biological matrix in which the target sequences to be examined are contained.

Such biological matrix can also comprise other sequences except the target nucleic acid chains. Isolation of target sequences leads often to co-isolation of these non-target sequences. Such nucleic acid chains (non-target sequences) can also be considered as an accompanying nucleic acid chains or contamination. Also by-products of an amplification reaction may represent such contamination.

In one embodiment of the invention, a labeling reaction of target nucleic acid sequences comprises other nucleic acid chains (accompanying nucleic acid chain) which should not be labeled or should not be detected. DNA or RNA from a biological material can be such nucleic acids.

The various combinations of components are shown below.

1.5.3 Examples of Solutions

Usable solutions should allow for an enzymatic incorporation of nucleotides into the growing strand of nucleic acid chains. Aqueous buffer solutions are preferred as solutions for the labeling reaction. Many buffers are commercially available as concentrated form, such 10× concentration, (e.g. from New England Biolabs, Roche Molecular Diagnostics, Abbott, Qiagen, etc.). Suitable buffer substances, for example, Tris, HEPES and phosphate are used. The pH value is typically between 7 and 9, though, many polymerases can also work between pH 5 and 10. Other monovalent cations such as Li (+), Na (+), K(+), NH4 (+) are used in combination with anions such as Cl (−), S04 (2−) often added. Divalent cations such as Mg (2+) or Mn (2+) are added together with anions. Organic additives such as DMSO, glycerol, detergents (e.g. Tween), Betaine, PEG, antioxidants (such as DTT) are also often added to reactions. EDTA is often used in low concentrations to complex heavy metals.

The compositions of the solutions can vary and an optimal concentration of individual components can be adjusted by titration.

The corresponding buffers are preferentially part of a kit for the labeling of target sequences with nuc-macromolecules. They are preferentially provided in concentrated or dry form.

1.5.4 Polymerases for Labeling Reaction

DNA-dependent DNA polymerases, RNA-dependent DNA polymerases (reverse transcriptases), DNA-dependent RNA polymerases and RNA-dependent RNA polymerases can be used for the labeling reaction. Examples of polymerases are shown in the "Terms and Definitions" section.

In a preferred embodiment, polymerases without 3'-5'-exonuclease activity are used. In another preferred embodiment, polymerases with 3'-5'-exonuclease activity are used.

In a preferred embodiment, polymerases without 5'-3'-exonuclease activity are used. In another preferred embodiment, polymerases with 5'-3'-exonuclease activity are used.

In one embodiment, thermally labile polymerase, such as Klenow fragment, are used. In a further embodiment, thermostable polymerases, such as Taq polymerase or Vent polymerase exo minus are used.

So-called hot start polymerases can be used. These are polymerases whose activity is reversibly inactivated by an antibody or by a chemical modification. Such polymerases are activated, for example, by heating.

Mixtures of several polymerases can be used. Such a mixture comprises, for example, polymerases with different substrate properties such as reverse transcriptase and DNA-dependent polymerase, or thermilabile and thermostable enzymes can be combined.

The polymerases can be provided in dissolved form or in dry form. They can be provided with other substances in compositions, for example, for storage, combined with stabilizing substances such as glycerol or PEG. Compositions with polymerases can be provided, which are intended for storage at 4° C. or room temperature, such preparations are commercially available, for example, from GE Healthcare.

In a preferred embodiment of the application, polymerases are provided as constituents of a composition, wherein the said composition is provided in a dry state. The activation of the polymerase can be achieved by the addition of a liquid.

In a preferred embodiment of the application, one or several polymerases or compositions thereof are constituents of a kit and are preferentially provided in concentrated form.

In one embodiment, the same polymerase can be used for the amplification and for the labeling reaction of target sequences.

Appropriate polymerases are preferentially part of a kit for the labeling of target sequences with nuc-macromolecules.

1.5.5 Primer for the Labeling Reaction

In an advantageous embodiment of the invention, at least one oligonucleotide is used as a primer for enzymatic labeling of the target sequences in a reaction. The primer must be accepted by the polymerase used. Examples of oligonucleotides having a primer function are known to those skilled in art.

A primer for the labeling reaction is provided preferentially in the form of DNA. In another embodiment, primer is provided in form of RNA.

The length of the primer is preferentially between 6 and 10, 10 and 15, 15 and 20, 20 and 25, 25 and 30, 30 and 40, 40 and 50, 50 and 100, or even longer than 100 nucleotides. At least a part of the primer sequence can bind to the target sequence to form a double strand, according to Watson-Crick base pairing.

Preferentially this portion of the primer is located at the 3'-end of the primer so that an enzymatic incorporation reaction can take place after the binding of the primer to the target sequence.

In one embodiment, a primer is fully complementary to the target sequence.

Since sequence variants often occur in nature, it can be useful in some applications, if the primer can differ such sequence variants. In a further embodiment, the composition of the primer deviates from the ideal complementary composition with regard to the target sequence so that a mismatch can occur in the vicinity of the 3' end of the primer (such as one or more bases within the primer are not complementary to a target sequence variant). Such mismatch can be used to differentiate between sequence variants.

There are different designs for position of the primer within the target. In one embodiment, the primer is located at one end of the target sequence. In another embodiment, the primer is located within the target sequence. In a further embodiment, at least one target sequence-specific primer pair is used for the amplification and the labeling. In a further embodiment, at least one primer in such a primer pair is labeled with a signal domain. In a further embodiment, at least one primer in such a primer pair is labeled with an anchor domain.

A common primer or a plurality of different primers can be used in an analysis of multiple target sequences.

In a further embodiment, several primers per one target sequence can be used for the labeling reaction, wherein a plurality of primers can be capable of binding to one strand, or both strands of the target sequence. In one embodiment, such a primer mix comprises primer sequences which have similar binding site in the target sequence and can bind different variants of the target sequence through the base variations in the primer compositions. Such primers can be used, for example, for SNP analysis. In another embodiment, such primer mix comprises primer sequences which have different binding sites along the target sequence. Such primers can be used, for example, for multiple labeling of target sequences.

In a further embodiment, a plurality of target sequences is labeled in a labeling reaction with nuc-macromolecules, wherein each target sequence is combined with at least one specific primer.

In a further embodiment, a plurality of target sequences is labeled in a labeling reaction with nuc-macromolecules, wherein at least one primer can bind to one or several target sequences.

In a further embodiment, uniform primers are used for different target sequences. Examples of such primer sequences are oligo-dT for cDNA synthesis. In another example, a uniform primer binding site can be introduced into all of the target sequences, for example by means of a ligation, for subsequent labeling reaction with a uniform primer.

In one embodiment, the Tm of the primer and the Tm of the target domain of the used nuc-macromolecules can be adapted to each other, wherein differences in Tm do not exceed +/−5° C.

In another embodiment, the sequence of the primer (or a pair of primers or a set of primers) is designed in such a way that the Tm of the primer is above the Tm of the target domain of the used nuc-macromolecule, wherein the difference exceeds for example 5° C. or even 50° C.

In another embodiment, the sequence of the primer (or a pair of primers or a set of primers) is designed in such a way that the Tm of the primer is below the Tm of the target domain of the used nuc-macromolecule, wherein the difference exceeds for example 5° C. or even 50° C.

Individual binding events (primer binding and nuc-macromolecule binding) can be controlled by temperature changes in combination with according adjustments in Tm of primers and of target domains of the nuc-macromolecules. Since DNA polymerases extend only bound primers, the process of primer extension can also be controlled. The binding of the target domain of the nuc-macromolecule to the target sequence favors its incorporation into the primer. Thus, by adjusting the Tm of the target domain to the reaction conditions, the incorporation of nuc-macromolecules can also be controlled.

Modifications

In a further embodiment, oligonucleotides with a primer function comprise one or several modifications. Examples of modifications are dyes, haptens (antigens), biotin, peptide-sequences, additional oligonucleotide sequences with other backbone structures, e.g. PTO, LNA, or PNA.

In a further embodiment, a primer comprises at least one anchor domain. In a further embodiment, a primer comprises at least one signal domain. The structures of the anchor domain or signal domain of the primers can be identical with those of the nuc-macromolecules or different as well. Examples of modified primers are known to one skilled in the art.

In one embodiment, the primers for the labeling reaction are provided in a solution form.

In a further embodiment, the primers immobilized on a solid phase are provided. The attached primers can be provided in combination with the solid phase, in which a unique association of the primer sequences to determined feature of the solid phase is possible, for example, to a position on the solid phase, for example, if a planar solid phase is used, or a color or a diameter, for example, if beads are used.

In one embodiment, primers for the labeling reaction differ from those used for the amplification of target sequences.

In a further embodiment, the same primers are used for the amplification and the labeling of target sequences.

The corresponding primers are preferentially part of a kit for the labeling of target sequences with nuc-macromolecules.

1.5.6 Target Sequence-Specific Hybridization Probes

A hybridization probe is an oligonucleotide which is capable of sequence specific binding to the target sequence.

In one embodiment of the invention, a hybridization probe can comprise a signal domain. Through the specific hybridization of labeled oligonucleotides to the respective target sequence labeled with nuc-macromolecules, a signal-giving or signal transmitting molecule can be introduced.

In a further embodiment of the invention, hybridization probes comprising an anchor domain are used. The hybridization probes can be bound to the solid phase via such anchor domain such as hapten, biotin, oligonucleotide. Target sequences labeled with nuc-macromolecules can be specifically bound to the solid phase through such oligonucleotides.

In a further embodiment of the invention, hybridization probes are used which are capable of competing with at least one target domain of a nucleotide conjugate for the binding to the target sequence and nucleic acid sequences similar to the target sequence. Due to different binding affinities resulting for example from differences in sequence composition of a hybridization probe and a target domain, an unspecific interaction between the target domain and nucleic acid sequences similar to the target sequence can be suppressed by such hybridization probes.

1.5.7 Nucleotides

In a preferred embodiment of the application, nuc-macromolecules comprising the following components (domains) are used in an enzymatic labeling reaction:

Nuc-linker-(target domain-1)-(anchor domain-1)

Wherein:
Nuc is a nuc-component
Linker is a linker component
Target-domain-1 can specifically bind/hybridize to a sequence segment in the target sequence in accordance with Watson-Crick base pairing. Oligonucleotides represent examples of target-domain-1. The structure of the oligonucleotides can be DNA, RNA, PNA, LNA, or morpholino.
Anchor-domain-1 can specifically bind to a binding partner. This binding partner is preferentially attached to a solid phase. Oligonucleotides (such as DNA, PTO, RNA, PNA, LNA or morpholino) or haptens (such as dyes) or biotin provide examples of anchor-domain-1. The respective binding partner attached to the solid phase can be, for example, oligonucleotides, antibodies, or streptavidin.

In a preferred embodiment of the application, several different kinds of nucmacromolecules comprising the following components (domains) are used in an enzymatic labeling reaction:

Nuc-linker-(target domain-n)-(anchor domain-n)

Wherein:
Nuc is a nuc-component
Linker is a linker component
Target-domains-n can specifically bind/hybridize to a sequence segment in the target sequence in accordance with Watson-Crick base pairing. The number of target domains (n) corresponds to the number of target sequences to be labeled.
Anchor-domains-n can specifically bind to the respective binding partner. These binding partners are preferentially attached to a solid phase. The number of anchor-domains (n) corresponds to the number of target sequences to be labeled.
The respective anchor domains are distinctly specific for the respective target domains.

In a preferred embodiment of the application, several different kinds of nuc-macromolecules comprising the following components (domains) are used in an enzymatic labeling reaction:

Nuc-linker-(target domain-1)-(anchor domain-n)

Wherein:
Nuc is a nuc-component
Linker is a linker component
Target-domain-1 can specifically bind/hybridize to a sequence segment in the target sequence in accordance with Watson-Crick base pairing.
Anchor-domains-n can specifically bind to the respective binding partner. These binding partners are preferentially bound to a solid phase. The number of anchor-domains (n) is in the range between 2 and 100 and corresponds to the number of target sequences to be labeled.
The target domain is uniform and is combined with the respective distinctly specific anchor domain.

In a preferred embodiment of the application, several different kinds of nuc-macromolecules comprising the following components (domains) are used in an enzymatic labeling reaction:

Nuc-linker-(target domain-n)-(anchor domain-1)

Wherein:
Nuc is a nuc-component
Linker is a linker component
Target-domains-n can specifically bind/hybridize to a sequence segment in the target sequence in accordance with Watson-Crick base pairing. The number of target-domains (n) corresponds to the number of target sequences to be labeled.
Anchor-domain-1 can specifically bind to the respective binding partner. These binding partners are preferentially bound to a solid phase.
The anchor domain is uniform and is combined with the respective distinctly specific target domain.

In a preferred embodiment of the application, several different kinds of nuc-macromolecules are used in an enzymatic labeling reaction, wherein at least two kinds of nuc-macromolecules are selected from the following group:
Nuc-linker-(target domain-1)-(anchor domain-1)
Nuc-linker-(target domain-n)-(anchor domain-n)
Nuc-linker-(target domain-1)-(anchor domain-n)
Nuc-linker-(target domain-n)-(anchor domain-1)

In a preferred embodiment of the application, several different kinds of nuc-macromolecules are used in an enzymatic labeling reaction, wherein at least two kinds of nuc-macromolecules are selected from the following group:
Nuc-linker-(target domain-1)-(anchor domain-1)
Nuc-linker-(target domain-2)-(anchor domain-2)
Nuc-linker-(target domain-3)-(anchor domain-3)
Nuc-linker-(target domain-4)-(anchor domain-4)

In a further preferred embodiment of the application, nuc-macromolecules comprising the following components are used:

Nuc-linker-(target domain-1)-(signal-domain-1)

Wherein:
Nuc is a nuc-component
Linker is a linker component
Target-domain-1 can specifically bind/hybridize to a sequence segment in the target sequence in accordance with Watson-Crick base pairing. Oligonucleotides represent examples of target-domain-1. The structure of the oligonucleotides can be DNA, RNA, PNA, LNA, or morpholino.
Signal-domain-1 can be identified through a distinctly specific signal, for example, a fluorescent signal, or it enables the binding of a further signal-generating partner (e.g. oligonucleotide or hapten or biotin). The respective signal-generating binding partner can be, for example, labeled oligonucleotides, labeled antibodies, or labeled streptavidin.

In a preferred embodiment of the application, several different kinds of nuc-macromolecules comprising the following components (domains) are used in an enzymatic labeling reaction:

Nuc-linker-(target domain-n)-(signal-domain-n)

Wherein:
Nuc is a nuc-component
Linker is a linker component
Target-domains-n can specifically bind/hybridize to a sequence segment in the target sequence in accordance with Watson-Crick base pairing. The number of target-domains (n) corresponds to the number of target sequences to be labeled.

Signal-domain-n can be differentiated through a distinctly specific signal. The number of signal-domains (n) corresponds to the number of target sequences to be labeled.

The respective signal domains are distinctly specific for the respective target domains.

In a preferred embodiment of the application, several different kinds of nuc-macromolecules comprising the following components (domains) are used in an enzymatic labeling reaction:

Nuc-linker-(target domain-1)-(signal domain-n)

Wherein:
Nuc is a nuc-component
Linker is a linker component
Target-domain-1 can specifically bind/hybridize to a sequence segment in the target sequence in accordance with Watson-Crick base pairing.

Signal-domain-n can be differentiated through a distinctly specific signal. The number of signal-domains (n) can be in the range between 2 and 100.

The target domain is uniform and is combined with the respective specific signal domains.

In a preferred embodiment of the application, several different kinds of nuc-macromolecules comprising the following components (domains) are used in an enzymatic labeling reaction:

Nuc-linker-(target domain-n)-(signal-domain-1)

Wherein:
Nuc is a nuc-component
Linker is a linker component
Target-domain-1 can specifically bind/hybridize to a sequence segment in the target sequence in accordance with Watson-Crick base pairing. The number of target-domains (n) corresponds to the number of target sequences to be labeled.

Signal-domain-1 can be identified through a distinctly specific signal (e.g. a fluorescent signal) or it enables the binding of a further signal-generating partner.

The signal domain is uniform and is combined with the respective specific target domains.

In a preferred embodiment of the application, several different kinds of nuc-macromolecules are used together in an enzymatic labeling reaction, wherein at least two kinds of nuc-macromolecules are selected from the following group:
Nuc-linker-(target domain-1)-(signal domain-1)
Nuc-linker-(target domain-n)-(signal domain-n).
Nuc-linker-(target domain-1)-(signal domain-n)
Nuc-linker-(target domain-n)-(signal domain-1)

In a preferred embodiment of the application, several different kinds of nuc-macromolecules are used together in an enzymatic labeling reaction, wherein at least two kinds of nuc-macromolecules are selected from the following group:
Nuc-linker-(target domain-1)-(signal domain-1)
Nuc-linker-(target domain-2)-(signal domain-2).
Nuc-linker-(target domain-3)-(signal domain-3)
Nuc-linker-(target domain-4)-(signal domain-4)

In a further preferred embodiment of the application, nuc-macromolecules are used, which comprise the following components (domains):

Nuc-linker-(target domain-1)-(anchor-domain-1)-(signal-domain-1)

Wherein:
Nuc is a nuc-component
Linker is a linker component
Target-domain-1 can specifically bind/hybridize to a sequence segment in the target sequence in accordance with Watson-Crick base pairing. Oligonucleotides represent examples of target-domain-1. The structure of the oligonucleotides can be DNA, RNA, PNA, LNA, or morpholino.

Signal-domain-1 can be identified through a distinctly specific signal, for example a fluorescent signal, or it enables the binding of a further signal-generating partner (e.g. oligonucleotide or hapten or biotin). The respective signal-generating binding partners can be, for example, labeled oligonucleotides, labeled antibodies, or labeled streptavidin.

Anchor-domain-1 can specifically bind to the respective binding partner. This binding partner is preferentially bound to a solid phase. Oligonucleotides (such as DNA, RNA, PNA, LNA or morpholino) or haptens (such as dyes) or biotin provide examples of anchor-domain-1. The respective binding partner attached to the solid phase can be, for example, oligonucleotides, antibodies, or streptavidin.

In a further preferred embodiment of the application, several different kinds of nuc-macromolecules are used in enzymatic labeling reactions, which comprise the following components (domains):

Nuc-linker-(target domain-n)-(anchor-domain-n)-(signal-domain-n)

Wherein:
Nuc is a nuc-component
Linker is a linker component
Target-domains-n can specifically bind/hybridize to a sequence segment in the target sequence in accordance with Watson-Crick base pairing. The number of the target-domains-n corresponds to the number of the target sequences which are supposed to be labeled.

Anchor-domains-n can specifically bind to the respective binding partner. These binding partners are preferentially bound to a solid phase. The number of the anchor-domains-n corresponds to the number of the target sequences which are supposed to be labeled.

Each of the signal-domain-n can have a distinctly specific signal property. The number of the signal-domains-n corresponds to the number of the target sequences which are supposed to be labeled.

The respective signal-domains and anchor-domains are specific for the respective target domains.

In one embodiment, non-labeled nucleotides, for example, dNTPs (dATP, dCTP, dTTP, dGTP, or analogs thereof, such as 7-deaza-dATP), NTPs (ATP, GTP, CTP, UTP, or analogues thereof) are used in addition to nuc-macromolecules in a labeling reaction for extension of the growing nucleic acid strand.

In another embodiment, conventionally labeled nucleotides, such as dUTP-biotin, fluorescein-dUTP, dCTP-Cy3, are used for labeling of the growing nucleic acid strand in addition to nuc-macromolecules.

In another embodiment, nuclease resistant nucleotides, e.g. alpha-thio-dNTP, are used in addition to nuc-macromolecules.

The nuc-macromolecules, dNTPs and conventionally modified nucleotides can be used in different combinations and compositions. Such compositions are preferentially components of kits. Below, some of advantageous compositions are presented.

1.5.8 Compositions of Nucleotides

Compositions including one or several different types of nuc-macromolecules without further nucleotides, e.g. without dNTP or NTP).

The labeling of nucleic acid chains occurs through the incorporation of nuc-components of nuc-macromolecules at the 3' end of the primer opposite the complementary bases in the target sequence.

Compositions, including one or more different types of nuc-macromolecules and a set of nucleotides, which allow a complete synthesis of nucleic acid chains, such as 4×dNTP or 4×NTP. Natural substrates for polymerases such as dNTP (dATP, dCTP, dGTP and dTTP) and their analogues can be used. These analogues may include modifications at the base such as dITP, dUTP, 7-Deaza-dATP oder 7-Deaza-dGTP or sugar modifications such as ddNTP or 3'-amino-3'-deoxy-NTP or phosphate modifications such as alpha-thio-dNTPs or tetraphosphates. Due to the use of dNTP, a primer extension can occur so that a complementary strand to the target sequence can be synthesized. Simultaneously, an incorporation of nuc-components of nuc-macromolecules occurs at the 3' end of the growing strand opposite complementary bases in the target sequence, which results in a labeling of the nucleic acid chains. The extent and the specificity of the labeling of the nucleic acid chains can be influenced by the varying of the concentrations and ratios between nuc-macromolecules and dNTPs; see below.

Compositions, including one or more different types of nuc-macromolecules and a set of nucleotides, which allows for only incomplete, limited primer extension such as only one or two or three dNTP or NTP. Natural substrates for polymerases such as dNTP (dATP, dCTP, dGTP and dTTP) and their analogues can be used. These analogues may include modifications at the base such as dITP and dUTP or sugar modifications such as ddNTP or 3'-amino-3'-deoxy-NTP or phosphate modifications such as alpha-thio-dNTPs or tetraphosphates. Due to the use of dNTP, a primer extension can occur so that a complementary strand to the target sequence can be synthesized. Simultaneously, an incorporation of nuc-components of nuc-macromolecules occurs at the 3' end of the growing strand opposite complementary bases in the target sequence, which results in a labeling of the nucleic acid chains. The extent and the specificity of the labeling of the nucleic acid chains can be influenced by the varying of the concentrations and ratios between nuc-macromolecules and dNTPs; see below. The length of the synthesized complementary strand can be controlled by limiting the composition of the dNTP set.

Compositions, including one or more different types of nuc-macromolecules and a set of nucleotides, which allow a complete synthesis of nucleic acid chains, such as 4×dNTP or 4×NTP, and one or several conventially labeled nucleotides. Natural substrates for polymerases such as dNTP (dATP, dCTP, dGTP and dTTP) and their analogues can be used. These analogues include modifications at the base such as dITP and dUTP or sugar modifications such as ddNTP or 3'-amino-3'-deoxy-NTP or phosphate modifications, such as alpha-thio-dNTPs or tetraphosphates. Conventionally labeled nucleotides can be used as modified nucleotides, which include, for example a dye or a fluorescent dye or an affinity moiety, such as Cy3, Rhodamine, Alexa dyes, or Atto-dyes, or biotin, or digoxigenin. Due to the use of dNTP, a primer extension can occur so that a complementary strand to the target sequence can be synthesized.

Simultaneously, an incorporation of nuc-components of nuc-macromolecules occurs at the 3' end of the growing strand opposite complementary bases in the target sequence, which results in a labeling of the nucleic acid chains. The extent and the specificity of the labeling of the nucleic acid chains can be influenced by the varying of the concentrations and ratios between nuc-macromolecules and dNTPs; see below A non-specific labeling of nucleic acid chains with dyes, fluorescent dyes or affinity moieties can take place due to the use of modified nucleotides.

In a preferred embodiment, nuc-macromolecules are used alone or together with other nucleotides (see above) in an aqueous buffer solution. Nuc-macromolecules can be used as components of kits in dissolved form (for example provided as a concentrated solution) or in dry form. The dried substances can be dissolved in a reaction mixture immediately before the test with an aqueous solution or an organic solution, for example DMSO.

In a further preferred embodiment, nuc-macromolecules are attached to a solid phase. The attachment is carried out in a way, which allows the target domain of the nuc-macromolecules not to lose its ability for specifically hybridization to the target sequences, and to retain the substrate property for polymerases. In one embodiment, the attachment is done in a way, which allows a specific identification of the individual types of nuc-macromolecules on a solid phase. For example, such identification can be achieved by a spatial arrangement of the solid phase, similar to a DNA microarray.

Hereinafter, embodiments are described which provide nuc-macromolecules in an aqueous buffer solution. Ratios of concentrations of nuc-macromolecules and unlabeled nucleotides (such as dNTP) can be adapted so that nuc-macromolecules can be incorporated by polymerases. Advantageous embodiments of the method include the following conditions and ranges between them:

Ratios of concentration of nuc-macromolecule and not labeled nucleotides (e.g. dNTP) comprise for example the following ranges: 1:100000000 to 1:10000000; 1:10000000 to 1:1000000; 1:1000000 to 1:100000; 1:100000 to 1:10000; 1:10000 to 1:1000; 1:1000 to 1:100; 1:100 to 1:10; 1:10 to 1:1; 1:1 to 10:1; 10:1 to 100:1; 100:1 to 1000:1; 1000:1 to 10000:1.

By changing the ratios of concentrations, it is possible to influence the portion of the nucleic acid chain which is labeled in an approach and which remains unlabeled due to incorporation of non labeled nucleotides (e.g. dNTP) instead of a nuc-macromolecule.

Nuc-macromolecules can be incorporated by a polymerase in the absence of non-labeled nucleotides (e.g. dNTP) of the same kind both sequence-specifically and sequence-unspecifically. The target sequence-specificity is strongly favored by the target domain of a nuc-macromolecule. The presence of the dNTP of the same base type as the base type of the nuc-component causes natural nucleotides and nuc-components of the nuc-macromolecule to compete for the incorporation. The target-sequence-non-specific incorporation of nuc-macromolecules can be increasingly competitively suppressed by dNTP at increasing concentrations of dNTP. This can be achieved for example by the use of concentrations of natural nucleotides in the range from 1 to 100 µmol/l. At still higher concentrations of natural nucleotides, the sequence-specific incorporation of nuc-macromolecules bound to the target sequence can also be increasingly suppressed; this can be achieved for example by the use of concentrations in the range from 1 mmol/l to 100 mmol/l.

The concentrations of nuc-macromolecules and unlabeled nucleotides can range between 100 pmol/l and 10 mmol/l. Particularly preferred ranges are between 100 nmol/l and 1 mmol/l.

Preferentially, the absolute concentrations of nuc-macromolecules in a reaction are in the following ranges (concentrations for nuc-macromolecules): 10 nmol/l to 100 nmol/l, 100 nmol/l to 1 µmol/l, 1 µmol/l to 10 µmol/l. Concentrations of non-labeled nucleotides: 1 µmol/l to 10 µmol/l, 10 µmol/l to 100 µmol/l, 100 µmol/l to 1 mmol/l, 1 mmol/l to 10 mmol/l, higher than 10 mmol/l.

Since more natural or modified nucleotides (for example labeled with a dye or biotin) can be used, their concentration is preferentially in the following ranges: 10 nmol/l to 100 nmol/l, 100 nmol/l to 1 µmol/l, 1 µmol/l to 10 µmol/l, 10 µmol/l to 100 µmol/l, 100 µmol/l to 1 mmol/l, 1 mmol/l to 100 mmol/l. In detail, a titration should be carried out to achieve an optimal labeling.

Concentrations of individual nucleotide species (nuc-macromolecules, dNTP, conventionally labeled nucleotides and other nuc-macromolecules) can be individually adjusted in a reaction mixture. When using multiple nuc-macromolecules, their concentrations and concentration ratios can be adjusted according to requirements of the analysis.

In one embodiment, a composition of nuc-macromolecules and other components of the test (for example such as primers and dNTPs) is assembled in such way, that in case of an occurring labeling reaction the nuc-macromolecules are consumed as completely as possible. The concentration of nuc-macromolecules in the reaction solution ranges for example between 10 pmol/l to 1 nmol/l, 1 nmol/l to 10 nmol/l, 10 nmol/l to 100 nmol/l, 100 nmol/l to 300 nmol/l, 300 nmol/l to 1 µmol/l, 1 µmol/l to 10 µmol/l.

Addition of individual reagents (primers, nucleotides, polymerase, and optionally also other reagents) can be done in one step or can be distributed over a number of individual steps. For example, nuc-macromolecules can be provided already at the begin of the labeling reaction in a particular test. The individual reagents can be provided in dried or concentrated form as a pre-mixed composition, for example, dNTP and nuc-macromolecules are premixed at a fixed ratio. By adding a solution with target sequences to such provided mixture, the components are dissolved in the reaction solution to allow a labeling reaction.

The nucleotide compositions comprising nuc-macromolecules are preferentially components of a kit.

1.5.9 Binding of Labeled Nucleic Acids to the Solid Phase and Detection

In a preferred embodiment of the invention, the binding of labeled target sequences to a solid phase follows a labeling reaction of target sequences with nuc-macromolecules. Subsequently, a detection of the binding of the target sequences to the solid phase is conducted. Examples are given in patent application Cherkasov et al WO2011050938.

Some examples of methods for labeling of target sequences and its subsequent binding to the solid phase are presented in FIGS. 6 to 15.

An example of a labeling method for a target sequence or its equivalents with a subsequent binding to the solid phase is shown in FIG. 6. The following components are provided (FIG. 6A): one type of nuc-macromolecules (1-4 in FIG. 6) with a target domain and an anchor domain, a single-stranded target sequence (7 in FIG. 6), one primer labeled with a signal domain (6 and 9 in FIG. 6), a DNA polymerase, and further nucleotides such as dNTPs. These components are incubated under conditions that allow the polymerase to incorporate dNTPs and nuc-macromolecules into the growing strand (FIG. 6B). A solid phase (12 in FIG. 6) which provides a binding partner (11 in FIG. 6) for the anchor domain is provided. The labeling reaction is preferentially designed in such a way that nuc-macromolecules are incorporated as completely as possible. If an excess of nuc-macromolecules should be used, labeled nucleic acid chains can be purified of excess free nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc-macromolecule (13 in FIG. 6). The detection is done via the signal domain of the primer.

A further example of a labeling method for a target sequence or its equivalents with a subsequent binding to the solid phase is shown in FIG. 7. The following components are provided: one type of nuc-macromolecules (1-4 in FIGS. 7A and 7B) with a target domain, an anchor domain (4a in FIG. 7A), and an antagonist of the anchor domain (4b in FIG. 7A). Further components such as single-stranded target sequence, one primer labeled with a signal domain, a DNA polymerase, and further nucleotides such as dNTPs (FIG. 7B) are provided.

The anchor domain and its antagonist are separated by the binding of the target domain to the target sequence. After the incorporation of the nuc-component into the growing strand, this state is fixed. In this embodiment of the method, polymerases that show little or no exonuclease activity and no or very little "strand-displacement" activity are preferentially used. In another embodiment, a nuc-component which leads to a termination in the synthesis is used; for example, a nuc-component comprises ddNTP (such as ddUTP or ddCTP). These components are incubated under conditions that allow the polymerase to incorporate the dNTPs and nuc-macromolecules into the growing strand (FIG. 7C).

A solid phase which comprises a binding partner for the anchor domain is provided. After the incorporation reaction, an incubation of the labeled target sequences or their equivalents with the solid phase is conducted under conditions which permit the specific binding of the anchor domain of incorporated nuc-macromolecules to the immobilized binding partner. Preferentially, the anchor domains of the un-incorporated nuc-macromolecules are blocked by their antagonists under these conditions. The labeled target sequence binds to the solid phase via the anchor domain of the incorporated nuc-macromolecule. The detection reaction is achieved by means of the signal domain of the primer. The non-incorporated, free nuc-macromolecules do not interfere with the binding of labeled target sequences because their anchor domains are blocked by the antagonists.

A further example of a labeling method for a target sequence or its equivalents with a subsequent binding to the solid phase is shown in FIG. 8. The following components are provided: one type of nuc-macromolecules with a target domain and an anchor domain, a single-stranded target sequence, one primer coupled with a signal domain, a DNA polymerase, and further nucleotides such as dNTPs. These components are incubated under conditions that allow the polymerase to incorporate dNTPs and nuc-macromolecules into the growing strand. A polymerase which has a "strand displacement" activity is used. A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc-macromolecule. Since the polymerase is able to displace the target domain of the nuc-macromolecules, several nuc-macromolecules can be incorporated into the same growing strand. The detection is done via the signal domain of the primer.

A further example of a labeling method for a target sequence or its equivalents with a subsequent binding to the solid phase is shown in FIG. 9. The following components are provided: one type of nuc-macromolecules with a target domain and an anchor domain, a single-stranded target sequence, a primer, a DNA polymerase, and further nucleotides such as dNTPs and one kind of labeled nucleotides such as nuc-macromolecules having a signal domain or conventionally labeled nucleotides such as dUTP-16-biotin or Cy3-dCTP. These components are incubated under conditions that allow the polymerase to incorporate dNTPs and nuc-macromolecules into the growing strand. A polymerase which has a "strand-displacement" activity is used. A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc-macromolecule. Since the polymerase is able to displace the target domain of the nuc-macromolecules, several nuc-macromolecules and several nucleotides labeled with the signal domain can be incorporated into the same growing strand.

A further example of a labeling method for a target sequence or its equivalents with a subsequent binding to the solid phase is shown in FIG. 10. The following components are provided: one type of nuc-macromolecules with a target domain and an anchor domain, a single-stranded target sequence, one primer labeled with a signal domain, a DNA polymerase having a 5-3 exonuclease activity, and further nucleotides such as dNTPs. The linker component is linked not to the target domain, but instead to an other part of the marker, e.g. to the anchor domain of the marker. These components are incubated under conditions that allow the polymerase to incorporate dNTPs and nuc-macromolecules into the growing strand. During the reaction, the target domain of the nuc-macromolecule bound to the target sequence is degradated while the reaction proceeds (FIG. 10). A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc-macromolecule. Since the polymerase is able to degrade the target domain of the nuc-macromolecule, multiple nuc-macromolecules can be incorporated into the same growing strand. The detection reaction is done via the signal domain of the primer.

An example is shown in FIGS. 11 and 12 demonstrating a possible design for a reaction to test a particular solution for presence of a target sequence. In the process shown in FIG. 11, the target sequence with the newly synthesized complementary strand is attached directly to the solid phase. In the method illustrated in FIG. 12, a separation of the double strand is included. A strand separation can result in a further increase of the specificity of the analysis.

A further example of a labeling method for a target sequence or its equivalents with a subsequent binding to the solid phase is shown in FIG. 13. The following components are provided: one type of nuc-macromolecules with a target domain, an anchor domain and a signal domain, a single-stranded target sequence, a primer, a DNA polymerase, and further nucleotides such as dNTPs. These components are incubated under conditions that allow the polymerase to incorporate dNTPs and nuc-macromolecules into the growing strand (FIG. 13B). A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc-macromolecule. The detection reaction is done by the signal domain of the nuc-macromolecule.

A further example of a labeling method for a target sequence or its equivalents with a subsequent binding to the solid phase is shown in FIG. 14. The following components are provided: one type of nuc-macromolecule with a target domain and a signal domain, a single-stranded target sequence, a primer with an anchor domain, a DNA polymerase, and further nucleotides such as dNTPs. These components are incubated under conditions that allow the polymerase to incorporate dNTPs and nuc-macromolecules into the growing strand (FIG. 14B). A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules and labeled primers by a known method. The labeled target sequences or their equivalents are incubated with the solid phase under conditions which permit the specific binding of the anchor domain to the immobilized binding partner. The labeled target sequence binds to the solid phase via the anchor domain of the primer. The detection is done via the signal domain of the nuc-macromolecule.

A further example of a labeling method for a target sequence or its equivalents with a subsequent binding to the solid phase is shown in FIG. 15. The following components are provided: one type of nuc-macromolecule with a target domain and the anchor domain-1, a single-stranded target sequence, a primer with the anchor domain-2, a DNA polymerase, and further nucleotides such as dNTPs. These components are incubated under conditions that allow the polymerase to incorporate dNTPs and nuc-macromolecules into the growing strand (FIG. 15B). The first solid phase (solid phase-1) which comprises a binding partner for the anchor domain-1 of the nuc-macromolecule is provided, as well as the second solid phase (solid phase-2) which comprises a binding partner for the anchor domain-2 of the primer is provided. Both solid phases are provided, for example, as particles in an aqueous suspension. The labeling reaction is preferentially conducted in such a way that nuc-macromolecules are incorporated as completely as possible. If an excess of nuc-macromolecules should be used, labeled nucleic acid chains can be purified from nuc-macromolecules and labeled primers by a known method. The labeled target sequences or their equivalents are incubated with both solid phases under conditions that allow the specific binding of the both anchor domains to the respective immobilized binding partner.

The labeled target sequence binds to both phase via the anchor domains. The detection reaction is done through the visual perception of the binding of the two solid phases to each other such as an agglutination.

In a further embodiment of the invention, a plurality of binding partners are attached to a solid phase in a spatial arrangement so that a correlation of particular binding partner to a specific position on the solid phase can be achieved. Individual components of a solid phase are combined to form an array. Microtiter plates or their analogs, BeadArrays, are examples of such arrays. Further examples of such solid phases are microarrays, bead arrays, western blot strips, "Lateral Flow Devices," and membrane arrays set with multiple reaction fields. Some examples of solid phases with one or more binding partners are described in the section "Terms and Definitions," and will be known to an expert.

A spacial attribution of the labeled nucleic acid chain is achieved by the binding of target sequences each labeled with a target-sequence-specific anchor domain to a solid phase with spatially arranged binding partners for the respective anchor domains (FIGS. 16, 17, and 19).

Target sequences which are labeled with nuc-macromolecules and bound to the solid phase can be detected with one of the known method of detection.

A further example is presented for a labeling method for a target sequence or its equivalents with a subsequent binding to the solid phase. The following components are provided: one type of nuc-macromolecules with a target domain and a signal domain, a single-stranded target sequence, a primer, a DNA polymerase, and further nucleotides such as dNTPs. These components are incubated under conditions that allow the polymerase to incorporate dNTPs and nuc-macromolecules into the growing strand.

A solid phase which comprises at least one nucleic acid chain (e.g. oligonucleotide) complementary to the target sequence or to their equivalents is provided. Such nucleic acid chains are preferentially immobilized on the solid phase. If the provided solid phase comprises a plurality of complementary nucleic acid chains, they are attached in a spatial arrangement, i.e. in form of an addressable array. An expert knows such solid phases, e.g. DNA microarray. The labeling reaction is preferentially conducted in such a way that nuc-macromolecules are incorporated as completely as possible. If an excess of nuc-macromolecules should be used, labeled nucleic acid chains can be purified of nuc-macromolecules and primers, if necessary, by a known method. The labeled target sequences or their equivalents are incubated with the solid phase under conditions which permit the specific binding of the labeled target sequence, or their equivalents, to the immobilized nucleic acid chains. The labeled target sequence binds to the solid phase directly via the formation of double strands with the complementary immobilized nucleic acid chains. The detection reaction is done by means of signal domain of the incorporated nuc-macromolecule.

In the following, examples of combinations of the solid phase and the anchor domains are presented. The anchor domain can be constituents of the nuc-macromolecules, or those of the modified primers, or those of the hybridization probes.

1.5.9.1 Use of Nuc-Macromolecules with a Uniform Anchor Domain

Nuc-macromolecules comprising at least one uniform anchor domain are provided for a labeling reaction. A solid phase with a binding partner which is able to bind specifically to that uniform anchor domain is provided.

Using nuc-macromolecules with only one type of anchor domains, the binding of labeled target sequences to the solid phase is conducted via one binding partner attached to the solid phase. The nuc-component and target sequences can be uniform or different.

For example, only one type of nuc-macromolecules is used in the reaction. A binding to the solid phase is achieved after incorporation of this nuc-macromolecule into the target sequence or its equivalent and a subsequent incubation with the solid phase.

For example, multiple nuc-macromolecules with different target domains and uniform anchor domains can be used for a test directed to a group of target sequences. If one of the target sequences of interest is presented in a sample, an incorporation of the nuc-macromolecule into the growing strand occurs. Subsequently, the labeled target sequence or its equivalent is bound to the solid phase.

The detection of the binding of the target sequence to the solid phase can be achieved, for example, via the signal domain of an incorporated nuc-macromolecule or a primer or a hybridization probe.

1.5.9.2 the Use of Nuc-Macromolecules with Different Anchor Domains

Nuc-macromolecules having different anchor domains can be used in the labeling reaction. A solid phase with several binding partners which are capable of specifically binding to each of these different anchor domains is provided. Preferentially, binding partners are attached in a particular spatial arrangement. The binding of labeled target sequences to such a solid phase results in the distribution of labeled nucleic acids with incorporated anchor domains on the solid phase with a specific binding partner.

After a subsequent detection based on the resulting signal pattern, a target sequence presented in a sample can be identified. Thus, multiple parameters (such as the presence of different target sequences) can be analyzed.

The detection of the binding of the target sequence to the solid phase can be conducted, for example, via the signal domain of the incorporated nuc-macromolecule or of the primer or of a hybridization probe.

1.5.9.2.1

In one embodiment, several different nuc-macromolecules with different specific combinations of target domain with anchor domains can be used for labeling. The nuc-components and signal domain of nuc-macromolecules can be uniform or different. In one embodiment, nuc-macromolecules are used which comprise the target domain, the anchor domain, and the signal domain. In a further embodiment, nuc-macromolecules are used which comprise the target domain and the anchor domain.

Through the specific combination of target domains and anchor domains within one type of nuc-macromolecule, an assignment of anchor domains to certain target sequences can be achieved. After the incorporation of the nuc-component into the growing strand by the polymerase, the anchor domain is also coupled in a target-sequence-specific way.

For example, a plurality of target sequences has to be analyzed. The target domains [T] of individual types of nuc-macromolecules are complementary to these target sequences. The respective anchor domain of nuc-macromolecules is selected specifically for each target sequence (i.e. the anchor domain [A] is assigned to the respective target sequence, for example nuc1-[T1, A1], nuc1-[T2, A2], nuc1-[Tn, An], etc.). During labeling, each target sequence obtains a respectively specific anchor domain. After the labeling reaction, labeled target sequences can bind to the solid phase specifically via the anchor domains. After the detection step, it can be determined which of the target sequences was bound to which position on the solid phase.

1.5.9.2.2

In another embodiment, a plurality of nuc-macromolecules with different specific combinations of nuc-component-anchor domain can be used for the labeling. The target domains or signal domains can be uniform or different or they can be even absent.

Preferentially in such an embodiment, at least four different specific anchor domains are used, each for a specific base of the nuc-component, for example dATP is combined with the anchor domain 1, dCTP is combined with the anchor domain 2, dGTP is combined with the anchor domain 3 and dUTP is combined with the anchor domain 4.

1.5.9.3 Binding to the Solid Phase by a Modified, Sequence Specific Primer

In one embodiment, the following components are used in the labeling reaction: a target sequence, at least one polymerase, at least one primer which comprises an anchor domain, at least one type of nuc-macromolecules which comprise at least one target domain and at least one signal domain, optionally further nucleotides.

Upon binding of the labeled target sequence to the solid phase via the anchor domain of the primer, this target sequence can be identified through the signal of the incorporated nuc-macromolecules.

In another embodiment, the following components are used in a labeling reaction: primers which comprise an anchor domain 1, at least one kind of nuc-macromolecules which comprise at least one target domain and at least one anchor domain 2. The anchor domain of primer is different from the anchor domain of nuc-macromolecules. Upon binding of the labeled target sequence to the solid phase via the anchor domain of the primer, the second solid phase can bind to the anchor domain of the nuc-macromolecule. Using microparticles, the binding of both solid phases can be detected as agglutination. Agglutination is taking place only, if the labeling reaction of the target sequences or their equivalents has been successful. Using a lateral flow device (FIG. 19), the binding of both solid phases can be detected through formation of a visible line (for example, when using colored microparticles or colloidal gold).

If a plurality of target sequences has to be detected, a plurality of different primers, each with a specific anchor domain, can be used in combination with several types of nuc-macromolecules, each with a specific target domain, and at least one signal domain or at least one anchor domain. The signal-domains and the anchor domains of the used nuc-macromolecules can be uniform or different.

1.5.9.4 Binding to the Solid Phase by Means of a Modified Hybridization Probe Hybridization probes comprising a target domain and an anchor domain can be used for the labeling reaction together with at least one kind of nuc-macromolecules comprising at least one target domain and at least one signal domain. Each target domain is specific for a particular target sequence. Upon binding of the labeled target sequence to the solid phase via the anchor domain 1 of the hybridization probe, this target sequence can be detected through the signal of the incorporated nuc-macromolecules.

If a plurality of target sequences has to be detected, a plurality of different hybridization probes, each having a specific anchor domain, can be used in combination with several types of nuc-macromolecules, each having a specific target domain, and for example at least one signal domain. The signal domains of the used nuc-macromolecules can be uniform or different.

1.5.9.5 Binding to the Solid Phase by a Modified Nucleotide

Modified nucleotides having a low molecular weight (e.g. dUTP-16-Biotin, or dUTP-digoxigenin, or dUTP-fluorescein) and comprising an anchor domain can be used in the labeling reaction together with at least one kind of nuc-macromolecules which comprise at least one target domain and at least one signal domain. A solid phase is provided which is able to bind the low molecular weight markers of conventional nucleotides, such as streptavidin or antibodies against digoxigenin or against fluorescein. Upon binding of the labeled target sequence to the solid phase via the said modified nucleotide with low molecular weight, this target sequence can be detected through the signal of the incorporated nuc-macromolecules.

1.5.9.6 Direct Binding of the Labeled Target Sequence, or the Equivalents Thereof to the Solid Phase with Attached, Addressable and Complementary to the Target Sequence Nucleic Acid Chains In one embodiment, a labeling reaction comprises the following components: a target sequence, at least one polymerase, at least one primer used in combination with at least one kind of nuc-macromolecules which comprise at least one target domain and at least one signal domain, and optionally other nucleotides. After labeling of the target sequences with the nuc-macromolecules, the strands are separated, for example by temperature or alkali, e.g. NaOH solution. A solid phase is provided which comprises addressable, to a respective target sequence complementary oligonucleotides. The mixture is brought in contact with the provided solid phase, wherein the labeled nucleic acid chains can bind to the complementary nucleic acid chains attached to the solid phase. The detection reaction is done via the signal domain of the incorporated nuc-macromolecules.

In one embodiment, the labeling reaction comprises a target sequence, at least one polymerase, at least one primer used in combination with at least one kind of nuc-macromolecules which comprises at least one target domain and at least one anchor domain, and optionally further nucleotides. After the labeling of the target sequences with the nuc-macromolecules, strands are separated, for example by temperature or alkali, e.g. NaOH solution. The mixture is brought in contact with the provided solid phase (1) so that the labeled nucleic acid chains can bind to the complementary nucleic acid chains attached to the solid phase.

After the binding of the labeled target sequence to the solid phase (1) through the formation of double strands with the attached nucleic acid strands of the solid phase, a second solid phase (2) can bind to the anchor domain of nuc-macromolecules. When microparticles are used, the detection can be achieved for example through the agglutination. Agglutination is only positive, if the target sequences or their equivalents have been successfully labeled. By the use of a lateral flow devices, the binding of the two solid-phase can be detected through the formation of a visible line (e.g. using colored micro-particles or colloidal gold).

Such a type of binding of labeled nucleic acid chains to the solid phase is known to one skilled in the art, e.g DNA microarray technology (for examples see references in section 1.3.20).

If multiple target sequences have to be analyzed, a solid phase with addressable attached nucleic acid chains can be used. Nuc-macromolecules are accordingly adapted to the target sequences to be examined.

1.5.10 Detection of Bound Labeled Nucleic Acid Chains

Many existing methods can be used for detection of nucleic acids labeled with nuc-macromolecules. On the one hand, incorporated nuc-macromolecules can comprise one or more signal domains with signaling or signal transmitting entities, on the other hand, other components of the system can comprise signaling or signal transmitting elements. Such elements are, for example, labeled primers, labeled nucleotides, hybridization probe and intercalating dyes.

Characteristic signals from dyes, chromogenic substances, fluorescent dyes, electrochemical markers or particles (e.g. nano or micro beads) can be used for detection. Examples of individual components are shown in the chapter "signal domain" and "detection methods" in more detail. Depending on signalling, different systems for detection of the signal can be used. Examples are known to one skilled in the art.

In one embodiment, for example, signaling is used to detect the binding of the labeled nucleic acid chains to the solid phase. In another embodiment, the signalling is used, for example, to detect different sequence variants within the target sequence.

Different methods of signal enhancement or signal amplification can be used for the signalling which are known to a person skilled in the art.

In an advantageous embodiment of the invention, the intensities of the received signals are measured. Signal intensities from the target sequences can be compared to signal intensities of the control sequences or to those of each other.

In an advantageous embodiment, these intensities can be recorded in digital form, stored and imaged.

In the following, some examples for detection reactions of nucleic acid chains on a solid phase are presented. Different detection methods can be combined with various structures of the nuc-macromolecules.

1.5.10.1 Nuc-Macromolecules with T-A-S-Domains

Using at least one kind of nuc-macromolecules with T-A-S-domains, the detection of bound labeled nucleic acid sequences can be done through the signal domain (S-domain of the nuc-macromolecules).

1.5.10.2 Nuc-Macromolecules with T-S-Domains or S-Domains

Using at least one kind of nuc-macromolecules with a target domain or a signal domain, the detection of the bound target sequences or their equivalents can be preferentially achieved through the signal domain of the incorporated nuc-macromolecules. The binding of the labeled nucleic acid chains to the solid phase can be done by means of other reactants.

For example, modified primers, hybridization probes or modified nucleotides can be used with an anchor domain (see above).

1.5.10.3 Signaling by a Sequence Specific, Modified Primer

Sequence-specific primers with signal domains can be used in the labeling reaction.

In this embodiment, the detection of the bound target sequences or equivalents thereof is done through the signal domain of these labeled primers. In a preferred embodiment, the binding of the labeled nucleic acid chains is to the solid phase is achieved via the incorporated nuc-macromolecules which comprise at least an anchor domain.

In a further embodiment, the binding of the labeled nucleic acid chains to the solid phase is achieved via the incorporated nuc-macromolecules comprising at least an anchor domain and a target domain.

1.5.10.4 Signaling Through a Modified Hybridization Probe

Sequence-specific probe with signal domains can be used in a labeling reaction.

In this embodiment, the detection of the bound target sequences or equivalents thereof is achieved via the signal domain of this labeled probe. In a preferred embodiment, the binding of the labeled nucleic acid chains is to the solid phase is achieved via the incorporated nuc-macromolecules which comprise at least an anchor domain.

In a further embodiment, the binding of labeled nucleic acid chains to the solid phase is achieved via the incorporated nuc-macromolecules comprising at least an anchor domain and a target domain.

1.5.10.5 Signaling by a Modified Nucleotide

Modified nucleotides having a signal domain (e.g. nucleotides labeled with fluorescent dyes or biotin, e.g. dUTP-16-Biotin) can be used in a labeling reaction. In this embodiment, the detection of the bound target sequences or equivalents thereof is achieved via the signal domain of these modified nucleotides. In a preferred embodiment, the binding of labeled nucleic acid chains is to the solid phase is achieved via the incorporated nuc-macromolecules which comprise at least an anchor domain.

In a further embodiment, the binding of labeled nucleic acid chains to the solid phase is achieved via the incorporated nuc-macromolecules comprising at least an anchor domain and a target domain.

Below, further examples of advantageous combinations are presented.

1.5.11 Process Variants: the Use of Nuc-Macromolecules for the Labeling

1.5.11.1 Labeling Reaction Through a Primer Extension

In one embodiment of the application, target sequences are provided in a single stranded form. In a further embodiment, double-stranded target sequences can be provided at the start. In this case, a denaturation step of the double strand, for example, by means of elevated temperature is included before or during the labeling step or a separation of double strands is achieved by an enzyme, for example, by means of a helicase. Typically, the target sequence is provided in a buffered aqueous solution.

An oligonucleotide having a primer function is added to the provided single stranded target sequence (hereinafter referred to as primer). The mixture is incubated under conditions which allow for the sequence-specific hybridization of the primer to the binding site within the target sequence. Such conditions are well known for an expert and are described in the literature. Under such conditions, an extendable primer-target sequence complex is established. At least one type of polymerases, at least one kind of nuc-macromolecules, and optionally further components (such as natural nucleotides, modified nucleotides, or hybridization probes) are added to these complexes. The solution is incubated under conditions which allow the polymerase to perform a primer extension. During this step, the nuc-component of nuc-macromolecules are incorporated into the growing nucleic acid strand by the added polymerase. Thus, the target sequence or a complementary strand to the target sequence (an equivalent to the target sequence) is labeled with a nuc-macromolecule.

In one embodiment, nuc-macromolecules comprising at least one target domain are used (for example, combinations of at least one target domain and one anchor domain, or at least one target domain and one signal domain, or at least one target domain and one anchor domain, and one signal domain). The target sequence-specific target domain of the nuc-macromolecules can bind to the provided target sequence downstream from the 3 position of the primer. The reaction conditions are adjusted in such a way that the target domain of the nuc-macromolecules can bind to its respective binding site within the target sequence.

Notably, the melting temperatures of the primer and the target domain should be considered for the choice of the reaction conditions. The temperature of the reaction is preferentially chosen so that both the primer and the target domain of the nuc-macromolecules can bind to the target sequence. The extent of the binding can be influenced. In one embodiment, the reaction temperature below the Tm of the primer and the Tm of the target domain is applied. In a further embodiment of the application, the temperature higher than the Tm of the primer and the Tm of the target domain is chosen, for example in the range of Tm+5° C. or in the range Tm+10° C.

Thus, only a small part of the target domains bind to the target sequences. In another embodiment, the reaction temperature is below the Tm of the primer but over the Tm of the target domain of the nuc-macromolecule. In a further embodiment, the reaction temperature is above the Tm of the primer but below the Tm of the target domain of the nuc-macromolecule. In another embodiment, a temperature gradient is used during the reaction, wherein the temperature is gradually adapted so that the hybridization of the primer and the target domain can occur successively, not simultaneously.

In one embodiment of the invention, the Tm of the target-sequence-specific target domains of a nuc-macromolecule is higher than the Tm of the corresponding specific primer. Thereby, the nuc-macromolecules can bind to the target sequences at higher temperatures than the primers. This can ensure that the primer being extended meets nuc-macromolecules already bound to the target sequence.

In another embodiment of the invention, the Tm of the target domain of the nuc-macromolecules is lower than that of the used primers. Thus, a primer-extension can take place at higher temperatures without interfering of the nuc-macromolecules with the incorporation reaction.

In another embodiment of the invention, the Tm of the target domain of the nuc-macromolecules and the Tm of the primers is approximately the same. Thus, the binding properties of the nuc-macromolecules and those of the primer are about the same.

The order of addition of the components may vary. For example, individual components of the labeling reaction can be added one by one or in combinations (compositions). For example, the required nucleotides are premixed in certain proportions. Buffers and salts can also be added in certain pre-mixed proportions. Other combinations are obvious to an expert. Such compositions can be provided as components of kits.

After this labeling step, the labeled nucleic acid chain (target sequence or its equivalents) can be isolated from excess of unincorporated nucleotides. Isolation and purification of nucleic acid chains is well known to a person skilled in the art. Subsequently, nucleic acid chains are brought in contact with a solid phase and detected, as described in the chapter "amplification".

Labeled nucleic acid chains can also be brought into contact with the solid phase and detected directly after the labeling reaction, without isolation and purification.

The binding of the nucleic acid chains to the solid phase can be achieved directly via complementary immobilized nucleic acid chains or indirectly, i.e. enabled via an anchor domain.

Other components can also be used in such reaction, e.g. labeled primers, hybridization probes, and labeled nucleotides, as described in other chapters.

One or more types of nuc-macromolecules can participate in such a reaction, as described in other chapters.

One or more target sequences can be amplified and labeled. The detection of the target sequence can be achieved via the binding to the solid phase with a subsequent detection reaction as described in other chapters.

Examples for labeling of one target sequence or multiple nucleic acid chains are given in patent application Cherkasov et al WO2011050938.

1.5.11.2 Amplification and Labeling

In a particularly advantageous embodiment of the application, the labeling reaction takes place in the same batch as the amplification, wherein amplification and labeling steps are conducted one after another. In another embodiment, the labeling is carried out parallel to the amplification of the target sequences. In this embodiment, amplification primers can be used as labeling primer.

Various examples of amplification of nucleic acid chains are known. As described in these methods, a segment of the target sequence or the complete target sequence is amplified using primers, often provided as a primer pairs. The amplification can be exponential such as PCR or linear.

The reaction can be characterized by the cyclic change of the temperature or can be carried out at a constant temperature (isothermal).

By the choice of temperature, buffer and concentration, a process comprising the conversion of the target sequences into single-stranded form, hybridization of the primer and its extension is conducted. This process can be repeated several times.

An expert should know hot to carry out a PCR.

In one embodiment, same primers are used for the amplification reaction and for the labeling reaction. In a further embodiment, an additional primer is used for the labeling reaction.

For carrying out a PCR, the following components are typically provided in a reaction mixture: at least one target sequence, at least one primer pair suitable for this target sequence, at least one appropriate polymerase such as a thermostable polymerase, at least one kind nuc-macromolecules having a target domain matching the target sequence, further natural nucleotides (such as dATP, dGTP, dCTP, dTTP), and an appropriate buffer solution.

The amplification reaction is carried out by cyclic changes of the temperature, wherein the following cyclic steps are repeated: annealing, primer extension and denaturation of newly formed strands.

By the addition of nuc-macromolecules comprising at least a target domain which can be hybridized to the target sequence (the target domain binds to the target sequence downstream from the 3' side of a corresponding primer), nuc-macromolecules can bind to the single-stranded target sequences (FIG. 18-21).

This occurs similar to the probe in a real-time PCR method. After the binding of the primers and the nuc-macromolecules to the target sequence (hybridiation step/annealing in PCR), a primer extension reaction proceeds including the incorporation of nuc-macromolecules. After completion of the primer extension, the resulting duplexes are denatured, for example, by an increase of the temperature. Then, a new cycle with hybridization of the primer and of the nuc-macromolecule, and a corresponding primer extension is conducted. These cycles can be repeated several times, so that an accumulation of extended primers is achieved. The newly synthesized strands contain nuc-macromolecules. Specifically labeled nucleic acid chains have been generated by the incorporation of nuc-macromolecules into the growing strand, The reaction conditions (e.g. buffer and temperature), the Tm of the primer and the Tm of the target domain of the nuc-macromolecules are selected so that both primer and nuc-macromolecule can bind to the target sequences during the hybridization step. In this embodiment, the amplification can proceed parallel to the labeling.

In one embodiment, the distance between the 3' end of the primer and the 5' end of the target domain is at least 10 nucleotides, in a further embodiment, at least 50 nucleotides, in a still further embodiment, at least 100 nucleotides, in a still further embodiment, at least 200 nucleotides.

Preferably, the 3'-end of the target domain is blocked so that the target domain can not serve as a primer.

Typically, a mixture of nuc-macromolecules and natural nucleotides is provided for the reaction. The concentration ratios in such a mixture can vary. For example, the concentrations of natural nucleotides ranges between 50 and 500 µmol/l and the concentration of the nuc-macromolecules between 0.1 and 2 µmol/l. Other examples of concentrations of nucleotides are described in section 1.5.8. The concentration of the primers ranges, for example, between 0.1 and 2 µmol/l.

The conditions of the reaction (temperature) and the structure and concentration of the individual components can be adjusted so that at the beginning of the process the amplification of the fragments of the target sequences, or their equivalents, predominates. With the increase of concentration of the amplified fragments (equivalent to the target sequence) in later stages of the amplification, the labeling of the amplified strands take place. At very low concentrations of target sequences at the beginning of the amplification process, the probability of the binding and of the incorporation of nuc-macromolecules into the target sequence, or their equivalents is low. With increasing concentrations of target sequences during the amplification process, the frequency of binding events and incorporation of nuc-macromolecules into the growing nucleic acid chains also increases.

In the following, some examples of combinations of PCR and labeling reaction are presented. Labeled primers comprising a signal domain are used for signal generation in these examples. One of the primers of a target sequence-specific primer pair is selected for this purpose.

In one embodiment, PCR is used as amplification method (FIG. 18). Nuc-macromolecules comprising a target domain complementary to the potential PCR fragment of the DNA and a target-sequence-assigned anchor domain can be used.

The Tm of the target domain, for example, is in the same range, as the Tm of the used primers, +/−5° C. The PCR primers are used as a labeling primer and comprise, for example, either a signal domain or an anchor domain. The appropriate combinations of labeled primers and nuc-macromolecules are described in previous chapters.

The concentration of primers range according to the known rules of a PCR, for example, between 10 nmol/l and 100 nmol/l, 100 nmol/l and 300 nmol/l, 300 nmol/l and 1 µmol/l, 1 µmol/l and 10 µmol/l The concentration of the nuc-macromolecules in the reaction solution ranges, for example, from 10 pmol/l to 100 pmol/l, 100 pmol/l to 1 nmol/l, 1 nmol/l to 10 nmol/l, 10 nmol/l to 100 nmol/l, 100 nmol/l to 300 nmol/l, 300 nmol/l pmol to 1 µmol/l, 1 µmol/l and 10 µmol/l. The ratios of the concentrations of the PCR primers and nuc-macromolecules are, for example, in the following areas (concentration of PCR primers to nuc-macromolecules): 1:100 bis 1:10, 1:10 bis 1:1, 1:1 bis 10:1, 10:1 bis 100:1, 100:1 bis 1000:1. The concentration of dNTPs (dATP, dCTP, dGTP, dTTP), for example, is between 10 µmol/l and 1 mmol/l of each.

The times for each temperature-step are, for example, between 1 sec and 10 min.

In some embodiments, the differences between the Tm of the primers and the Tm of the target domain of the used nuc-macromolecules can exceed 5° C., for example, differences can be up to 50° C. These differences can be used to control amplification reaction and labeling reaction. In one embodiment, the Tm of the primer is, for example, 15° to 20° higher than the Tm of the target domain of the nuc-macromolecules. The nuc-macromolecules can be used in concentrations that are significantly lower than the concentrations of dNTPs. During the initial cycles of the PCR, temperatures for the annealing step can be selected around the Tm of the primer (for example, calculated as Tm of the primer minus 5-10 degree), whereby an extension of the primer and the complementary strand with natural nucleotides can occur.

The target domains of the nuc-macromolecules, however, can not bind to the target sequences, as their Tm is much lower than the used hybridization temperature. Since the target domain does not bind to the target sequence under these conditions and their concentration is significantly lower than that of the dNTP, the dNTPs are incorporated preferentially. Subsequently, further cycles are conducted with the temperature in the annealing step below the Tm of the target domain of the nuc-macromolecule. Due to the change of the temperature (the temperature was reduced from that around the Tm of the primer to that around the Tm of the target domain), both primers and the target domains of the nuc-macromolecules can bind to the target sequence.

Due to high local concentrations of nuc-components of the bound nuc-macromolecules to the target sequences, these nuc-macromolecules can be incorporated into the growing strand, despite the presence of the dNTPs so that the target sequences are labeled. In this embodiment, the target domain is located preferentially further apart in 3' direction from the primer. Preferentially, the distance between the 3' end of the primer and the 5' end of the target domain is at least 2 to 10 nucleotides, in a further embodiment, at least 10 to 50 nucleotides, in a further embodiment at least 50 to 100 nucleotides, in a further embodiment at least 100 to 200, in a further embodiment at least 200 nucleotides.

By controlling the reaction temperatures, the binding of the primers and the target domains can be made variable so that either the amplification reaction only or both amplification and labeling reaction can proceed.

In a further embodiment, a further primer (labeling primer) is used for the labeling the target sequence in addition to the amplification primers. This primer can specifically bind the same strand of the target sequence as the target domain of a nuc-macromolecule. Preferentially, the labeling primer is located within the target sequence and upstream from the 5' side of the bound target domain of a nuc-macromolecule. During the amplification, PCR fragments of the target sequence are generated using the amplification primer. The labeling primer binds preferentially between one amplification primer and the target domain of the bound nuc-macromolecule.

The Tm of the labeling primer is preferentially in the same temperature range as the Tm of the target domain of the nuc-macromolecule. For example, the Tm of the labeling primer can differ from the Tm of amplification primer (the Tm of labeling primer is lower than the Tm of amplification primers) so that during a PCR, initially the PCR fragments are generated and then a labeling reaction can proceed with a labeling primer. In a reaction, the concentration of a labeling primer can be higher than the concentration of PCR primers.

In a further embodiment, more than one labeling primers having different binding sites within a target sequence are used together with several corresponding specific nuc-macromolecules. The labeling primers bind to the target sequence on the 5' side of the binding site of the target domain of a nuc-macromolecule so that an incorporation reaction can take place. Preferentially, those labeling primers are provided with a signal-domain or an anchor domain.

In a further embodiment, additional oligonucleotides are used to compete with the target domain of a nuc-macromolecule for the binding position in the target sequence. In one embodiment, such oligonucleotides have the same sequence composition as the target domain of the nuc-macromolecules. In another embodiment, their sequence composition differs from the target domain in at least one nucleotide.

In a further embodiment, a plurality of oligonucleotides differing in their sequence composition from the target domain in at least one nucleotide is provided. Due to the presence of such oligonucleotides in the mixture, the target domains compete for the binding site within the target sequence. Therefore, less specific binding of the target domain to the target sequence, can be suppressed, thus contributing to higher specificity of the analysis.

After the PCR, PCR fragments can be purified from the excess of primers or nuc-macromolecules or be used directly in the analysis. The analysis is performed for example by the binding to a solid phase having addressable binding partners.

In one embodiment, the concentrations of the nuc-macromolecules are preferentially chosen in a way that after the labeling reaction most nuc-macromolecules are incorporated into the target sequences and no additional purification of the labeled nucleic acid chains for the subsequent binding to the solid phase is required.

In a further embodiment, the concentration of one PCR primer may be higher than that of the other primer. This allows a certain degree of asymmetry in the generation of the PCR fragments to be achieved: thereby, the concentration of one strand can be increased.

In another embodiment, various primers for the labeling reaction and for the amplification reaction are combined in an assay. For example, primer pairs with higher Tm are used for the amplification and at least one primer with a lower Tm for the labeling reaction of newly generated PCR products. The Tm of the primer for the labeling reaction is, for example, in the same range as the Tm of the target domain of nuc-macromolecules.

In a further embodiment, multiple target sequences are amplified by means of PCR (FIG. 19). Such multiplex PCR is well known to an expert. Several primer pairs are used for amplification, so that multiple PCR fragments arise. Nuc-macromolecules can be used in such reaction, each of which comprises a specific target domain and a corresponding specific anchor domain. The target domains of the nuc-macromolecules are chosen in such a way that they can specifically bind to the resulting PCR fragments.

The anchor domains of the nuc-macromolecules are specifically combined together with the respective target domains so that respective anchor domain with the corresponding target domain of a nuc-macromolecule forms a specific pair. For example, it is expected that four target sequences may be present in a mixture.

A multiplex PCR with four specific primer pairs and four specific nuc-macromolecules is conducted (FIG. 19). The nuc-macromolecules can have the following composition: (Nuc1-Linker)[T1;A1], (Nuc1-Linker)[T2;A2], (Nuc1-Linker)[T3;A3], (Nuc1-Linker)-[T4;A4] (in the figure, an indication to the linker is omitted).

The detection of the presence of three of the four expected target sequences is achieved by means of the binding to the solid phase and visualization. The binding is achieved via the binding partners having addressable positions on the solid phase.

In another embodiment, nuc-macromolecules comprising a target domain, an anchor domain and an antogonist to the anchor domain are used in a PCR (FIG. 20).

The structure of the nuc-macromolecule and the cyclic reaction conditions are selected in such a way that during the reaction, the target domain of the nuc-macromolecules can bind to the target sequence. Further, the conditions of the reaction are selected so that the anchor domain of the free, unincorporated nuc-macromolecules can be present during the reaction in an open or a locked state, but preferentially in the open state.

After the incorporation of the nuc-macromolecules, the anchor domain is presented in the open state. This is achieved, for example, through the spatial separation of the anchor domain and the antagonist after the hybridization of the target domain. After the labeling reaction, the temperature is decreased so that antagonist can bind the anchor domain within the unincorporated nuc-macromolecules and thus block it.

The anchor domains of the incorporated nuc-macromolecules remain open and capable of binding to the solid phase. This mixture is brought into contact with a solid phase and incubated under conditions that permit the binding of the anchor domains of the incorporated nuc-macromolecules to the immobilized binding partner. Since the anchor domains of the unincorporated nuc-macromolecules are blocked, they do not interfere with the binding of the labeled target sequences.

In another embodiment, a polymerase having a strand displacement activity is used in the PCR reaction (FIG. 21). Nuc-macromolecules comprising a target domain and an anchor domain are used. During the PCR, the binding and the incorporation of nuc-macromolecules occurs into the PCR fragments of the target sequence. As the polymerase is able to displace the target domain of the target sequence, additional natural dNTPs or nuc-macromolecules are incorporated.

The labeled PCR fragments can be bound to a solid phase. In such a reaction, for example, one type of nuc-macromolecules comprises a target domain [T1] and an anchor domain [A1], and a different type of nuc-macromolecules comprises another target domain [T2] and a signal-domain [S1]. By the incorporation of both types of nuc-macromolecules, PCR fragments are specifically labeled with the signal domain and the anchor domain.

Other components can also be used in such reaction, e.g. labeled primers, hybridization probes, and labeled nucleotides, as described in other chapters.

One or more types of nuc-macromolecules can participate in such a reaction, as described in other chapters.

One or more target sequences can be amplified and labeled.

Detection of the target sequence can be achieved via the binding to the solid phase with a subsequent detection reaction as described in other chapters.

Detection of a Specific Target Sequence in a Material

Many examples of diagnostic tests will be known to a person skilled in the area. Usually, internal controls for amplification, binding, and detection are included in a test designed for the detection of one or more specific sequences from an organism in a test material.

With regard, for example, to the target sequences of the desired organisms and the structures of the nuc-macromolecules, such control sequences are designed according to the rules described in other chapters. A labeling reaction is performed as described above.

Such a labeling reaction comprises, for example, several nuc-macromolecules with target domains which are complementary to the target sequences of interest.

The target sequences can be amplified with different techniques, for example using a multiplex PCR. In a further embodiment, such a reaction comprises a plurality of primers specific to the target sequences or primer pairs which allow amplification of the desired target sequences.

Following the amplification and labeling reaction, detection of the labeled target sequences is conducted. In the case of the presence of a target in the material, it is detected by specific labeling with nuc-macromolecules.

In one embodiment, the strength of the generated signal is measured. The amount of target sequences in the starting material can be estimated by correlating this signal strength to that from internal controls.

The individual reagents are preferentially provided in pre-mixed form so that only the addition of the material is necessary to start the reaction. Provided reagents are preferentially provided as a kit.

Examples of the Detection of Sequence Variants in a Specific Target Sequence (Distinction of Related Target Sequences Such as SNP Detection)

In some cases, sequence variants of a target sequence which differ by one or few nucleotides have to be differentiated. An assay for such a task can be designed in different ways.

In one embodiment, the differentiation is accomplished by primers: only primers supporting an extension reaction of a specific sequence are used. For example, a primer has a discriminatory nucleotide in the 3' end position which can bind to only a particular type of the sequence. Another type of the sequence would form a mismatch, and thus it cannot be extended or the extension is insufficient. In such an embodiment, the nuc-macromolecules can be used for binding to the solid phase (i.e. nuc-macromolecules include at least one anchor domain) or they can be used for detection (i.e. nuc-macromolecules include at least one signal domain).

In another embodiment, sequence-specific or sequence-selective amplification is conducted with selective primers, for example by means of a PCR reaction. The nuc-macromolecules can be used for binding to the solid phase (i.e. nuc-macromolecules include at least one anchor domain) or they can be used for detection (i.e. nuc-macromolecules include at least one signal domain).

In another embodiment, the differentiation can be carried out by the target domain of the nuc-macromolecules. Multiple nuc-macromolecules whose target domains are complementary to different variants of the target sequence (FIG. 16) can be used. Nuc-macromolecules having perfectly complementary target domains are preferentially incorporated into the growing strand. The target domains within a single type of nuc-macromolecules are used, for example, in combinations such as at least a target domain and an anchor domain or at least a target domain and a signal domain or of a target domain, an anchor domain, and a signal domain.

An appropriate variation of the target sequence can be identified through the binding to the solid phase and a detection reaction.

In another embodiment, the differentiation can be achieved by the incorporation of a nuc-component of a nuc-macromolecule. The nuc-component is combined with a specific anchor domain (FIG. 17) or signal domain, which allows for a specific attribution of the incorporated nuc-component after the binding to a solid phase.

For example, dATP is combined with the anchor domain 1, dCTP with the anchor domain 2, dGTP with the anchor domain 3, and dUTP with the anchor domain 4. In one embodiment, the nuc-macromolecules comprise only an anchor domain.

In another embodiment, the nuc-macromolecules comprise at least one target domain and an anchor domain. The signal domain can be bound to the corresponding primers.

After a labeling reaction, a binding reaction to the solid phase with addressable binding partners is conducted. By known encoding of nuc-components by means of the anchor domain/binding partner on the solid phase, the type of nuc-component can be determined.

Combinations of various methods are possible.

In one embodiment, nuc-macromolecules comprise at least one target domain and at least one anchor domain. The detection is performed by the use of nuc-macromolecules with signal domains or modified primers with signal domains or hybridization probes with signal domains or conventionally labeled nucleotides.

In a further embodiment, nuc-macromolecules comprises at least one target domain and at least one signal domain. The binding to the solid phase is performed by the use of nuc-macromolecules with anchor domains or modified primers with anchor domains or hybridization probes with anchor domains or by direct hybridization of labeled target sequences to the complementary nucleic acid strands which are immobilized on the solid phase.

Incubation of labeled nucleic acid chains with the solid phase allows the anchor domains to bind to the binding partners immobilized on the solid phase. Thereby, the labeled target sequences or their equivalents can also be bound to the solid phase.

After a detection reaction, an optical attribution of the bound nucleic acid chains to the respective positions of the binding partners can be made. Thus, a conclusion about the presence of specific target sequences in the reaction mixture is possible.

The binding of the nucleic acid chains to the solid phase can be conducted directly through a complementary immobilized nucleic acid chain or indirectly transmitted via an anchor domain.

In such a reaction, other components such as labeled primers, hybridization probes, labeled nucleotides can be used, as described in other sections.

One or several types of nuc-macromolecules can participate in such a reaction as described in other sections.

One or several target sequences can be amplified and labeled. The detection of the target sequence can be achieved through the binding to the solid phase with a subsequent detection reaction, as described in other sections.

1.5.12 Composition Kit for Labeling and/or Amplification of Nucleic Acids

Generally, one or more kits comprise components which are necessary for the performance of enzymatic incorporation reactions with inventive nuc-macromolecules and an optional subsequent analysis (for example individual substances such as nuc-macromolecules, polymerase, dNTPs and primers or their compositions, reaction mixtures, and solid phase).

The composition of the kit can vary depending on the application, wherein the type of application can range from a simple primer extension reaction to an amplification with labeling and a subsequent analysis by means of a solid phase.

The kits can optionally comprise either positive and/or negative controls and instructions for performance of the method.

Optionally, kits can comprise materials and reagents for the preparation of components of the kit for the biochemical reactions or the genetic material such as components for preparation of the target sequence. Means for purification of labeled nucleic acid chains from an excess of nuc-macromolecules can be components of kits.

Usually, the kit components are provided in commercial reaction vessels, wherein the volume of the vessels can vary between 0.2 ml and 1 l. Vessel arrays such as microtiter plates can be preloaded with components which support the automatic delivery of reagents.

A kit for labeling nucleic acid chains (target sequences) can optionally include multiple components for practicing the invention disclosed in the specification.

Below, some examples are given:
Means and solutions for isolating target sequences from a biological material
One or more devices for handling of the solutions.
One or more primers for amplification and labeling of target sequences.
These primers can optionally comprise at least one anchor domain and/or a signal domain.
One or more DNA polymerases or RNA polymerases or reverse transcriptases.
For example, Klenow Fragment Polymerase, Klenow exo minus Fragment, phi29 DNA Polymerase, T7 DNA Polymerase, Sequenase 2™, Taq Polymerase, Vent™ Polymerase, Deep Vent™ Polymerase, Vent™ exo minus DNA Polymerase, Deep Vent™ exo minus DNA Polymerase, Pwo DNA Polymerase, Tli DNA Polymerase, Tth DNA Polymerase, so called Hot-Start-Polymerases, T7 RNA Polymerase, T4 RNA Polymerase, reverse Transcriptasen, e.g. Moloney Murine Lekemia Virus (M-MLV), Rous Sarcoma Virus (RSV), Avian Myeloblastosis Virus (AMV), Rous Associated Virus (RAV), Myeloblastosis Associated Virus (MAV), Human Immunodeficiency Virus (HIV).

The polymerases are preferentially provided in a storage solution, this storage solution, for example, comprises the following substances:
Buffer Tris-HCl, HEPES, Borate, Phosphate, Acetate (concentrations range for example from 10 mM to 200 mM)
Salt, e.g. NaCl, KCl, NH4Cl, concentrations range for example from 10 mM to 500 mM.
PEG or other inert polymer, e.g. Mowiol (concentrations range for example from 1 to 50% (w/v)
Glycerol (concentrations range for example from 1% to 70%)
Reducing agents, e.g. DTT (concentrations range for example from 0.1 to 50 mM)
Further substances can be included in a storage solution which support the stability of an enzyme. Examples of such substances are known, see description of products from enzyme manufacturers such as Promega, Invitrogen, Roche, etc.

One or several kinds of nuc-macromolecules (nucleotide analogs) that can be present as in form of acid or as salts (e,g, sodium, potassium, ammonium or lithium can be used as an ion). Nuc-macromolecules can be provided in dry form or in form of a solution, e.g. solved in water or in a buffer, e.g. Tris-HCl, HEPES, borate, phosphate, acetate, or in a storage solution, which can comprise the following components individually or in combination:

buffer Tris-HCl, HEPES, borate, phosphate, acetate (concentrations range for example from 10 mM and 200 mM)

salts, e.g. NaCl, KCl, NH4Cl, MgCl2,

PEG or other inert polymer, such as Mowiol in concentration from 1 to 20% (w/v)

glycerol in concentration between 1% and 50% marker or marker units of modified nuc-macromolecules, in particular in the embodiments, in which affine bound is used between the linker and the marker or between marker and core component.

DMSO

One or more reaction buffers for performing the amplification and/or the labeling reaction and/or the binding to the solid phase and/or the detection of the binding events on the solid phase One or more sets of natural nucleotides or analogs thereof (e.g. dATP, dGTP, dCTP, dTTP, dUTP, dITP or ATP, CTP, GTP, UTP)

One or more sets of terminators (e.g. ddATP, ddGTP, ddCTP, ddTTP, ddUTP)

One or more types of conventionally labeled nucleotides, such as fluoresently labeled or biotin-labeled dUTP or dCTP analogues One or more target-sequence-specific hybridization probes with an anchor domain or a signal domain Other enzymes which support amplification or labeling method, proteins and cofactors, such as helicase and ATP, single strand binding protein One or more reaction vessels for carrying out individual reactions Solid phase for the binding of labeled target sequences, such as a lateral flow device or an array. Such a solid phase can comprise, for example, a binding partner for anchor domains of nuc-macromolecules, or those of primers, or those of hybridization probes.

Such a solid phase can also comprise oligonucleotides which can bind to the target sequence.

One or more reagents for the detection of binding events of the labeled target sequences to the solid phase (e.g. enzymes and chromogenic substrates, or nanoparticles)

Where appropriate, control sequences to verify the success of individual steps

A guide to conduct and analyse of the reactions

1.5.13 Suggestions for the Synthesis of Nuc-Macromolecules

The nuc-macromolecules according to the invention can be synthesized in different ways. Examples for the synthesis of sequence specific nucleotide conjugates are given in patent application Cherkasov et al WO2011050938. Further suggestions for the synthesis of nuc-macromolecules are presented in patent applications Cherkasov et al WO2005044836 and Cherkasov et al WO2006097320.

Nuc-macromolecules can be synthesized by the Genovoxx GmbH company as customer service.

1.5.14 Examples of Synthesis of Nuc-Macromolecules

In the following, synthesis of nuc-macromolecules in which the target domain consists of DNA is described. There are many known methods for covalent labeling of the DNA. The labeling can be conducted at different positions of the nucleic acid chain (5' position, 3 position, internal portions). Multiple labels can be attached to one DNA.

The modification can be conducted via chemical or enzymatic reactions. On the one hand, the coupling of a substance can be carried out already during the chemical/enzymatic synthesis of nucleic acids (for example, by the use of phosphoroamidites or by the use of modified nucleotides and a polymerase or by the use of a ligase reaction).

On the other hand, the coupling can proceed via one or more intermediate steps such as through the introduction of a reactive group and be accomplished after the synthesis.

Below, examples which describe some of these variants are presented for demonstration.

Synthesis of Nuc Linker Components with Reactive Groups.

The coupling of nuc-components and marker components such as oligonucleotides can be achieved by many methods. For example, many methods are known which describe the linking of two structures each having a reactive amino group by a crosslinker. Oligonucleotides modified with one or more amino groups can be purchased commercially. Optionally, the amino group can be present at the 5' end or at the 3' end, or in the internal area of an oligonucleotide. In the following examples, amino-reactive nuc-components which are provided as precursors are described. Such amino-reactive nucleotides can be linked to the oligonucleotides.

1.5.14.1 Synthesis of dUTP-PEG(8)-NH2

Aminoallyl-dUTP, 5 mg (AA-dUTP purchased from Jena Biosciences) was dissolved in phosphate buffer, pH 8.0 solution, to a concentration of 50 mmol/l.

Fmoc-PEG(8)-NHS (obtained from Iris Biotech GmbH) was dissolved in DMSO to a concentration of 100 mmol/l.

The solution of Fmoc-PEG(8)-NHS (approx. 8 equivalents) was added to the solution of dUTP-AA, until AA-dUTP was completely reacted (control via TLC).

Purification of dUTP-PEG(8)-Fmoc was carried out on DEAE-HPLC in a Tris-HCl buffer and NaCl gradient. The fractions containing product were collected and further purified by reversed-phase C-18 column with water-ethanol gradient. The eluate containing dUTP-PEG(8)-Fmoc was evaporated, dried, and dissolved in anhydrous DMF.

Pipiridin was added to the solution of dUTP-PEG(8)-Fmoc in DMF up to a concentration of 1%. The product, dUTP-PEG(8)-NH2, was precipitated and dried.

Further, dUTP-PEG3400-NH2 and dUTP-PEG5000-NH2 were obtained by a similar method, wherein Fmoc-PEG3400-NHS and Fmoc-PEG5000-NHS have been used (obtained from Iris Biotech GmbH). For materials and methods see Cherkasov et al. WO 2005 044836.

Thus, further reactive groups can be coupled to the amino group on the linker. At this stage, various cross-linkers can be used for the preparation of an amino-reactive derivative. An expert will be familiar with many examples of cross-linkers.

1.5.14.2 Synthesis of dUTP-PEG(8)-NHS

Glutarate-(NHS)2 was first dissolved in DMF and after that was added in excess to a solution of dUTP-PEG(8)-

NHS in DMF (5 mmol/l). The product, dUTP-PEG(8)-NHS was precipitated, washed with DMF, and dried.

Similarly, dUTP-PEG(3400)-NHS and dUTP-PEG(5000)-NHS were obtained.

In another embodiment of this example, phenyldiisothiocyanate can be used instead of glutarate-(NHS)2, resulting in products dUTP-(PEG)8-ITC or dUTP-PEG(3400)-ITC accordingly.

An expert will recognize that other cross-linkers with other functionalities such as other linker lengths or other amino-reactive groups can be used. Further additional functionalities such as cleavability of the linker can be introduced by an appropriate choice of the cross-linker such as reductively or oxidatively cleavable linkers (e.g. dithiodipropionic acid-(NHS)2, tartrate-(NHS)2). Many cross-linkers are commercially available, for example from Thermo Scientific or Sigma-Aldrich or IRIS GmbH.

1.5.14.3 (A) Synthesis of dUTP-Glutarate-NHS and dUTP-PEG(5)-NHS and dUTP-PEG(9)-NHS dUTP-AA (aminoallyl-dUTP, by Trilink Biotechnologies, pH 7.0), was dried and suspended in dry DMSO up to a calculated concentration of 50 mmol/l. Glutarate-(NHS)2 (obtained from Thermo Scientific Germany) was dissolved in DMSO to concentrations of 300 mmol/l.

The suspension of dUTP-AA was added to solution of Glutarate-(NHS)2 and incubated for 2 h at 37° C. under vigorous stirring until the solution became transparent.

The conversion of dUTP-AA was monitored by TLC.

The purification of dUTP-glutarate-NHS was carried out by precipitation from diethyl ether/DMF mixture (v:v 90:10). The pellet contained the product. The product was dissolved in DMSO and frozen.

In a similar manner, further dUTP-R-X analogs can be synthesized, wherein (R) represents any linker and (X) can be any reactive group. The reactive group can, for example, react with amino groups or thio groups or carboxyl groups.

Examples of other commercially available short linkers (cross-linkers) are presented in the cross-linker Guide Thermo Scientific (www.piercenet.com).

In a similar manner, dUTP-PEG(5)-NHS and dUTP-PEG(9)-NHS were synthesized and purified. These analoga contain a PEG-Linker with 5 and 9 PEG-monomers (Crosslinker were obtained from Thermo Scientific: BS(PEG)5 or BS(PEG)9).

These linkers can also comprise a cleavable linkage such as a reductively cleavable bond, for example dithiodispropionic acid-(NHS)2 or an oxidative cleavable bond such as tartrate-(NHS)2.

Other nucleotide analogs (e.g. N-(6-Aminohexyl)-dCTP (available from AmpliChem), N6 (6-Amino)hehyl-dATP, 5-Propargylamino-dCTP, 7-Propargylamino-7-deaza-dATP, 7-Propargylamino-7-deaza-dGTP are available from Jena Bioscience and can be modified in a similar manner.

The NHS group of the linker can react with an amino group of another molecule, for example with one of an oligonucleotide.

1.5.14.3 (B) Synthesis of ddUTP-PEG (9)-NHS and PEG-ddUTP (5)-NHS 1 mg of ddUTP-PA (5-propargylamino-ddUTP from Jena Bioscience, Germany) was dissolved in dry DMSO (3 mmol/l). PEG(9)-(NHS)2 (Thermo Scientific Germany) was dissolved in dry DMSO (100 mmol/l).

The ddUTP-PA solution was added to the PEG(9)-(NHS)2 solution and incubated at RT for 12 h. The extent of the reaction was checked by TLC.

The purification of ddUTP-PEG(9)-NHS was carried out by precipitation from diethyl ether/DMF mixture (v:v 90:10). The pellet contained the product. The product was dissolved in DMSO and frozen.

ddUTP-PEG(5)-NHS was synthesized in analogous manner.

Further ddNTP-R-X analogs can be synthesized in a similar manner, wherein (R) represents any linker and (X) any reactive group. The linker can be coupled, for example, to the nucleobase or to the sugar moiety of the nucleotide. The reactive group can, for example, react with amino groups or thiol groups or carboxyl groups. Examples of other commercially available short linkers (crosslinkers) are presented in the Crosslinker Guide of Thermo Scientific (www.piercenet.com). Such crosslinkers can also comprise a cleavable linkage, such as a reductively cleavable bond (e.g. dithiobispropionic acid-(NHS)2), or an oxidatively cleavable bond (e.g. tartrate-(NHS)2).

Thus, the NHS group of the linker can be coupled to an amino group of another molecule such as of an oligonucleotide.

Coupling of Amino-Reactive Nuc-Components to the Oligonucleotide.

Such coupling will be known to one skilled in the area: oligonucleotides with one or more amino groups are reacted with an excess of amino-reactive components in a solution, such as with NHS derivatives or with isothiocyanate derivatives. The purification of the modified oligonucleotide can be done for example by means of HPLC (DEAE and RP) and will also be known to a person skilled in the area.

Below, some examples of the preparation of nuc-macromolecules which contain a nuc-component, a linker, and an oligonucleotide are described. All oligonucleotides were synthesized by MWG Operon Germany.

1.5.14.4 (A): dU-PEG(8)-[T1,A1]-TAMRA

This example illustrates the coupling of the nuc-component at the 5' end of a sequence-specific oligonucleotide with a target domain and an anchor domain. The oligonucleotide, target domain-1, anchor domain 1-TAMRA, abbreviated as [T1, A1]-TAMRA were synthesized by MWG (see list of sequences):

Target domain-1, anchor domain 1-TAMRA, abbreviated as [T1, A1]-TAMRA NH2-cgtattaccgcggctgctggca-cAAAAAAAAAAAAAAAAAAAAAAAA-TAMRA (SEQ ID NO: 1)

This sequence contains a target sequence: cgtattaccgcggctgctggcac (SEQ ID NO: 2), and an anchor sequence AAAAAAAAAAAAAAAAAAAAAAAA (SEQ ID NO: 3). This oligonucleotide contains an amino group at the 5' end, which is coupled via a spacer-C6. The TAMRA reporter is coupled as a fluorescent marker at the 3' end.

The oligonucleotide was dissolved in a phosphate buffer, pH 8.0. An excess of dUTP-PEG(8)-NHS (5 mmol/l, in DMF) was added to this solution. The reaction proceeded at room temperature in good yields. The subsequent purification of the product was carried out by DEAE column and RP-C18 column. The product (dU-PEG(8)-[T1,A1]-TAMRA) was dried and then dissolved in water at 50 µmol/l concentration and frozen. Other nuc-macromolecules were synthesized in a similar manner (Table 1).

1.5.14.4 (B): ddUTP-PEG(9)-[T4, S4] (Chain-Terminating Nucleotide Conjugate)

This example illustrates synthesis of a sequence-specific chain-terminating nuc-macromolecule.

The nuc-component is coupled to the 5"-end of an oligonucleotide with sequence-specific target domain. The oligonucleotide consists of a target domain-4 (sequence: cgt att acc gcg gct gct gg cac (SEQ ID NO: 2)) and a spacer dA (10) (SEQ ID NO: 4). An amino-group, NH2-group, is bound to the 5'-end via C6 linker and a dye (fluorescein) is attached to the 3'-end (see list of sequences):

[T4]-FAM or [T4, S4]: Target domain-4, spacer, fluorescein, 5"NH2-cgt att acc gcg gct gct gg cac AAAAAAAAAA FAM (SEQ ID NO: 5)

The oligonucleotide was dissolved in a phosphate buffer, pH 8.0 (1 mmol/l). A 5× excess of ddUTP-PEG(9)-NHS (dissolved in DMSO) was added to this solution. The reaction proceeded at room temperature with good yield. The subsequent purification of the product was carried out by means of DEAE and RP-C18 column chromatography. The product (ddUTP-PEG(9)-[T4;S4]) was dried and subsequently dissolved in water to obtain a concentration of 50 µmol/l, and frozen.

Other sequence-specific terminating nuc-macromolecules can be synthesized in similar manner.

Other chain-terminating nucleotides can be used instead of ddUTP. For example, the 3'-OH group can be replaced with an amino or azido group or other groups that lead to chain-termination. Examples thereof are known to a person skilled in the art. Reversible terminating groups can also be used. The coupling of the nuc-components can be accomplished at the 5'-end of the oligonucleotide or at an internal position or at the 3'-end.

1.5.14.5: dU-PEG(4)-[T1,A1]-TAMRA

Synthesis of nuc-macromolecules with "click chemistry" (components obtained from Baseclick GmbH, Germany).

This example illustrates the coupling of the nuc-component at the 5' end of a sequence-specific oligonucleotide having a anchor domain at the 3' end. The oligonucleotide [T1, A1]-TAMRA was used, sequence see Example 1.5.14.4 and in the list of sequences.

The oligonucleotide was dissolved in a phosphate buffer, pH 8.0. An excess of NHS-PEG4-N3 (10 mmol/l, in DMSO, obtained from Baseclick GmbH, Germany) was added to this solution. The reaction proceeded at room temperature in good yields.

The subsequent purification of the product was carried out by DEAE column and RP-C18 column. The product was dried and then dissolved in water resulting in 1 mmol/l concentration. The resulted N3-PEG4-oligonucleotide carries an azide group, which is coupled via a short PEG linker.

The coupling of the nuc-component:
dU-Alkyne-C8, 5 µl, (10 mmol/l dissolved in water, obtained from Baseclick GmbH, Germany) was added to N3-PEG4-Oligonucleotide (5 µl, 1 mmol/l) and then 10 µl DMSO/t-Butanol was added. After that, a fresh Click-solution (1 V 0.1 M CuBr in DMSO/t-butanol and 2 V 0.1 M TBTA in DMSO/t-butanol) was added. The reaction proceeded at room temperature for 24 hours.

The subsequent purification of the product was carried out by DEAE and RP-C18.

The product was dried and then dissolved in water resulting in 100 µmol/l concentration. The product (dU-PEG(4)-[T1, A1]-TAMRA) contains a nuc-component which is coupled via a short linker to the oligonucleotide.

An azide functionality or alkynes functionality can be introduced into various positions of a nucleotide (e.g. at the base or sugar) or an oligonucleotide (e.g. at the 3' end or 5' end or in the internal positions). Also several functionalities can be added. Nuc-macromolecules with one or more nuc-components can be obtained with by coupling of corresponding nuc-components.

Examples of the coupling of nucleic acid molecules via click chemistry are given in the following references:

A. H. El-Sagheer, T. Brown, *Chem. Soc. Rev.* 2010, 39, 1388-1405. Click Chemistry with DNA.

J. Lahann, Wiley VCH 2009. Click Chemistry for Biotechnology and Materials Science.

F. Morvan, A. Meyer, G. Pourceau, S. Vidal, Y. Chevolot, E. Souteyrand, J.-J. Vasseur *Nucleic Acids Symposium Series* 2008, 52, 47-48. Click Chemistry and Oligonucleotides: How a simple reaction can do so much.

1.5.14.6 Synthesis of dUTP-PEG(5)[T5-MB;S5] and dUTP-PEG(9)[T5-MB;S5] with a Target Domain of the Type "Molecular Beacon"

A modified oligonucleotide was synthesized (Eurofin MWG, Germany) comprising a sequence segment (target domain sequence) complementary to a target sequence (M2). A further sequence segment that is complementary to part of said target domain sequence adjoins the target domain. Such a structure can be present free in solution as a fully or partially double-stranded oligonucleotide, which is called "molecular beacon". A person skilled in the art knows that oligonucleotides of this composition can allow for better discrimination of sequences.

dUTP-PEG(5)-NHS or dUTP-PEG(9)-NHS were used as nuc-components with a linker (synthesis see above). The oligonucleotide had the following structure:

[T5-MB]-FAM or [T5-MB; S5]: Target domain-5, spacer, fluorescein, 5' NH2-cgt att acc gcg gct gct GTAATAC AAAAA AAAAA FAM (SEQ ID NO: 6) (Stem regions are underlined)

The oligonucleotide was dissolved in a phosphate buffer solution, at pH 8, and added to dUTP-PEG(5)-NHS or PEG-dUTP(9)-NHS. The reaction proceeded at the NH2 group at the 5'-end with good yield. Purification of the product was carried out by means of DEAE and RP-18 column chromatography.

Other modified nucleotides with target domain oligonucleotides of the type "molecular beacon" were synthesized in similar manner.

1.5.14.7 Synthesis of dUTP-PEG(9)-[T4;aT1;S4] with a Target Domain and with an Oligonucleotide Complementary to the Target Domain (Antagonist)

Initially dUTP-PEG(9)-[T4;S4] was synthesized. dUTP-PEG(9)-NHS and an oligonucleotide with the following structure were used:

[T4]-FAM or [T4, S4]: Target domain-4, spacer, fluorescein, 5'NH2-cgt att acc gcg gct gct gg cac AAAAAAAAAA FAM (SEQ ID NO: 5)

The synthesis conditions used were similar to those described for other examples of coupling of a nucleotide-linker-NHS to a terminal amino group of an oligonucleotide. dUTP-PEG(9)-[T4;S4] was purified by means of DEAE and RP-18 column chromatography and dissolved in a buffer solution (incorporation buffer 1). An equivalent of a complementary oligonucleotide with the following structure was added to this solution:

Antagonist oligonucleotide 1 [aT1]

5' agc cgc ggt aat acg 3'phosphate (SEQ ID NO: 7)

This oligonucleotide can undergo complementary binding at the sequence of the target domain, thereby blocking a portion of the target sequence at the 5'-end of the target domain (here underlined)

domain, for example by raising the temperature. The melting temperature (Tm) of oligonucleotide antagonists (62° C.) is lower than the Tm of the entire target domain (73° C.) (measured in incorporation buffer 1).

Other nuc-macromolecules with antagonists of the target domain oligonucleotides were synthesized in similar manner.

Overview of the Synthesized Nuc-Macromolecules

TABLE 1

| name of the nuc-macromolecule (conjugate) | nuc-component | Position of the nuc-component | Linker component | Target Domain [Tn] | Anchor Domain [An] |
|---|---|---|---|---|---|
| dU-P4-[T1,A1] | dU | 5' end | PEG 4 | Target Domain 1 | Anchor Domain 1 |
| dU-P8-[T1,A1] | dU | 5' end | PEG 8 | Target Domain 1 | Anchor Domain 1 |
| dU-P3000-[T1,A1] | dU | 5' end | PEG 3000 | Target Domain 1 | Anchor Domain 1 |
| dU-P8-SS-P8-[T2] | dU | 5' end | PEG8-SS-PEG8 | Target Domain 2 | |
| dU-P3000-[T2] | dU | 5' end | PEG 3000 | Target Domain 2 | |
| dU-P3000-[T2] | dU | 5' end | PEG 5000 | Target Domain 2 | |
| dU-P3000-[T2]-3' | dU | 3' end | PEG 3000 | Target Domain 2 | |
| dU-P5000-[T2]-3' | dU | 3' end | PEG 5000 | Target Domain 2 | |
| dU-Glut-[T3,A3] | dU | 5' end | Glutarate | Target-Domain 3 | Anchor-Domain 3 |
| dC-Glut-[T3,A3] | dC | 5' end | Glutarate | Target Domain 3 | Anchor Domain 3 |
| dU-Tart-[T1,A1] | dU | 5' end | Tartrate | Target Domain 1 | Anchor Domain 1 |
| dU-DTBP-[T1,A1] | dU | 5' end | Dithiobis-propionate | Target Domain 1 | Anchor Domain 1 |
| dU-P8-[T3,A3]-FAM | dU | 5'-end | PEG 8 | Target Domain 3 | Anchor Domain 3 with fluorescein |
| ddU-P5-[T4; S4] | ddU | 5'-end | PEG 5 | Target Domain 4 | |
| ddU-P9-[T4; S4] | ddU | 5'-end | PEG 9 | Target Domain 4 | |
| dU-P5-[T5-MB; S5] | dU | 5'-end | PEG 5 | Target Domain 5 as molecular beacon | |
| dU-P9-[T5-MB; S5] | dU | 5'-end | PEG 9 | Target Domain 5 as molecular beacon | |
| dU-P9-[T4; aT1; S4] | dU | 5'-end | PEG 9 | Target Domain 4 + Antagonist-Oligo 1 | |

5"NH2-cgt att acc gcg gct gct gg cac AAAAAAAAAA FAM (SEQ ID NO: 5)

3'phosphate gca taa tgg cgc cga (SEQ ID NO: 7)

The solution containing dUTP-PEG(9)-[T4;S4] and the antagonist oligonucleotide [aT1] was heated to 90° C. C for 1 minute and then cooled to RT. Cooling causes the complementary oligonucleotide antagonist to bind to the corresponding position of the target domain oligonucleotide, resulting in formation of dUTP-PEG(9)-[T4;aT1;S4]. Thus, the target domain of the nuc-macromolecule now has a single-stranded as well as a double-stranded segment. The antagonist oligonucleotide can be released from the target The oligonucleotides with a target domain and optionally with an anchor domain used for the synthesis are shown in the list of sequences.

1.5.15 Examples of Enzymatic Labeling Reactions of Target Sequences with Nuc-Macromolecules All polymerases were purchased from commercial suppliers (e.g. New England Biolabs or Promega).

Incorporation of Nuc-Macromolecules in a Primer-Dependent Reaction:

The substrate properties of synthesized nuc-macromolecules were tested for several polymerases in incorporation reactions.

An incorporation reaction was performed in an incorporation of buffer 1 (50 mmol/l Tris-HCl, 50 mmol/l NaCl, 5 mmol/l MgCl2, 10% glycerol), or an incorporation of buffer 2 (1× reaction buffer (1× ThermoPol thermophilic polymerases) from New England Biolabs).

Different polymerases were tested (e.g. Klenow exo minus, Taq polymerase, Vent exo minus polymerase, Terminator, Terminator II, Deep Vent exo minus, Sequenase, Tth polymerase, Tli polymerase).

Reactions were performed in a total volume of 10 to 20 µl. The following concentrations of components were typically used: primer (labeled with a fluorescent dye or unlabeled) 0.1 to 1.5 µmol/l, templates (M1-M10) from 1 nmol/l to 1.5 µmol/l, nuc-macromolecules from 0.1 to 10 µmol/l, natural nucleotides (dATP, dCTP, dGTP, dTTP) were used in concentrations of 0.1 µmol/l to 10 mmol/l (the concentrations used are indicated in the respective experiment).

The concentrations of polymerases obtained from commercial suppliers were arbitrarily designated as 1× concentration. The dilutions of polymerases (for example 1:10 to 1:1000) relate to this initial concentration and are specified in the respective experiment.

The solid phase was represented by streptavidin-magnetic beads, which comprise a binding partner for the respective anchor domain, such as dT48 (SEQ ID NO: 8) for a dA25-anchor domain (SEQ ID NO: 3).

The analysis of the extended fragments was carried out using gel electrophoresis in a 10% polyacrylamide gel under denaturing conditions (approximately 85-90° C.), The gel images were made using a gel documentation system.

In the summary, the following properties of nucleic macromolecules were determined:

The synthesized nuc-macromolecules (comprising at least one nuc-macromolecule, a linker, at least one target domain, at least one anchor domain, and at least one signal domain) are suitable as substrates for DNA polymerases and can be incorporated into the primer in a primer extension reaction in a template-dependent reaction at a corresponding complementary position for the respective nuc-components.

Nuc-macromolecules can be accepted as substrates by thermolabile and thermostable polymerases.

The novel nuc-macromolecules can be used in a primer-dependent labeling reaction such as a primer extension.

Nuc-macromolecules compete with the corresponding natural nucleotides for incorporation into the growing strand opposite the respective complementary position in the template. The ability of the nuc-macromolecules to compete for the incorporation depends on whether the target domain of the nuc-macromolecule is hybridized to the respective template or not:

The incorporation of nuc-macromolecules hybridized to the respective template is clearly preferred. It takes up to 10 mmol/l concentration of natural nucleotides to suppress the incorporation of a hybridized nuc-macromolecule.

The incorporation of nuc-macromolecules non-hybridized to the template is strongly suppressed by natural nucleotides of the same type as nuc-components of the corresponding nuc-macromolecule.

Nuc-macromolecules with structures comprising a relatively short linker between the nuc-component and the marker component (for example up to 200 chain atoms, more preferentially up to 100 chain atoms, more preferentially up to 50 chain atoms, more preferentially up to 20 chain atoms) are preferred in labeling reactions in the presence of natural nucleotides of the same type as the nuc-component of the nuc-macromolecules (e.g. dTTP presence in a reaction with nuc-macromolecules comprising dUTP).

Nuc-macromolecules having structures comprising a relatively short linker (see above) and at least one nuc-component attached to the 5' end or in the vicinity of the 5' end of the target domain are preferred in labeling reactions in the presence of natural nucleotides of the same type as the nuc-component of the nuc-macromolecules (e.g. dTTP presence in a reaction with nuc-macromolecules comprising dUTP).

The inventive nuc-macromolecules can be used in a labeling reaction comprising cycles. The cyclic labeling reaction includes at least one cycle wherein a change of the reaction temperature is carried out. For example, one such cycle includes at least a denaturation step (for example at 95° C.) in which the target sequences can be converted from double-stranded form into a single-stranded form. Furthermore, such a cycle includes at least one hybridization step of a primer and of a target domain of a nuc-macromolecule. Furthermore, such a cycle includes at least one step for the extension of the primer and incorporation of nuc-macromolecules. The steps of the hybridization and extension can take place at the same or different temperatures. These steps can be repeated at least two times.

The labeling can be performed on nucleic acid chains which are immobilized on a solid phase.

Nuc-macromolecules which are attached to a solid phase can be used for labeling of target sequences.

Under appropriate reaction conditions, for example at hybridization temperature, nuc-macromolecules can distinguish target sequences by their target domains and label only specific target sequences.

Under appropriate reaction conditions, for example at hybridization temperature, nuc-macromolecules can distinguish target sequences by their target domains, wherein a group of target sequences with similar binding sites for target domain of a nuc-macromolecule can be labeled.

Several nuc-macromolecules can be provided in a labeling reaction and label their specific target sequences under appropriate reaction conditions, for example at hybridization temperature.

Nuc-macromolecules can selectively label their specific target sequences in the presence of another type of nucleic acid chains (for example genomic DNA) under appropriate reaction conditions.

Nuc-macromolecules can label single-stranded forms of the target sequence.

Nuc-macromolecules can label double-stranded forms of the target sequence (e.g. PCR fragments) when double strands were separated from each other and an appropriate hybridization step is included in a cyclic labeling reaction for a respective target domain of a nuc-macromolecule.

Nuc-macromolecules can label target sequences during a PCR.

Target sequences which were labeled with nuc-macromolecules can be bound to a solid phase via the coupled/introduced anchor domain of nuc-macromolecules.

The extent of labeling of target sequences and, hence, the signal intensity of the labeled target sequences can be influenced by the reaction conditions. For example, by changing the concentration of competing natural nucleotides of the same kind as the nuc-component of the nuc-macromolecules or by the number of cycles in a cyclic labeling reaction or by the initial amount of target sequences or by hybridization temperature for the target domain or primer.

Parts of nuc-macromolecules (e.g. target domain of nuc-macromolecules) can be degraded by the 5'-3' exonuclease activity of a polymerase (e.g. Taq polymerase).

The "strand displacement" activity of the polymerases can displace the target domain of a nuc-macromolecule from the bound state to the target sequence, and continue the synthesis of the labeled strand.

Below, some examples are given to demonstrate the substrate properties of nuc-macromolecules.

1.5.15.1 Enzymatic Incorporation of dU-PEG(8)-[T1,A1]-TAMRA (I)

In this experiment, incorporation of dU-PEG(8)-[T1,A1]-TAMRA (I) into the primer in the presence of different sets of further natural nucleotides was tested.
Components:
Incorporation buffer 1
Nuc-macromolecule: dU-PEG(8)-[T1,A1]-TAMRA (5 µmol/l)
Natural nucleotides (dTTP, dATP, dCTP, dGTP) were added to the final concentrations, as described in the legend

```
Polymerase:
Klenow exo minus, 1:10

Primer:
A50-T719 (1 µmol/I)
(this primer has an anchor domain A50)

Template:
M1 (1 µmol/I)
5' GTT TTC CCA GTC ACG ACG GGAG gtg cc agc agc cgc ggt aat acg ACCA cctatagtgagtcgtatta 3' (SEQ ID NO: 9)
Binding site for nuc-macromolecule is underlined.
```

Primer, templates, natural nucleotides and nuc-macromolecule (dU-PEG(8)-[T1,A1]-TAMRA) were combined to a reaction solution and were heated to 90° C. and then allowed to cool down to room temperature, so that the primers and the target domain of the nuc-macromolecule could bind/hybridize to the template (target sequence). Polymerase was added to this solution and the reaction was allowed to proceed at room temperature for 10 min. Then the reaction was loaded directly onto a gel, and the reaction products were separated. The result is presented in FIG. 26. The composition of individual reactions is given in the legend.

It can be seen that dU-PEG(8)-[T1,A1]-TAMRA can be used as a substrate by Klenow exo minus (Lane 1). It can be incorporated into the primer in the presence of dTTP at increasing concentrations (up to 1 mmol/l) (Lanes 2 to 7), and in the presence of additional nucleotides (dATP, dGTP, dCTP, Lane 7).

The compound, dU-PEG(8)-[T1,A1]-TAMRA, can compete with free dTTP (1 mmol/l) for incorporation into the primer by polymerase due to its binding to the template.

In control experiments (not shown here), it was determined that dU-PEG(8)-[T1,A1]-TAMRA can be incorporated into the primer even when it is not hybridized to the template. However, the presence of dTTP resulted in suppression of this reaction.

Thus, dTTP presented at a concentration of only 5 µmol/l could significantly reduce the incorporation of the compound, dU-PEG(8)-[T1,A1]-TAMRA, if it was not bound to the template. The presences of competing nucleotides in a concentration of 100 µmol/l resulted in a complete suppression of the incorporation of dU-PEG(8)-[T1,A1]-TAMRA if it was not hybridized to the template.

Taken together, the specific binding of dU-PEG(8)-[T1,A1]-TAMRA to the template resulted in a significant favoring of incorporation of this nuc-macromolecule in the presence of competing nucleotides. This effect was interpreted as follows: the local concentration of the nuc-component is increased greatly due to binding to the template, so that polymerase can preferentially incorporate this nucleotide.

1.5.15.2 Enzymatic Incorporation of dU-PEG(8)-[T1,A1]-TAMRA.(II)

In this experiment, incorporation of dU-PEG(8)-[T1,A1]-TAMRA.(II) into the primer by several polymerases was tested in the presence of other natural nucleotides.
Components:
Incorporation buffer 1
Nuc-macromolecule: dU-PEG(8)-[T1,A1]-TAMRA (5 µmol/l)
Natural nucleotides (dTTP, dATP, dCTP, dGTP) were added to the final concentrations, as described in the legend

```
Polymerase:
Klenow exo minus, 1:10 bis 1:1000

Taq Polymerase 1:100

Vent exo minus -Polymerase 1:100

Primer:
A50-T719 (1 µmol/I)
(this primer has an anchor domain A50)
```

-continued

Template:
M2 (1 µmol/I)

Template 2:
5' GTT TTC CCA GTC ACG ACG GGAG gtg cc agc agc cgc ggt aat acg AGT CTT CTCA cctatagtgagtcgtatta (SEQ ID NO: 10)
The binding site for the nuc-macromolecule is underlined.

The reaction solution was prepared as in 1.5.15.1. Primer, templates and nuc-macromolecules were hybridized by heating the reaction solution to 90° C. and subsequently allowing it to cool to RT.

DATP, dGTP, dCTP were added to this solution at a final concentration of 100 µmol/l and dTTP at 0 to 10 mmol/l (details in the legend to FIG. 27). The reaction was started by the addition of an appropriate polymerase (Klenow exo minus in dilution 1:10, 1:100, 1:1000, Taq 1:100 and Vent exo minus, 1:100). The labeling reaction was conducted for 12 hrs at 37° C. The reaction mixtures were analyzed by gel electrophoresis. The result is depicted in FIG. 27. The composition of individual reactions is given in the legend.
Results:
Acceptance of dU-PEG(8)-[T1,A1]-TAMRA.

All used polymerases accepted dU-PEG(8)-[T1,A1]-TAMRA as substrate in the primer extension reaction (FIG. 27, Lanes 1, 4, 7, 10, 15). The presence of dATP, dCTP, and dGTP did not disturb the incorporation. Only a partial extension of the primer was achieved (FIG. 27, arrow A2), since the absence of dTTP prevented full primer extension.

Competition with dTTP

Incorporation of dU-PEG(8)-[T1,A1]-TAMRA by all polymerases was observed in the presence of dTTP up to 100 µmol/l concentration (Lanes 2, 5, 8, 11, and 14). The incorporation of dU-PEG(8)-[T1,A1]-TAMRA by Vent minus and by Taq Polymerase was strongly or even completely suppressed under applied reaction conditions in the presence of dTTP, at 10 mmol/l, (Lane 12 for Taq, Lane 13 for Vent exo minus). In contrast, Klenow exo minus can incorporate dU-PEG(8)-[T1,A1]-TAMRA hybridized to the template even at this high concentration of competing nucleotides (Lanes 3, 6, and 9).

Strand-Displacement Activity of Polymerases

The ability of Klenow exo minus to effect strand displacement resulted in a complete synthesis of the complementary strand to M2 in the presence of dTTP (Lanes 2, 3, and 5).

Taq polymerase and Vent exo minus were unable to detach the target domain of nuc-macromolecule hybridized to the matrix under the same conditions, for which reason these polymerases did not show strand displacement activity. The incorporation by Vent exo minus and Taq proceeded only up to the target domain; a complete synthesis of the complementary strand was not observed under the applied conditions. A complete synthesis of the complementary strand could be achieved, however, under cyclic labeling conditions (see below).

5'-3' Exonuclease Activity of Taq

Taq polymerase has a 5'-3' exonuclease activity. Despite this activity, the primer was labeled with the inventive nucleotides.

Effect of the Polymerase Concentration

Klenow fragment was used at different concentrations, from 1:10 to 1:1000. The best results for the strand displacement reaction were achieved at higher concentrations of Klenow exo minus.

1.5.15.3 Choice of Nuc-Macromolecules and Polymerases for a Labeling Reaction

For a specific labeling reaction of target sequences (nucleic acid chains), it is crucial that nuc-macromolecules can be incorporated depending on their binding to these target sequences. Several reaction parameters have influence on the result. The choice of polymerases, the reaction conditions (such as concentration of competing natural nucleotides) as well as the structure of nuc-macromolecules can have such an influence. For illustrative purposes, some of these parameters were varied (polymerases, concentration of competing nucleotides, structure of nuc-macromolecules).

In the following, various polymerases were compared with regard to their ability to incorporate the nuc-macromolecules, hybridized to a template, in the presence of competing nucleotides (in these examples, dTTP).

Very good incorporation: Klenow exo minus, Taq, Therminator polymerase, Therminator Polymerase II (all enzymes from New England Biolabs)

Good incorporation: Vent exo minus, Tth polymerase

Moderate incorporation: Sequenase 2, Deep Vent exo minus

The structure of the nuc-macromolecules can have an effect on their ability to be incorporated by the polymerase in the presence of competing nucleotides. The best incorporation results (in the presence of competing nucleotides) were achieved with structures of nuc-macromolecules having a nuc-component which is coupled via a relatively short linker at the 5' end of the target domain.

The role of the binding and the role of the position of the target domain on a target sequence.

Comparison of the incorporation capability of the nuc-macromolecules "with" and "without" binding to the template indicated that the presence of dTTP (100 µmol/l) can completely prevent incorporation of nuc-macromolecules with dUTP (as nuc-component) but without binding of the target domain to the template. The presence of dTTP at lower concentrations (1 to 10 µmol/l) can significantly reduce the incorporation of such nuc-macromolecules.

This situation changes dramatically upon the binding of the target domains to the corresponding complementary position of the template downstream from the 3' direction of the primer (wherein there is at least one nucleotide position in the template between the 5'end of the target domain and the 3' end of the primer, which is able to form a base pair with the nuc-component of the hybridized nuc-macromolecule): the nuc-macromolecules bound to the template are preferentially incorporated. Even concentrations of natural nucleotides in the solution up to 100 µmol/l or even 10 mmol/l cannot completely suppress the incorporation.

The position of the binding of a target domain to the target sequence can be varied depending on the experiment. Typically, the target domain is designed in such a way that its potential binding site is located in the 3' direction from the labeling primer. Preferentially, the position of the target domain in the target sequence is selected in such a way as to provide at least one nucleotide position in the template between the target domain and the primer which is able to form a complementary base pair with the nuc-component of the hybridized nuc-macromolecule.

The degree of labeling of a target sequence can be managed in accordance with a reaction procedure, the respective concentrations of the natural nucleotides, the polymerase and the reaction conditions: coupling of the nuc-component at the 5' end of the target domain or to the parts close to the 5' end of the target domain (with short linkers having only 10 to 100 chain atoms, for example) allows an incorporation of the nuc-macromolecules bound to the template in the presence of high concentrations of natural nucleotides.

1.5.15.4 Cyclic Primer Extension Reaction

The labeling of target sequences can be conducted in a single step of primer extension or during multiple cycles of primer extension. Here, an example for the labeling of target sequences in multiple cyclic steps is presented.

For better illustration of the importance of the hybridization of a target domain to the target sequence for labeling, a plurality of different target sequences were used with the same primer-binding site. The primer is labeled with a fluorescent dye (T7-19-Cy3) at the 5' position. The nuc-macromolecule (dU-PEG(4)-[T1,A1]-TAMRA) used for the labeling has dUTP as its nuc-component, which is coupled via a short linker at the 5' end of the target domain. Further, this nuc-macromolecule has an anchor domain and a signal domain (TAMRA) at the 3' end.

Components:

Template M2 and the target domain have a completely complementary sequence along the entire length of the target domain (complementary region is underlined).

Template M4 has complementary sequences for both ends of the target domain (complementary region is underlined).

Template 8 has complementary sequences only for the 3' end of the target domain. (complementary region is underlined). The 5' end of the target domain is not hybridized to the target sequence.

Template 9 has complementary sequences for the 5' end of the target domain (complementary region is underlined). The 3' end of the target domain is not hybridized to the target sequence.

Such sequences can be considered as examples of deviations from the target sequence (e.g. mutations in the target sequence). Likewise, such sequences can be considered as pairs of the target sequence/target domains, wherein the target domain is not completely complementary to the target sequence (template 4). This experiment serves as example of a reaction process wherein the Tm of the target domain is less than the Tm of primers. Further, this experiment represents the case when the 5' end of the target domain is not hybridized to the target sequence.

The reaction solution was prepared as in example 1.5.15.1.

Primer, templates, natural nucleotides (dNTPs) and nuc-macromolecules were provided in a buffer solution. The solutions were initially incubated at 95° C. for 15 min. During this time, the Taq polymerase was added to the reaction (Hot Start of the reaction to avoid side reactions). To stop the reaction, EDTA was added to the final concentration of 10 mmol/l. The reaction mixtures were subsequently separated on a gel.

The cyclic labeling reactions were carried out under different temperatures in several cyclic steps.

```
ThermoPol Buffer 1x

Nuc-macromolecule:
dU-PEG(4)-[T1, A1]-TAMRA (0.5 µmol/I)

Natural nucleotides (dTTP 50 µmol/II, dATP, dCTP, dGTP each 100 µmol/I)

Polymerase:
Taq Polymerase 1:100

Primer:
T719-Cy3 (0.5 µmol/I)
(This primer has a signal domain, Cy3-dye)

Templates:
M2, M4, M8, M9 (each 0.1 µmol/I)

Template 2:
5' GTT TTC CCA GTC ACG ACG GGAG gtg cc agc agc cgc ggt aat acg AGT CTT CTCA cctatagtgagtcgtatta (SEQ ID NO: 10) (already present)

Template 4:
5' GTT TTC CCA GTC ACG ACG GGAG gtg cc agc ggt aat acg AGT CTT

CTGA cctatagtgagtcgtatta (SEQ ID NO: 11)

Template 8:
5' GTT TTC CCA GTC ACG ACG GGAG gtg cc agc agc cgc AGT TTT TTT AGT CTT CTGA cctatagtgagtcgtatta (SEQ ID NO: 12)

Template 9:
5' GTT TTC CCA GTC ACG ACG GGAG cgc ggt aat acg AGT CTT

CTCA cctatagtgagtcgtatta (SEQ ID NO: 13)
(The potential binding sites for the target domain are underlined)
```

A cycle comprised a hybridization step, an extension step and a denaturation step.

The extension step (70° C. for 1 min) and the denaturation step (95° C. for 30 sec) were carried out equally for all templates.

Since the given target domain and target sequences comprised differences in complementary areas, it was interesting to test at which hybridization temperature the incorporation of nuc-macromolecules occurs. Consequently, different hybridization temperatures were tested. Since in preliminary experiments the ability of the nuc-macromolecule to be incorporated on the target sequence (M2, full complementary to the target domain) had already been tested, this reaction was used as a positive control (hybridization at 55° C.).

The following temperatures were chosen as hybridization temperatures: 35° C., 45° C., and 55° C.

Cyclic reactions (each 20 cycles) were conducted in a PCR device under the following conditions:

| Cycler Program: hybridization at 35° C. | | |
| --- | --- | --- |
| Denaturation: | 95° C. | 30 sec |
| Hybridization: | 45° C. | 1 min |
| Extension: | 70° C. | 1 min |
| Cycler-Program: hybridization at 35° C. | | |
| Denaturation: | 95° C. | 30 sec |
| Hybridization: | 45° C. | 1 min |
| Extension: | 70° C. | 1 min |
| Cycler Program: hybridization at 55° C. | | |
| Denaturation: | 95° C. | 30 sec |
| Hybridization: | 55° C. | 1 min |
| Extension: | 70° C. | 1 min |

As a control of the signal intensity and the position of the extension product in the gel, primer extension (1× cycle) of the respective template without a nuc-macromolecule was used (37° C., 12 hrs). The concentration of individual components (primer, template, polymerase, dNTPs were the same as in the cyclic labeling). In this reaction, primer was extended with natural nucleotides.

The results of the reaction are summarized in FIG. 28

It can be seen that the primer extension has taken place during the cyclic primer extension, the amount of extended primers has increased (compare the intensity of the bands in a simple cyclic reaction and primer extension).

The labeling of the newly synthesized strands depends significantly on whether the nuc-macromolecule has bound to the template under particular reaction conditions via its target domain. The reaction at M2 template with Taq polymerase at 55° C. hybridization temperature resulted in a good yield: the labeled product is clearly visible (FIG. 28, M2, Lane 1, Arrow A1). The labeling with the template (M8) at all hybridization temperatures (35° C., 45° C., 55° C.) is clearly visible, too (see FIG. 28, M8, Lanes 2-4, Arrow A2). In the reaction with template (M4), only a very weak labeling is visible at a hybridization temperature of 35° C. and 45° C. (see FIG. 28, M4, Lanes 1, 2, Arrow A2). No labeling could be detected at 55° C. In the reaction with template 9, no labeling was detected at any hybridization temperature; the incorporation of dU-PEG(4)-[T1,A1]-TAMRA was completely suppressed by natural nucleotides.

This example illustrates that the binding of the target domain of a nuc-macromolecule can be used for the specific recognition of a target sequence: under stringent hybridization conditions only nuc-macromolecules which were bound to the target sequence could be incorporated into the growing strand. Changes in the binding site in the target sequence can lead to a loss of or reduction in the labeling. On the other hand, the target domain can still bind to the changed position in the target sequence if less stringent conditions (e.g. lower temperatures) are used.

The example with template 8 illustrates that polymerase accepts nuc-macromolecules even if their 5' end is not hybridized to the template.

1.5.15.5 Labeling of Target Sequences During or Parallel to their Amplification in the PCR and Subsequent Binding and Isolation of Labeled Target Sequences with a Solid Phase Via the Anchor Domain of the Incorporated Nuc-Macromolecules The labeling of target sequences can take place parallel to their amplification. PCR is one of the usual methods for amplification of nucleic acid chains. Here, an example is shown for the labeling of target sequences parallel to the amplification. After PCR, labeled DNA fragments were isolated by a specific binding to a solid phase. This isolation is enabled by a specific binding of the anchor domain of incorporated nuc-macromolecules to the binding partner immobilized on a solid phase.

Components:

| | | |
| --- | --- | --- |
| ThermoPol Buffer 1x | | |
| Nuc-macromolecule: | dU-PEG(4)-[T1,A1]-TAMRA | (0.5 µmol/l) |
| Nuc-macromolecule: | dU-PEG(8)-[T1,A1]-TAMRA | (0.5 µmol/l) |
| Natural nucleotides | | |
| (dTTP 50 µmol/ll, dATP, dCTP, and dGTP each 100 µmol/l) | | |
| Polymerase: | Taq-Polymerase | 1:100 |
| | Vent exo minus | 1:100 |
| Primer: | T719-Cy3 | (0.5 µmol/l) |
| | U19 | |
| (T7-19-Cy3 Primer has a signal domain: Cy3-dye) | | |
| Template: | M2 | (10 nmol/l) |
| | dT48-Magnetic beads | (1 vial) |
| | (SEQ ID NO: 8) | |

One PCR primer was labeled with a fluorescent dye (Cy3) at the 5' end. The other PCR primer was unlabeled. Nuc-macromolecules used for the labeling (dU-PEG(4)-[T1,A1]-TAMRA and dU-PEG(8)-[T1,A1]-TAMRA) had dUTP as their nuc-component, which was coupled via a short linker (PEG 4 or PEG 8) at the 5' end of the target domain.

Further, these nuc-macromolecules had an anchor domain and a signal domain (TAMRA) at the 3' end. The binding site of the template 2 for the target domain is fully complementary.

Both PCR primers, template (M2), natural nucleotides (dNTPs), and nuc-macromolecules were provided in a buffer solution. The solution was initially incubated at 95° C. for 15 min. During this time Taq Polymerase or Vent exo minus polymerase was added to the reaction (hot start of the reaction, to minimize side reactions). To stop the reaction, EDTA was added to the final concentration of 10 mmol/l. Subsequently, the reaction mixtures were separated on a gel.

The following PCR conditions were used:

Cycler Program:

| | | |
| --- | --- | --- |
| Denaturation: | 95° C. | 30 sec |
| Hybridization: | 55° C. | 1 min |
| Extension: | 70° C. | 1 min |
| Cycling: 20 cycles | | |
| Hold: | 4° C. | |

Subsequently, a part of the reaction was brought in contact with a suspension of magnetic beads with dT48 (SEQ ID NO: 8). After an incubation period of 5 min in Thermo-Pollx, the beads were washed with incorporation buffer 1. The beads were loaded directly onto the gel. The detachment of the PCR fragments of beads was achieved by the use of elevated temperature of about 85° C.

The solid phase was prepared prior to the experiment as follows: Streptavidin Magnetic beads (Promega) were loaded with an oligonucleotide dT48 (SEQ ID NO: 8) having a biotin moiety at the 3' end and washed. The dT48 oligonucleotide (SEQ ID NO: 8) represents an example of a binding partner for an anchor domain. Such beads were able to bind nucleic acid chains labeled with nuc-macromolecules.

The result of the reaction is summarized in FIG. 29. A significant formation of PCR fragments was observed: labeled nuc-macromolecules PCR products (Arrow A1 and A2, FIG. 29 A) and PCR products without nuc-macromolecules (Arrow B1, FIG. 29 A). Interestingly, Taq polymerase was able to generate only low amounts of fully extended labeled PCR fragments (Arrow A1) vs. (Arrow A2). On the other hand, Vent exo minus polymerase could generate significantly a higher proportion of fully extended fragments through their strand-displacement activity under reaction conditions (Arrow A2).

Specific isolation of PCR fragments modified with nuc-macromolecules by solid phase is shown in FIG. 29 (B). It can be recognized, that only PCR fragments with incorporated nuc-macromolecules having an anchor domain could be isolated (Arrow A1, Lane 3). PCR products without incorporated nuc-macromolecules did not bind to the solid phase and therefore could not be isolated (Lane 4 has no signals).

1.5.15.6 Detection of Bacterial DNA by PCR Amplification and Labeling with Nuc-Macromolecules An expert will know many methods based on the real-time PCR method. In such methods, for example, a labeled probe capable of binding to the complementary target sequence is added into the reaction and the amount of product is measured during the reaction.

The signal or measurable increment of the signal is detected if the probe has hybridized to the respective target sequence, and is partially degraded by the 5'-3' activity of a thermostable polymerase (e.g. U.S. Pat. Nos. 5,538,848, 5,723,591, 5,876,930, 6,030,787, 6,171,785, 5,487,972).

Such methods for the detection of specific DNA segments in biological material can be found in a very large number of publications. The authors describe the isolation conditions of the nucleic acid chains, the specific primers, the probe composition and the appropriate reaction conditions for the amplification and detection of target sequences. Numerous variants of this method, including multiplex PCR methods, real-time PCR diagnostic methods, and combinations with reverse transcriptases (RT-PCR) have been published since the introduction of real-time PCR in the 90s.

The present application makes use of this state of the art. In one advantageous embodiment of this application, the specific binding of a target domain of a nuc-macromolecule to the target sequence takes place under conditions which allow an amplification of nucleic acid chains (such as PCR), similar to real-time PCR. An expert can therefore apply the existing knowledge of the real-time PCR. In particular, this relates to the composition of PCR primers, the target domain, and reaction conditions, as well as other combinations such as multiplexing and combinations with reverse transcriptases.

For demonstration purposes, primers and probe composition published in a publication (Nadkarni M. A. et al, Microbiology, 2002, v. 148 257-) were used for labeling with nucmacromolecules during a PCR reaction.

The primers (forward and reverse primers, see the list of sequences) were adopted without changes. The sequence composition of the described double-labeled probe (FAM/TAMRA) was adopted for the sequence composition of the target domain of the nuc-macromolecule with the following changes. Instead of fluorescein, a nuc-component was coupled via a short linker at the 5' end of the target domain and an anchor domain consisting of 25 dA residues was added to the 3' end of the target domain. The 3'end of the anchor domain carried a fluorescent dye (TAMRA).

The resulting oligonucleotide was [T1, A1]-TAMRA, which was used for the synthesis of nuc-macromolecules as an example of the marker.

Some properties of the resulting nuc-macromolecule with this oligonucleotide (e.g. dU-PEG(4)-[T1,A1]-TAMRA or dU-PEG(8)-[T1,A1]-TAMRA) have been already described in the preceding examples; see examples 1.5.15.1 to 1.5.15.5.

In this example, the application of this nuc-macromolecule for detection of a presence of bacterial DNA is shown. A real-time PCR for detection of the 16 S ribosomal genomic portion of bacteria was selected. The primer and the probe were placed within conserved regions of the 16 S sequence.

ThermoPol Buffer 1x
| | | |
|---|---|---|
| Nuc-macromolecule: | dU-PEG(4)-[T1,A1]-TAMRA | (0.5 µmol/l) |
| Natural nucleotides (dTTP, dATP, dCTP, and dGTP each 200 µmol/l) | | |
| Polymerase: | Taq Polymerase | 1:100 |
| Primer: | Forward Primer | (1 µmol/l) |
| | Reverse Primer | (1 µmol/l) |
| Probe (FAM/TAMRA) | | (1 µmol/l) |
| Template: | genomic DNA from E. coli | (0.5 ng/µl) |
| | dT48-Magnetic beads (SEQ ID NO: 8) | (1 vial) |

The composition of the primer and the probe (FAM/TAMRA) corresponded to those described in the cited paper (see the list of sequences). Preparation of the dT48 beads (SEQ ID NO: 8) was described in the previous example.

Reagents were pipetted at RT and heated up to 95° C., then Taq Polymerase was added. Following this, PCR cycles were carried out according to the following scheme:

| First 25 cycles: | | |
|---|---|---|
| Denaturation: | 95° C. | 30 sec |
| Hybridization: | 55° C. | 1 min |
| Extension: | 70° C. | 1 min |
| Next 25 cycles: | | |
| Denaturation: | 95° C. | 30 sec |
| Hybridization: | 55° C. | 1 min |
| Extension 1: | 60° C. | 1 min |
| Extension 2: | 70° C. | 1 min |
| Hold: | 4° C. | |

The PCR fragments were purified in part via ultrafiltration and/or via binding to the dT48 Magnetic Beads (SEQ ID NO: 8).

The analysis was performed by gel electrophoresis (10% acrylamide gel, acrylamide/bisacrylamide mixture Rotiphorese Roth) under denaturing conditions at 90° C., 150V. The detection of the signals was performed using TAMRA dyes of the nuc-macromolecule or by staining of the nucleic acid chains with ethidium bromide after electrophoresis.

Figure 31:
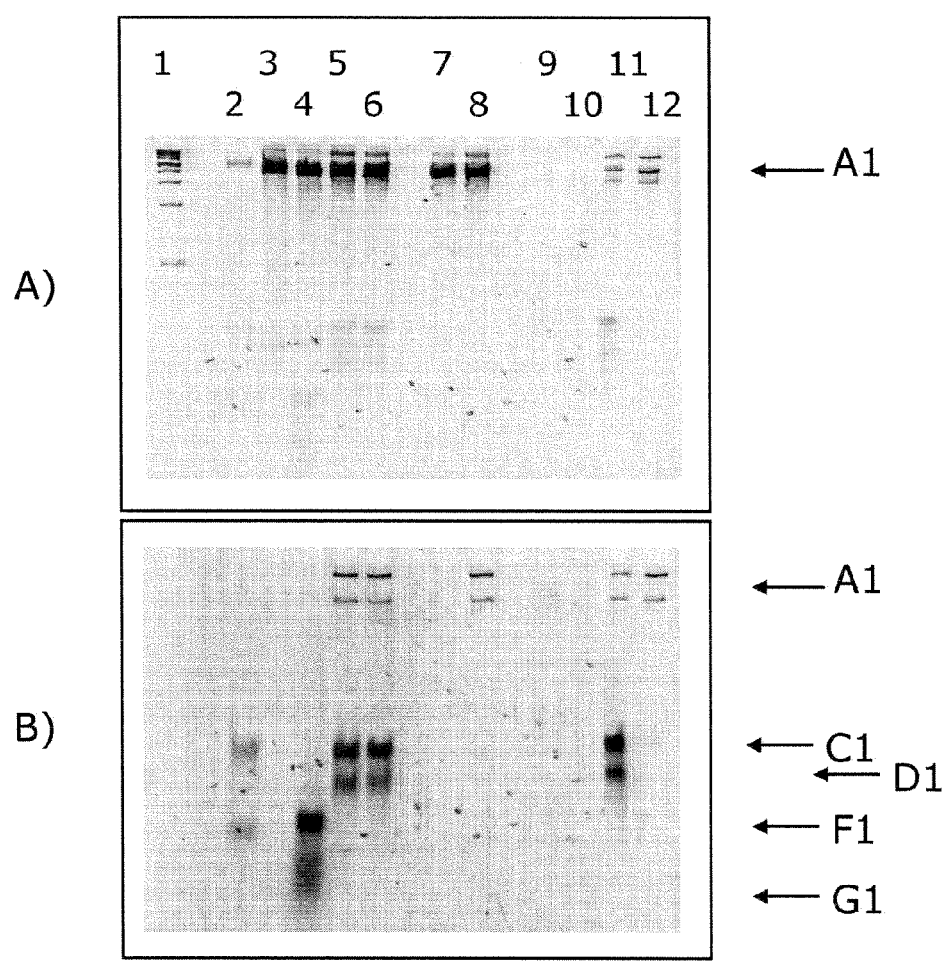

The result of the labeling is shown in FIG. 31.

The PCR was successful under the applied conditions (bands of approximately 500 bp).

The nuc-macromolecules (dU-PEG(4)-[T1,A1]-TAMRA) were incorporated into the PCR products (Arrow A1, Lanes 5 and 6, FIG. 31 B). This was achieved despite a relatively high concentration of dTTP (200 µmol/l at the start of the reaction). The added DMSO (5%) in this reaction had no effect (the intensity of the bands in Lanes 5 and 6 is approximately equal). Two bands of high molecular mass correspond to a completely (upper band) and an incompletely labeled PCR product.

In a control reaction, the real-time PCR probe (FAM/TAMRA) was not incorporated (Lane 4), because it is not a nuc-macromolecule. In this reaction, the PCR products did not carry a fluorescent label. The probe was partly degraded by the 5'-3' exonuclease activity of Taq polymerase, since it was hybridized to the target sequence during the reaction, as was expected for a real-time PCR test.

The labeled PCR products could be purified of primers and unincorporated nuc-macromolecules via ultrafiltration MWCO 100 kDa (Lanes 7 and 8).

1.5.15.7 Incorporation of Nuc-Macromolecules with Target Domain Containing a Double-Stranded Portion Two types of double strand formation within a target domain oligonucleotides were tested. First, an oligonucleotide of the type "molecular beacon" was synthesized and used as target domain of a nuc-macromolecule (dU-PEG (9)-[T5-MB;S5] see synthesis example 1.5.14.6). Second, a nuc-macromolecule with a single-stranded target domain was synthesized. Another, shorter oligonucleotide was hybridized with the target domain oligonucleotide by complementary binding, with the result that the target domain formed both a single-stranded segment and a double stranded segment with this oligonucleotide (dU-PEG(9)-[T4;aT1;S4] see synthesis example 1.5.14.7).

At lower temperatures, the target domain oligonucleotide of such nuc-macromolecules is present partly in the form of a double strand. This prevents the target domain sequence of the nuc-macromolecule from binding to other nucleic acid chains (both specific and non-specific binding are prevented). With increasing temperature the double strand opens, which means that the target domain can adopt the single-stranded form and bind to target sequences. This principle makes it possible to increase specificity in an assay, because the target sequence and a target domain only interact at higher temperatures.

Components:

```
Incorporation buffer 1

Nuc-macromolecules
dU-P9-[T5-MB, S5] (1 µmol/I)

dU-P9-[T4, S4] (1 µmol/I)

dU-P9-[T4, aT1, S4] = dU-P9-[T4, S4] + antagonist-oligonucleotide (1 µmol/I)

Natural nucleotides (dTTP, dATP, dCTP, dGTP) 300 µmol/I

Polymerase:
Bst Polymerase Large Fragment 1:20

Primer:
T719-Cy3 (0.5 µmol/I)

Templates:
M2 (0.5 µmol/I)

Template 2:
5' GTT TTC CCA GTC ACG ACG GGAG gtg cc agc agc cgc ggt aat acg AGT CTT CTCA cctatagtgagtcgtatta (SEQ ID NO: 10)
The binding site for dU-P9-[T4, S4] is underlined
```

The labeled PCR fragments could be bound to the dT48 magnetic beads (SEQ ID NO: 8) via introduced nuc-macromolecules caning anchor domain directly after the PCR. The non-labeled PCR fragments did not bind to the dT48 beads (SEQ ID NO: 8), because they had no anchor domain.

Since the reaction also contained unincorporated nuc-macromolecules, they also were bound to the beads (Lane 11). The labeled PCR fragments purified with ultrafiltration were free of nuc-macromolecules and could be isolated in pure form by the beads (Lane 12).

This example shows how reagents and methods developed using real-time PCR can be used in combination with nuc-macromolecules.

The reaction mixture was prepared as described in 1.5.15.1. Primer, templates and modified nucleotides were hybridized by heating the reaction mixture to 90° C. with subsequent cooling to RT.

dATP, dGTP, dCTP, dTTP were added to this solution to obtain a final concentration of 300 µmol/l. The reaction was initiated by adding polymerase. The labeling reaction was carried out for 10 min at 55° C. The reaction mixtures were analyzed by gel electrophoresis. The result is depicted in FIG. 46. The makeup of individual reactions is provided in the legend.

Results:
Bst Polymerase Large Fragment accepted the nucleotide conjugates as substrates in the primer extension reaction.

The Bst Polymerase Large Fragment was able to incorporate nucleotide conjugates into the complementary strand at dTTP concentrations of 300 µmol/l.

The strand displacement activity of Bst Polymerase Large Fragment resulted in complete synthesis of the complementary strand to the template M2 in the presence of dTTP.

1.5.15.8 Amplification and Labeling of a DNA with Nuc-Macromolecules in a Thermostable Helicase-Dependent Amplification (tHDA) Under Isothermal Conditions and Detection of Amplification by Means of a Strip Test (Lateral Flow Device)

A target sequence was amplified and labeled by means of tHDA. The kit components (Bst DNA polymerase large fragment and thermostable helicase) together with specific primers make it possible to amplify DNA fragments. The sequence-specific incorporation of dU-PEG(8)-[T3,A3]-FAM on template M8 with primer T7-19 was first validated in a separate assay. This showed that the large fragment of Bst DNA polymerase (Bst polymerase large fragment) is able to incorporate such a nuc-macromolecule in a sequence-specific manner and can synthesize a complete nucleic acid strand complementary to M8. Sequence-specific incorporation of dU-PEG(8)-[T3,A3]-FAM was then tested for in a tHDA-assay. Commercially available test strips, which detect molecules that are labeled with fluorescein and biotin (e.g. PCR fragments), were used for the detection of the amplified product. The dU-PEG(8)-[T3,A3]-FAM used in the assay contained a fluorescein moiety at the 3'-end. A primer comprising a biotin-moiety at the 5'-end was used in the reaction. If amplification and labeling are successful, one can expect the appearance of a color mark at a predetermined position on the test strip.

Reagents: IsoAmp II Universal tHDA Kit (BioHelix Corporation, sales in Germany from New England Biolabs, NEB), Milenia GenLine HybriDetect 2T (strip test for the detection of PCR fragments, Milenia Biotec, Germany).

Components:

| | | |
|---|---|---|
| Nuc-macromolecule: | dU-PEG(8)-[T3,A3]-FAM | (1 µmol/l) |
| Primer: | T7-19 and U19-Biotin | (each 0.2 µmol/l) |
| Template: | M8 | (1 nmol/l) |

The reaction mixture (50 µl) was pipetted according to the manufacturer's instructions (One Step tHDA, BioHelix Corporation product information). The reaction was incubated at 60° C. for 1 h. Following this, a strip (Milenia GenLine HybriDetect 2T) was immersed in the reaction mixture. A color signal appeared after about 2 min at the expected position on the test strip (detection of a DNA fragment with fluorescein and biotin). Gel electrophoresis confirmed that the nuc-macromolecule had been incorporated as envisaged.

A person skilled in the art knows various ways of implementing HDA reactions (Tong et al. Biotechniques, 2008, 45, 543-; Jeong et al. Cell Mol life Science 2009 v. 66, 3325-, Vincent et al. EMBO Reports 2004 v. 5 795-), during which (both chain-terminating and non-terminating) nuc-macromolecules as described in the present invention can be used. Combinations of these techniques with different means for detection are obvious to an expert.

1.5.15.9 Examples of Synthesis of DNA with Nuclease-Resistant Sequence-Specific Nucleotide Conjugates and their Isolation by Means of Nuclease Treatment (FIG. 47-56)

One example of the present invention describes components and methods for the synthesis of a nuclease-resistant information carrier ("smart DNA"), FIG. 47, as well as methods for its detection. This information carrier ("smart DNA") is produced in an enzymatic primer extension reaction or in an amplification reaction.

In one embodiment, compositions used for the synthesis comprise the following components:
- At least one target sequence
- At least one type of sequence-specific nucleotide conjugate (smart nucleotide) comprising a nuclease-resistant oligonucleotide segment and at least one nucleotide-specific signaling domain or anchor domain
- At least one nuclease-resistant primer carrying a biotin moiety,
- Four dNTP or a mixture of natural and alpha-thio dNTPs at a concentration at which the non-specific incorporation of smart nucleotides is suppressed
- At least one polymerase The synthesis is preferably carried out under conditions that allow for sequence-specific labeling of the target sequences by nucleotide conjugates.

The product of the synthesis reaction (primer extension or amplification) is a modified DNA which contains sequence-specific nuclease-resistant smart nucleotides and which is labeled with a specific signal domain or anchor domain.

In one embodiment of the invention, the labeled DNA segment is subsequently isolated. The isolation can be effected by various means, for example by affinity purification of the labeled fragment, or isolation by means of gel electrophoresis, or by HPLC (reverse-phase or ion exchange chromatography).

In an advantageous embodiment of the invention, the newly synthesized labeled DNA is isolated with the help of nucleases. In such an embodiment, DNA labeled with sequence-specific nuclease-resistant nucleotide conjugates is more resistant to DNA-degrading or DNA-cleaving enzymes such as nucleases than unlabeled DNA. Such DNA can withstand treatment with particular nucleases, while the remaining unlabeled DNA is completely or partly destroyed by such treatment.

In one embodiment, single strands of the unlabeled nucleic acids are preferably degraded. Double-stranded fragments remain in the reaction. Such fragments are usually not able to interact with other nucleic acid chains via hybridization.

In another embodiment, preferably both single strands and double strands of unlabeled nucleic acids are degraded.

After the nuclease degradation step, the labeled DNA and cleavage fragments of the unlabeled DNA are present as a mixture. Preferably, such cleavage fragments (Mono-, di- and tri-nucleotide fragments) will not interact with labeled DNA by hybridization and do not interfere with detection. If so, labeled DNA can be detected in the presence of cleaved fragments.

The following advantages are available in subsequent process steps such as detection, if the fragments of labeled DNA are isolated and the remaining sequences are eliminated, for example with the help of nuclease:

A. The possibility of non-specific interactions between other sequences and the DNA to be detected is significantly reduced since all non-labeled sequences are enzymatically degraded.
B. The possibility of non-specific interaction between other sequences and particular components of the detection system, for example between labeled oligonucleotides and non-labeled DNA fragments, is significantly reduced because all unlabeled sequences are enzymatically degraded.
C. The analysis does not require maintenance of the double-stranded state for the labeled DNA (all fragments of the molecule to be detected are covalently linked to each other within one strand)
D. The analysis does not require stringent conditions to achieve specific hybridization of labeled probes (e.g. oligonucleotide) on the single strand of the target sequence: all fragments of the molecule to be detected are already specifically covalently coupled to each other.

Overall, detection is greatly simplified after nuclease isolation of labeled DNA fragments, and potentially this also increases the specificity of the analysis. The signal-to-noise ratio can be significantly improved: for example, non-specifically amplified, but unlabeled DNA fragments will not interfere with detection.

A further advantage of isolation by nuclease digestion is that the amplification potential of the labeled nucleic acid chains is eliminated. In this preferred embodiment of the invention, after isolation with nucleases the information carrier is incapable of undergoing amplification with the same primers as the target sequence during the amplification reaction.

In such an embodiment, the degradation step with nucleases is designed in such a way that no full-length amplification products of the target sequence remain in the mixture, which could serve as a template in a further amplification reaction. This can be achieved for example by nuclease treatment of sufficient duration.

An information carrier equivalent to DNA can be produced by a combination of target sequence-specific labeling during amplification and isolation of labeled DNA fragments. These information carriers predominantly have the following properties:
  The information carrier was produced during amplification of the target sequence: amplified fragments of the nucleic acid chains provide templates for synthesis of the information carrier. Sensitivity ranges comparable to, for example, PCR-based methods can be achieved in this manner.
  The information carrier preferably comprises at least one specific marker that can withstand nuclease degradation (e.g. haptens, proteins, nucleic acid analogs).
  All components comprising the information carrier are preferably covalently linked to each other.
  The information carrier has an information content equivalent to a part of the target sequence or the entire target sequence, owing to the ability of certain sequence-specific nucleotide conjugates (e.g. with target domain in form of a molecular beacon) to discriminate between the target sequence and other sequences down to a single nucleotide
  After isolation the information carrier is preferably not amplifiable with the same primers as the target sequence
  After isolation the information carrier is preferably present in a composition that does not include any nucleic acid chains.
  The detection step/Detection of the information carrier preferably requires neither maintenance of specific stringent conditions nor of conditions at which the double-strandedness of DNA is maintained: Since all components of the information carrier are covalently linked to each other, one can work at conditions that are not usually compatible with DNA detection, such as de-denaturing pH ranges, temperature or presence of nucleases.

In the following, the preparation, the isolation, and the detection of sequence-specifically labeled DNA (nuclease-resistant information carrier) are described.

In this example sequence-specific labeling of target sequences with a resolution down to a single nucleotide of the target sequence is demonstrated. A person skilled in the art is aware of probes with appropriate structures which can differentiate nucleic acid sequences down to one nucleotide. For example, probes with partially double-stranded regions (e.g. molecular beacons) can achieve this level of discrimination in real-time PCR. LNA or PNA-based probes are available as further examples.

In the present example, oligonucleotides with molecular beacon structure were used to discriminate between target sequences. These sequences are components of the target domain of the respective nucleotide conjugate. The sequences of the target domain of the sequence-specific nucleotide conjugate and the target sequence were partly taken from the following reference: Marras et al. "Multiplex detection of single-nucleotide variations using molecular beacons" Genetic Analysis: Biomedical Engineering, 1999, v. 14, 151-. In this article, the ability of partially double-stranded oligonucleotide probes (molecular beacons) is used to discriminate between four sequences that differ in only one nucleotide.

Material and Methods:

The sequences can be found in Table 2. All sequences were synthesized by MWG-EurofinOperon (Germany).

Table 2

Sequences of target domain oligonucleotides of nucleotide conjugates in Example 1.5.15.9

Name Sequence 5'->3' Modification at 5' Modification at 3'

MB-Tbc1-PTO 5'AC6-ccacgcttgtgggtcaaccccgtgg-3'FLU (SEQ ID NO: 14) NH2-C6 Fluorescein MB-Tbc4-PTO 5'AC6-ccacgcttgtcggtcaaccccgtgg-3'FLU (SEQ ID NO: 15) NH2-C6 Fluorescein MB-Tbc1 PTO/DNA Mix1 5'AC6-ccacgcTTGTGGGTCAACCcccgtgg-3'FLU (SEQ ID NO: 14) NH2-C6 Fluorescein MB-Tbc1 PTO/DNA-Mix2 5'AC6-ccAcGcTtGtGgGt-CaAcCcCcGtgg-3'FLU (SEQ ID NO: 14) NH2-C6 Fluorescein MB-Tbc1 PTO/DNA-Mix3 5'AC6-ccAcgCttGtgGgt-CaaCccCcGtgg-3'FLU (SEQ ID NO: 14) NH2-C6 Fluorescein Note on Table 2: Capital letters represent nucleotides with phosphodiester linkage; lowercase letters represent nucleotides with PTO linkage (Eurofin Operon MWG)

TABLE 2

Sequences of target domain oligonucleotides of nucleotide
conjugates in Example 1.5.15.9

| Name | Sequence 5'->3' | Modification at 5' | Modification at 3' |
|---|---|---|---|
| MB-Tbc1-PTO | 5'AC6-ccacgcttgtgggtcaacccccgtgg-3'FLU (SEQ ID NO: 14) | NH2-C6 | Fluorescein |
| MB-Tbc4-PTO | 5'AC6-ccacgcttgtcggtcaacccccgtgg-3'FLU (SEQ ID NO: 15) | NH2-C6 | Fluorescein |
| MB-Tbc1 PTO/DNA Mix1 | 5'AC6-ccacgcTTGTGGGTCAACCcccgtgg-3' FLU (SEQ ID NO: 14) | NH2-C6 | Fluorescein |
| MB-Tbc1 PTO/DNA-Mix2 | 5'AC6-ccAcGcTtGtGgGtCaAcCcCcGtgg-3' FLU (SEQ ID NO: 14) | NH2-C6 | Fluorescein |
| MB-Tbc1 PTO/DNA-Mix3 | 5'AC6-ccAcgCttGtgGgtCaaCccCcGtgg-3' FLU (SEQ ID NO: 14) | NH2-C6 | Fluorescein |

Note on Table 2:
Capital letters represent nucleotides with phosphodiester linkage; lowercase letters represent nucleotides with PTO linkage (Eurofin Operon MWG)

Synthesis of Sequence-Specific, Nuclease Resistant Nucleotide Conjugates with Signaling Domains or Anchor Domains Oligonucleotides (Table 2) were coupled to dUTP-PEG (9)-NHS (synthesis see Example 1.5.14.3) at the NH2-C6-linker at the 5'-end of the respective oligonucleotide. The final concentrations of dUTP-PEG9-NHS and oligonucleotides in the reaction mixture were: approximately 4 mmol/l and 0.3 mmol/l respectively. The reaction proceeded at room temperature in phosphate buffer pH 7.5 for 1 hr. Under these conditions, nearly complete selective modification of the terminal amino group takes place, without modification of the PTO backbone of the oligonucleotide. Purification was subsequently carried out by means of ultrafiltration via MWCO 10 kDa and Tris-HCl buffer pH 8, 100 mmol/l. If required, purification was performed with RP-HPLC and DEAE-HPLC. Nucleotide conjugates were diluted to a concentration of 50 µmol/l and frozen.

Primer Extension
Incorporation Buffer
(50 mmol/l Tris-HCl, 50 mmol/l NaCl, 5 mmol/l MgCl2, 10% glycerol, 0.2 mmol/l EDTA) for Klenow Fragment Exo-minus or a buffer supplied by the manufacturer for the particular polymerase.

dNTP:
dATP, dCTP, dTTP, dGTP (a concentration of 200 µmol/l was used as standard for dATP, dCTP, dGTP, and of 100 µmol/l for dTTP). Variations from these conditions have been noted below.

Alpha-Phosphorothioate dNTP:
Sp-dATP-a-S, Sp-dCTP-a-S Sp-dGTP-a-S Sp-dUTP-a-S (BIOLOG Life Science Institute, Germany) were used in concentrations similar to those of dNTP.

Polymerases:
Klenow Fragment Exo minus (NEB), Taq-Polymerase (Omni-Lab), Apto-Taq-Polymerase (Roche), HotStarTaq DNA-Polymerase (Qiagen), OneTaq-Hot Start Polymerase (NEB), Vent-Polymerase exo minus (NEB), Bst-Polymerase and Bst-Polymerase Large Fragment (NEB), phi29 DNA Polymerase (NEB) AMV-Reverse Transcriptase (NEB), MMLV-Reverse-Transcriptase (NEB)

Polymerases were used in the reaction in 1:50 dilution of the respective stock solution. Different hot start polymerases were used:

Apto-Taq polymerase (Roche) and OneTaq polymerase (NEB) are inactivated by an aptamer and only develop full synthetic capacity above a temperature of approximately 45° C. They do not require pre-activation. Synthetic capacity is reversibly suppressed when the temperature falls below 45° C.

HotStarTaq DNA Polymerase (Qiagen) is activated at 95° C. and subsequently retains its activity even if the temperature falls below 45° C.

Templates, Primers, Probes and Filter Oligonucleotides

TABLE 3-1

Templates for primer extension and PCR

| Name | Sequence 5'->3' |
|---|---|
| M40-MBTbc | GTT TTC CCA GTC ACG ACG GGAG TCT GGGGTTGACCGACAAG AGT CA CTCA cctatagtgagtcgtatta (SEQ ID NO: 16) |

TABLE 3-1-continued

Templates for primer extension and PCR

| Name | Sequence 5'->3' |
|---|---|
| M41-MBTbc | GTT TTC CCA GTC ACG ACG GGAG TCT GGGGTTGACCCACAAG AGT CA CTCA cctatagtgagtcgtatta (SEQ ID NO: 17) |
| M51-MBTbc | GTT TTC CCA GTC ACG ACG GGAG TCT GGGGTTGACCAACAAG AGT CA CTCA cctatagtgagtcgtatta (SEQ ID NO: 18) |
| M52-MBTbc | GTT TTC CCA GTC ACG ACG GGAG TCT GGGGTTGACCTACAAG AGT CA CTCA cctatagtgagtcgtatta (SEQ ID NO: 19) |
| M42-MBTbc (minus 3xNT) | GTT TTC CCA GTC ACG ACG GGAG TCT GGGGTTGA___ACAAG AGT CA CTCA cctatagtgagtcgtatta (SEQ ID NO: 20) |
| M43-MBTbc (minus 6x NT) | GTT TTC CCA GTC ACG ACG GGAG TCT GGGGTTGA_____-AAG AGT CA CTCA cctatagtgagtcgtatta (SEQ ID NO: 21) |

Note on Table 3-1:
Templates consisted of DNA; the primer binding site of T7-19 primer has been indicated in lowercase letters; the binding site for the target domain of the nucleotide conjugates is shown in italics. The sequences differ at a single position, which is underlined.

TABLE 3-2

| Name | Sequence 5'->3' |
|---|---|
| RNA M46-MBTbc | GGGGUUGACCGACAAGAAAACccUaUagUgagUcgUaUUa (SEQ ID NO: 22) |

Note on Table 3-2:
The following template was used for testing reverse transcriptases.

TABLE 4

Primers for primer extension and PCR

| Name | Sequence 5'->3' |
|---|---|
| T7-19 DNA | TAATACGACTCACTATAGG (SEQ ID NO: 23) |
| T7-19 DNA Biotin | 5' BIO-TAATACGACTCACTATAGG (SEQ ID NO: 23) |
| U19 DNA | GTT TTC CCA GTC ACG ACG (SEQ ID NO: 24) |
| T7-19-PTO-Biot | 5'BIO-taatacgactcactatagg (SEQ ID NO: 23) |
| T719-Cy3-3PTO | 5'-Cy3-taaTACGACTCACTATagg (SEQ ID NO: 23) |
| T719-PTO2-Biot | 5'BIO-tAaTaCgAcTcCcTaTagg (SEQ ID NO: 25) |
| T719-PTO3-Biot | 5'BIO-tAatAcgActCacTatAgg (SEQ ID NO: 23) |

Note on Table 4:
Capital letters represent nucleotides with phosphodiester linkage; lowercase letters represent nucleotides with PTO linkage (Eurofin Operon MWG)

Utilization of Filter-1-Oligonucleotides (Hybridization Probes) During Amplification.

Filter-1-oligonucleotides are oligonucleotides that competitively interfere with the binding of the target domain of a nucleotide conjugate to sequences resembling the target sequence during a labeling reaction or amplification.

TABLE 5

Filter-1-oligonucleotides

| Name | Sequence 5'->3' |
|---|---|
| MB-1Tbc1-P | 5'-CCACGCTTGTGGGTCAACCCCCGTGG-3'PHO (SEQ ID NO: 26) |
| MB-1Tbc 2-P | 5'-CCACGCTTGTTGGTCAACCCCCGTGG-3'PHO (SEQ ID NO: 27) |
| MB-1Tbc 3-P | 5'-CCACGCTTGTAGGTCAACCCCCGTGG-3'PHO (SEQ ID NO: 28) |
| MB-1Tbc 4-P | 5'-CCACGCTTGTCGGTCAACCCCCGTGG-3'PHO (SEQ ID NO: 29) |

Note on Table 5:
All filter-oligonucleotides consist of DNA. Their sequences differ at a single position, which is underlined. Their concentration in the solution was 0.5 µmol/l.

Utilization of Filter-2-Oligonucleotides (Target Domain Antagonists) Before or During Detection.

Filter-2-oligonucleotides were used to suppress the binding capacity of the target domain of nucleotide conjugates after incorporation is complete.

TABLE 6

Filter-2-oligonucleotides for binding to the target domain before or during detection (target domain antagonists)

| Name | Sequence 5'->3' |
|---|---|
| MB-1Tbc 5 | GGGGTTGACCAACAAG (SEQ ID NO: 30) |
| MB-1Tbc 6 | GGGGTTGACCCACAAG (SEQ ID NO: 31) |
| MB-1Tbc 7 | GGGGTTGACCGACAAG (SEQ ID NO: 32) |
| MB-1Tbc 8 | GGGGTTGACCTACAAG (SEQ ID NO: 33) |

Note on Table 6:
All filter-oligonucleotides consist of DNA. Their sequences differ at a single position, which is underlined. Their concentration in the solution was 5 µmol/l.

Reaction Conditions:

Primers were used in concentrations ranging from 0.1 µmol/l to 1 µmol/l respectively, and sequence-specific nucleotide conjugates were used in variable concentrations ranging from 0.01 µmol/l to 5 µmol/l respectively.

Primer Extension (FIG. 48)

Prior to a primer extension, the respective nucleic acid components were combined in an appropriate buffer solution and briefly heated to 80° C. and then cooled to RT (pre-hybridization of sequence-specific nucleotide analogs). Subsequently, each incorporation reaction was initiated by addition of polymerase and an increase in temperature (RT: Klenow Fragment exo minus, 37° C.: Klenow Fragment exo minus, Taq Polymerase, phi29 DNA polymerase, AMV-RT, MMLV-RT, Vent exo minus polymerase, 50° C.: Apto-Taq polymerase, OneTaq-Hot Start polymerase, Bst polymerase, Vent polymerase, HotStarTaq DNA polymerase). The reactions proceeded for approximately 10-20 minutes at indicated temperature conditions. Prior to use of HotStarTaq DNA polymerase (Qiagen), the reaction mixture was heated and maintained at 95° C. for 15 minutes and then cooled to the appropriate temperature.

Amplification Reaction (FIG. 48-50)

The starting concentration of the respective template in the reaction (Table 2) was varied in a range between approximately 1 fmol/l to 10 pmol/l. The concentrations of primers and other reagents were similar to those of the primer extension reaction. At least two primers (forward and reverse primer) were used. Likewise, combinations of multiple primers in one reaction were used. PCR was carried out with conventional PCR equipment. At least 20 PCR amplification cycles were used:

Denaturation, 95° C. (15 sec),
Annealing temperature, X° C. (for example for 1 min)
Extension temperature, 65° C. (for example for 1 min)

Finally, the mixture was cooled to 4° C.

For template concentrations of less than 1 fmol/l, 45 PCR cycles were performed.

The annealing temperature was varied between 40 and 60° C. The influence of the respective annealing temperature on the results of the labeling reaction is documented in the results section.

In another embodiment, additional hybridization probes (filter-1-oligonucleotides) were added to the primer extension reaction or amplification reaction. These filter-1-oligonucleotides were used in concentrations of 0.5 µmol/l. The 3'-OH group of these oligonucleotides was blocked by means of a phosphate moiety. Therefore these filter oligonucleotides cannot serve as primers in the reaction. They bind to the template during the annealing step, and they compete with the target domains of the nucleotide conjugates in binding the template. In this way, it is possible to influence the binding efficiency of the target domains of the nucleotide analogs. The efficiency with which sequence-specific nucleotide conjugates are incorporated may likewise be influenced in this manner.

Nuclease Degradation (FIG. 51)

Nuclease Degradation Followed a Similar Procedure:

10 µl of the reaction mixture containing labeled DNA (e.g. after a primer extension or amplification) was directly added into 90 µl of a solution of nuclease in a buffer supplied by the manufacturer. The following nucleases were tested (purchased from NEB or Fermentas): DNase I, Micrococcal nuclease, uracil-DNA glycosylase, S1 nuclease, exonuclease III (Exo III), exonuclease I (Exo I), mung bean nuclease. The manufacturer's recommended reaction conditions for degradation were used.

Isolation and Detection (FIG. 51-55):

The isolation of labeled DNA fragments was effected by means of different methods, for example by means of ultrafiltration, affinity binding to solid phase, or nuclease treatment.

After reaction, various techniques were used to analyze each labeled DNA. Gel electrophoresis (flat gel or capillary electrophoresis) as well as immunochromatographic technique (lateral flow device, also called dip-stick method) (Milenia GenLine HybriDetect 2T, Milenia Biotec GmbH) were employed in analysis and detection.

Capillary electrophoresis was carried out under double strand denaturing conditions (ABI 310 sequencer, POP6 gel, 50° C.). Dipstick detection was performed at room temperature and up to 37° C.

In one embodiment (method 1), nucleic acids labeled with biotin/fluorescein were analyzed with a dip stick immediately after the labeling reaction (primer extension/amplification).

In one other embodiment (method 2), nucleic acids labeled with biotin/fluorescein were analyzed with a dip stick immediately after the nuclease reaction (primer extension/amplification).

In yet another embodiment (method 3), nucleic acids labeled with biotin/fluorescein were heated to 90° C. in a solution containing approximately 5 µmol/l filter-2-oligonucleotides (target domain antagonists) after the labeling reaction (primer extension or amplification), then cooled to RT, and only analyzed with dip stick after these steps.

Results and Evaluation:

Knowledge of the melting temperatures of complexes formed by the target domain and the target sequence is important for sequence-specific binding. During the incorporation reaction, only nucleotide conjugates that are able to bind to the target sequence under the respective conditions can be incorporated.

Therefore, melting temperatures (Tm) were initially determined for complexes of templates/target domains. Both perfect matches and mismatches were tested. The measurement was performed with intercalating dye at oligonucleotide concentrations of approximately 0.5 µmol/l. Some of the results for selected pairs are summarized below in Table 7.

TABLE 7

Comparison of Tm for Match vs. Mis-match hybridization

| Template | Oligos | Match vs. Mis-Match | Tm, ° C. | Notes |
| --- | --- | --- | --- | --- |
| M40-MBTbc | MB-1Tbc1-P | 1x Mismatch | 50 | DNA/DNA |
| M41-MBTbc | MB-1Tbc1-P | Match | 60 | DNA/DNA |
| M51-MBTbc | MB-1Tbc1-P | 1x Mismatch | 50 | DNA/DNA |
| M52-MBTbc | MB-1Tbc1-P | 1x Mismatch | 50 | DNA/DNA |
| M40-MBTbc | MB-Tbc1 PTO | 1x Mismatch | 42 | DNA/PTO |
| M41-MBTbc | MB-Tbc1 PTO | Match | 52 | DNA/PTO |
| M51-MBTbc | MB-Tbc1 PTO | 1x Mismatch | 42 | DNA/PTO |
| M52-MBTbc | MB-Tbc1 PTO | 1x Mismatch | 42 | DNA/PTO |
| M40-MBTbc | MB-Tbc1 PTO/DNA-Mix3 | 1x Mismatch | 44 | DNA/PTO/DNA-Mix3 |
| M41-MBTbc | MB-Tbc1 PTO/DNA-Mix3 | Match | 54 | DNA/PTO/DNA-Mix3 |
| M51-MBTbc | MB-Tbc1 PTO/DNA-Mix3 | 1x Mismatch | 44 | DNA/PTO/DNA-Mix3 |
| M52-MBTbc | MB-Tbc1 PTO/DNA-Mix3 | 1x Mismatch | 44 | DNA/PTO/DNA-Mix3 |

According to Marras et al., the calculated Tm of the hairpin structure of a molecular beacon is about 64° C. and is in the same range as the Tm of a perfectly bound probe.

Mismatches exhibit a Tm that is about 13° C. lower than that of a perfect match. Despite some deviations, our data are in good agreement with those of Marras et al. Authors (Marras et al.) propose that the annealing and detection temperature should be chosen in such a manner that perfectly hybridized probes are guaranteed to bind; in the case of DNA/DNA hybrids this temperature corresponds to about 56° C. The drop in Tm for DNA/PTO hybrids was likewise expected.

Different annealing temperatures were explored for amplification and labeling of target sequences. The annealing temperatures were chosen so that they were within +/−10° C. of the melting temperature. The specificity of incorporation was subsequently assessed by means of different detection methods (see above). The most important findings are summarized as follows.

Labeling During Primer Extension (FIG. 48)

The incorporation of sequence-specific nucleotide conjugates was first examined in a primer extension.

It was established that all of the synthesized nucleotide conjugates of the structure dU-PEG (9)-oligonucleotide were able to be incorporated into the primer by the polymerases used, and that they competed successfully with 100 µmol/l dTTP for incorporation into the growing strand. Only at concentrations of 1 mmol/l, complete suppression of sequence-specific incorporation of nucleotide conjugates was observed, for example for Taq Polymerases.

It was established that very good sequence differentiation and sequence-dependent incorporation could be achieved in a wide temperature range for 3 or 6 nucleotide mutations. Perfect match complexes (template-target domain) and single nucleotide mismatch complexes (template-target domain) were therefore investigated in detail.

As expected, the sequence specificity of incorporation depended on the incorporation reaction temperature. In reaction mixtures with only one sequence-specific nucleotide conjugate present and temperatures significantly below the Tm of the mismatch-complex (for example at RT or 37° C.), no discrimination between single nucleotide variants was found. The target domain of the nucleotide conjugate bound both to perfect match and to mismatch; the nuc-component was thus incorporated by polymerases.

At temperatures near the Tm of mismatch complexes, the incorporation yield with a nucleotide mismatch at the template was substantially lower than with perfect-match hybridization at the template.

When the temperature of the extension reaction is raised to the Tm of the perfect-match complex (e.g. approximately 50° C. for target domains MB-Tbc1 PTO or MB-Tbc4 PTO), the nucleotide conjugate is only incorporated if a perfect-match target sequence is present in the mixture (FIG. 48). Even a single nucleotide difference in such a system may lead to a lack of labeling. Such a system can therefore discriminate sequences down to single nucleotide differences at the binding site of the target domain.

Further increases in the reaction temperature lead to a reduction in the yield of incorporation.

At reaction temperatures in the range of Tm+15° C. (relative to the Tm of the perfect-match complex), labeling ceases, even if the target domain is theoretically able to form a perfect-match complex with the template.

This behavior was observed for all the sequence-specific nucleotide conjugates that were synthesized. When the Tm of the target domain was changed (e.g. from PTO to a PTO-DNA mix), the optimal conditions for detection of single nucleotide differences changed accordingly.

Primer Extension in the Presence of Filter-1-Oligonucleotides

The effect of additional oligonucleotides which influence target domain binding on the specificity of the incorporation reaction was investigated.

A sequence-specific nucleotide conjugate (e.g. dU-PEG (9)-MB-Tbc1-PTO) formed a perfect-match complex with template M41-MBTbc, which had a Tm of about 52° C. The same nucleotide conjugate formed a mismatch complex with template M40-MBTb, which had a Tm of approximately 42° C.

Further experiments showed that filter-1-oligonucleotide MB-1Tbc 4-P formed a perfect-match complex with template M40-MBTbc, which had a Tm of about 60° C., and a mismatch complex with M41-MBTbc, which had a Tm of approximately 50° C.

When both templates M40-MBTbc and M41-MBTbc are simultaneously incubated with dU-PEG(9)-MB-Tbc1-PTO and filter-1 oligonucleotide MB-1Tbc-4-P, then the templates compete for perfect-match complexes.

To a large extent, the oligonucleotide prevents the formation of a mismatched complex between M40-MBTbc and dU-PEG(9)-MB-Tbc1 PTO.

A primer extension reaction with this composition reveals that nucleotide conjugate may still be incorporated in a sequence-specific manner, while the temperature range within which sequence-specific incorporation occurs was significantly greater.

In summary, the experiments showed: the incorporation of nucleotide conjugates that form a perfect-match complex with a sequence was not significantly disturbed by filter-1-oligonucleotides that form a perfect-match complex said sequence, while the incorporation of nucleotide conjugates that form a mismatch complex with said sequence was greatly reduced.

A similar effect could be achieved when all nucleotide conjugates variants that form a perfect-match complex are present in the reaction. They compete with each other for perfect match and prevent mismatch formation. This is the case for example in a mixture containing templates M40-MBTbc and M41-MBTbc as well as nucleotide conjugates dU-PEG(9)-MB-Tbc1-PTO and dU-PEG(9)-MB-Tbc-4-PTO.

The structure of the filter-1-oligonucleotides may comprise not only DNA, but also other types of oligonucleotides, including, for example PNA, LNA, etc. The binding specificity can be increased by means of a partial double strand, such as by molecular beacon formation.

A plurality of filter-1-oligonucleotides can be simultaneously present in a reaction.

Synthesis of Nuclease-Resistant DNA Fragments

Oligonucleotides may be rendered nuclease resistant by means of PTO modifications. Other modifications, such as PNA, LNA, or 2'-O-methyl modifications are also known to one skilled in the art.

Several nucleases were examined. The use of DNase I and Micrococcal nuclease made it possible to eliminate non-labeled DNA fragments after a reaction. This example is presented in more detail.

Primers consisting of DNA (T7-19-biotin-DNA) and various PTO-containing primers (see above) were used, as well as nucleotide conjugates with PTO-containing target domains (see above). Biotin-labeled primers and fluorescein-labeled nucleotide conjugates were covalently linked during a primer extension reaction with M41-MBTbc as template. Subsequent treatment with DNase I resulted in degradation of sequences containing longer DNA segments that had not been protected by PTO, such as T7-19-biotin-DNA, as well as template M41-MBTbc within a few minutes. In contrast, some variants of modified DNA could withstand degradation by DNase I. Such variants resulted from reactions that involved the following components: one of the following primers (T7-19-PTO-Biot, T719-PTO2-Biot, T719-PTO3-Biot), one of the dUTP conjugates with one of the following target domains (MB-Tbc1-PTO, MB-Tbc1 PTO/DNA-Mix2, MB-Tbc1 PTO/DNA-Mix3) and four dNTPs.

On the other hand, only labeled DNA arising from the reaction of T7-19-PTO-Biot and dU-PEG(9)-MB-Tbc1-PTO was able to survive degradation with Micrococcal Nuclease. Other variants of the labeled DNA were digested within a few minutes.

An increased resistance to nucleases could be imparted to the newly synthesized DNA strands in a sequence-specific manner through modification of the primers and of the components of nucleotide conjugates.

The choice of a nuclease allows for degradation of different parts of the resulting DNA. By way of example, all non-labeled nucleic acid chains can be eliminated from the reaction mixture.

The synthesis of nuclease-resistant labeled DNA can also be achieved by using alpha-phosphorothioate dNTPs for example. Compositions can be used, which comprise both alpha-phosphorothioate dNTPs and natural dNTPs.

A selective protection of labeled DNA fragments can also be combined with other types of nucleases degradation. For example, a composition containing several nucleases can be used. In another embodiment, different restriction endonucleases may be used to cleave sequences in a sequence-specific manner.

Detection with Dipstick (FIG. 53-54)

Labeled nucleic acid fragments may be rapidly detected by means of immunochromatographic methods. Many such methods are known to one skilled in the art. Depending on the features and the design, several analytes may be analyzed simultaneously, or alternatively the intensity of individual signals may be measured. Fluorescent, chromogenic, electrochemical or other signals may be used for detection.

The detection process with the Milenia GenLine HybriDetect 2T strip test, a dipstick, detects molecules that carry biotin and fluorescein labels simultaneously.

In the current example, primers carried a biotin moiety, while sequence-specific nucleotide conjugates carried a fluorescein moiety. Biotin binds to membrane-bound streptavidin, and fluorescein can be detected with nanogold particles conjugated with anti-fluorescein antibodies.

A specific signal is generated when a molecule simultaneously carries both labels: biotin and fluorescein. If the concentration of such doubly labeled molecules is sufficiently high, the specific signal becomes visible to the naked eye as a band on the strip. In our experiments, the detection limit with such a strip was found at a concentration of doubly labeled nucleic acid molecules of 100 pmol/l. Appearance of a specific band was deemed to be sufficient for qualitative detection of a specific signal. Appropriate positive and negative controls were included in each experiment.

An expert is aware of the application of such test strips. Usually, labeled probes bind to a single strand of a nucleic acid via hybridization. The specificity of the analysis depends on the stringency of the hybridization conditions and on the complexity of the mixture. The assay parameters are optimized so that specifically labeled probes are detected only if they hybridize to the target sequences with sufficient specificity. Often, several wash steps are carried out under increasingly stringent conditions in order to achieve the required specificity of the analysis by eliminating non-specifically bound fragments.

Combination of Isolation Through a Nuclease Degradation and Detection by Means of a Dipstick In the example described above, the two labels (biotin and fluorescein) are covalently integrated into a single DNA molecule after sequence-specific incorporation of the nucleotide conjugate. As a consequence of the use of PTO analogs, particular nucleotide conjugate labeled segments of the newly synthesized DNA are protected from nucleases.

Such covalent coupling makes it possible to use isolation methods and detection conditions that may cause the destruction of unprotected DNA duplexes, or of unprotected single strands for example. The elimination of non-labeled nucleic acid chains will substantially reduce non-specific binding of the labeled nucleic acids to other nucleic acid chains, resulting in an increase in specificity or an increase in the robustness of an assay.

In one embodiment, labeled DNA is detected by means of a strip test after isolation through nuclease degradation (e.g. DNase I or Micrococcal nuclease as described above). This involves the detection of fragments of DNA which have been labeled via covalent incorporation of sequence-specific nucleotide conjugates. The following components are degraded by nucleases, for example: single-stranded DNA templates and double-stranded segments not protected by PTO. The degradation products (mono-, di-, trinucleotides) do not interact with labeled products through non-specific hybridization and therefore do not interfere with dipstick detection.

There is no need for maintenance of stringent conditions during the detection of labeled DNA fragments: all unlabeled DNA segments are degraded, which means that interference due to non-specific hybridization cannot arise.

Labeled DNA may be synthesized under conditions that allow for sequence discrimination (e.g. at a reaction temperature near the Tm of the perfect match complex between template DNA and sequence-specific nucleotide conjugates; see above). In such an example, nucleotide conjugates can distinguish target sequence with an accuracy of a single nucleotide (see above). A subsequent degradation of non-labeled fragments eliminates all template molecules, which means that non-specific binding between nucleotide conjugates and DNA cannot take place. The sequence of the target sequence can thus be inferred from the detection signal of the sequence-specifically labeled DNA.

Combination of Selective Saturation of the Target Domain by an Antagonist with Detection by Means of a Dipstick In a further realization of the detection of labeled DNA with a dipstick, the target domains of smart nucleotides are saturated with specific target domain antagonists (filter-2-oligonucleotides) prior to detection. Examples of filter-2-oligonucleotides are provided in Table 6. These filter-2-oligonucleotides may be added to labeled DNA in high concentration after the labeling reaction. Subsequent heating destabilizes target domain-DNA complexes, and, after subsequent cooling, the target domains of the nucleotide conjugates become saturated with filter-2-oligonucleotides.

Through the use of filter-2-oligonucleotides the discrimination of an assay can be increased even without isolation of labeled DNA, via nuclease degradation for example. As sequence-specific nucleotide conjugates are covalently incorporated, there is no strict requirement for a target domain after incorporation. The target domain may therefore be removed during the incorporation reaction, or after an incorporation event, or its sequence binding capacity may be inactivated by an antagonist (in this example filter-2-oligonucleotide).

In this execution of the example, filter-2-oligonucleotides (e.g. MB-1Tbc 6) were hybridized with the target domain of the nucleotide conjugates (e.g. dU-PEG(9)-MB-Tbc1-PTO) after the incorporation reaction. The hybridization results in a perfect match between the target domain and the filter-2-oligonucleotide. A specific or non-specific interaction with complementary or non-complementary templates is thereby suppressed. The filter-2-oligonucleotide suppresses such binding events competitively. Owing to a significant excess of filter-2-oligonucleotides (5 µmol/l) over the applied concentrations of nucleotide conjugates, all target domains were preferably saturated. Filter-2-oligonucleotides can be used not only for saturation of the target domain of nucleotide conjugates. Various other segments of the target sequences can be blocked by means of these oligonucleotides.

The structure of the filter-2-oligonucleotides may comprise not only DNA, but also other types of oligonucleotides, including, for example, PNA, LNA, etc. The specificity of the binding to the target domain can be increased by a partial double strand, for example by molecular beacon formation.

Multiple filter-2-oligonucleotides can be present in a composition.

In summary, various techniques may be used in combination to increase the specificity of the analysis during synthesis, labeling, isolation or detection with sequence-specific nucleotide conjugates. As a consequence of the sequence-specific nature of labeling, novel combinations may be used at each individual step. Such methods would not be feasible without the use of sequence-specific nucleotide conjugates.

The aforementioned individual examples for increasing specificity can also be combined by a person skilled in the art. For example, utilization of filter-1-oligonucleotides during labeling can be combined with nuclease degradation after labeling.

Labeling During Amplification with PCR

Various thermostable polymerases were used during incorporation reactions with sequence-specific nucleotide conjugates. Both Hotstart polymerases and non-Hotstart polymerases were used. Amplification reactions were performed with various templates and primers (see above) in the presence of the synthesized nucleotide conjugates. Different levels of discrimination were achieved by changing the annealing temperatures.

By way of example, differentiation of sequences with only one nucleotide difference could be achieved with dU-PEG (9)-MB-Tbc1-PTO (0.1 µmol/l) and Primer T719-PTO3-Biot (0.5 µmol/l) at annealing temperatures between 48° C. to 54° C.

Mismatch discrimination was further improved by addition of dU-PEG(9)-MB-Tbc1-PTO in combination with appropriate filter-1-oligonucleotides (0.5 µmol/l); the annealing temperature, for example, could be lowered further.

In reactions with multiple templates (four variants of the template were identical except in one nucleotide position), sequence-specific labeling of the correct sequence was likewise feasible due to the formation of a perfect match between the target sequence and the target domain of the nucleotide conjugate and subsequent incorporation of the nucleotide component.

In one embodiment, nucleases were used to isolate DNA fragments labeled with sequence-specific nucleotide conjugates. DNase I was able to isolate PTO-protected segments of DNA within a few minutes. In one embodiment, the detection of the isolated, PTO-protected fragments of labeled DNA was performed by means a strip-test (see above).

By combining the above techniques, discrimination of a single nucleotide difference in the target sequence could be achieved, if required. The following results were achieved:

Labeled DNA was synthesized during an amplification reaction

Amplification yielded labeled DNA in sufficient quantity for detection by means of a strip test It was possible to chose the synthesis conditions such that the target domains of nucleotide conjugates discriminated target sequence to a single nucleotide.

This specificity was further enhanced both by means of sequence-specific nucleotide conjugates and by means of additional filter-1-oligonucleotides.

Labeled DNA could be isolated.

The isolation of labeled fragments of DNA could be achieved by nucleases for example.

A wide variety of nucleases with different substrate specificities is available to an expert, and this provides scope for customizing the structure of the labeled DNA in light of the prevalent nuclease isolation conditions. Both the choice of the nuclease and the composition of the labeled DNA are important in this respect.

A wide variety of possible oligonucleotides modifications (e.g. PTO, LNA, PNA, morpholino, 2'-O-Me, etc.) offers a wide spectrum of possible primer and target domain adaptations to a specific nuclease.

Multiple sequences present in the same reaction mixture can be distinguished with an accuracy of a single nucleotide through the appropriate choice of target domain and reaction conditions.

The detection of labeled DNA can be achieved in several ways. Among other methods, the simple detection conditions of test strips can be used.

Various other components (e.g. as filter-1-oligonucleotides, filter-2 oligonucleotides, alpha-phosphorothioate dNTPs, Hotstart polymerases, nucleases) can be employed to increase the specificity of an assay with sequence-specific nucleotide conjugates.

As other amplification reactions (e.g. HDA, SDA) are based on similar principles, similar conditions can also be employed in these reactions.

Many examples for amplification of nucleic acid chains and detection with specific probes are given in patent application Cherkasov et al WO2011050938. The composition of the primers and reaction conditions for the labeling with nuc-macromolecules can be obtained from this literature. The composition of the target domain of a particular type of nuc-macromolecules that are specific to a respective target sequence can be derived from the composition of the probes described for real-time PCR in analogy to the example provided above.

1.5.15.7 Labeling of Target Sequences with Solid-Phase-Bound Nuc-Macromolecules

This reaction was performed in a manner similar to that detailed in Example 1.5.15.1. The target sequence (template 2, M2) was hybridized with a primer and nuc-macromolecule (dU-PEG(8)-[T1,A1]-TAMRA) and then specifically bound to the solid phase via the anchor domain of the nuc-macromolecule. This nuc-macromolecule had dUTP as nuc-component, a target domain which can bind to the target sequence, an anchor domain (dA25 (SEQ ID NO: 3)), and a fluorescent dye (TAMRA) at the 3' end of the anchor domain, which serves as a signal domain. A solid phase which was capable of binding these anchor domains (dT48 magnetic beads (SEQ ID NO: 8), preparation see section 1.5.15.5) was used. After binding, the solid phase was washed and suspended in incorporation buffer 1.

Natural nucleotides (dATP, dCTP, dGTP, each 100 µmol/l) were added to this solid phase with bound reaction components. The dTTP was omitted in reaction 1 (Lane 1) and added to reaction 2 (Lane 2) up to 100 µmol/l concentration. The reaction was started by adding Klenow fragment exo minus (1:50) and conducted at RT for 30 min. After the reaction, the solid phase was directly loaded onto the gel and products were separated by denaturing electrophoresis under 85° C.

The result is depicted in FIG. 30.

An incorporation of nuc-macromolecules into the extended primer can be observed, wherein no complete synthesis of the complementary strand was achieved in the absence of dTTP (Arrow A1.1 and A1.2, Lane 1). In the presence of dTTP, Klenow fragment exo minus could conduct the strand synthesis in full length (Arrow A 2, Lane 2). Since in this experiment the nuc-macromolecule carried a fluorescent dye, unused nucleotide can also be seen (arrow C1). The incompleteness of the consumption of nuc-macromolecules is attributed to the steric effects of the surface.

Examples of the Application of Sequence-Specific Nucleotide Conjugates with Chain-Terminating Properties Preventing the extension of the complementary strand of particular sequences in an amplification reaction can be important, for example, in the following areas:

Use during in vitro analysis:

In a preferred embodiment of the invention, one or more sequences (population N1-Nx) may be amplified in presence of one or more other sequences (population Z1-Zx).

In a preferred embodiment, the population N1-Nx comprises sequences derived from a tumor, while sequences in the population Z1-Zx represent native, wild-type sequences of a particular species. Tumor sequences (population N1-Nx) differ from wild-type sequences (population Z1-Zx).

In a further preferred embodiment, the population N1-Nx comprises mutated sequences derived from a virus, while sequences in the population Z1-Zx represent unchanged, wild-type sequences of a virus.

In a further preferred embodiment, the population of N1-Nx comprises sequences derived from a fetus, while sequences of the population Z1-Zx represent sequences of the maternal organism.

In biological samples, target sequences are generally not present in pure form, but are contaminated by sequences of similar composition. In an assay, however, only one type of target sequence is to be detected and the signal from other potential target sequences is to be suppressed.

In an advantageous embodiment, inventive sequence-specific nucleotide conjugates with terminating nuc-components (such as 2',3'-dideoxy-nucleosid-triphosphates) are used in conventional assays. The use of sequence-specific terminators makes it possible, for example, to suppress the amplification and/or labeling and/or detection of specific sequence variants (negatively selected target sequences). Assays with improved signal-to-noise ratio can be provided in this way. The suppression of the amplification of wild-type sequences and detection of mutated sequences represents one example of this approach. Frequently, mutated sequences are only present in low copy number in a sample. In contrast, the wild-type sequence variant is present in high copy number. The suppression of the amplification of wild-type sequences makes it possible to enrich mutated sequences for further analysis during amplification.

List of sequences used:

Name, modification, sequence

```
Primer and probes/anchor
Primer T7-19:
5'- taatacgactcactatagg (SEQ ID NO: 23)

Primer T7-19-Biotin:
5'-Biotin- taatacgactcactatagg (SEQ ID NO: 23)

Primer T7-19-Cy3:
5'-Cy3- taatacgactcactatagg (SEQ ID NO: 23)

Primer dA50-T7-19:
5'- aaaaaaaaaa aaaaaaaaaa aaaaaaaaaa aaaaaaaaaa aaaaaaaaaa taatacgactcactatagg (SEQ ID NO: 34)

U19 Primer:
5'- GTT TTC CCA GTC ACG ACG (SEQ ID NO: 24)

Primer U 19-Biotin:
5'- Biotin-GTT TTC CCA GTC ACG ACG (SEQ ID NO: 24)

Primer forward:
5'-tcc tac ggg agg cag cagt (SEQ ID NO: 35)

Primer reverse:
5'-gga cta cca ggg tat cta atc ctg tt (SEQ ID NO: 36)

Probe (FAM/TAMRA):
5' FAM-cgt att acc gcg gct gct gg cac-TAMRA (SEQ ID NO: 2)

dT48-Biotin (Binding partner for anchor domain 1):
5' tttttttttt tttttttttt tttttttttt tttttttttt tttttttt-Biotin (SEQ ID NO: 8)
```

-continued

B1-Biotin-Anchor (Binding partner for anchor domain 2)
5'-Biotin- agtgaattcgagctcggtaC (SEQ ID NO: 37)

Oligonucleotide component of the nuc-macromolecules
[T1, A1]-TAMRA: Target-Domain-1, Anchor-Domain-1, TAMRA
5'NH2-cgt att acc gcg gct gct gg cac AAAAAAAAAA AAAAAAAAA AAAAA -TAMRA
(SEQ ID NO: 1)

[T2, A2]-TAMRA: Target-Domain-2, Anchor-Domain-2, TAMRA,
5'NH2-CGAGACGAAATGGGAtttttttttttttttttttt-3' TAMRA (SEQ ID NO: 38)

[T3, A3]-FAM: Target-Domain-3, Anchor-Domain-3, Fluorescein,
5'NH2-AAA AAA ACT gcg gct gct gg cac Gtaccgagctcgaattcact -FAM (SEQ ID NO: 39)

[T4]-FAM or [T4, S4]: Target-Domain-4, Spacer, Fluorescein,
5'NH2-cgt att acc gcg gct gct gg cac AAAAAAAAAA FAM (SEQ ID NO: 5)

[T5-MB]-FAM or [T5-MB, S5]: Target-Domain-5, Spacer, Fluorescein,
5' NH2-cgt att acc gcg gct gct GTAATAC AAAAA AAAAA FAM (SEQ ID NO: 6)
(Stem regions are underlined)

[T6-MB]-FAM or [T6-MB, S6]: Target-Domain-6, Spacer, Fluorescein,
5' NH2-cgt att acc gcg gct gct gg cac GTAATAC AAAAA FAM (SEQ ID NO: 40)
(Stem regions are underlined)

[T7-MB]-FAM or [T7-MB, S7]: Target-Domain-7, Spacer, Fluorescein,
5' NH2-cgt att acc gcg AATACG AAAAA FAM (SEQ ID NO: 41)
(Stem regions are underlined)

Antagonist oligonucleotides [aT(n)]

Antagonist oligonucleotide 1 [aT1]
5' agc cgc ggt aat acg 3'Phosphate (SEQ ID NO: 7)

Templates used:

Template 1 (M1):
5' GTT TTC CCA GTC ACG ACG GGAG gtg cc agc agc cgc ggt aat acg ACCA cctatagtgagtcgtatta (SEQ ID NO: 9)

Template 2 (M2):
5' GTT TTC CCA GTC ACG ACG GGAG gtg cc agc agc cgc ggt aat acg AGT CTT CTCA cctatagtgagtcgtatta (SEQ ID NO: 10)

Template 3 (M3):
5' GTT TTC CCA GTC ACG ACG GGAG gtg cc agc agc ggt aat acg AGT CTT CTGA cctatagtgagtcgtatta (SEQ ID NO: 42)

Template 4 (M4):
5' GTT TTC CCA GTC ACG ACG GGAG gtg cc agc ggt aat acg AGT CTT CTGA cctatagtgagtcgtatta (SEQ ID NO: 11)

Template 5 (M5):
5' GTT TTC CCA GTC ACG ACG GGAG gtg cc agc agc AAA AAA aat acg AGT CTT CTGA cctatagtgagtcgtatta (SEQ ID NO: 43)

Template 6 (M6):
5' GTT TTC CCA GTC ACG ACG GGAG gtg Ac agc Agc cgc Agt aat Acg AGT CTT CTGA cctatagtgagtcgtatta (SEQ ID NO: 44)

Template 7 (M7):
5' GTT TTC CCA GTC ACG ACG GGAG gtg cc agc agc cgc AAA AAA AAA AGT CTT CTGA cctatagtgagtcgtatta (SEQ ID NO: 45)

Template 8 (M8):
5' GTT TTC CCA GTC ACG ACG GGAG gtg cc agc agc cgc AGT TTT TTT AGT CTT CTGA cctatagtgagtcgtatta (SEQ ID NO: 12)

-continued

Template 9 (M9):
5' GTT TTC CCA GTC ACG ACG GGAG cgc ggt aat acg AGT CTT CTCA cctatagtgagtcgtatta (SEQ ID NO: 13)

Template 10 (M10)
5'-(A)48 TCC CAT TTC GTC TCG TTC CGC TTT GTcctatagtgagtcgtatta (SEQ ID NO: 46)

All publications, patents, and patent applications that have been cited herein are incorporated into this application at full extent (even if it was not explicitly noted for a respective publication) and are subject to regulations in accordance with the USPTO for "incorporated by reference" for all purposes in the United States.

Individual embodiments are intended to illustrate the invention and can be further combined with each other by persons skilled in the area. Combinations of various embodiments also constitute the subject of the present invention.

LEGENDS FOR FIGURES

FIG. 26, Example 1.5.15.1, Incorporation in Presence of Competing Nucleotides

Image of a gel after electrophoretic separation of the reaction products.

The following components were added into individual reactions in addition to the template, primer and polymerase. Individual lanes correspond to individual reactions.
1. +dU-PEG(8)-[T1,A1]-TAMRA
2. +dU-PEG(8)-[T1,A1]-TAMRA+dTTP 10 µmol/l
3. +dU-PEG(8)-[T1,A1]-TAMRA+dTTP 100 µmol/l
4. +dU-PEG(8)-[T1,A1]-TAMRA+dTTP 1 mmol/l
5. +dU-PEG(8)-[T1,A1]-TAMRA+dTTP 100 µmol/l+ dGTP 100 µmol/l
6. +dU-PEG(8)-[T1,A1]-TAMRA+dTTP 1 mmol/l+ dGTP 100 µmol/l
7. +dU-PEG(8)-[T1,A1]-TAMRA+dTTP+dATP+dCTP+ dGTP je 100 µmol/l
8. Control: only dU-PEG(8)-[T1,A1]-TAMRA, no Polymerase Position of the extended primer with the incorporated dU-PEG(8)-[T1,A1]-TAMRA (arrow A), Position of the dU-PEG(8)-[T1,A1]-TAMRA in gel (arrow B).

FIG. 27, Example 1.5.15.2 Competition with 10 Mmol/l dTTP

Image of a gel after electrophoretic separation of the reaction products.

The following components were included into individual reactions in addition to the template, primers, dATP, dGTP, dCTP (each 100 µmol/l), and polymerase (individual concentrations see below). Individual lanes correspond to individual reactions. An estimation of observed incorporation is given.

Klenow 1:10
1. +dU-PEG(8)-[T1,A1]-TAMRA incorporation
2. +dU-PEG(8)-[T1,A1]-TAMRA+dTTP 100 µmol/l incorporation
3. +dU-PEG(8)-[T1,A1]-TAMRA+dTTP 10 mmol/l incorporation Klenow 1:100
4. +dU-PEG(8)-[T1,A1]-TAMRA incorporation
5. +dU-PEG(8)-[T1,A1]-TAMRA+dTTP 100 µmol/l incorporation
6. +dU-PEG(8)-[T1,A1]-TAMRA+dTTP 10 mmol/l yield about 50%

Klenow 1:1000
7. +dU-PEG(8)-[T1,A1]-TAMRA incorporation
8. +dU-PEG(8)-[T1,A1]-TAMRA+dTTP 100 µmol/l incorporation
9. +dU-PEG(8)-[T1,A1]-TAMRA+dTTP 10 mmol/l low yield Taq 1:100
10. +dU-PEG(8)-[T1,A1]-TAMRA incorporation
11. +dU-PEG(8)-[T1,A1]-TAMRA+dTTP 100 µmol/l incorporation
12. +dU-PEG(8)-[T1,A1]-TAMRA+dTTP 10 mmol/l low yield Vent exo-1:100
13. +dU-PEG(8)-[T1,A1]-TAMRA+dTTP 10 mmol/l no incorporation
14. +dU-PEG(8)-[T1,A1]-TAMRA+dTTP 100 µmol/l incorporation
15. +dU-PEG(8)-[T1,A1]-TAMRA incorporation Position of the extended primer with the incorporated dU-PEG(8)-[T1,A1]-TAMRA (arrow A1). Position of the partially extended primer with incorporated dU-PEG(8)-[T1,A1]-TAMRA in gel (arrow A2). Position of the dU-PEG(8)-[T1,A1]-TAMRA in gel (arrow B).

FIG. 28, Example 1.5.15.4, Cyclic Labeling Reaction, Different Target Sequences, Different Temperatures Image of a gel after electrophoretic separation of the reaction products.

Individual lanes correspond to individual reactions.
FIG. 28, M2
(Reactions with Template 2, M2)
1. Cyclic primer extension (20 cycles) with Taq polymerase and the following components: M2, primer, four dNTPs, dU-PEG(4)-[T1,A1]-TAMRA;
2. Primer extension with Taq polymerase and the following components: M2, primer, four dNTPs, no dU-PEG(4)-[T1,A1]-TAMRA;
3. ladder: dU-PEG(4)-[T1,A1]-TAMRA, labeled primer Arrow A1: primer extension product labeled with the dU-PEG(4)-[T1,A1]-TAMRA (incomplete strand extension)
Arrow B1: primer extension product without dU-PEG(4)-[T1,A1]-TAMRA (labeling by primer Cy3)
Arrow C1: dU-PEG(4)-[T1,A1]-TAMRA (nuc-macromolecule)
Arrow D1: degradation of dU-PEG(4)-[T1,A1]-TAMRA by 5-3 exonuclease activity of the Taq polymerase
Arrow E1: labeled primer (T7-19-Cy3)

FIG. 28, M4
(Reactions with Template 4, M4)
1. Cyclic primer extension (20 cycles) with Taq polymerase, 35° C., the following components: M4, primer, four dNTPs, dU-PEG(4)-[T1,A1]-TAMRA;
2. Cyclic primer extension (20 cycles) with Taq polymerase, 45° C., the following components: M4, primer, four dNTPs, dU-PEG(4)-[T1,A1]-TAMRA;
3. Cyclic primer extension (20 cycles) with Taq polymerase, 55° C., the following components: M4, primer, four dNTPs, dU-PEG(4)-[T1,A1]-TAMRA;

4. Primer extension with Taq polymerase and the following components: M4, primer, four dNTPs, no dU-PEG(4)-[T1,A1]-TAMRA;
5. ladder: dU-PEG(4)-[T1,A1]-TAMRA, labeled primer
Arrow A2: primer extension product labeled with the dU-PEG(4)-[T1,A1]-TAMRA (complete strand extension)
Arrow B1: primer extension product without dU-PEG(4)-[T1,A1]-TAMRA (labeling by primer Cy3)
Arrow C1: dU-PEG(4)-[T1,A1]-TAMRA (nuc-macromolecule)
Arrow E1: labeled primer (T7-19-Cy3)
FIG. 28, M8
(Reactions with Template 8, M8)
1. ladder: dU-PEG(4)-[T1,A1]-TAMRA, labeled primer
2. Cyclic primer extension (20 cycles) with Taq polymerase, 35° C., the following components: M8, primer, four dNTPs, dU-PEG(4)-[T1,A1]-TAMRA;
3. Cyclic primer extension (20 cycles) with Taq polymerase, 45° C., the following components: M8, primer, four dNTPs, dU-PEG(4)-[T1,A1]-TAMRA;
4. Cyclic primer extension (20 cycles) with Taq polymerase, 55° C., the following components: M8, primer, four dNTPs, dU-PEG(4)-[T1,A1]-TAMRA;
5. Primer extension with Taq polymerase and the following components: M8, primer, four dNTPs, no dU-PEG(4)-[T1,A1]-TAMRA;
Arrow A2: primer extension product labeled with the dU-PEG(4)-[T1,A1]-TAMRA (complete strand extension)
Arrow B1: primer extension product without dU-PEG(4)-[T1,A1]-TAMRA (labeling by primer Cy3)
Arrow C1: dU-PEG(4)-[T1,A1]-TAMRA (nuc-macromolecule)
Arrow D1: degradation of dU-PEG(4)-[T1,A1]-TAMRA by 5-3 exonuclease activity of the Taq polymerase
Arrow E1: labeled primer (T7-19-Cy3)
FIG. 28, M9
(Reactions with Template 8, M8)
1. Cyclic primer extension (20 cycles) with Taq polymerase, 35° C., the following components: M9, primer, four dNTPs, dU-PEG(4)-[T1,A1]-TAMRA;
2. Cyclic primer extension (20 cycles) with Taq polymerase, 45° C., the following components: M9, primer, four dNTPs, dU-PEG(4)-[T1,A1]-TAMRA;
3. Cyclic primer extension (20 cycles) with Taq polymerase, 55° C., the following components: M9, primer, four dNTPs, dU-PEG(4)-[T1,A1]-TAMRA;
4. Primer extension with Taq polymerase and the following components: M4, primer, four dNTPs, no dU-PEG(4)-[T1,A1]-TAMRA;
Arrow B1: primer extension product without dU-PEG(4)-[T1,A1]-TAMRA (labeling by primer Cy3)
Arrow C1: dU-PEG(4)-[T1,A1]-TAMRA (nuc-macromolecule)
Arrow E1: labeled primer (T7-19-Cy3)
FIG. 29, Example 1.5.15.5, Labeling During PCR
Image of a gel after electrophoretic separation of the reaction products.
FIG. 29 Part A
Result of PCR reactions with a labeled primer. Individual lanes correspond to individual reactions. The components of the reactions are shown below. Template 2 (M2) was used as the target sequence.
1. PCR (20 cycles) with Taq polymerase, M2, both PCR-primer, four dNTPs, dU-PEG(4)-[T1,A1]-TAMRA;
2. PCR (20 cycles) with Vent exo minus polymerase, M2, both PCR-primer, four dNTPs, dU-PEG(4)-[T1,A1]-TAMRA;
3. ladder: dU-PEG(4)-[T1,A1]-TAMRA, labeled primer
4. PCR (20 cycles) with Taq polymerase, M2, both PCR-primer, four dNTPs, dU-PEG(8)-[T1,A1]-TAMRA;
5. PCR (20 cycles) with Vent exo minus polymerase, M2, both PCR-primer, four dNTPs, dU-PEG(8)-[T1,A1]-TAMRA;
6. PCR (20 cycles) with Taq polymerase, M2, both PCR-primer, four dNTPs, no dU-PEG(8)-[T1,A1]-TAMRA (control);
7. PCR (20 cycles) with Vent exo minus polymerase, M2, both PCR-primer, four dNTPs, no dU-PEG(8)-[T1,A1]-TAMRA (control);
Arrow A1: PCR product labeled with the dU-PEG(4)-[T1,A1]-TAMRA or with dU-PEG(8)-[T1,A1]-TAMRA (incomplete strand extension)
Arrow A2: PCR product labeled with the dU-PEG(4)-[T1,A1]-TAMRA or with dU-PEG(8)-[T1,A1]-TAMRA (complete strand extension)
Arrow B1: PCR product without dU-PEG(4)-[T1,A1]-TAMRA or dU-PEG(8)-[T1,A1]-TAMRA (labeling by primer Cy3)
Arrow C1: dU-PEG(4)-[T1,A1]-TAMRA (nuc-macromolecule)
Arrow D1: degradation of dU-PEG(4)-[T1,A1]-TAMRA or dU-PEG(8)-[T1,A1]-TAMRA by 5-3 exonuclease activity of the Taq polymerase
Arrow E1: labeled primer (T7-19-Cy3)
FIG. 29 Part B
Comparison of PCR products with and without specific isolation by solid phase (dT48-anchor beads (SEQ ID NO: 8)). Individual lanes correspond to individual reactions. The components of the reactions are shown below.
1. PCR (20 cycles) with Taq polymerase, M2, both PCR primers, four dNTPs, dU-PEG(4)-[T1,A1]-TAMRA;
2. PCR (20 cycles) with Taq polymerase, M2, both PCR primers, four dNTPs, no dU-PEG(4)-[T1,A1]-TAIVIRA (control);
3. Labeled PCR product (corresponding to PCR reaction in lane 1) isolated by binding to the solid phase via anchor domain of the incorporated nuc-macromolecule (residues of unused nuc-macromolecules and nuc-macromolecules degraded by the exonuclease but still having an anchor domain are also visible)
4. No isolated PCR product without labeling by nuc-macromolecule (corresponding PCR reaction in lane 2). The product did not bind to the solid phase because it had no anchor domain.
The reactants purified with beads were detached from the beads by the temperature increase during electrophoresis. This event has occurred with a delay so that the migration distance in the gel is slightly less than that of the PCR products loaded directly onto the gel. Arrows on the left indicate the positions for Lane 1 and 2, arrows on the right for Lanes 3 and 4.
Arrow A1: PCR product labeled with the dU-PEG(4)-[T1,A1]-TAMRA (incomplete strand extension)
Arrow A2: PCR product labeled with the dU-PEG(4)-[T1,A1]-TAMRA (complete strand extension)
Arrow B1: PCR product without dU-PEG(4)-[T1,A1]-TAMRA (labeling by primer Cy3)
Arrow C1: dU-PEG(4)-[T1,A1]-TAMRA (nuc-macromolecule)
Arrow D1: degradation of dU-PEG(4)-[T1,A1]-TAMRA by 5-3 exonuclease activity of the Taq polymerase
Arrow E1: labeled primer (T7-19-Cy3)
FIG. 31, Example 1.5.15.6, PCR and Labeling of the Bacterial DNA Image of a gel after electrophoretic separation of the reaction products.

FIG. 31, Part A and B (first, imaging of fluorescence signals from nuc-macromolecules was conducted (Part B), then the gel was stained with ethidium bromide and a further image was made (A)). Electrophoresis at 85-90° C.
1. ladder 100 bp
2. dU-PEG(4)-[T1,A1]-TAMRA, +T7-19-Cy3 Primer, +PCR-Produkt (from Lane 3, diluted 1:10)
3. PCR Reaktion without Probe and without nuc-macromolecule
4. PCR Reaktion with Probe (FAM/TAMRA) but without nuc-macromolecule
5. PCR Reaktion with nuc-macromolecule dU-PEG(4)-[T1, A1]-TAMRA
6. PCR Reaktion with nuc-macromolecule dU-PEG(4)-[T1, A1]-TAMRA+DMSO 5%
7. PCR as in Lane 4, PCR-Product purified with ultrafiltration MWCO 100 kDa
8. PCR as in Lane 5, PCR-Product purified with ultrafiltration MWCO 100 kDa
9. PCR as in Lane 4, incubation with dT48-Beads ("dT48" disclosed as SEQ ID NO: 8), washed with incorporation buffer 1
10. PCR and purification as in lane 7, then incubation with dT48-Beads ("dT48" disclosed as SEQ ID NO: 8), washed with incorporation buffer 1
11. PCR as in Lane 5, then binding to dT48-Beads ("dT48" disclosed as SEQ ID NO: 8), washed with incorporation buffer 1
12. PCR as in Lane 8, then binding to dT48-Beads ("dT48" disclosed as SEQ ID NO: 8), washed with incorporation buffer 1
Arrow A1: PCR product labeled with the dU-PEG(4)-[T1, A1]-TAMRA (complete and incomplete strand extension)
Arrow C1: dU-PEG(4)-[T1,A1]-TAMRA (nuc-macromolecule)
Arrow D1: degradation of dU-PEG(4)-[T1,A1]-TAMRA by 5-3 exonuclease activity of the Taq polymerase
Arrow F1: probe (FAM/TAMRA), lane 4
Arrow G1: degradation of probe (FAM/TAMRA) by 5-3 exonuclease, lane 4

FIG. 46

Use of Nuc-Macromolecules with Double Stranded Segments by Bst Polymerase Large Fragment. (Example 1.5.15.7)

An image of a gel after electrophoretic separation of the reaction products is shown.

Below the individual reagents are specified that were added in addition to template, primer and dATP, dGTP, dCTP, dTTP.

Each lane corresponds to an individual reaction.
1. +dU-P9-[T4; S4]+Bst-Polymerase large fragment
2. +dU-P9-[T4;aT1; S4]+Bst-Polymerase large fragment
3. +dU-P9-[T5-MB;S5]+Bst-Polymerase large fragment
4. +dU-P9-[T4;S4] without Polymerase
5. +dU-P9-[T5-MB;S5] without Polymerase Arrow (A) indicates the position of the fully synthesized complementary strand with incorporated dU-P9-[T4; S4] or dU-P9-[T5-MB; S5]. Arrow (B) shows the position of fully extended complementary strand lacking incorporation of nuc-macronucleotides. Arrow (C) shows the position of free, non-incorporated dU-P9-[T4; S4] or dU-P9-[T5-MB;S5], arrow (D) indicates the position of free, unused T7-19-Cy3 (A higher concentration of T7-19-Cy and dU-P9-[T4; S4] or dU-P9-[T5-MB; S5] was added to control reactions 4 and 5).

FIG. 47

Structure of a Labeled Fragment of a Nucleic Acid after Incorporation of a Sequence-Specific Nucleotide Conjugate and a Subsequent DNase I Degradation.

Primers and components of the nuc-macromolecule were protected by PTO modifications. Unprotected segments of the DNA were degraded by DNase I.

FIGS. 48 and 49

Comparison of the Binding and Incorporation of Nuc-Macromolecules with Complementary and Non-Complementary Target Domains (Perfect Match and Mismatch) Under Discriminating Reaction Conditions, for Example at a Reaction Temperature Equal to Tm for Perfect Match The structure of molecular beacons allows for good differentiation between perfectly hybridized and imperfectly hybridized target domains of nuc-macromolecules. Only bound nucleotide conjugates are incorporated into the growing strand.

FIG. 50 Retardation of the Synthesis of Labeled Fragments.

After incorporation of the nuc-components of nuc-macromolecules, synthesis can proceed further. The rate of synthesis may decrease, however. Thus, the extension of labeled strands can be retarded or suppressed (FIG. 50 A).

Continuation of synthesis beyond the incorporated nucleotide conjugate may be achieved by adjusting various parameters, such as longer incubation times or through the use of polymerases with strand displacement activity or higher temperatures (FIG. 50 B).

If premature termination of synthesis occurs, these strands are not available for polymerase chain reaction, since they lack the second primer binding site. This allows for the specific suppression of the amplification of particular fragments during PCR.

FIG. 51

Separation of Labeled Fragments from Non-Labeled Fragments by Means of Nuclease Degradation.

Well-defined segments of the labeled nucleic acid chains can be protected from nuclease by means sequence-specific nucleotide conjugates. The unlabelled segments can be removed by nuclease.

FIG. 52

Saturation of the Target Domain after an Incorporation Reaction

The binding of complementary oligonucleotides to target domains may be used to hamper their ability to bind non-specifically to other nucleic acid chains.

FIG. 53-55

Detection of Labeled Fragments of DNA by Means of a Strip Test.

Reactants (streptavidin) for the corresponding anchor domain (biotin) are fixed on a strip. If successful labeling has taken place, the labeled fragment (comprising biotin and fluorescein) binds at the respective location on the strip. Fluorescein and biotin are co-located on the same molecule only after a successful sequence-specific labeling. Non-specifically bound fragments have been eliminated by DNase for example and not interfere with specific detection.

The invention claimed is:

1. A method for detection of at least one target nucleic acid chain present in a reaction mixture, comprising the steps:
  (1) labelling the at least one target nucleic acid chain by enzymatic synthesis of one or more nucleic acid chains, comprising the step of enzymatic incorporation of nucleotides into the complementary strand of the at least one target nucleic acid chain to provide at least one labelled target nucleic acid chain,
  wherein at least one of the nucleotides is a target nucleic acid chain-specific nucleotide-conjugate having the structure: (Nuc-linker)n-marker
  wherein:
  Nuc is a nucleotide component (nuc-component) selected from the group consisting of a nucleoside-triphosphate, nucleoside-tetraphosphate, nucleoside-pentaphosphate, and an alpha-nucleoside thiotriphosphate;
  Linker is a linker component comprising a water soluble polymer, which links the nuc-component to a macromolecular marker component, wherein said;
  Marker is a macromolecular marker component which comprises at least one target domain having an oligonucleotide sequence complementary to at least a portion of the target nucleic acid chain; and n is a positive integer from 1 to 100;
  wherein the nucleotide-conjugate comprises at least one synthetic chemical nucleotide modification that is resistant to nuclease;
  wherein the Linker is covalently attached to the base of the nuc-component and covalently attached to the oligonucleotide sequence of the macromolecular marker component and
  wherein binding of the at least one target domain of the nucleotide-conjugate to the complementary portion of the target nucleic acid chain facilitates selective incorporation of the nucleotide component of the nucleotide-conjugate into newly synthesized target nucleic acid chains by a polymerase;
  (2) isolating the at least one labelled target nucleic acid chain by adding to the reaction mixture at least one type of nuclease to which the nucleotide-conjugate is resistant and incubating the reaction mixture under conditions that enable nuclease degradation of the nucleic acid chains in the reaction mixture that are not resistant to nuclease degradation by said nuclease; and
  (3) detecting the at least one labelled target nucleic acid chain.

2. The method of claim 1,
  wherein the labelling of the at least one target nucleic acid chain comprises the step of (1) primer extension using the target nucleic acid chain as a template or (2) amplification of the at least one target nucleic acid chain;
  wherein at least one polymerase and at least one type of nucleotide that is not a nucleotide-conjugate are used to conduct the enzymatic synthesis of one or more nucleic acid chains; and at least one primer is used in the step of primer extension or amplification.

3. The method according to claim 1,
  wherein the step of detecting comprises detecting a characteristic signal moiety, and optionally comparing the detected signal with at least one reference signal.

4. The method according to claim 1 wherein the Marker comprises at least one oligonucleotide sequence that is fully or partially complementary to the target nucleic acid chain and which comprises at least one chemically modified nucleotide that is resistant to nuclease.

5. The method according to claim 1, wherein the chemical nucleotide modification of the macromolecular marker component comprises at least one chemical modification selected from the group consisting of PTO, LNA; PNA, morpholino, and 2'-O-Me.

6. The method according to the claim 2, wherein the at least one primer comprises at least one nuclease resistant modification.

7. The method according to claim 2, wherein the at least one type of nucleotide that is not a nucleotide-conjugate is selected from the group consisting of dATP, dGTP, dCTP, dTTP, dUTP, ATP, GTP, CTP, UTP, nucleotides labeled with biotin, terminator nucleotides, fluorescent dye labeled nucleotides, and alpha-phosphorothioate nucleotides.

8. The method according to claim 2, wherein the amplification step comprises a polymerase chain reaction (PCR).

9. The method according to claim 2, wherein the amplification step comprises an isothermal amplification.

10. The method of claim 1, wherein the at least one nuclease is selected from the group consisting of DNase I, Micrococcal nuclease, Exonuclease III (Exo III), Exonuclease I (Exo I), Mung Bean Nuclease, S1 Nuclease, and sequence-specific endonuclease.

11. A kit for detection of the target nucleic acid chains according to claim 1, comprising: at least one type of the nucleotide-conjugate, at least one nuclease to which the nucleotide-conjugate is resistant, and optionally, components for labelling the target nucleic acid chains and/or detecting the labelled target nucleic acid chains,
  wherein the at least one nucleotide conjugate has the structure: (Nuc-linker)n-marker
  wherein:
  Nuc is a nucleotide component (nuc-component) selected from the group consisting of a nucleoside-triphosphate, nucleoside-tetraphosphate, nucleoside-pentaphosphate, and a an alpha-nucleoside thiotriphosphate derivative;
  Linker is a linker component comprising a water soluble polymer, which links the nuc-component to a macromolecular marker component, wherein said;
  Marker is a macromolecular marker component which comprises at least one target domain having an oligonucleotide sequence complementary to at least a portion of the target nucleic acid chain; and n is a positive integer from 1 to 100;

wherein the nucleotide-conjugate comprises at least one synthetic chemical nucleotide modification that is resistant to nuclease;

wherein the Linker is covalently attached to the base of the nuc-component and covalently attached to the oligonucleotide sequence of the macromolecular marker component and wherein binding of the at least one target domain of the nucleotide-conjugate to the complementary portion of the target nucleic acid chain facilitates selective incorporation of the nucleotide component of the nucleotide-conjugate into newly synthesized target nucleic acid chains by a polymerase.

12. The method according to claim 6, wherein the primer comprises at least one nucleotide modified with a group selected from PTO, LNA, PNA, morpholino and 2'-O-Me.

13. The method according to claim 1, further comprising binding the labelled target nucleic acid chains to a solid substrate prior to detecting said labelled target nucleic acid chains.

14. The method according to claim 1, wherein in the labelling step, the reaction mixture comprises at least one target nucleic acid chain and at least one non-target nucleic acid chain.

15. The kit according to claim 11, further comprising at least one primer for synthesis of target nucleic acid chain, wherein said primer comprises at least one chemical modification that is resistant to nuclease and a nuclease to which the primer is resistant.

16. The kit according to claim 15, further comprising at least one alpha-phosphorothioate nucleotide selected from the group consisting of Sp-dATP-alpha-S, Sp-dCTP-alpha-S, Sp-dGTP-alpha-S and Sp-dUTP-alpha-S.

17. A method for synthesizing at least one copy of a target nucleic acid chain, comprising the steps:
(1) labelling the target nucleic acid chain by enzymatic synthesis of one or more nucleic acid chains in a reaction mixture, comprising the step of enzymatic incorporation of nucleotides into the complementary strand of the target nucleic acid chain to provide at least one labelled target nucleic acid chain,
wherein at least one of the nucleotides is a target nucleic acid chain-specific nucleotide-conjugate having the structure: (Nuc-linker) n-marker
wherein:
Nuc is a nucleotide component (nuc-component) selected from the group consisting of nucleoside-triphosphate, nucleoside-tetraphosphate, nucleoside-pentaphosphate, and an alpha-nucleoside thiotriphosphate;
Linker is a linker component comprising a water soluble polymer, which links the nuc-component to a macromolecular marker component,
wherein said;
Marker is a macromolecular marker component which comprises at least one target domain having an oligonucleotide sequence complementary to at least a portion of the target nucleic acid chain; and n is a positive integer from 1 to 100;
wherein the Linker is covalently attached to the base of the nuc-component and covalently attached to the oligonucleotide sequence of the macromolecular marker component wherein the nucleotide-conjugate comprises at least one synthetic chemical nucleotide modification that is resistant to nuclease; and wherein binding of the at least one target domain of the nucleotide-conjugate to the complementary portion of the target nucleic acid chain facilitates selective incorporation of the nucleotide component of the nucleotide-conjugate into newly synthesized target nucleic acid chains by polymerase;

2) isolating the at least one labelled target nucleic acid chain by adding to the reaction mixture at least one type of nuclease to which the nucleotide-conjugate is resistant and incubating the reaction mixture under conditions that enable nuclease degradation of the nucleic acid chains in the reaction mixture that are not resistant to nuclease degradation by said nuclease.

18. The method of claim 1, wherein the Linker is selected from the group consisting of polyethylene-glycol (PEG), polyamide, polypeptides, polysaccharides and derivatives thereof, dextran and derivatives thereof, polyphosphate, polyacetate, poly(alkyleneglycol), copolymers of ethyleneglycol and propyleneglycol, poly(olefinic alcohol), poly(vinylpyrrolidone), poly(hydroxyalkylmethacrylamide), poly(hydroxyalkylmethacrylate), poly(x-hydroxy acid), polyacrylic acid and derivatives thereof, poly-acrylamide and derivatives thereof, poly(vinylalcohol), polylactic acid, polyglycolic acid, poly(epsilon-caprolactone), poly(beta-hydroxybutyrate), poly(beta-hydroxyvalerate), polydioxanone, poly(ethylene terephthalates), poly(malic acid), poly(tartronic acid), poly(ortho ester), polyanhydride, polycyanoacrylate, poly(phosphoester), polyphosphazenes, hyaluronidate, and polysulfones.

19. The method of claim 11, wherein the Linker is selected from the group consisting of polyethylene-glycol (PEG), polyamide, polypeptides, polysaccharides and derivatives thereof, dextran and derivatives thereof, polyphosphate, polyacetate, poly(alkyleneglycol), copolymers of ethyleneglycol and propyleneglycol, poly(olefinic alcohol), poly(vinylpyrrolidone), poly(hydroxyalkylmethacrylamide), poly(hydroxyalkylmethacrylate), poly(x-hydroxy acid), polyacrylic acid and derivatives thereof, poly-acrylamide and derivatives thereof, poly(vinylalcohol), polylactic acid, polyglycolic acid, poly(epsilon-caprolactone), poly(beta-hydroxybutyrate), poly(beta-hydroxyvalerate), polydioxanone, poly(ethylene terephthalates), poly(malic acid), poly(tartronic acid), poly(ortho ester), polyanhydride, polycyanoacrylate, poly(phosphoester), polyphosphazenes, hyaluronidate, and polysulfones.

20. The method of claim 17, wherein the Linker is selected from the group consisting of polyethylene-glycol (PEG), polyamide, polypeptides, polysaccharides and derivatives thereof, dextran and derivatives thereof, polyphosphate, polyacetate, poly(alkyleneglycol), copolymers of ethyleneglycol and propyleneglycol, poly(olefinic alcohol), poly(vinylpyrrolidone), poly(hydroxyalkylmethacrylamide), poly(hydroxyalkylmethacrylate), poly(x-hydroxy acid), polyacrylic acid and derivatives thereof, poly-acrylamide and derivatives thereof, poly(vinylalcohol), polylactic acid, polyglycolic acid, poly(epsilon-caprolactone), poly(beta-hydroxybutyrate), poly(beta-hydroxyvalerate), polydioxanone, poly(ethylene terephthalats), poly(malic acid), poly(tartronic acid), poly(ortho ester), polyanhydride, polycyanoacrylate, poly(phosphoester), polyphosphazenes, hyaluronidate, and polysulfones.

21. The method of claim 1, wherein the Linker is attached to the base at one of positions 4 or 5 when the base is a pyrimidine or one of positions 6, 7 or 8 when the base is a purine.

22. The method of claim 11, wherein the Linker is attached to the base at one of positions 4 or 5 when the base is a pyrimidine or one of positions 6, 7 or 8 when the base is a purine.

23. The method of claim 17, wherein the Linker is attached to the base at one of positions 4 or 5 when the base is a pyrimidine or one of positions 6, 7 or 8 when the base is a purine.

* * * * *

SEQUENCE LISTING

<160> NUMBER OF SEQ ID NOS: 46

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgtattaccg cggctgctgg cacaaaaaaa aaaaaaaaa aaaaaaaa                          48

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtattaccg cggctgctgg cac                                                    23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa aaaaaaaaaa aaaaa                                                  25

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaaa                                                                   10

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtattaccg cggctgctgg cacaaaaaaa aaa                                         33

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgtattaccg cggctgctgt aatacaaaaa aaaaa                                       35

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agccgcggta atacg                                                    15

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttttttttt tttttttttt tttttttttt tttttttttt tttttttt               48

<210> SEQ ID NO 9
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gttttcccag tcacgacggg aggtgccagc agccgcggta atacgaccac ctatagtgag    60
tcgtatta                                                            68

<210> SEQ ID NO 10
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gttttcccag tcacgacggg aggtgccagc agccgcggta atacgagtct tctcacctat    60
agtgagtcgt atta                                                     74

<210> SEQ ID NO 11
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gttttcccag tcacgacggg aggtgccagc ggtaatacga gtcttctgac ctatagtgag    60
tcgtatta                                                            68

<210> SEQ ID NO 12
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
gttttcccag tcacgacggg aggtgccagc agccgcagtt tttttagtct tctgacctat    60
agtgagtcgt atta    74

<210> SEQ ID NO 13
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gttttcccag tcacgacggg agcgcggtaa tacgagtctt ctcacctata gtgagtcgta    60
tta    63

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccacgcttgt gggtcaaccc ccgtgg    26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccacgcttgt cggtcaaccc ccgtgg    26

<210> SEQ ID NO 16
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttttcccag tcacgacggg agtctggggt tgaccgacaa gagtcactca cctatagtga    60
gtcgtatta    69

<210> SEQ ID NO 17
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gttttcccag tcacgacggg agtctggggt tgacccacaa gagtcactca cctatagtga    60
gtcgtatta    69

```
<210> SEQ ID NO 18
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gttttcccag tcacgacggg agtctggggt tgaccaacaa gagtcactca cctatagtga      60
gtcgtatta                                                              69

<210> SEQ ID NO 19
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gttttcccag tcacgacggg agtctggggt tgacctacaa gagtcactca cctatagtga      60
gtcgtatta                                                              69

<210> SEQ ID NO 20
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gttttcccag tcacgacggg agtctggggt tgaacaagag tcactcacct atagtgagtc      60
gtatta                                                                 66

<210> SEQ ID NO 21
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gttttcccag tcacgacggg agtctggggt tgaaagagtc actcacctat agtgagtcgt      60
atta                                                                   64

<210> SEQ ID NO 22
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gggguugacc gacaagaaaa cccuauagug agucguauua                            40

<210> SEQ ID NO 23
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 23
taatacgact cactatagg                                              19

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttttcccag tcacgacg                                               18

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
taatacgact ccctatagg                                              19

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccacgcttgt gggtcaaccc ccgtgg                                      26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccacgcttgt tggtcaaccc ccgtgg                                      26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccacgcttgt aggtcaaccc ccgtgg                                      26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 29
ccacgcttgt cggtcaaccc ccgtgg                                  26

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggggttgacc aacaag                                             16

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggggttgacc cacaag                                             16

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggggttgacc gacaag                                             16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggggttgacc tacaag                                             16

<210> SEQ ID NO 34
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaaaaaaaaa aaaaaaaaaa aaaaaaaaaa aaaaaaaaaa aaaaaaaaaa taatacgact    60
cactatagg                                                     69

<210> SEQ ID NO 35
<211> LENGTH: 19
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 35
tcctacggga ggcagcagt                                                   19

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggactaccag ggtatctaat cctgtt                                           26

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agtgaattcg agctcggtac                                                  20

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgagacgaaa tgggattttt tttttttttt ttttt                                 35

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaaaaaactg cggctgctgg cacgtaccga gctcgaattc act                        43

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cgtattaccg cggctgctgg cacgtaatac aaaaa                                 35

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 41
cgtattaccg cgaatacgaa aaa                                           23

<210> SEQ ID NO 42
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gttttcccag tcacgacggg aggtgccagc agcggtaata cgagtcttct gacctatagt    60
gagtcgtatt a                                                        71

<210> SEQ ID NO 43
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttttcccag tcacgacggg aggtgccagc agcaaaaaaa atacgagtct tctgacctat    60
agtgagtcgt atta                                                     74

<210> SEQ ID NO 44
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gttttcccag tcacgacggg aggtgacagc agccgcagta atacgagtct tctgacctat    60
agtgagtcgt atta                                                     74

<210> SEQ ID NO 45
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gttttcccag tcacgacggg aggtgccagc agccgcaaaa aaaaaagtct tctgacctat    60
agtgagtcgt atta                                                     74

<210> SEQ ID NO 46
<211> LENGTH: 93
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 46
aaaaaaaaaa aaaaaaaaaa aaaaaaaaaa aaaaaaaaaa aaaaaaaatc ccatttcgtc      60
tcgttccgct ttgtcctata gtgagtcgta tta                                    93
```